United States Patent
Praveen et al.

(10) Patent No.: US 12,258,627 B2
(45) Date of Patent: *Mar. 25, 2025

(54) KELCH DOMAIN CONTAINING 7B (KLHDC7B) VARIANTS AND USES THEREOF

(71) Applicant: Regeneron Pharmaceuticals, Inc., Tarrytown, NY (US)

(72) Inventors: Kavita Praveen, Tarrytown, NY (US); Giovanni Coppola, Tarrytown, NY (US); Manuel Allen Revez Ferreira, Tarrytown, NY (US); Lauren Gurski, Tarrytown, NY (US); Aris Baras, Tarrytown, NY (US); Meghan Drummond Samuelson, Tarrytown, NY (US); Goncalo Abecasis, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 159 days.

This patent is subject to a terminal disclaimer.

(21) Appl. No.: 18/303,193

(22) Filed: Apr. 19, 2023

(65) Prior Publication Data

US 2023/0366024 A1   Nov. 16, 2023

Related U.S. Application Data

(63) Continuation of application No. 17/307,653, filed on May 4, 2021, now Pat. No. 11,674,177.

(Continued)

(51) Int. Cl.
    *C12Q 1/68*     (2018.01)
    *C12Q 1/6851*   (2018.01)
    (Continued)

(52) U.S. Cl.
    CPC ........ *C12Q 1/6874* (2013.01); *C12Q 1/6851* (2013.01); *C12Q 1/6876* (2013.01);
    (Continued)

(58) Field of Classification Search
    None
    See application file for complete search history.

(56) References Cited

U.S. PATENT DOCUMENTS

| 2016/0090597 | A1  | 3/2016  | Smith et al. |
| 2017/0226570 | A1* | 8/2017  | Weksberg ............ C12Q 1/6827 |
| 2017/0306406 | A1* | 10/2017 | Weksberg ............ C12Q 1/6883 |

FOREIGN PATENT DOCUMENTS

| WO | 2017161387      |    | 9/2017 |              |
| WO | WO-2017161387 A1 | *  | 9/2017 | ............. A61K 31/12 |

OTHER PUBLICATIONS

Kalra et al., Biological insights from multi-omic analysis of 31 genomic risk loci for adult hearing difficulty, https://doi.org/10.1101/562405, Now published in PLOS Genetics doi: 10.1371/journal.pgen.1009025, Feb. 27, 2019.*

(Continued)

*Primary Examiner* — Aaron A Priest
(74) *Attorney, Agent, or Firm* — Armstrong Teasdale LLP

(57) ABSTRACT

The present disclosure provides methods of treating subjects having hearing loss, methods of identifying subjects having an increased risk of developing hearing loss, and methods of detecting Kelch Domain Containing 7B (KLHDC7B) variant nucleic acid molecules and variant polypeptides.

19 Claims, 4 Drawing Sheets

Specification includes a Sequence Listing.

Related U.S. Application Data

(60) Provisional application No. 63/087,245, filed on Oct. 4, 2020, provisional application No. 63/020,746, filed on May 6, 2020.

(51) Int. Cl.
    *C12Q 1/6874*     (2018.01)
    *C12Q 1/6876*     (2018.01)
    *G01N 33/68*     (2006.01)
    *A61K 38/00*     (2006.01)

(52) U.S. Cl.
    CPC .......... *G01N 33/6818* (2013.01); *A61K 38/00* (2013.01); *C12Q 2600/118* (2013.01); *C12Q 2600/158* (2013.01)

(56) References Cited

OTHER PUBLICATIONS

Cherny et al., "Self-reported hearing loss questions provide a good measure for genetic studies: a polygenic risk score analysis from UK Biobank", European Journal of Human Genetics, 2020, 28(8), pp. 1056-1065.

Helena et al., "GWAS Identifies 44 Independent Associated Genomic Loci for Self-Reported Adult Hearing Difficulty in UK Biobank", The American Journal of Human Genetics, 2019, 105(4), pp. 788-802.

Kalra et al., "Biological insights from multi-omic analysis of 31 genomic risk loci for adult hearing difficulty", PLOS Genetics, 2020, 16(9), pp. 1-32.

International Search Report and Written Opinion dated Aug. 9, 2021 for International Patent Application No. PCT/US2021/030669.

* cited by examiner

C) Position: 22:50549676:G:A; cDNA: c.1510G>A; Amino acid: Val504Met

| Study | Cases | Controls | AAF | | OR | p-value |
|---|---|---|---|---|---|---|
| UKB 300K imputed | 92,009 | 9,039 | 280 | 221,108 | 19,348 | 371 | 0.0434 | | 1.14 | 1.3E-27 |
| GHS 85K IDT imputed | 1,711 | 156 | 2 | 53,828 | 4,324 | 101 | 0.0410 | | 1.11 | 1.2E-01 |
| GHS 60K VCRome imputed | 2,915 | 298 | 12 | 41,580 | 3,370 | 62 | 0.0391 | | 1.07 | 1.1E-01 |
| Malmo Freeze Two imputed | 305 | 20 | 1 | 25,624 | 1,813 | 37 | 0.0356 | | 1.00 | 7.1E-01 |
| Sinai Freeze Two imputed | 189 | 13 | 0 | 9,504 | 667 | 10 | 0.0385 | | 0.99 | 4.9E-01 |
| Meta | 97,129 | 9,466 | 298 | 351,644 | 29,522 | 581 | 0.0417 | | 1.17 | 3.3E-28 |

SEQUENCE LISTING

```
Sequence total quantity: 48
SEQ ID NO: 1            moltype = DNA   length = 5125
FEATURE                 Location/Qualifiers
source                  1..5125
                        mol_type = genomic DNA
                        organism = Homo sapiens
SEQUENCE: 1
agaagcaggt tggctgtgat gacagcacag agctcaggaa cgctgcctga ggaccctggg   60
gcctacgagg aggagaagag ggcaggagct ggtggggtgc ttgcagagac cctgggctcc  120
tatcctgcca taagcctcgc tgtctcctga tatctgcagc caggccctac tgacaccccc  180
aggcctgagt gcaagcagag acccaccat tcccaggccc tggaggactg gtccaccta   240
actgggcagc ccttggggca ggcgctggcc ggtgcctcag cccaggcctc tgtgctctgc  300
atgcactgcc agcctgccat caggcctcta ttgcagccct gaaccatgat ccagggcacc  360
ttggagccag atggtcccct ctggggctgg gactgggaca gtgacaatga ctgggatagt  420
gctgtgctgg ccctcctggc gctggctgtg gtggctgcca cagcgctggc cttacactgg  480
tttggctccg ggcacgatca agaggcggca gaaccggtgt ccacagccct cggggctcaa  540
cctcatcagg caggaggagc tgagctggcc ctgcaaccga agtctaaggt cagtgatggc  600
agcgaggggc agagcccagg gcaggggaaa ccagagcccc caggacgcgg ccagcagagc  660
```

```
cctgtccctg ctgcagcgcc gggcggggc ctggccgcca tggcccggct tccactcaag  720
acggctgtcg aggaggcccg cagagaggca ttaggacagc aacgggcag tgccaccccc   780
gcggcccccc gagcggaagg aaaggagcct cccaggccag gcactgccct cctgggcagg  840
agcgaagcag gggggatgtc cgccccctc ctgatccact tcactcctcg gagccctggc   900
agcgaagcgg aggcggagac aggtggtgtc agggcgtcct ctcgccaggc cgcaggcccc  960
gcggggcaac aggacactgg cccctggcag gcgggcgcgg ggcctcgggg ctcgatgggg  1020
agaggccggg gccggcggcg gcggatggac gctggctcgg gagacagagc ccgccgcccc  1080
cggaaactgg acccgctccg cctgggcgcc gcggggagcg tgtgggacgc ggtggacggg  1140
gccgccgccc tggacgccca cgcgcgcggc ctccccacag gaccccccact cgccccaggag  1200
cccgcactcc cggcgctgcc cgctccccgc gccctgcagc ctgggtctca gacggaaggc  1260
tctggggcca agggtggctg gagcaggag gcctcgggg tccctgcccc cggaggaggc  1320
tggccctggg tcagcaggga ggtccggc accggagct ttggcccagc ccagactcc    1380
acgcgccct ggctagagag tccgcctcaa ggtcgcccac tctcgtccca agggccgggt  1440
gccacagggg cctacgatgc cggcgaggcc gggggctgaca gctcccgaga taacagtcct  1500
gccgctgacc tggggcccac ccggccccg gagcaagcaa agccggctgc agccggccac   1560
agccgcgcgc cctcccggag ccgtgagcct cgccccgcgct ccgcctcccc gcccgcagct  1620
cccggcccgg ggttcccacc tgaagccctg actctcccct ctccttcaga cttttttgcc   1680
ctggaggtta cccaggatcc ttccgtgggc gaaaatctca gagcggcgcc agcccaagt   1740
tcagcctcag cccaagtctt aacttcagct ccagcctcag tcctagcccc agccctggct  1800
tcatccccca gctcagcacc aacctcagcc accacctcaa cctcatcccc cacctcagcc  1860
ccagcccag ctccaacctc agctccaact tcaaccccag cccagcccc aagtccagct    1920
gcagccgcaa ctccagcccc agccccagtc ccagtccgca gcccagcca cccatcccca  1980
gccctaaccc cagtcccaac cccagcccta agcccagct caactccagc cctaaccca    2040
gccgcatccc cagcccaac cccagtccca acccagccc taagcccagc tccaactca    2100
gccccaaccc cagccgcatc cctgccccag gcccccacct cagccccaac cccaaccca   2160
gccgcatccc ctgccccagc tgacgggtca aagcctcagg agagtgtggc tctccccagg  2220
cgctaccagg aggggcaggt ctcagccagc tgggaaacc ttatgccat ggttcttaga    2280
agccacccct tccccaggca agacaggcc aagggagtg tccgagggc ggttcccggg    2340
agccccgtgg gtcccagcac ttccacacac tctgaggaca gacacggccc ctcttcttca  2400
gtggggacag tcataggggac aggtacaggg ggcctggtttg aggctggagg tcagccaggg  2460
ccaagaagct ccgagaccaa cggatcgcc agcccagacc ctcccccagg cctaagagga  2520
gagggaacca gggagaaaag tctagacccg ctgcccaag ccgcgatgcc cagggcccc   2580
gcacagcccc ccgcgcagag gccgcctggc cccgcggcct cctcctctgc gaggcgctca   2640
cagccggtac cccagctacg gaaacgcagc aggtgcgaaa tcgcccgag ctcggagcag   2700
gaggtcaggc cggccgcctc gggggaccct caaggggagg cgcggggga ggggggcagc   2760
cctgccggcc gcagcgggc gctcacgaa aagcaggagg aggcccggaa gctcatggtg    2820
tttctgcaga ggcccggggg ttgggggtg gtggaggggc cccggaagcc cagctcccgg    2880
gccctggagc ccgccacggc ggcagccctg cggcggcggc tggacctggg cagttgcctg   2940
gacgtcggg cctttgccca gcagcacgga gagcccggcc tggcgcagga gacctacgcg   3000
ctgatgagcg acaacctgct gcgagtgctg ggagacccgt gcctctaccg ccggctgagc  3060
gcggccgacc gcgagcgcat cctcagcctg cggaccggcc ggggccggc ggtgctgggc   3120
gtcctcgtac tgcccagcct ctaccagggg ggccgctcag ggctccccag ggggccctcgt  3180
ggcgaggagc ctcctgcggc ggccctgtg tccctgcctc tacctgcgca cctgcatgtg   3240
ttcaaccccc gggagaacac ctggcggccc ctgacccagg tgcccgagga ggccccgctt   3300
cggggctgcg gtctctgcac catgcacaac tacctgttc tggcgggggg catccgtggc   3360
tccggtgcca aggccgtctg ctccaacgag gtcttctgct acaaccctct gaccaacatc  3420
tggagccagg ttcggcccat gcagcaggcc cgagcccagc tcaactgtgg ggccctggac  3480
gggctgctct atgccatcgg tggcgaatgc ctgtacagca tggagtgcta cgacccgcga  3540
acagacgcct ggaccccacg cgcgccactc cccgcaggca ccttcccgt ggcccacgag   3600
gctgtggcct gccgtgggga catctacgtc accgggggtc acctcttcta ccgcctgctc  3660
aggtacagcc ccgtgaagga tgcttggac gagtgcccat acagtgccag cacccggcgt  3720
tccagcgaca tcgtgggcact gggggggcttc ctgtaccgct tcgacctgct gcggggcgtg  3780
ggcgccgccg tgatgcgcta caacacagtg accggctcct ggagcagggc tgcctcctg   3840
cccctgcccg cccccgcccc actgcactgc accaccctgg gcaacaccat ttactgcctc  3900
aaccccaag tcactgccac ctttcacgtc tctgggggga ctgcccagtt ccaggccaag   3960
gagctgcagc ccttccccctt ggggagcacc ggggtcctca gtccattcat cctgactctg  4020
ccccctgagg accggctgca gacctcactc tgagtggcag gcagagaacc aaagctgctt   4080
cgctgctctc cagggagacc ctcctgggat gggcctgaga ggccggggct cagggaaggg   4140
gctgggatcg gaacttcctg ctcttgtttc tggacaactt tcccctttctg ctttaaaggt   4200
tgtcgattat tttgaagccc agactccctc agcctctttc tgcccctcac tccacaccca  4260
gactgttttcc tgactcaatt ccgtacctac ttacagaccc tctcagcttg ctgacaccc   4320
cctgtctgtg ggactcccta ttccctagag ccagggactg atgcgtctcc acagacaagg  4380
acttggctcg ctggagctct gctgagccga gagaggaggg ggtagaaaac attcacactt   4440
cctatgctct gtcagcagga cagggagcaa aaacgtcccc aggcaacgcc ctcgcctctg  4500
ggactttctg cctgtcctaa ggcctcccca ggtaccaacc ccgtagctat ctgggtctgt  4560
ttggcactgt ggattctcaa gggcctagaa cccttgcctc tgaaactggt ccgctggtgc  4620
agccctgctg tctgcagctc ctgccatac ccccagccca caccggcca ggcccactcc     4680
gggctcacca ccctctgcag ccttgtgggg ctctcccagc ccctccagaa gcccaccca   4740
cttctcgcca accccgatc tctaaatgag gcctgagcgt caccctagtt ctgcccttt     4800
ttagctgtgt agacttggac gagacatttg acttccctttt ctccttgtct ataaaatgtg  4860
gacagtggac gtctgtcacc caagagagtt gtgggagaca agatcacagc tatgagcacc  4920
tcgcacggtt tccaggatgc acagcacaat ccatgatgcg ttttctcccc ttacgcactt   4980
tgaaacccat gctagaaaag tgaatacatc tgactgtgct ccactccaac ctccagcctg   5040
gatgtccctg ttttctgttt tttattctat gttcagcacc actggcacca                5100
aatacatttt aattcaccga aagca                                        5125

SEQ ID NO: 2        moltype = DNA  length = 5125
FEATURE             Location/Qualifiers
source              1..5125
``` mol_type = genomic DNA
organism = Homo sapiens

SEQUENCE: 2

```
agaagcaggt tggctgtgat gacagcacag agctcaggaa cgctgcctga ggaccctggg    60
gcctacgagg aggagaagag ggcaggagct ggtggggtgc ttgcagagac cctgggctcc   120
tatcctgcca taagcctcgc tgtctcctga tatctgcagc caggccctac tgacacccc    180
aggcctgagt gcaagcagag accccaccat tcccaggccc tggaggactg gtccaccta    240
actgggcagc ccttggggca ggcgctggcc ggtgcctcag cccaggcctc tgtgctctgc    300
atgcactgcc agcctgccat caggcctcta ttgcagcctg gaaccatgat ccagggcacc    360
ttggagccag atggtcccct ctgggggctgg gactgggaca gtgacaatga ctggatagt    420
gctgtgctgg ccctcctggc gctggctgtg gtggctgcca cagcgctggc cttacactgg    480
tttggctccg ggcacgatca agaggcggca gaaccggtgt ccacagccct cggggctcaa    540
cctcatcagg caggaggagc tgagctggcc ctgcaaccga agtctaaggt cagtgatggc    600
agcgagggc agagcccagg gcaggggaaa ccagagccca caggacgcgg ccagcagagc    660
cctgtccctg ctgcagcgcc gggcggggc ctggccgcca tggcccggct tccactcaag    720
acggctgtcg aggaggcccg cagagaggca ttaggacagc aacggggcag tgccaccccc    780
gcggcccccc gagcggaagg aaaggagcct cccaggccag gcactgccct cctgggcagg    840
agcgaagcag gggggatgtc cgccccccctc ctgatccact tcactcctcg gagccctggc    900
agcgaagcgg aggcggagac aggtggtgtc agggcgtcct ctcgccaggc cgcaggcccc    960
gcggggcaac aggacactgg ccctggcag gcgggcgcgg ggcctcggg ctcgatgggg    1020
agaggccggg gccggcggcg gcggatggac gctggctcgg gagacagagc ccgccgcccc    1080
cggaaactgg acccgctccg cctggccgcc gcggggacgg tgtgggacgc ggtggacggg    1140
gccgccgccc tggacgccca cgcgcgcggg ctccccacag gaccccact cgcccaggag    1200
cccgcactcc cggcgctgcc cgctccccgc gccctgcagc ctgggtctca gacgaaggc    1260
tctgggcca agggtggctg gagcaggag gcctcggggg tccctgcccc cggaggaggc    1320
tggccctggg tcagcaggga ggtcccgggc acccggagct ttggcccagc cccagactcc    1380
acgcgcccct ggctagagag tccgcctcaa ggtcgcccac tctcgtccca agggccgggt    1440
gccacagggg cctacgatgc cggcgaggcc gggctgaca gctcccgaga taacagtcct    1500
gccgctgacc tggggcccac ccggcccccg gagcaagcaa agccggctgc agccggccac    1560
agccgcgcgc cctcccggag ccgtgagcct cgccccgcgct ccgcctcccc gcccgcagct    1620
cccgcccggg ggttccacc tgaagccctg actctcccct ctccttcaga cttttttgccc    1680
ctggaggtta cccaggatcc ttccgtgggc gaaaatctca gagcggcgcc agccccaagt    1740
tcagcctcag cccaagtctt aacttcagct ccagcctcag tcctagcccc agccctggct    1800
tcatccccca gctcagcacc aacctcagcc accacctcag cctcatcccc cacctcagcc    1860
ccagccccag ctccaacctc agctccaact tcaacccccag cccagcccc aagtccagct    1920
gcagccgcaa ctccagcccc agcccagtc ccagtcccaa ccctcacacc cccatcccca    1980
gccctaaccc cagtcccaac cccagcccta agcccagctc caactccagc cctaacccca    2040
gccgcatccc cagcccctaac cccagtccca accccagccc taagcccagc tccaactcca    2100
gccccaaccc cagccgcatc cctgccccag gcccccacct cagccccaac cccaaccca    2160
gccgcatccc ctgccccagc tgacgggtca aagcctcagg agagtgtggc tctcccagg    2220
cgctaccagg aggggcaggt ctcagccagc tggggaaacc ttattgccat ggttcttaga    2280
agccacccct tccccaggca agacaggccc caagggagtg tcccgagggc ggttcccggg    2340
agccccgtgg gtcccagcac ttccacacac tctgaggaca gacacggcc ctcttcttca    2400
gtggggacag tcatagggac aggtacaggg ggcctggttg aggctggagg tcagccacag    2460
ccaagaagct ccgagaccaa cggatcgccc agcccagacc ctccccagg cctaagagga    2520
gagggaacca gggagaaaag tctagacccg ctgcccaag ccgcgatgcc caggggcccc    2580
gcacagcccc ccgcgcagag gccgcctggc cccgcgcct cctcctctgc gaggcgctca    2640
cagccggtac cccagctacg gaaacgcagc aggtgcgaaa tcgccccgag ctcggagcag    2700
gaggtcaggc cggccgcctc ggggggaccct caaggggagg cgccggggga ggggggcagc    2760
cctgccggcc gcagcgggc gctcacgaaa aagcaggagg aggcccggaa gctcatggtg    2820
tttctggaca ggcccggggg ttgggggggtg gtggagggc cccggaagcc cagctccggg    2880
gccctggagc ccgccacggc ggcagccctg cggcggcggc tggacctggg cagttgcctg    2940
gacgtgctgg cctttgccca gcagcacgga gagcccggcc tggcgcagga gacctacgcg    3000
ctgatgagca caacctgct gcgagtgctg ggagacccgt gcctctaccg ccggctgagc    3060
gcggccgacc gcgagcgcat cctcagcctg cggaccgagc ggggccggc ggtgctgggc    3120
gtcctcgtac tgcccagcct ctaccagggg ggccgctcag ggctcccag gggccctcgt    3180
ggcgaggagc ctcctgcggc ggcccctgtg tccctgcctc tacctgcgca cctgcatgtg    3240
ttcaaccccc gggagaacac ctggcggccc ctgacccagg tgcccgagga ggccccgctt    3300
cggggctgcg gtctctgcac catgcacaac tacctgtttc tggcggggggg catccgtggc    3360
tccggtgcca aggccgtctg ctccaacaga gtcttctgct acaacccctc gaccaacatc    3420
tggagccagg ttcggcccat gcagcaggcc cgagcccagc tcaagctggt ggccctggac    3480
gggctgctct atgccatcgg tggcgaatgc ctgtacagca tggagtgcta cgacccgcga    3540
acagacgcct ggaccccacg cgcgccactc cccgcaggca ccttccctgt ggcccacgag    3600
gctgtggcct gccgtgggga catctacgtc accgggggtc acctcttcta ccgcctgctc    3660
aggtacagcc ccgtgaagga tgcttgggac gagtgcccat acagtgccag ccaccggcgt    3720
tccagcgaca tcgtggcact ggggggcttc ctgtaccgct tcgacctgct gcggggcatg    3780
ggcgccgccc tgatgcgcta caacacagtg accggctcct ggagcagggc tgcctccctg    3840
cccctgcccg cccccgcccc actcactgcc accaccctgg gcaacaccat ttactgcctc    3900
aacccccagg tcactgccac cttcacggtc tctgggggag ctgcccagtt ccaggccaag    3960
gagctgcagc ccttcccctt ggggagcacc gggggtcctca gtccattcat cctgactctg    4020
cccccctgagg accggctgca gacctcactc tgagtggcag gcagagaacc aaagctgctt    4080
cgctgctctc cagggagacc ctcctgggat gggcctgaga ggccggggct cagggaaggg    4140
gctgggatcg gaacttcctg ctcttgtttc tggacaactt tccccttctg ctttaaaggt    4200
tgtcgattat tttgaagccc agactccctc agcctcttc tgcccctcac tccacaccca    4260
gactgttttc tgactcaatt ccgtacctac ttacagaccc tctccagcttg ctgacacccca    4320
cctgtctgtg ggactccta ttccctgag ccagggactg atgcgtctcc acagacaagg    4380
acttggctcg ctggagctct gctgagccga gagaggaggg ggtagaaaac attcacactt    4440
cctatgctct gtcagcagga cagggagcaa aaacgtcccc aggcaacgcc ctcgcctctg    4500
ggactttctg cctgtcctaa ggcctcccca ggtaccaacc ccgtagctat ctgggtctgt    4560
```

```
ttggcactgt ggattctcaa gggcctagaa cccttgcctc tgaaactggt ccgctggtgc   4620
agccctgctg tctgcagctc ctgcccatac ccccagccca caccaggcca ggccactcc    4680
gggctcacca ccctctgcag ccttgtgggg ctctcccagc cctccagaa gcccacccca    4740
cttctcgcca accccgatc tctaaatgag gcctgagcgt caccctagtt ctgcccttt     4800
ttagctgtgt agacttggac gagacatttg acttcccttt ctccttgtct ataaaatgtg   4860
gacagtggac gtctgtcacc aagagagtt gtgggagaca agatcacagc tatgagcacc    4920
tcgcacggtg tccaggatgc acagcacaat ccatgatgcg ttttctcccc ttacgcactt   4980
tgaaacccat gctagaaaag tgaatacatc tgactgtgct ccactccaac ctccagcctg   5040
gatgtccctg tctgggccct ttttctgttt tttattctat gttcagcacc actggcacca   5100
aatacatttt aattcaccga aagca                                         5125
```

SEQ ID NO: 3        moltype = RNA  length = 5125
FEATURE             Location/Qualifiers
source              1..5125
                    mol_type = mRNA
                    organism = Homo sapiens
SEQUENCE: 3

```
agaagcaggt tggctgtgat gacagcacag agctcaggaa cgctgcctga ggaccctggg   60
gcctacgagg aggagaagag ggcaggagct ggtggggtgc ttgcagagac cctgggctcc   120
tatcctgcca taagcctcgc tgtctcctga tatctgcagc caggccctac tgacaccccc   180
aggcctgagt gcaagcagag accccaccat tcccaggccc tggaggactg gtccacctta   240
actgggcagc ccttggggca ggccgtcggcc ggtgcctcaa cccaggcctc tgtgctctgc   300
atgcactgcc agcctgccat caggcctcta ttgcagccct gaaccatgat ccagggcacc   360
ttggagccag atggtcccct ctggggctgg gactgggaca gtgacaatga ctgggatagt   420
gctgtgctgg ccctcctggc gctggctgtg gtggctgcca cagcgctggc cttacactgg   480
tttggcctccg ggcacgatca agaggcggca gaaccggtgt ccacagcccc cgggctcaa   540
cctcatcagg caggaggagc tgagctggcc ctgcaaccga agtctaaggt cagtgatggc   600
agcgagggc agagcccagg gcaggggaaa ccagagcccc caggacgcgg ccagcagagc   660
cctgtccctg ctgcagcgcc gggcggggc ctggccgcca tgcccggct ccactcaag    720
acggctgtcg aggaggcccg cagagaggca ttaggacagc aacgggcag tgccacccc    780
gcggccccc gagcggaagg aaaggagcct cccaggccag gcactgccct cctgggcagg   840
agcgaagcag gggggatgtc cgcccccctc ctgatccact tcactcctcg gagccctggc   900
agcgaagcgg aggcggagac aggtggtgtc agggcgtcct ctcgccaggc cgcaggccc    960
gcggggcaac aggacactgg cccctggcag gcgggcgcgg ggcctcggg ctcgatgggg   1020
agaggccggg gccgcggcg gcggatggac gctggctcgg gagacagagc ccgccgcccc   1080
cggaaactgg accccgctccg cctgggcgcc gcggggagcg tgtggacgc ggtgacggg   1140
gccgccgccc tggacgccca cgcgcgcggc ctccccacag accccccact cgcccaggag   1200
cccgcactcc cggcgctgcc cgctcccgc gccctgcagc ctgggtctca gacggaaggc   1260
tctggggcca agggtggctg gagcagggag gcctcgggg tccctgcccc cggaggaggc   1320
tggcctgggg tcagcaggga ggtcccgggc accggagctc ttggcccagc cccagactcc   1380
acgcgccccc ggctagagag tccgcctcaa ggtcgcccac tctcgtccca agggccgggt   1440
gccacagggg cctacgatgc cggcgaggcc ggggctgaca gctcccgaga taacagtcct   1500
gccgctgacc tggggcccac ccggccccg gagcaagcaa agccggctgc agccggccac   1560
agccgcgcgc cctccccggag ccgtgagcct cgcccgcgct ccgcctcccc gcccgcagct   1620
cccggcccgg ggttcccacc tgaagccctg actctcccct ctcttcaga ctttttgccc   1680
ctggaggtta cccaggatcc ttccgtgggc gaaaatctca gagcggcgcc agcccccagt   1740
tcagcctcag cccaagtctt aacttcagct ccagcctcca tcctagccc aaccctggct   1800
tcatccccca gctcagcacc aacctcagcc accacctcaa cctcatcccc cacctcagcc   1860
ccagcccag ctccaacctc agctccaact tcaaccccag cccagcccc aagtccagct    1920
gcagccgcaa ctccagcccc agcccagtc ccagtcccaa ccctcacacc ccatccccca   1980
gccctaaccc cagtcccaac cccagccta agcccagcc caactccagc ctaacccca     2040
gccgcatccc cagccctaac cccagtccca accccagccc taagcccagc tccaactcca   2100
gccccaaccc cagccgcatc cctgcccca gccccacct cagccccaac cccaacccca    2160
gccgcatccc ctgccccagc tgacgggtca agcctcagg agagtgtggc tctcccagg     2220
cgctaccagg aggggcaggt ctcagccagc tggggaaacc ttattgccat ggttcttaga   2280
agccaccect tccccaggca agacaggccc caagggagtg tcccgagggc ggttcccggg   2340
agccccgtgg gtcccagcac ttccacacac tctgaggaca gacacggccc ctcttcttca   2400
gtggggacag tcatagggac aggtacaggg ggcctggttg aggctggagg tcagccacag   2460
ccaagaagct ccgagaccaa cggatcgccc agcccagacc ctccccagg cctaagagga    2520
gagggaacca gggagaaaag tctagacccg ctgccccaag ccgcgatgcc caggggcccc   2580
gcacagcccc ccgcgcagag gccgcctggc cccgcggcct cctcctctgc gaggcgctca   2640
cagccggtac cccagctacg gaaacgcagc aggtgcgaaa tcgccccgag ctcggagcag   2700
gaggtcaggc cggccgcctc gggggaccct caaggggagg cgccgggga gggggcagc    2760
cctgccgccc gcagcgggc gctcacggaa aagcaggagg aggcccggaa gctcatgggc   2820
tttctgcaga ggcccggggg ttgggggtg gtggagggc cccggaagcc agctcccgg    2880
gccctggagc ccgccacggc ggcagccctg cggcggcggc tggacctggg cagttgcctg   2940
gacgtgctgg cctttgccca gcagcacgga gagcccggcc tggcgcagga gacctacgcg   3000
ctgatgagcg acaacctgct gcgagtgctg ggagaccgt gcctctaccg ccggctgagc   3060
gcggccgacc gcgagcgcat cctcagcctg cggaccgcg gggccgggc ggtgctgggc   3120
gtcctcgtac tgcccagcct ctaccagggg ggccgctcag ggctcccag ggccctcgt     3180
ggcgaggagc ctcctgcggc ggccctgtgt ccctgcctc tacctgcgca cctgcatgtg   3240
ttcaaccccc gggagaacac ctggcggccc ctgcccagg tgcccgagga ggcccgcttt   3300
cggggctgcg gtctctgcac catgcacaac tacctgtttc tggcgggggg catccgtggc   3360
tccggtgcag ggccgtctg ctccaacgag gtcttctgga caaccctct gaccaacatc   3420
tggagccagg ttcggcccat gcagcaggcc cgagcccagc tcaagctggt ggccctggac   3480
gggctgctct atgccatcgg tggcgaatgc ctgtacagca tggagtgcta cgacccgcga   3540
acagacgcct ggaccccacg cgcgccactc cccgcaggca ccttccctgt ggcccacgag   3600
gctgtggcct ccgtgggga catctacgtc accggggtc acctcttcta ccgcctgctc   3660
aggtacagcc ccgtgaagga tgcttgggac gagtgccat acagtgccag ccaccggcgt   3720
```

```
tccagcgaca tcgtggcact gggggcttc ctgtaccgct tcgacctgct gcggggcgtg  3780
ggcgccgccg tgatgcgcta caacacagtg accggctcct ggagcagggc tgcctccctg  3840
cccctgcccg ccccgcccc actgcactgc accaccctgg gcaacaccat ttactgcctc  3900
aaccccagg tcactgccac cttcacggtc tctgggggga ctgccagtt ccaggccaag  3960
gagctgcagc ccttccccct gggagcacc ggggtcctca gtccattcat cctgactctg  4020
cccctgagg accggctgca gacctcactc tgagtggcag gcagagaacc aaagctgctt  4080
cgctgctctc cagggagacc ctcctgggat gggcctgaga ggccggggct cagggaaggg  4140
gctgggatcg gaacttcctg ctcttgtttc tggacaactt tccccttctg ctttaaaggt  4200
tgtcgattat tttgaagccc agactccctc agcctctttc tgcccctcac tccacaccca  4260
gactgtttcc tgactcaatt ccgtaccctac ttacagaccc tctcagcttg ctgacacccc  4320
cctgtctgtg ggactcccta ttccctagag ccagggactg atgcgtctcc acagacaagg  4380
acttggctcg ctggagctct gctgagccga gagaggaggg ggtagaaaac attcacacatt  4440
cctatgctct gtcagcagga cagggagcaa aaacgtcccc aggcaacgcc ctcgcctctg  4500
ggactttctg cctgtcctaa ggcctcccca ggtaccaacc ccgtagctat ctgggtctgt  4560
ttggcactgt ggattctcaa gggcctagaa cccttgcctc tgaaactggt ccgctggtgc  4620
agccctgctg tctgcagctc ctgcccatac ccccagccca caccaggcca ggcccactcc  4680
gggctcacca ccctctgcag ccttgtgggg ctctcccagc cctccagaa gcccacccca  4740
cttctcgcca acccccgatc tctaaatgag gcctgagcgt caccctagtt ctgcccctt  4800
ttagctgtgt agacttggac gagacattg acttccttt ctccttgtct ataaaatgtg  4860
gacagtggac gtcgtcacc caagagagtt gtgggagaca agatcacagc tatgagcacc  4920
tcgcacggtg tccaggatgc acagcacaat ccatgatgcg ttttctcccc ttacgcactt  4980
tgaaacccat gctagaaaag tgaatacatc tgactgtgct ccactccaac ctccagcctg  5040
gatgtccctg tctgggccct ttttctgttt tttattctat gttcagcacc actggcacca  5100
aatacatttt aattcaccga aagca                                         5125

SEQ ID NO: 4         moltype = RNA   length = 2990
FEATURE              Location/Qualifiers
source               1..2990
                     mol_type = mRNA
                     organism = Homo sapiens
SEQUENCE: 4
ccacctcagc cccaaccccca accccagccg catcccctgc cccagctgac gggtcaaagc  60
ctcaggagag tgtggctctc cccaggcgct accaggaggg gcaggtctca gccagctggg  120
gaaaccttat tgccatggtt cttagaagcc accccttcca caggcaagac aggccccaag  180
ggagtgtccc gagggcggtt cccgggagcc ccgtgggtcc cagcacttcc cacacactctg  240
aggacagaca cggcccctct tcttcagtgg ggacagtcat agggacaggt caggggggcc  300
tggttgaggc tggaggtcag ccacagccaa gaagctccga gaccaacgga tcgcccagcc  360
cagaccctcc ccaggcccta agaggagagg gaaccaggga gaaaagtcta gacccgctgc  420
cccaagccgc gatgcccagg ggccccgcac agccccccgc gcagaggccg cctggcccga  480
cggcctcctc ctctgcgagg cgctcacagc cggtacccca gctacggaaa cgcagcaggt  540
gcgaaatcgc cccgagctcg gagcaggagg tcaggccggc cgcctcgggg acccctcaag  600
gggaggcgcc ggggagggg gcagccctg ccggccgcag cgggcgctc acggaaaagc  660
aggaggaggc ccggaagctc atggtgtttc tgcagaggcc cggggttgg ggggtggtgg  720
aggggcccg gaagcccagc tcccgggccc tggagcccgg cacggcggca gccctgcgcc  780
ggcggctgga cctgggcagt tgcctggacg tgctggcctt tgcccagcag cacggagagc  840
ccggcctggc gcaggagacc tacgcgctga tgagcgcaca cctgctgcga gtgctgggag  900
acccgtgcct ctaccgccgg ctgagcgcgg ccgaccgcga gcatcctc agcctgcgga  960
ccggccgggg ccgggcggtg ctgggcgtcc tcgtactgcc cagcctctac cagggggggc  1020
gctcagggct cccaggggc cctcgtggcg aggagcctcc tgcggcggcc cctgtgtccc  1080
tgcctctacc tgcgcacctg catgtgttca acccccggga gaacacctgg cggccctga  1140
cccaggtgcc cgaggaggcc ccgcttcggg gctgcgcggct ctgcaccatg cacaactacc  1200
tgtttctggc ggggggcatc cgtggctccg gtgccaaggc cgtctgctcc aacgaggtct  1260
tctgctacaa ccctctgacc aacatctgga gccaggttcg gcccatgcag caggcccgag  1320
cccagctcaa gctggtggcc ctggacgggc tgctctatgc catcggtggc gaatgcctgt  1380
acagcatgga gtgctacgac ccggcgaacag acgcctgcac cccacgcgcg ccactccccg  1440
caggcacctt ccctgtggcc cacgaggctg tggcctgccg tggggacatc tacgtcaccg  1500
ggggtcacct cttctaccgc ctgctcaggt acagccccgt gaaggatgct tgggacgagt  1560
gcccatacag tgccagccac cggcgttcca gcgacatcgt ggcactgggg ggcttcctgt  1620
accgcttcga cctgctgcgg ggcgtgggcg ccgcctgtat gcgctacaac acagtgaccg  1680
gctcctggag cagggctgcc tccctgcccc tgcccccc gccccactg cactgcacca  1740
ccctgggcaa caccatttac tgcctcaacc ccaggtcac tgccaccttc acggtctctg  1800
gggggactgc ccagttccag gccaaggagc tgcagccctt cccccttgggg agcaccgggg  1860
tcctcagtcc attcatcctg actctgcccc tgaggaccg gctgcagacc tcactctgag  1920
tggcaggcag agaaccaaag ctgcttcgct gctctccag ggagaccctc tgggatgggc  1980
ctgagaggcc ggggctcagg gaaggggctg ggatcggaac ttcctgctct gtttctgga  2040
caactttccc cttctgcttt aaaggttgtc gattattttg aagcccagac tccctcagcc  2100
tctttctgcc cctcactcca cacccagact gtttcctgac tcaattccgt acctacttac  2160
agaccctctc agcttgctga caccccctgt ctgtgggac tccctattcc ctagagcag  2220
ggactgatgc gtctccacag acaaggactt ggctcgctg agctctgctg agccgagaga  2280
ggaggggta gaaaacattc acacttccta tgctctgtca gcaggacagg gagcaaaaac  2340
gtccccagc aacgccctcg cctctgggac tttctgcctg tcctaaggcc tccccaggta  2400
ccaacccgt agctatctgg gtctgtttgg cactgtggat tctcaaggc ctagaaccct  2460
tgcctctgaa actggtccgc tggtgcagcc ctgctgtctg cagctcctgc cataccccc  2520
agcccacacc aggccaggcc cactccgggc tcaccccctc tgccaacccc cgatctcta aatgaggcct  2580
cccagccccc cagaagccc acccacttc tcgccaaccc ccgatctcta aatgaggcct  2640
gagcgtcacc ctagttctgc ccttttag ctgtgtagac ttggacgaga catttgactt  2700
ccctttctcc ttgtctataa aatgtggaca gtggacgtct gtcacccaag agagttgtgg  2760
gagacaagat cacagctatg agcacctcgc acggtgtcca ggatgcacag cacaatccat  2820
gatgcgtttt ctccccttac gcactttgaa acccatgcta gaaaagtgaa tacatctgac  2880
```

```
tgtgctccac tccaacctcc agcctggatg tccctgtctg ggccctttt ctgtttttta    2940
ttctatgttc agcaccactg gcaccaaata cattttaatt caccgaaagc              2990

SEQ ID NO: 5            moltype = RNA   length = 4837
FEATURE                 Location/Qualifiers
source                  1..4837
                        mol_type = mRNA
                        organism = Homo sapiens
SEQUENCE: 5
actgccagcc tgccatcagg cctctattgc agccctgaac catgatccag ggcaccttgg    60
agccagatgg tccctctgg  ggctgggact gggacagtga caatgactgg gatagtgctg    120
tgctggccct cctggcgctg gctgtggtgg ctgccacagc gctggcctta cactggtttg    180
gctccgggca cgatcaagag gcggcagaac cggtgtccac agccctcggg gctcaacctc    240
atcaggcagg aggagctgag ctggccctgc aaccgaagtc taaggtcagt gatggcgacg    300
aggggcagag cccagggcag gggaaaccag agccccagg  acgcggccag cagagccctg    360
tccctgctgc agccgcgggc gggggcctgg ccgccatggc ccggcttcca ctcaagacgg    420
ctgtcgagga ggcccgcaga gaggcattag acagcaacg  gggcagtgcc accccgcgg    480
cccccgagc  ggaaggaaag gagcctccca ggccaggcac tgccctcctg ggcaggacg    540
aagcagggg  gatgtccgcc cccctcctga tccacttcac tcctcggagc cctggcagcg    600
aagcggaggc ggagacaggt ggtgtcaggg cgtcctctcg ccaggccgca ggccccgcgg    660
ggcaacagga cactggcccc tggcaggcgg gcgcggggcc ctcgggctcg atggggagag    720
gccgggccg  gcggcggcgg atggacgctg gctcgggaga cagagcccgc cgccccccga    780
aactggaccc gctccgcctg ggcgccgcgg ggagcgtgtg ggacgcggtg gacggggccg    840
ccgccctgga cgccacgcg  gcggcctcc  ccacaggacc cccactcgcc caggagcccg    900
cactcccggc gctgccgct  ccccgcgccc tgcagcctgg gtctcagacg gaaggctctg    960
gggccaaggg tggctggagc agggaggcct cgggggtccc tgccccgga  ggaggctggc    1020
cctgggtcag cagggaggtc ccgggcaccc ggagctttgg cccagcccca gactccacgc    1080
gcccctggct agagagtccg cctcaaggtc gcccactctc gtcccaaggg ccgggtgcca    1140
caggggccta cgatgccggc gaggccgggg ctgacagctc ccgagataac agtcctgccg    1200
ctgacctggg gcccaccgg  cccccggag  aagcaaagcc tggcgcagcc ggccacagcc    1260
gcgcgccctc ccggagccgt gagcctcgcc cgcgctccgc ctccccgccc gcagctcccg    1320
gcccggggtt cccacctgaa gcccgacta  tccctctcc  ttcagactt  ttgccccgg    1380
aggtacccca ggatccttcc gtgggcgaaa atctcagagc ggcgccagcc caagttcag    1440
cctcagccca agtcttaact tcagctccag cctcagtcct agccccagcc ctggcttcat    1500
ccccagctc  agcaccaacc tcagccacca cctcaacctc atccccccacc tcagccccag    1560
ccccagctcc aacctcagct ccaacttcaa ccccagccca agccccaagt ccagctgcag    1620
ccgcaactcc agcccagcc  ccagtcccag tccaaccct  cacaccccca tccccagccc    1680
taacccccagt cccaaccca gccctaagcc cagctccaac tccagcccta accccagccg    1740
catccccaagc cctaacccca gtccccaaccc cagcctcca actccagccc                1800
caacccccagc cgcatcccct gccccagccc ccacctcagc cccaacccca accccagccg    1860
catccccctgc cccagctgac gggtcaaagc ctcaggagag tgtggctctc cccaggcgct    1920
accaggaggg gcaggtctca gccagctggg gaaaccttat tgccatggtt cttagaagcc    1980
accccttccc caggcaagac aggccccaag ggagtgcggt cccgggagcg                   2040
ccgtgggtcc cagcacttcc acacactctg aggacagaca cggcccctct tcttcagtg      2100
ggacagtcat agggacaggt acaggggcc tggttgagggc tggaggtcag ccacagccaa     2160
gaagctccga ccaacggaa tcgcccagcc cagaccctcc cccaggccta agaggagagg     2220
gaaccagggga gaaaagtcta gacccgctgc cccaagccgc gatgcccagg ggccccgcac     2280
agcccccgc  gcagaggccg cctggcccccg cggcctcctc ctctgcgagg cgctcacagc    2340
cggtacccca gctacggaaa cgcagcaggt gcgaaatcgc ccgagctcg  gagcaggagg     2400
tcaggccggc cgcctcgggg gaccctcaag ggggaggcgcc ggggagggg gcagccctg      2460
ccgggccgcag cgggggcgctc acggaaaagc aggaggagcc ccggaagctc atggtgtttc   2520
tgcagaggcc cggggttgg  ggggtggtgg aggggccccg gaagcccagc tcccgggccc   2580
tggagcccgc cacggcggca gcccctgcgg ggcggctgga cctgggcagt tgcctggacg   2640
tgctggcctt tgcccagcag cacggagagc ccggcctggc gcaggagacc tacgcgctga     2700
tgagcgacaa cctgctgcga gtgctgggag acccgtcgc  ctaccgcgg ctgagcgcgg    2760
ccgaccgcga gcgcatcctc agcctgcgga ccggccggg  ccggcgcgtg ctgggcgtcc    2820
tcgtactgcc cagcctctac cagggggcc gctcagggct cccaggggc  cctcgtggcg     2880
aggagcctcc tgcggcggcc cctgtgtccc tgcctctacc tgcgcacctg catgtgttca    2940
accccggga  gaacacctgg cggccccctga cccaggtgcc cgaggaggcc ccgcttcggg     3000
gctgcggtct ctgcaccatg cacaactacc tgtttctggc ggggggcat  cgtggcctgg    3060
gtgccaagggc cgtctgctcc aacgaggtct tctgctacaa ccctctgacc aacatctgga    3120
gccaggttcg gcccatgcag caggcccgag cccagctcaa gctggtggcc ctggacgggc    3180
tgctctatgc catcggtggc gaatgcctgt acagcatgga gtgctacgac ccgcgaacag    3240
acgcctggac cccacgcgcg ccactccccg caggcaccctt ccctgtggcc cacgaggctg    3300
tggcctgccg tgggggacatc tacgtcaccg ggggtcacct cttctaccgc ctgctcaggt    3360
acagccccgt gaaggatgct tgggacagt  gcccatacag tgccagccac cggcgttcca    3420
gcgacatcgt ggcactgggg ggcttcctgt accgcttcga cctgctgcgg ggcgtgggcg    3480
ccgccgtgat gcgctacaac acagtgaccg gctcctggag cagggctgcc tccctgcccg    3540
tgccgccgac cgcccactg  cactgcacca cctgggaac accatttac tcctcaacc      3600
cccaggtcac tgccaccttc acggtctctg ggggactgc  ccagttccag gccaaggagc    3660
tgcagccctt cccctttggg gcaccgggg  tcctcagtcc attcatcctg actctgcccc    3720
ctgaggaccg gctgcagacc tcactctgag tggcaggcag agaaccaaag ctgcttcgct    3780
gctctccagg agacccctcc tgggatgggc ctgagaggcc gggctcagg  gaagggctg     3840
ggatcggaac ttcctgtct  tgttctggaa caactttcct aaaggtgtc                     3900
gattatttt  aagcccagac tccctcagcc tctttctgcc cctcactcca cacccagact    3960
gtttcctgac tcaattccgt acctacttac agacccctct agcttgctga cacccccctg     4020
tctgtgggac tccctattcc ctagagccag ggactgatgc gtctcacag  acaaggactt    4080
ggctcgctgg agctctgctg agccgagaga ggaggggta  gaaaacattc acacttccta    4140
tgctctgtca gcaggacagg gagcaaaaac gtccccagcc aacgcccctcg cctctgggac    4200
```

-continued

```
tttctgcctg tcctaaggcc tccccaggta ccaaccccgt agctatctgg gtctgtttgg 4260
cactgtggat tctcaagggc ctagaaccct tgcctctgaa actggtccgc tggtgcagcc 4320
ctgctgtctg cagctcctgc ccataccccc agcccacacc aggccaggcc cactccgggc 4380
tcaccaccct ctgcagcctt gtggggctct cccagcccct ccagaagccc accccacttc 4440
tcgccaaccc ccgatctcta aatgaggcct gagcgtcacc ctagttctgc cccttttag 4500
ctgtgtagac ttggacgaga catttgactt ccctttctcc ttgtctataa aatgtggaca 4560
gtggacgtct gtcacccaag agagttgtgg gagacaagat cacagctatg agcacctcgc 4620
acggtgtcca ggatgcacag cacaatccat gatgcgtttt ctcccttac gcactttgaa 4680
acccatgcta gaaaagtgaa tacatctgac tgtgctccac tccaacctcc agcctggatg 4740
tccctgtctg ggcctttt ctgttttta ttctatgttc agcaccactg gcaccaaata 4800
cattttaatt caccgaaagc aaaaaaaaaa aaaaaaa                          4837

SEQ ID NO: 6               moltype = RNA   length = 2099
FEATURE                    Location/Qualifiers
source                     1..2099
                           mol_type = mRNA
                           organism = Homo sapiens
SEQUENCE: 6
ccacctcagc cccaacccca accccagccg catcccctgc cccagctgac gggtcaaagc 60
ctcaggagag tgtggctctc cccaggcgct accaggaggg gcaggtctca gccagctggg 120
gaaaccttat tgccatggtt cttagaagcc accccttccc caggcaagac aggccccaag 180
ggagtgtccc gagggcggtt cccgggagcc ccgtgggtcc cagcacttcc acacactctg 240
aggacagaca cggcccctct tcttcagtgg ggacagtcat agggacaggt acaggggccc 300
tggttgaggc tggaggtcag ccacagccaa gaagctccga gaccaacgga tcgcccagcc 360
cagaccctcc cccaggccta agaggagagg gaaccaggga gaaaagtcta gacccgctgc 420
cccaagccgc gatgccaggg ggcccccgca gcccccgc gcagaggccg cctgcccgg 480
cggcctcctc ctctgcgagg cgctcacagc cggtacccca gctacggaaa cgcagcaggt 540
gcgaaatcgc cccgagctcg gagcaggagg tcaggccggc cgcctcgggg gaccctcaag 600
gggaggcgcc ggggagggg ggcagccctg ccggccgcag cggggcgctc acggaaaagc 660
aggaggaggc ccggaagctc atggtgttc tgcagagcc cggggtggg ggggtggtgg 720
aggggccccg gaagcccagc tcccgggccc tggagcccgc cacggcggca gcctgtcgcc 780
ggcggctgga cctgggcagt tgcctggacg tgctggcctt tgcccagcag cacggagagc 840
ccggcctggc gcaggagacc tacgcgctga tgagcgacaa cctgctgcga gtgctgggag 900
acccgtgcct ctaccgccgg ctgagcgcgg ccgaccgcga gcgcatcctc agcctgcgga 960
ccggcgaggg ccgggcgtg ctgggcgtcc tcgtactgcc cagcctctac caggggggcc 1020
gctcagggct cccagggggc cctcgtggcg aggagcctcc tgcggcggcc cctgtgtccc 1080
tgcctctacc tgcgcacctg catgtgttca accccgggga gaacacctgg cggcccctga 1140
cccaggtgcc cgaggaggcc ccgcttcggg gctgcgtgtc ctgcaccatg cacaactacc 1200
tgtttctggc gggggcatc cgtgtcctg gtgccaaggc cgtctgctcc aacgaggtct 1260
tctgctacaa ccctctgacc aacatctgga gccaggttcg gcccatgcag caggcccgag 1320
cccagctcaa gctggtggcc ctggacgggc tgctctatgc catcggtggc gaatgcctgt 1380
acagcatgga gtgctacgac ccgcgaacag acgcctggac cccacgcgcg ccactccccg 1440
caggcacctt ccctgtggcc cacgaggctg tggcctgacc tggggacatc tacgtcaccg 1500
ggggtcacct cttctaccgc ctgctcaggt acaccccgt gaaggatgct tgggacgagt 1560
gcccatacag tgccagccac cggcgttcca gcgacatcgt ggcactgggg ggcttcctgt 1620
accgcttcga cctgctgcgg ggcgtgggcg ccgccgtgat gcgctacaac acagtgaccg 1680
gctcctggag cagggctgcc tccctgcccc tgcccgccg ccccactg cactgcacca 1740
ccctgggcaa caccatttac tgcctcaacc cccaggtcac tgccaccttc acggtctctg 1800
gggggactgc ccagttccag gccaaggagc tgcagcccct tcccctgggg agcaccgggg 1860
tcctcagtcc attcatcctg actctgcccc ctgaggaccg gctgcagacc tcactctgag 1920
tggcaggcag agaaccaaag ctgcttcgct gctctccagg gagaccctcc tgggatggc 1980
ctgagaggcc ggggctcagg aagggctg ggatcggaac ttcctgctct tgtttctgga 2040
caactttccc cttctgcttt aaaggttgtc gattattttg aaaaaaaaa aaaaaaaaa 2099

SEQ ID NO: 7               moltype = RNA   length = 5125
FEATURE                    Location/Qualifiers
source                     1..5125
                           mol_type = mRNA
                           organism = Homo sapiens
SEQUENCE: 7
agaagcaggt tggctgtgat gacagcacag agctcaggaa cgctgcctga ggaccctggg 60
gcctacgagg aggagaagag ggcaggagct ggtgggtgc ttgcagagac cctgggctcc 120
tatcctgcca taagcctcgc tgtctcctga tatctgcagc caggccctac tgacaccccc 180
aggcctgagt gcaagcagag accccaccat tcccaggctg gtgaggactg gtccaccta 240
actgggcagc ccttgggca ggcgctggcc ggtgcctcag cccaggcctc tgtgctctgc 300
atgcactgcc agcctgccat caggcctcta ttgcagccct gaaccatgat ccagggcacc 360
ttggagccaa atggtcccct ctgggctgg gactgggaca gtgacaatga ctgggatagt 420
gctgtgctgg ccctcctggc gctggctgtg gtggctcaga cagcgctggc cttacactgg 480
tttggctccg ggacgatca agaggcggca gaaccggtgt ccacagccct gggggctcaa 540
cctcatcagg caggaggagc tgagctggcc ctgcaaccga agtctaaggt cagtgatgcc 600
agcgagggc agagcccagg gcaggggaaa ccagagcccc caggacgcgg ccagcagagc 660
cctgtccctg ctgcagcgcc gggcggggc ctggccgcca tggcccggct tccactcaag 720
acggctgtcg aggaggcccg cagagaggca ttaggacagc aacggggcag tgccacccc 780
gcggcccccc gagcggaagg aaaggagcct ccaggccag gcatcccct cctgggcagg 840
agcgaagcag gggggatgtc cgccccctc ctgatccact tcactcctcg gagccctggc 900
agcgaagcgg aggcggagac aggtggtgtc agggcgtcct ctcgcaggc cgcaggcccc 960
gcggggcaac aggacactgg cccctggcag gcgggcgcgg ggcctcgggg ctcgatgggg 1020
agaggccggg gcctggcgg gcgatggac gctggctcgg gagacagagc ccgccgcccc 1080
cggaaactgg acccgctccg cctgggcgcc gcggggagcg tgtgggacgc ggtggacggg 1140
```

```
gccgccgccc tggacgccca cgcgcgcggc ctccccacag gaccccccact cgcccaggag    1200
cccgcactcc cggcgctgcc cgctccccgc gccctgcagc ctgggtctca gacggaaggc    1260
tctggggcca agggtggctg gagcaggag gcctcggggg tccctgcccc cggaggaggc    1320
tggccctggg tcagcaggga ggtcccggc acccggagct ttggcccagc cccagactcc    1380
acgcgcccct ggctagagag tccgcctcaa ggtcgccac tctcgtccca agggccggt    1440
gccacagggg cctacgatgc cggcgaggcc ggggctgaca gctcccgaga taacagtcct    1500
gccgctgacc tggggcccac ccggcccccg gagcaagcaa agccggctgc agccggccac    1560
agccgcgcgc cctcccggag ccgtgagcct cgcccgcgct ccgcctcccc gcccgcagct    1620
cccggcccgg ggttcccacc tgaagccctg actctccccct ctccttcaga cttttttgcct   1680
ctggaggtta cccaggatcc ttccgtgggc gaaaatctca gagcggcgcc agccccaagt    1740
tcagcctcag cccaagtctt aacttcagct ccagctcag tcctagcccc agccctggct    1800
tcatccccca gctcagcacc aacctcagcc accacctcaa cctcatcccc cacctcagcc    1860
ccagccccag ctccaacctc agctccaact tcaacccag cccagcccc aagtccagct    1920
gcagccgcaa ctccagcccc agcccccagtc ccagtcccaa ccctcacacc cccatcccca    1980
gccctaaccc cagtcccaac cccagcccta agcccagctc caactccagc cctaacccca    2040
gccgcatccc cagccctaac cccagtccca acccagccc taagcccagc tccaactcca    2100
gccccaaccc cagccgcatc ccctgcccca gcccccacct cagccccaaa cccaaccca    2160
gccgcatccc ctgcccagc tgacgggtca aagcctcagg agagtgtggc tctccccagg    2220
cgctaccagg aggggcaggt ctcagccagc tggggaaacc ttattgccat ggttcttaga    2280
agccacccct tccccaggca agacaggccc caagggagtg tccgagggc ggttcccggg    2340
agccccgtgg gtcccagcac ttccacacac tctgaggaca gacacggccc ctcttcttca    2400
gtggggacag tcatagggac aggtacaggg ggctggttg aggctggagg tcagccacag    2460
ccaagaagct ccgagaccaa cggatcgccc agcccagacc ctcccccagg cctaagagga    2520
gagggaacca gggagaaaag tctagacccg ctgcccaag ccgcgatgcc caggggcccc    2580
gcacagcccc ccgcgcagag gccgcctggc cccgcgcct cctcctctgc gaggcgctca    2640
cagccggtac cccagctacg gaaacgcagc aggtgcgaaa tcgccccgag ctcgagcag    2700
gaggtcaggc cggccgcctc gggggaccct caagggagg cgccggggga gggggcagc    2760
cctgccggcc gcagcggggc gctcacgaaa aagcaggagg aggcccggaa gctcatggtg    2820
tttctgcaga ggcccggggg ttgggggtg gtggaggggc cccggaagcc cagctcccgg    2880
gccctggcc ccgccacggc ggcagcctg cggcggccgc tggacctggg cagttgcctg    2940
gacgtgctgg cctttgccca gcagcacgga gagcccggcc tggcgcagga gacctacgcg    3000
ctgatgagcg acaacctgct gcgagtgctg ggagacccgt gcctctaccg ccggctgagc    3060
gcggccgacc gcgagcgcat cctcagcctg cggaccggcc ggggccggggc ggtgctgggc    3120
gtcctcgtac tgcccagcct ctaccagggg ggcgctccag ggctccccag gggcgcatgt    3180
ggcgaggagc ctcctgcggc ggccctgtg tccctgcctc tacctgcgca cctgcatgtg    3240
ttcaaccccc gggagaacac ctggcggcc ctgacccagg tgcccgagga ggccccgctt    3300
cggggctgcg gtctctgcac catgcacaac tacctgtttc tggcgggggg catccgtggc    3360
tccggtgcca aggccgtctg ctccaacgag gtcttctgct acaaccctct gaccaacatc    3420
tggagccagg ttcggcccat gcagcaggcc cgagcccagc tcaagctggt ggccctgggc    3480
gggctgctct atgccatcgg tggcgaatgc ctgtacagca tggagtgcta cgacccgcga    3540
acagacgcct ggaccccacg cgcgccactc cccgcaggca ccttccctgt ggcccacgag    3600
gctgtggcct gccgtgggga catctacgtc accggggtc acctcttcta ccgcctgctc    3660
aggtacagcc ccgtgaagga tgcttgggac gagtgcccat acagtgccag ccaccggcag    3720
tccagcgaca tcgtgggcact gggggggcttc ctgtaccgct tcgacctgct gcggggcatg    3780
ggcgccgccg tgatgcgcta caacacagtg accggctcct ggagcagggc tgcctccctg    3840
cccctgcccg cccccgcccc actgcactgc accaccctgg gcaacaccat ttactgcctc    3900
aaccccaggg tcactgccac cttcacggtc tctggggga ctgcccagtt ccaggccaag    3960
gagctgcagc ccttcccctt ggggagcacc ggggtcctca gtccattcat cctgactctg    4020
cccctgagg accggctgca gacctcactc tgagtggcag gcagagaacc aaagctgctt    4080
cgctgctctc cagggagacc ctcctgggat gggcctgaga ggccggggct cagggaaggg    4140
gctgggatcg gaacttcctg ctcttgttttc tggacaactt tccccttgtg cttttaaagagt    4200
tgtcgattat tttgaagccc agactccctc agcctctttc tgcccctcac tccacccca    4260
gactgtttcc tgactcaatt ccgtacctac ttacagaccc tctcagcttg ctgacacccc    4320
cctgtctgtg ggactcccta ttccctagag ccagggactg atgcgtctcc acagacaagg    4380
acttggctcg ctggagctct gctgagccga gagaggggg ggtagaaaac attcacactt    4440
cctatgctct gtcagcagga cagggagcaa aaacgtcccc aggcaacgcc ctcgcctctg    4500
ggactttctg cctgtcctaa ggcctcccca ggtaccaacc ccgtagctat ctgggtctgt    4560
ttggcactgt ggattctcaa gggcctagaa cccttgcctc tgaaactggt ccgctggtgc    4620
agccctgctg tctgcagctc ctgcccatac cccagccca caccaggcca ggcccatcc    4680
gggctcacca ccctctgcag ccttgtgggg ctctcccagc ccctccagaa gcccacccca    4740
cttctcgcca accccgatc tctaaatgag gcctgagcgt cacccagtt ctgccccttt    4800
ttagctgtgt agacttggac gagacatttg acttccctttt ctccttgtct ataaaatgtg    4860
gacagtggac gtctgtcacc caagagagtt gtgggagaca agatcacagc tatgagcacc    4920
tcgcacggtg tccaggatgc acagcacaat ccatgatgc ttttctcccc ttacgcactt    4980
tgaaacccat gctagaaaag tgaatacatc tgactgtgct ccactccaac ctccagcctg    5040
gatgtccctg tctgggcct ttttctgttt ttattctat gttcagcacc actggcacca    5100
aatacatttt aattcaccga aagca                                         5125
```

```
SEQ ID NO: 8            moltype = RNA   length = 2990
FEATURE                 Location/Qualifiers
source                  1..2990
                        mol_type = mRNA
                        organism = Homo sapiens
SEQUENCE: 8
ccacctcagc cccaacccca accccagccg catcccctgc cccagctgac gggtcaaagc      60
ctcaggagag tgtggctctc cccaggcgct accaggaggg gcaggtctca gccagctggg    120
gaaaccttat tgccatggtt cttagaagcc acccctccc caggcaagac aggccccaag    180
ggagtgtccc gagggcggtt cccggagcc ccgtgggtcc cagcacttcc acacactctg    240
aggacagaca cggcccctct tcttcagtgg ggacagtcat agggacaggt acaggggcc    300
```

```
tggttgaggc tggaggtcag ccacagccaa gaagctccga gaccaacgga tcgcccagcc    360
cagaccctcc cccaggccta agaggagagg gaaccaggga gaaaagtcta gacccgctgc    420
cccaagccgc gatgcccagg ggccccgcac agccccccgc gcagaggccg cctggccccg    480
cggcctcctc ctctgcgagg cgctcacagc cggtacccca gctacggaaa cgcagcaggt    540
gcgaaatcgc cccgagctcg gagcagggga tcaggccggc cgcctcgggg gaccctcaag    600
gggaggcgcc gggggagggg ggcagccctg ccggccgcag cggggcgctc acggaaaagc    660
aggaggaggc ccggaagctc atggtgtttc tgcagaggcc cggggggttgg ggggtggtgg    720
aggggccccg gaagcccagc tcccgggccc tggagcccgc cacggcggca gccctgcggc    780
ggcggctgga cctgggcagt tgcctggacg tgctggcctt tgcccagcag cacggagagc    840
ccggcctggc gcaggagacc tacgcgctga tgagcgacaa cctgctgcga gtgctgggag    900
acccgtgcct ctaccgccgg ctgagcgcgg ccgaccgcga gcgcatcctc agcctggcgga    960
ccggccgggg ccggccggtg ctgggcgtcc tcgtactgcc cagcctctac caggggggcc   1020
gctcagggct cccccagggc cctcgtggcg aggagcctcc tgcggcggcc cctgtgtccc   1080
tgcctctacc tgccgcacctg catgtgttca accccgggga gaaccacctgg cggccccctga   1140
cccaggtgcc cgaggaggcc ccgcttcggg gctgcggtct ctgcaccatg cacaactacc   1200
tgtttctggc ggggggcatc cgtggctccg gtgccaaggc cgtctgctcc aacgaggtct   1260
tctgctacaa ccctctgacc aacatctgga gccaggttcg gcccatgcag caggcccgag   1320
cccagctcaa gctggtggcc ctggacgggc tgctctatgc catcggtggc gaatgcctgt   1380
acagcatgga gtgctacgac ccgcgaacag acgcctggac cccacgcgcg ccactccccg   1440
caggcacctt ccctgtggcc cacgaggctg tggcctgccg tggggacatc tacgtcaccg   1500
ggggtcacct cttctaccgc ctgctcaggt acagccccgt gaaggatgct tgggacgagt   1560
gcccatacag tgccagccac cggcgttcca gcgacatcgt ggcactggg ggcttcctgt   1620
accgcttcga cctgctgcgg ggcatggggc ccgccgtgat gcgctacaac acagtgaccg   1680
gctcctggag cagggctgcc tccctgcccc tgcccgcccc cgcccactg cactgcacca   1740
ccctgggcaa caccatttac tgcctcaacc ccaggtcac tgccaccttc acggtctctg   1800
gggggactgc ccagttccag gccaaggagc tgcagccctt cccttgggg agcaccgggg   1860
tcctcagtcc attcatcctg actctgcccc ctgaggaccg gctgcagacc tcactctgag   1920
tggcaggcag agaaccaaag ctgcttcgct gctctccagg gagaccctcc tgggatgggc   1980
ctgagaggcc gggggctcagg gaaggggctg ggatcggaac ttcctgctct tgtttctgga   2040
caactttccc cttctgcttt aaaggttgtc gattattttg agcccagac tccctcagcc   2100
tctttctgcc cctcactcca cacccagact gtttcctgac tcaattccgt acctactac    2160
agaccctctc agcttgctga cacccccctg tctgtgggac tccctattcc ctagagccag   2220
ggactgatgc gtccacag acaaggactt ggctcgctgg agctctgctg agccgagaga     2280
ggaggggta gaaaacattc acacttccta tgctctgtca gcaggacagg gagcaaaaac    2340
gtccccaggc aacgccctcg cctctgggac tttctgcctg tcctaaggcc tccccaggta   2400
ccaaccccgt agctatctgg gtctgtttgg cactgtggat tctcaagggc ctagaaccct   2460
tgcctctgaa actggtccgc tggtgcagcc ctgctgtctg cagctcctgc ccatacccc    2520
agcccacacc aggccaggcc cactccgggc tcaccaccct ctgcagcctt gtggggctct   2580
cccagccct ccagaagccc acccccattc tcgccaaccc ccgatctcta aatgaggcct   2640
gagcgtcacc ctagttctgc cccttttag ctgtgtagac ttggacgaga catttgactt   2700
cccttttctcc ttgtctataa aatgtggaca gtggacgtct gtcacccaag agagttgtgg   2760
gagacaagat cacagctatg agcacctcgc acggtgtcca ggatgcacag cacaatccat   2820
gatgcgtttt ctcccttac gcactttgaa acccatgcga gaaaagtgaa tacatctgac   2880
tgtgctccac tccaacctcc agcctggatg tccctgtctg ggccttttt ctgtttttta   2940
ttctatgttc agcaccactg gcaccaaata cattttaatt caccgaaagc              2990

SEQ ID NO: 9            moltype = RNA   length = 4837
FEATURE                 Location/Qualifiers
source                  1..4837
                        mol_type = mRNA
                        organism = Homo sapiens
SEQUENCE: 9
actgccagcc tgccatcagg cctctattgc agccctgaac catgatccag ggcaccttgg     60
agccagatgt tccctctgg ggctgggact gggacagtga caatgactgg gatagtgctg    120
tgctgcccct cctggcgctg gctgtggtgg ctgccacagc gctggcctta cactggtttg    180
gctccgggca cgatcaagag gcggcagaac cggtgtccac agccctcggg gctcaacctc    240
atcaggcagg aggagctgag ctggccctgc aaccgaagtc taaggtcagt gatggcagcc    300
aggggcagag cccagggcag gggaaaccag agccccagg acgcggccag cagagccctg    360
tccctgctgc agccgccggc gggggcctgg ccgccatggc ccggcttcca ctcaagacgg    420
ctgtcgagga ggcccgcaga gaggcattag gacagcaacg ggcagtgcc accccgcgg    480
ccccccgagc ggaaggaaag gagcctccca ggccaggcac tgcccctctg ggcaggagcg    540
aagcagggg gatgtccgcc cccctcctga tccacttcac tcctcggagc cctggcagcg    600
aagcggaggc ggagacaggt ggtgtcaggg cgtcctctcg ccaggccgca ggccccgcgg    660
ggcaacagga cactgccccc tggcaacggg gcgcgggccc ctcgggctcg atgggagag    720
gccggggccg gcggcggcgg atggacgctg gctcggagag cagagccgc cgccccgga    780
aactggaccc gctccgcctg ggccgccgcg ggagcgtgtg ggacgcggtg gacggggccg    840
ccgccctgga cgcccacgcg cgcggcctcc cacaggacc ccactcgcc caggagcccg    900
cactcccggc gctgccgct cccccgcgcc tgcagcctg gtctcagacg gaaggctctg    960
gggccaaggg tggctggagc aggggaggcct gggggtcct tgcccccgga ggaggctggc   1020
cctgggtcag cagggaggtc ccgggcaccc ggagctttgg cccagcccca gactccacgc   1080
gccctggct agagagtccg cctcaaggtc gcccactctc gtcccaaggg ccgggtgcca   1140
caggggccta cgatgccggc gaggccgggg ctgacagctc ccgagataac agtcctgccg   1200
ctgacctggg gccaccegg ccccggagc aagcaaagcc ggctgcagcc ggccacagcc   1260
gcgcgcctcc ccggagccgt gagccctcgc cgcgctccgc ctccccgccc gcagctcccg   1320
gcccggggtt cccacctgaa gccctgactc tcccctctcc ttcagacttt ttgccctgg    1380
aggttaccca ggatccttcc gtgggcgaaa atctcagagc ggcgcagcc caagttcag    1440
cctcagccca agtcttaact tcagctccag cctcagtcct agcccagcc ctggcttcat   1500
cccccagctc agcaccaacc tcagccacca cctcaacctc atccccccacc tcagcccag   1560
cccagctcc aacctcagct ccaacttcaa cccagccccc agccccaagt ccagctgcag   1620
```

```
ccgcaactcc agcccagcc ccagtcccag tcccaaccct cacacccca tccccagccc    1680
taacccagt cccaaccccc gcctaagcc cagctccaac tccagccta accccagccg     1740
catcccagc cctaacccca gtccaaccc cagcctaag cccagctcca actccagccc    1800
caacccagc cgcatccct gccccagccc ccacctcagc ccaaccccca accccagccg    1860
catccctgc cccagctgac gggtcaaagc ctcaggagag tgtggctctc cccaggcgct   1920
accaggaggg gcaggtctca gccagctggg gaaaccttat tgccatggtt cttagaagcc  1980
accccttccc caggcaagac aggcccaag ggagtgtccc gagggcggtt cccgggagcc   2040
ccgtgggtcc cagcacttcc acacactctg aggacagaca cggcccctct tcttcagtgg  2100
ggacagtcat agggacaggt acagggggcc tggttgaggc tggaggtcag ccacagccaa  2160
gaagctccga gaccaacgga tcgcccagcc cagaccctcc cccaggccta agaggagagg  2220
gaaccaggga gaaaagtcta gacccgctgc cccaagccgc gatgcccagg ggcccgcac   2280
agcccccgc gcagaggccg cctggccccg cggcctcctc ctctgcgagg cgctcacagc   2340
cggtaccca gctacggaaa cgcagcaggt gcgaaatcgc cccgagctcg gagcaggagg   2400
tcaggccggc cgcctcgggg gaccctcaag gggaggcgcc gggggagggg gcagccctg   2460
ccggccgcag cggggcgctc acggaaaagc aggaggagc ccggaagctc atggtgtttc   2520
tgcagaggcc cggggttgg gggtggtgg agggccccg gaagcccagc tcccgggccc    2580
tggagcccgc cacggcggca gccctgcggc ggcggctgga cctgggcagt tgcctggacg  2640
tgctgccctt tgcccagcag cacggagagc ccggcctgac caggagacc tacgcgcgtga 2700
tgagcgacaa cctgctgcga gtgctgggag acccgtgcct ctaccgccgg ctgagcgcgg  2760
ccgaccgcga gcgcatcctc agcctgcgga cggccgggg ccgggcggtg ctgggcgtcc   2820
tcgtactgcc cagcctctac caggggggcc gctcagggct cccagggggc cctcgtggcg  2880
aggagcctcc tgcggcggcc cctgtcctcc tgcctctacc ctgcgcacctg catgtgttca  2940
accccgga gaacctggg cggccctga cccaggtgcc cgaggaggcc ccgcttcgg     3000
gctgcggtct ctgcaccatg cacaactacc tgtttctggc gggggcatc cgtggctccg   3060
gtgccaaggc cgtctgctcc aacgaggtct tctgctacaa ccctctgacc aacatctgga   3120
gccaggttcg gcccatgcag caggccgag cccagctcag gctggtggcc ctggacggg    3180
tgctctatgc catcggtgg gaatgcctgt acagcatga gtgctacgac ccgcgaacag    3240
acgcctggac cccacgcgcg ccactcccg caggcacctt ccctgtgccc cacgaggctg   3300
tggcctgccg tggggacatc tacgtcaccg ggggtcacct cttctaccgc ctgctcaggt   3360
acagcccgt gaaggatgct tgggacgagt gcccatacag tgccagccac cggcgttcca   3420
gcgacatcgt ggcactgggg ggcttcctgt accgcttcga cctgctgcgg ggcatgggcg   3480
ccgccgtgat gcgctacaac acagtgaccg gctcctggag cagggctgcc tcctgcccc    3540
tgcccgcccc cgcccactg cactgcacca ccctgggcaa caccatttac tgcctcaacc   3600
cccaggtcac tgccaccttc acggtctctg ggggactgc ccagttccag gccaaggagc   3660
tgcagcccc ttcccctggg agcaccgggg tcctcagtcc attcatcctg actctgctcc   3720
ctgaggaccg gctgcagacc tcactctgag tggcaggcag agaaccaaag ctgcttcgct   3780
gctctccagg gagaccctcc tgggatgggc ctgagaggcc ggggctcagg gaaggggctg   3840
ggatcggaac ttcctgctct tgtttctgga caactttccc cctttgcttt aaaggttgtc   3900
gattatttg aagcccagac tccctcagcc tcttctgcc cctcactcca cacccagact   3960
gtttcctgac tcaattccgt acctacttac agacccctc agcttgctga cacccccctg   4020
tctgtgggac tccctattcc ctagagccag ggactgatgc gtctcacag acaaggactt   4080
ggctcgctgg agctctgctg agccgagaga ggaggggta gaaaacattc acacttccta   4140
tgctctgtca gcaggacagg gagcaaaac gtccccagc aacgccctcg cctctgggaa   4200
tttctgcctg tcctaaggcc tcccaggta ccaaccccgt agctatctgg gtctgtttgg   4260
cactgtggat tctcaagggc ctagaaccct tgcctctgaa actggtccgc tggtgcagcc   4320
ctgctgtctg cagctcctgc ccataccccc agccacacc aggccaggcc cactccgggc   4380
tcaccaccct ctgcagcctt gtggggctct cccagccct ccagaagccc accccacttc   4440
tcgccaaccc ccgatctcta aatgaggcct gagcgtcacc ctagttctgc cccttttttag   4500
ctgtgtagac ttgacgagac catttgactt cccttcctcc ttgtctataa aatgtggaca   4560
gtggacgtct gtcacccaag agagttgtgg gagacaagat cacagctatg agcacctcgc   4620
acggtgtcca ggatgcacag cacaatccat gatgcgtttt ctccccttac gcactttgca   4680
acccatgcta gaaaagtgaa tacatctgac tgtgctccac tccaacctcc agcctggatg   4740
tccctgtctg ggccctttt ctgttttta ttctatgttc agcaccactg gcaccaaata   4800
catttttaatt caccgaaagc aaaaaaaaa aaaaaa                             4837

SEQ ID NO: 10          moltype = RNA   length = 2099
FEATURE                Location/Qualifiers
source                 1..2099
                       mol_type = mRNA
                       organism = Homo sapiens
SEQUENCE: 10
ccacctcagc cccaaccccca accccagccg catcccctgc cccagctgac gggtcaaagc    60
ctcaggagag tgtggctctc cccaggcgct accaggaggg gcaggtctca gccagctggg   120
gaaaccttat tgccatggtt cttagaagcc accccttccc caggcaagac aggcccaag    180
ggagtgtccc gagggcggtt cccgggagcc ccgtgggtcc cagcacttcc acacactctg   240
aggacagaca cggcccctct tcttcagtgg ggacagtcat agggacaggt acagggggcc   300
tggttgaggc tggaggtcag ccacagccaa gaagctccga gaccaacgga tcgcccagcc   360
cagaccctcc cccaggccta agaggagagg gaaccaggga gaaaagtcta gacccgctgc   420
cccaagccgc gatgcccagg ggcccgcac agcccccgc gcagaggccg cctggccccg    480
cggcctcctc ctctgcgagg cgctcacagc cggtaccca gctacggaaa cgcagcaggt   540
gcgaaatcgc cccgagctcg gagcaggagg tcaggccggc cgcctcgggg gaccctcaag   600
gggaggcgcc gggggagggg gcagccctg ccggccgcag cggggcgctc acggaaaagc    660
aggaggagc ccggaagctc atggtgtttc tgcagaggcc cggggttgg gggtggtgg     720
agggccccg gaagcccagc tcccgggccc tggagcccgc cacggcggca gccctgcggc   780
ggcggctgga cctgggcagt tgcctggacg tgctgccctt tgcccagcag cacggagagc   840
ccggcctggc caggagacc tacgcgctga tgagcgacaa cctgctgcga gtgctgggag   900
acccgtgcct ctaccgccgg ctgagcgcgg ccgaccgcga gcgcatcctc agcctgcgga   960
cggccgggg ccgggcggtg ctgggcgtcc tcgtactgcc cagcctctac caggggggcc   1020
gctcagggct cccagggggc cctcgtggcg aggagcctcc tgcggcggcc cctgtgtccc   1080
```

```
tgcctctacc tgcgcacctg catgtgttca accccggga gaacacctgg cggcccctga   1140
cccaggtgcc cgaggaggcc ccgcttcggg gctgcggtct ctgcaccatg cacaactacc   1200
tgtttctggc gggggggcatc cgtggctccg gtgccaaggc cgtctgctcc aacgaggtct   1260
tctgctacaa ccctctgacc aacatctgga gccaggttcg gcccatgcag caggcccgag   1320
cccagctcaa gctggtggcc ctggacgggc tgctctatgc catcggtggc gaatgcctgt   1380
acagcatgga gtgctacgac cgcgaacag acgcctggac cccacgcgcg ccactccccg   1440
caggcacctt ccctgtggcc cacgaggctg tggcctgccg tggggacatc tacgtcaccg   1500
ggggtcacct cttctaccgc ctgctcaggt acagccccgt gaaggatgct tgggacgagt   1560
gccatacag tgccagccac cggcgttcca gcgacatcgt ggcactgggg ggcttcctgt   1620
accgcttcga cctgctgcgg ggcatgggcg ccgccgtgat gcgctacaac acagtgaccg   1680
gctcctggag cagggctgcc tccctgcccc tgcccgcccc cgcccactg cactgcacca   1740
ccctgggcaa caccatttac tgcctcaacc cccaggtcac tgccaccttc acggtctctg   1800
ggggggactgc ccagttccag gccaaggagc tgcagccctt ccccttgggg agcaccgggg   1860
tcctcagtcc attcatcctg actctgcccc ctgaggaccg gctgcagacc tcactctgag   1920
tggcaggcag agaaccaaag ctgcttcgct gctctccagg gagaccctcc tgggatgggc   1980
ctgagaggcc ggggctcagg gaaggggctg ggatcggaac ttcctgctct tgtttctgga   2040
caactttccc cttctgcttt aaaggttgtc gattattttg aaaaaaaaaa aaaaaaaa    2099

SEQ ID NO: 11          moltype = DNA   length = 5125
FEATURE                Location/Qualifiers
source                 1..5125
                       mol_type = other DNA
                       organism = Homo sapiens
SEQUENCE: 11
agaagcaggt tggctgtgat gacagcacag agctcaggaa cgctgcctga ggaccctggg   60
gcctacgagg aggagaagag ggcaggagct ggtggggtgc ttgcagagac cctgggctcc   120
tatcctgcca taagcctcgc tgtctcctga tatctgcagc caggcccctac tgacaccccc   180
aggcctgagt gcaagcagag accccaccat tcccaggccc tggaggactg gtccaccctta  240
actgggcagc ccttggggca ggcgctggcc ggtgcctcag cccaggcctc tgtgctctgc   300
atgcactgcc agcctgccat caggcctcta ttgcagccct gaaccatgat ccagggcacc   360
ttggagccag atggtcccct ctggggctgg gactgggaca gtgacaatga ctgggatagt   420
gctgtgctgg ccctcctggc gctggctgtg gtggctgcca cagcgctggc cttacactgg   480
tttggctccg ggcacgatca agaggcggca gaaccggtgt ccacagccct cggggctcaa   540
cctcatcagg caggaggagc tgagctgggc ctgcaaccga agtcagaggt cagtgatggc   600
agcgagggc agagcccagg gcaggggaaa ccagagcccc caggacgcgg ccagcagagc   660
cctgtccctg ctgcagcgcc gggcggggc ctggccgcca tggcccggct tccactcaag   720
acggctgtcg aggaggcccg cagagaggca ttaggacagc aacggggcag tgccaccccc   780
gcggccccc gagcggaagg aaaggagcct cccaggccag gcactgccct cctgggcagg   840
agcgaagcag ggggatgtc cgcccccctc ctgatccact tcactcctcg gagccctggc   900
agcgaagcgg aggcggagac aggtggtgtc agggcgtcct ctcgccaggc cgcaggcccc   960
gcggggcaac aggacactgg cccctggcag gcgggcgcgg ggcccctcggg ctcgatgggg   1020
agaggccggg gccggcggcg gcggatggac gctggctcgg gagacagagc ccgccgcccc   1080
cggaaactgg acccgctccg cctgctgcgc gcggggacgg tgtgggacgc ggtggacggg   1140
gccgccgccc tggacgccca cgcgcgcggg ctccccacag gacccccact cgcccaggag   1200
cccgcactcc cggcgctgcc cgctcccccgc gccctgcagc ctgggtctca gacgaaggc    1260
tctggggcca agggtggctg gagcaggagg gcctcggggg tccctgcccc cggaggaggc   1320
tggccctggg tcagcaggga ggtcccgggc acccggagct ttggccagc cccagactcc   1380
acgcgcccct ggctagagag tccgcctcaa ggtcgcccac tctcgtccca agggccgggt   1440
gccacagggg cctacgatgc cggcgaggcc ggggctgaca gctcccgaga taacagtcct   1500
gccgctgacc tggggcccac ccggcccccg gagcaagcaa agccggctgc agccggccac   1560
agccgcgcgc cctcccggag ccgtgagcct cgcccgcctc cgcctcccc gccctccct    1620
cccggcccgg ggttcccacc tgaagccctg actctcccct ctccttcaga cttttttgccc   1680
ctggaggtta cccaggatcc ttccgtgggc gaaaatctca gagcggcgcc agccccaagt   1740
tcagcctcag cccaagtctt aacttcagct ccagcctcag tcctagcccc agccctggct   1800
tcatccccca gctcagcacc aacctcagcc accacctcaa cctcatcccc cacctcagcc   1860
ccagccccag ctccaacctc agctccaact tcaaccccag cccagccccc aagtccagct   1920
gcagccgcaa ctccagcccc agcccagtc cagtccaa ccctcacacc cccatcccca    1980
gccctaaccc cagtcccaac cccagcccta agcccagctc caactccagc ctaaccccca   2040
gccgcatccc cagcccctaac cccagtccca accccagccc taagcccagc tccaactcca   2100
gcccccaacc cagccgcatc ccctgcccca gccccccct cagccccaaac cccaaccca     2160
gccgcatccc ctgcccagc tgacgggtca agcctcagg agagtgtggc tctcccagg     2220
cgctaccagg aggggcaggt tcagccagc tggggaaacc ttattgccat ggttcttaga   2280
agccacccct tccccaggca agacaggccc aagggagtg tcccgagggc ggttcccggg   2340
agcccgtgg gtcccagcac ttccacacac tctgaggaca gacacggccc ctcttcttcca   2400
gtggggacag tcatagggac aggtacaggg ggcctggttg aggctggagg tcagccacag   2460
ccaagaagct ccgagaccaa cggatcgccc agccagacc ctcccccagg cctaagagga   2520
gagggaacca gggagaaaag tctagaccc gctgcccaag ccgcgatgcc caggggcccc   2580
gcacagccca ccgcgcagag gccgcctggc cccgcggcct cctcctctgc gaggcgctca   2640
cagccggtac cccagctacg gaaacgcagc aggtgcgaaa tcgccccgag tccgagcag   2700
gaggtcaggc cggccgcctc gggggaccct caagggggag cgccggggga ggggggcagc   2760
cctgccggcc gcagcggggc gctcacggaa aagcaggagg aggcccggaa gctcatggtg   2820
tttctgcaga ggccccgggg ttgggggggtg gtggagggg cccggaagcc cagctcccgg   2880
gccctggagc ccgcacggc ggcagccctg cggcggcggc tggacctggg cagttgcctg   2940
gacgtgctgg ccttttgccca cagcacgga gagccccggc tggccaggag gacctacgcg   3000
ctgatgagcg acaacctgct gcgagtgctg ggagacccgt gcctctaccg cggctgagc   3060
gcggccgacc gcgagcgcat cctcagcctg cggaccggcc ggggccggc ggtgctgggc   3120
gtcctcgtac tgcccagcct ctaccagggg ggccgctcag ggctcccag ggggcctcgt   3180
ggcgaggagc ctcctgcggc ggccccctgt g tcctgcctc tacctgcgca cctgcatgtg   3240
ttcaaccccc gggagaacac ctggcggccc ctgacccagg tgcccgagga ggcccgcgtt   3300
```

```
cggggctgcg gtctctgcac catgcacaac tacctgtttc tggcggggggg catccgtggc   3360
tccggtgcca aggccgtctg ctccaacgag gtcttctgct acaaccctct gaccaacatc   3420
tggagccagg ttcggcccat gcagcaggcc cgagcccagc tcaagctggt ggccctggac   3480
gggctgctct atgccatcgg tggcgaatgc ctgtacagca tggagtgcta cgacccgcga   3540
acagacgcct ggaccccacg cgcgccactc cccgcaggca ccttccctgt ggccacgagg   3600
gctgtggcct gccgtgggga catctacgtc accgggggtc acctcttcta ccgcctgctc   3660
aggtacagcc ccgtgaagga tgcttgggac gagtgcccat acagtgccag ccaccggcgt   3720
tccagcgaca tcgtggcact ggggggcttc ctgtaccgct tcgacctgct gcggggcgtg   3780
ggcgccgccg tgatgcgcta caacacagtg accggctcct ggagcagggc tgcctccctg   3840
ccoctgcccg ccccgcccc actgcactgc accaccctgg gcaacaccat ttactgcctc   3900
aaccccccagg tcactgccac cttcacggtc tctgggggga ctgcccagtt ccaggccaag   3960
gagctgcagc ccttcccctt ggggagcacc ggggtcctca gtccattcat cctgactctg   4020
cccctgagg accggctgca gacctcactc tgagtggcag gcagagaacc aaagctgctt   4080
cgctgctctc cagggagacc ctcctgggat gggcctgagc ggccggggct caggggaaggg   4140
gctgggatcg gaacttcctg ctcttgtttc tggacaactt tccccttctg ctttaaaggt   4200
tgtcgattat tttgaagccc agactccctc agcctctttc tgccctcac tccacaccca   4260
gactgtttcc tgactcaatt ccgtacctac ttacagaccc tctcagcttg ctgacaccccc   4320
cctgtctgtg ggactcccta ttccctagag ccaggggactg atgcgtctcc acagacaagg   4380
acttggctcg ctggagctct gctgagccga gagaggaggg ggtagaaaac attcacactt   4440
cctatgctct gtcagcagga cagggagcaa aaacgtcccc aggcaacgcc ctcgcctctg   4500
ggactttctg cctgtcctaa ggcctcccca ggtaccaacc ccgtagctat ctgggtctgt   4560
ttggcactgt ggattctcaa gggcctagaa cccttgcctc tgaaactggt ccgctggtgc   4620
agccctgctg tctgcagctc ctgcccatac ccccagccca caccaggcca ggcccactcc   4680
gggctcacca ccctctgcag ccttgtgggg ctctcccagc ccctccagaa gcccacccca   4740
cttctcgcca accccgatc tctaaatgag gcctgagcgt cacctagtt ctgcccttt   4800
ttagctgtgt agacttggac gagacatttg acttccctt ctccttgtct ataaaatgtg   4860
gacagtggac gtctgtcacc caagagagtt gtgggagaca agatcacagc tatgagcacc   4920
tcgcacggtg tccaggatgc acagcacaat ccatgatgcg ttttctcccc ttacgcactt   4980
tgaaacccat gctagaaaag tgaatacatc tgactgtgct ccactccaac ctccagcctg   5040
gatgtccctg tctgggccct ttttctgttt tttattctat gttcagcacc actggcacca   5100
aatacatttt aattcaccga aagca                                          5125
```

SEQ ID NO: 12        moltype = DNA   length = 2990
FEATURE              Location/Qualifiers
source               1..2990
                     mol_type = other DNA
                     organism = Homo sapiens
SEQUENCE: 12
```
ccacctcagc cccaaccca ccccagccg catcccctgc cccagctgac gggtcaaagc   60
ctcaggagag tgtggctctc cccaggcgct accaggaggg gcaggtctca gccagctggg   120
gaaaccttat tgccatggtt cttagaagcc accccttccc caggcaagac aggccccaag   180
ggagtgtccc gagggcggtt cccgggagcc ccgtgggtcc cagcacttcc acacactctg   240
aggacagaca cggcccctct tcttcagtgg ggacagtcat agggacaggt acaggggcgc   300
tggttgaggc tggaggtcag ccacagccaa gaagctccga gaccaacgga tcgcccagcc   360
cagaccctcc cccaggccta agaggagagg gaaccaggga gaaaagtcta gacccgctgc   420
cccaagccgc gatgcccagg ggccccgcac agccccccgc gcagaggccg cctggccccg   480
cggcctcctc ctctgcgagg cgctcacagc cggtacccca gctacggaaa cgcagcaggt   540
gcgaaatcgc cccgagctcg gagcaggagg tcaggccggc cgcctcgggg gaccctcaag   600
gggaggcgcc ggggaggggg ggcagccctg ccggccgcag cggggcgctc acggaaaagc   660
aggaggaggc ccggaagctc atggtgttc tgcagaggcc cgggggttgg ggggtggtgg   720
aggggcccccg gaagcccagc tcccgggccc tggagcccgc cacggcggca gccctgcggc   780
ggcggctgga cctgggcagt tgccctggacg tgctggcctt tgcccagcag cacggagagc   840
ccggcctggc gcaggagacc tacgcgctga tgagcgacaa cctgctgcga gtgctgggag   900
acccgtgcct ctaccgccgg ctgagcgcgg ccgaccgcga gcgcatcctc agcctgcgga   960
ccggccgggg gcggggcggtg ctgggcgtcc tcgtactgcc cagcctctac caggggggcg   1020
gctcagggct cccagggggc cctcgtggcg aggagcctcc tgcggcggcc cctgtgtccc   1080
tgcctctacc tgcgcacctg catgtgttca acccccggga gaacacctgg cggccctga   1140
cccaggtgcc cgaggaggcc ccgcttcggg gctgcggtct ctgcaccatg cacaactacc   1200
tgtttctggc gggggggcatc cgtggcccg gtgccaaggc cgtctgctgg aacgaggtct   1260
tctgctacaa ccctctgacc aacatctgga gccaggttcg gcccatgcag caggcccgag   1320
cccagctcaa gctggtggcc ctggacgggc tgctctatgc catcggtggc gaatgcctgt   1380
acagcatgga gtgctacgac ccgcgaacag acgcctggac cccacgcgcg ccactccccg   1440
caggcacctt ccctgtggcc acgagggctg tggcctgccg tggggacatc tacgtcaccg   1500
ggggtcaacct cttctaccgc ctgctcaggt acagccccgt gaaggatgcg tgggacgagt   1560
gcccatacag tgccaccac cggcgttcca gcgacatcgt ggcactgggg ggcttcctgt   1620
accgcttcga cctgctgcgg ggcgtgggcg ccgccgtgat gcgctacaac acagtgaccg   1680
gctcctggag cagggctgcc tcctgcccc tgcccgcccc cgcccactg cactgcacca   1740
ccctgggcaa caccatttac tgcctcaacc ccaggtcac tgccaccttc acggtctctg   1800
ggggactgc ccagttccag gccaaggagc tgcagccctt ccccttgggg agcaccctg   1860
tcctcagtcc attcatcctg actctgcccc tgaggaccg gctgcagacc tcactctgag   1920
tggcaggcag agaaccaaag ctgcttcgct gctctccagg gagaccctcc tgggatgggc   1980
ctgagaggcc ggggctcagg gaaggggctg ggatcgaac ttcctgctct gtttctgga   2040
caactttccc cttctgcttt aaaggttgtc gattattttg aagcccagac tccctcagcc   2100
tctttctgcc cctcactcca cacccagact gtttcctgac tcaattccgt acctacttac   2160
agaccctctc agcttgctga cacccccctg tctgtgggac tccctattcc ctagagccag   2220
ggactgatgc gtctccacag acaaggactt ggctcgctgg agctctgctg agccgagaga   2280
ggaggggta gaaaacattc acacttccta tgctctgtca gcaggacagg gagcaaaaac   2340
gtccccaggc aacgccctcg cctctgggac tttctgcctg tcctaaggcc tccccaggta   2400
ccaacccccgt agctatctgg gtctgtttgg cactgtggat tctcaagggc ctagaaccct   2460
```

```
tgcctctgaa actggtccgc tggtgcagcc ctgctgtctg cagctcctgc ccataccccc   2520
agcccacacc aggccaggcc cactccgggc tcaccaccct ctgcagcctt gtggggctct   2580
cccagcccct ccagaagccc accccacttc tgccaaccc ccgatctcta aatgaggcct   2640
gagcgtcacc ctagttctgc ccctttttag ctgtgtagac ttggacgaga catttgactt   2700
cccttctcc ttgtctataa aatgtggaca gtggacgtct gtcacccaag agagttgtgg    2760
gagacaagat cacagctatg agcacctcgc acggtgtcca ggatgcacag cacaatccat   2820
gatgcgtttt ctccccttac gcactttgaa acccatgcta gaaaagtgaa tacatctgac   2880
tgtgctccac tccaacctcc agcctggatg tccctgtctg ggcccttttt ctgttttta   2940
ttctatgttc agcaccactg gcaccaaata cattttaatt caccgaaagc               2990

SEQ ID NO: 13          moltype = DNA   length = 4837
FEATURE                Location/Qualifiers
source                 1..4837
                       mol_type = other DNA
                       organism = Homo sapiens
SEQUENCE: 13
actgccagcc tgccatcagg cctctattgc agccctgaac catgatccag ggcaccttgg    60
agccagatgg tcccctctgg ggctgggact gggacagtga caatgactgg gatagtgctg   120
tgctggccct cctggcgctg gctgtggtgg ctgccacagc gctggcctta cactggtttg   180
gctccgggca cgatcaagag gcggcagaac cggtgtccac agccctcggg gctcaacctc   240
atcaggcagg aggagctgag ctggccctgc aaccgaagtc taaggtcagt gatggcagcg   300
aggggcagag cccaggggcag gggaaaccag agccccaggg acgcggccag cagagccctg   360
tccctgctgc agcgccgggc gggggcctgg ccgccatggc ccggcttcca ctcaagacgg   420
ctgtcgagga ggcccgcaga gaggcattag acagcaacg gggcagtgcc accccgcgg    480
cccccccgagc ggaaggaaag gagcctccca ggccaggcac tgccctcctg ggcaggagcg   540
aagcgggg gatgtccgcc ccctcctga tccacttcac tcctcggagg cctggcacgg     600
aagcggaggc ggagacaggt ggtgtcaggg cgtcctctcg ccaggccgca ggccccgcgg    660
ggcaacagga cactgccccc tgcaggcgg gcgcggggcc ctcgggctcg atggggagag     720
gccggggccg gcggcggcgg atggacgctg gctcgggaga cagagcccgc cgcccccgga   780
aactggaccc gctccgcctg ggcgcgcggg ggagcgtgtg ggacgcggtg gacggggccg    840
ccgccctgga cgcccacgcg cgcggcctcc ccacagacc cccactcgcc caggagcccg     900
cactcccggc gctgccgct cccgcgccc tgcagcctgg gtctcagacg gaaggctctg    960
gggccaaggg tggctggagc agggaggcct cgggggtccc tgccccggga ggaggctggc   1020
cctgggtcag cagggaggtc ccggggcacc ggagctttgg cccagcccca gactccacgc   1080
gccctctggct agagagtccg cctcaaggtc gcccactctc gtcccaaggg ccgggtgcca   1140
caggggccta cgatgccggc gaggccgggg ctgacagctc ccgagataac agtcctgccg   1200
ctgacctggg gcccacccgg cccccggagc aagcaaagcc ggctgcagcc ggccacagcc   1260
gcgcgccctc ccggagccgt gagcctgcc cgcgctccgc ctccccgccc gcagctcccg    1320
gcccggggtt cccacctgaa gccctgactc tcccctctcc ttcagacttt ttgccccttgg   1380
aggttaccca ggatccttcc gtgggcgaaa atctccgagc ggcgccagcc ccaagttcag   1440
cctcagccca agtcttaact tcagctcag cctcagtcct agcccagcc ctggcttcat    1500
cccccagctc agcaccaacc tcagccacca cctcaacctc atccccacc tcagcccag    1560
cccagctcc aacctcagct ccaacttcaa cccagcccg agcccaagt cagctgcag      1620
ccgcaactcc agcccagcc ccagtccag tccaacccct cacccccca tcccagccc      1680
taacccagt cccaacccca gcctaagcc cagctccaac tccagcccta accccagccg    1740
catcccagc cctaaccca gtcccaaccc cagcctaag cccagctcca actccagccc      1800
caacccgac cgcatcccct gccccagcc ccacctcagc cccaacccca accccagcg     1860
catcccctgc cccagctgac gggtcaaag ctcaggagag tgtggctctc ccaggcgct     1920
accaggaggg gcaggtctca gccagctggg gaaaccttat tgccatggtt cttagaagcc   1980
accccttccc caggcaagac aggccccaag ggagtgtccc gagggcggtt cccgggagcc   2040
ccgtgggctcc cagcacttcc acacactctg aggacagaca cggcccctct tcttcagtgg   2100
ggacagtcat agggacaggt acaggggccc tggttgaggc tggaggtcag ccacagccaa   2160
gaagctccga gaccaacgga tcgcccagcc cagaccctcc cccaggccta agaggagagg   2220
gaaccaggga gaaaagtcta gacccgctgc cccaagccgc gatgcccagg ggccccgcac   2280
agccccccgc gcagaggccg cctggccccg cggcctcctc ctctgcgagg cgctcacag    2340
cggtaccca gctacggaaa cgcagcaggt gcgaaatcgc cccgagctcg gagcaggagg   2400
tcaggccggc cgcctcgggg gaccctcaag ggaggcgcc gggggaggg ggcagccctg     2460
ccggccgcag cggggcgctc acggaaaagc aggagagc ccggaagctc atggtgttc      2520
tgcagaggcc cggggttgg ggggtggtgg aggggcccg gaagcccag tcccgggccc      2580
tggagcccgc cacggcggca gccctgcggg gccggctga cctgggcagt tgcctggacg   2640
tgctggcctt tgcccagcag cacggagagc ccggcctggc gcaggagacc tacgcgctga   2700
tgagcgacaa cctgctgcga gtgctgggag accgtgccct ctaccgcgg ctgagcgcgg    2760
ccgaccgcga gcgcatcctc agcctgcgga ccggccgggg ccgggcggtg ctgggcgtcc   2820
tcgtactgcc cagcctctac cagggggcc gctcaggcct cctcagtgga cctcgtgcag   2880
aggagcctcc tgcggcggcc cctgtgtccc tgcctctacc tgcgcacctg catgtgttca   2940
acccccggga gaacctggg cggccctga ccaggtgcc cgaggaggcc ccgcttcggg      3000
gctgcggtct ctgcaccatg cacaactacc tgtttctggc gggggggcatc cgtggctccg   3060
gtgccaaggc cgtctgctcc aacgaggtct tctgctacaa ccctctgacc aacatctgga   3120
gccaggttcg gcccatgcag caggcccgag cccagctcaa gctggtggcc ctggacgggc   3180
tgctctatgc catcggtggc gaatgcctgt acagcatgga gtgctacgac ccgcgaacag   3240
acgcctggac cccacgcgcg ccactcccg caggcacctt cctgtgccca acgaggctg    3300
tggcctgccg tggggacatc tacgtcaccg ggggtcacct cttctaccgc ctgctcaggt   3360
acagcccgt gaaggatgct tgggacgagt gcccatacag tgccagccac cggcgttcca   3420
gcgacatcgt gcactgtggg ggcttcctgt accgcttcga ggcgtgggcg              3480
ccgccgtgat gcgctacaac acagtgaccg gctcctggag cagggctgcc tcctgcccc    3540
tgccgcccc cgcccactg cactgcacca cctgggcaa caccatttac tgcctcaacc     3600
cccaggtcac tgccaccttc acggtctctg ggggactgc ccagtccag gccaaggagc    3660
tgcagccctt cccctggg agcaccgggg tcctcagtcc attcatcctg actctgcccc   3720
ctgaggaccg gctgcagacc tcactctgag tggcaggcag agaaccaaag ctgcttcgct   3780
```

```
gctctccagg gagaccctcc tgggatgggc ctgagaggcc ggggctcagg gaaggggctg   3840
ggatcggaac ttcctgctct tgtttctgga caactttccc cttctgcttt aaaggttgtc   3900
gattattttg aagcccagac tccctcagcc tctttctgcc cctcactcca cacccagact   3960
gtttcctgac tcaattccgt acctacttac agaccctctc agcttgctga cacccccctg   4020
tctgtgggac tccctattcc ctagagccag ggactgatgc gtctccacag acaaggactt   4080
ggctcgctgg agctctgctg agccgagaga gggaggggta gaaaacattc acacttccta   4140
tgctctgtca gcaggacagg gagcaaaaac gtccccaggc aacgccctcg cctctgggac   4200
tttctgcctg tcctaaggcc tccccaggta ccaaccccgt agctatctgg gtctgtttgg   4260
cactgtggat tctcaagggc ctagaaccct tgcctctgaa actggtccgc tggtgcagcc   4320
ctgctgtctg cagctcctgc ccataccccc agcccacacc aggtcaggcc cactccgggc   4380
tcaccaccct ctgcagcctt gtggggctct cccagcccct ccagaagccc acccactcc   4440
tcgccaaccc ccgatctcta aatgaggcct gagcgtcacc ctagttctgc ccttttttag   4500
ctgtgtagac ttggacgaga catttgactt ccctttctcc ttgtctataa aatgtggaca   4560
gtggacgtct gtcacccaag agagttgtgg gagacaagat cacagctatg agcacctcgc   4620
acggtgtcca ggatgcacag cacaatccat gatgcgtttt ctcccttac gcactttgaa   4680
acccatgcta gaaaagtgaa tacatctgac tgtgctccac tccaacctcc agcctggatg   4740
tccctgtctg ggccctttt ctgtttttta ttctatgttc agcaccactg gcaccaaata   4800
catttaatt caccgaaagc aaaaaaaaaa aaaaaa                              4837

SEQ ID NO: 14           moltype = DNA   length = 2099
FEATURE                 Location/Qualifiers
source                  1..2099
                        mol_type = other DNA
                        organism = Homo sapiens
SEQUENCE: 14
ccacctcagc cccaacccca accccagccg catcccctgc cccagctgac gggtcaaagc    60
ctcaggagag tgtggctctc cccaggcgct accaggaggg gcaggtctca gccagctggg   120
gaaaccttat tgccatggtt cttagaagcc acccctcccc caggcaagac aggccccaag   180
ggagtgtccc gagggcggtt cccggagccc cgtgggtcc cagcacttcc acacactctg    240
aggacagaca cggcccctct tcttcagtgg ggacagtcag acaggacaggt acaggggcc   300
tggttgaggc tggaggtcag ccacagccaa gaagctccga gaccaacgga tcgcccagcc   360
cagaccctcc cccaggccta agaggagagg gaaccaggga gaaaagtcta gacccgctgc   420
cccaagccgc gatgcccagg ggccccgcac agccccccgc gcagaggccg cctgcccccg   480
cggcctcctc ctctgcgagg cgctcacagc cggtacccca gctacggaaa cgcagcaggt   540
gcgaaatcgc cccgagctcg gagcaggagg tcaggccggc ccgctcgggg gaccctcaag   600
gggaggcgcc gggggagggg ggcagccctg ccggccgcag cggggcgctc acggaaaagc   660
aggaggaggc ccggaagctc atggtgtttc tgcagaggcc cgggggttgg ggggtggtgg   720
aggggccccg gaagcccagc tcccgggccc tggagcccgc cacggcggca gccctgcggc   780
ggcggctgga cctgggcagt tgcctggacg tgctggcctt tgcccagcag cacggagagc   840
ccggcctggc gcaggagacc tacgcgctga tgagcgacaa cctgctgcga gtgctgggag   900
acccgtgcct ctaccgccgg ctgagcgcgg ccgaccgcga gcgcatcctc agcctgcgga   960
ccggccgggg ccggccggtg ctgggcgtcc tcgtactgcc cagcctctac caggggggcc  1020
gctcagggct cccccagggc cctcgtgcg aggagcctcc tgcggcggcc cctgtgtccc  1080
tgcctctacc tgcgcacctg catgtgttca accccgggga gaacacctgg cggcccctga  1140
cccaggtgcc cgaggaggcc ccgcttcggg gctgcggtct ctgcaccatg cacaactacc  1200
tgtttctggc gggggggcatc cgtggctccg gtgccaaggc cgtctgctcc aacgaggtct  1260
tctgctacaa ccctctgacc aacatctgga gccaggttcg accatgcag caggcccgag  1320
cccagctcaa gctggtggcc ctggacgggc tgctctatgc catcggtggc gaatgcctgt  1380
acagcatgga gtgctacgac ccgcgaacag acgcctggac cccacgcgcg ccactccccg  1440
caggcacctt ccctgtggcc cacgaggctg tggcctgccg tggggacatc tacgtcaccg  1500
ggggtcacct cttctaccgc ctgctcaggt acagccccgt gaaggatgct tgggacgagt  1560
gcccatacag tgccagccac cggcgttcca gcgacatcgt ggcactgggg gcttcctgt   1620
accgcttcga cctgctgcgg ggcgtggggcg ccgccgtgat gcgctacaac acagtgaccg  1680
gctcctggag cagggctgcc tccctgcccc tgcccgcccc cgcccactg cactgcacca  1740
ccctgggcaa caccatttac tgcctcaacc ccaggtcac tgccaccttc acggtctctg  1800
ggggggactgc ccagttccag gccaaggagc tgcagcccct cccccttgggg agcaccgggg  1860
tcctcagtcc attcatcctg actctgcccc tgaggaccg gctgcagacc tcactctgag   1920
tggcaggcag agaaccaaag ctgcttcgct gctctccagg gagaccctcc tgggatgggc   1980
ctgagaggcc ggggctcagg gaaggggctg ggatcggaac ttcctgctct tgtttctgga   2040
caactttccc cttctgcttt aaaggttgtc gattattttg aaaaaaaaaa aaaaaaaa     2099

SEQ ID NO: 15           moltype = DNA   length = 5125
FEATURE                 Location/Qualifiers
source                  1..5125
                        mol_type = other DNA
                        organism = Homo sapiens
SEQUENCE: 15
agaagcaggt tggctgtgat gacagcacag agctcaggaa cgctgcctga ggacccggg     60
gcctacgagg aggagaagag ggcaggagct ggtgggggtgc ttgcagagac cctgggctcc   120
tatcctgcca taagcctcgc tgtctcctga tatctgcagc caggcccta tgacacccc    180
aggcctgagt gcaagcagag accccaccat tcccaggccc tggaggactg tccacctta    240
actgggcagc ccttggggca ggcgctggcc ggtgcctcag cccaggcctc tgtgctctgc   300
atgcactgcc agcctgccat caggcctcta ttgcagccct gaaccatgat ccagggcacc   360
tggagcacag atggtcccct ctggggctgg gactgggaca gtgacaatga ctgggatagt   420
gctgtgctgg ccctcctggc gctggctgtg gtgctgccaa cagcgctggc cttacactgg   480
tttggctccg gcacgatca agaggcggca gaaccggtgt ccacagccct cgggggctcaa   540
cctcatcagg caggaggagc tgagctgcc ctgcaaccga agtctaaggt cagtgatggc   600
agcgagggggc agagcccagg gcaggggaaa ccagagcccc caggacgcgg ccagcagagc   660
cctgtccctg ctgcagcgcc gggcgggggc ctggccgcca tggcccggct tccactcaag   720
```

```
acggctgtcg aggaggcccg cagagaggca ttaggacagc aacggggcag tgccaccccc    780
gcggccccc  gagcggaagg aaaggagcct cccaggccag gcactgccct cctgggcagg    840
agcgaagcag gggggatgtc cgccccctc  ctgatccact tcactcctcg gagccctggc    900
agcgaagcgc aggcggagac aggtggtgtc agggcgtcct ctcgccaggc cgcaggcccc    960
gcggggcaac aggacactgg cccctggcag gcgggcgggg ggcctcggg  ctcgatgggg   1020
agaggccggg gccggcggcg gcggatggac gctggctcgg gagacagagc ccgccgcccc   1080
cggaaactgg acccgctccg cctgggcgcc gcggggagcg tgtggacgc  ggtggacggg   1140
gccgccgccc tggacgccca cgcgcgcggc ctccccacag gaccccact  cgcccaggag   1200
cccgcactcc cggcgctgcc cgctccccgc gccctgcagc ctgggtctca gacggaaggc   1260
tctgggccca agggtggctg gagcagggag gcctcggggg tccctgcccc cggaggaggc   1320
tggccctggg tcagcaggga ggtcccggc  acccggagct ttggcccagc cccagactcc   1380
acgcgcccct ggctagagag tccgcctcaa ggtcgcccac tctcgtccca agggccgggt   1440
gccacagggg cctacgatgc cggcgaggcc ggggctgaca gctcccgaga taacagtcct   1500
gccgctgacc tgggcccac  ccggccccg  gagcaagcaa agccggctgc agccggccac   1560
agccgcgcgc cctccggag  ccgtgagcct cgcccgcgct ccgcctcccc gcccgcagct   1620
cccggcccgg ggttcccacc tgaagccctg actctccct  ctccttcaga ctttttgccc   1680
ctggaggtta cccaggatcc ttccgtgggc gaaaatctca gagcggcgcc agcccaagt   1740
tcagcctcag cccaagtctt aacttcagct ccagcctcag tcctagcccg agccctggct   1800
tcatccccca gctcagcacc aacctcagcc accacctcaa cctcatcccc cacctcagcc   1860
ccagcccag  ctcaacctc  agctccaact tcaaccccag cccagcccc  aagtccagct   1920
gcagccgcaa ctccagcccc agcccagtc  ccagtcccaa ccctcacacc cccatcccca   1980
gccctaaccc cagtcccaac cccagcccta agcccagcct ccaactccag cctaaccca   2040
gccgcatccc cagccctaac cccagtccca accccagccc taagcccagc tccaactcca   2100
gccccaaccc cagccgcatc ccctgcccca gcccccacct cagccccaac cccaacccca   2160
gccgcatccc ctgcccagc  tgacgggtca agcctcagg  agagtgtggc tctccccagg   2220
cgctaccagg aggggcaggt ctcagccagc tgggaaacc  ttattgccat ggttcttaga   2280
agccaccccct tccccaggca agacaggccc caagggagtg tcccgagggc ggttcccggg   2340
agccccgtgg gtcccagcac ttccacacac tctgaggaca gacacggccc ctcttcttca   2400
gtggggacag tcatagggac aggtacaggg ggcctggttg aggctggagg tcagccacag   2460
ccaagaagct ccgagaccaa cggatcgccc agcccagacc ctcccccagg cctaagagga   2520
gagggaacca gggagaaaag tctagaccc  ctgccccaag ccgcgatgcc caggggcccc   2580
gcacagcccc ccgcgcagag gccgcctggc cccgcggcct cctcctctgc gaggcgctca   2640
cagccggtac cccagctacg gaaacgcagc aggtgcgaaa tcgccccgag ctcggagcag   2700
gaggtcaggc cggccgcctc ggggggaccct caaggggagg cgccgggga  gggggcagc   2760
cctgccggcc gcagcggggc gctcacggaa aagcaggagg aggcccggaa gctcatgggg   2820
tttctgcaga ggcccggggg ttggggggtg gtggagggc  cccggaagcc cagctcccgg   2880
gccctggagc ccgccacggc ggcagccctg cggcggcggc tggacctggg cagttgcctg   2940
gacgtgctgg cctttgccca gcagcacgga gagcccggcc tggcgcagga gacctacgcg   3000
ctgatgagcg acaacctgct gcgagtgctg gagacccgt  gcctctaccg ccggctgagc   3060
gcggccgacc gcgagcgcat cctcagcctg cggaccgcc  ggggccgggc ggtgctgggc   3120
gtcctcgtac tgcccagcct ctaccagggg ggccgctcag ggctcccag  gggccctcgt   3180
ggcgaggagc ctcctgcggc ggcccctgtg tccctgcctc tacctgcgca cctgcatgtg   3240
ttcaaccccc gggagaacac ctggcggccc ctgacccagg tgcccgagga ggcccgcgtt   3300
cggggctgcg gtctctgcac catgcacaac tacctgtttc tggcgggggg catccgtggc   3360
tccggtgcca aggccgtctg ctccaacgag gtcttctgct acaaccctct gaccaacatc   3420
tggagccagg ttcggcccat gcagcaggcc cgagcccagc tcaagctggt ggccctggac   3480
gggctgctct atgccatcgg tggcgaatgc tgtatacagca tggagtgcta cgaccgcgca   3540
acagacgcct ggaccccacg cgcgccactc cccgcaggca ccttccctgt ggcccacgag   3600
gctgtggcct gccgtgggga catctacgtc accggggggtc acctcttcta ccgcctgctc   3660
aggtacagcc ccgtgaagga tgcttgggac gagtgcccat acagtgccag ccaccggcgt   3720
tccagcgaca tcgtggcact gggggggcttc tgtgtaccgct tcgacctgct gcgggggcatg   3780
ggcgccgccg tgatgcgcta caacacagtg accggctcct ggagcagggc tgcctccctg   3840
cccctgcccg ccccgcccc  actgactgc  accaccctgg gcaacaccat ttactgcctc   3900
aacccccagg tcactgccac cttcacggtc tctggggga  ctgccagtt  ccaggccaag   3960
gagctgcagc ccttcccctt ggggagcacc gggtcctca  gtccattcat cctgactctg   4020
cccccctgagg accggctgca gacctcactc tgagtggcag gcagagaacc aaagctgctt   4080
cgctgctctc cagggagacc ctcctgggat gggcctgaga ggccgggct  cagggaaggg   4140
gctgggatcg gaacttcctg ctcttgtttc tggacaactt tcccctttctg ctttaaggt   4200
tgtcgattat tttgaagccc agactcccctc agcctctttc tgcccctcac tccacaccca   4260
gactgtttcc tgactcaatt ccgtacctac ttacagaccc tctcagcttg ctgacacccc   4320
cctgtctgtg ggactccta  ttccctagag ccagggactg atgcgtctcc acagacaagg   4380
acttggctcg ctggagctct gctgagccga gagaggaggg ggtagaaac  attcacactt   4440
cctatgctct gtcagcagga cagggagcaa aaacgtcccc aggcaacgcc ctcgcctctg   4500
ggactttctg cctgtcctaa ggcctcccca ggtaccaacc ccgtagctat ctgggtctgt   4560
ttggcactgt ggattctcaa gggcctagaa cccttgcctc tgaaactggt ccgctggtgt   4620
agccctgctg tctgcagctc ctgcccatac ccccagccca caccaggcca ggcccactcc   4680
gggctcacca ccctctgcag ccttgtgggg ctctcccagc ccctcagaa  gcccacccca   4740
cttctcgcca accccgatc  tctaaatgag gcctgagcgt cacccctagtt ctgcccctt   4800
ttagctgtgt agacttggac gagacatttg acttcccttt ctccttgtct ataaaatgtg   4860
gacagtggac gtctgtcacc caagagagtt gtgggagaca agatcacagc tatgagcacc   4920
tcgcacggtg tccaggatgc acagcacaat ccatgatgcg ttttctcccc ttacgcactt   4980
tgaaacccat gctagaaaag tgaatacatc tgactgtgct ccactccaac ctccagcctg   5040
gatgtccctg tctgggccct ttttctgttt tttattctat gttcagcacc actggcacca   5100
aatacatttt aattcaccga aagca                                         5125

SEQ ID NO: 16         moltype = DNA  length = 2990
FEATURE               Location/Qualifiers
source                1..2990
                      mol_type = other DNA
```

```
                        organism = Homo sapiens
SEQUENCE: 16
ccacctcagc cccaacccca accccagccg catcccctgc cccagctgac gggtcaaagc    60
ctcaggagag tgtggctctc cccaggcgct accaggaggg gcaggtctca gccagctggg   120
gaaaccttat tgccatggtt cttagaagcc accccttccc caggcaagac aggccccaag   180
ggagtgtccc gagggcggtt cccgggagcc ccgtgggtcc cagcacttcc acacactctg   240
aggacagaca cggcccctct tcttcagtgg ggacagtcat agggacaggt acaggggggcc   300
tggttgaggc tggaggtcag ccacagccaa aagctccga gaccaacgga tcgcccagcc   360
cagaccctcc cccaggccta agaggagagg gaaccaggga gaaaagtcta gacccgctgc   420
cccaagccgc gatgcccagg ggccccgcac agccccccgc gcagaggccg cctggccccg   480
cggcctcctc ctctgcgagg cgctcacagc cggtacccca gctacggaaa cgcagcaggt   540
gcgaaatcgc cccgagctcg gagcaggagg tcaggccggc cgcctcgggg gaccctcaag   600
gggaggcgcc gggggagggg ggcagccctg ccggccgcag cggggcgctc acggaaaagc   660
aggaggaggc ccggaagctc atggtgtttc tgcagaggcg cggggttgg ggggtggtgg   720
aggggccccg gaagcccagc tcccgggccc tggagcccgc cacggcggca gcctgcgcgc   780
ggcggctgga cctgggcagt tgcctggacg tgctggcctt tgcccagcag cacggagagc   840
ccggcctggc gcaggagacc tacgcgctga tgagcgacaa cctgctgcga gtgctgggag   900
acccgtgcct ctaccgcggc ctgagcgcgg ccgaccgcga gcgcatcctc agcctgcgga   960
ccggccgggg ccgggcggtg ctgggcgtcc tcgtactgcc cagcctctac caggggggcc  1020
gctcagggct cccccagggg c cctcgtggcg aggagcctcc tgcggcggcc cctgtgtccc  1080
tgcctctacc tgcgcacctg catgtgttca accccgggga gaacacctgg cggccctga   1140
cccaggtgcc cgaggaggcc ccgcttcggg gctgcggtct ctgcaccatg cacaactacc  1200
tgtttctggc gggggggcatc cgtgcctccg gtgccaaggc cgtctgctcc aacgaggtct  1260
tctgctacaa ccctctgacc aacatctgga gccaggttcg gcccatgcag caggcccgag  1320
cccagctcaa gctggtggcc ctggacgggc tgctctatgc catcgtggc gaatgcctgt  1380
acagcatgga gtgctacgac ccgcgaacag acgcctggca ccacgcgcg ccactcccga  1440
caggcacctt ccctgtggcc cacgaggctg tggcctgccg tggggacatc tacgtcaccg  1500
ggggtcacct cttctaccgc ctgctcaggt acagccccgt gaaggatgct tgggacgagt  1560
gcccatacag tgccagccac cggcgttcca gcgacatcgt ggcactgggg ggcttcctgt  1620
accgcttcga cctgctgcgg ggcatgggcc ccgccgtgat ggctacaac acagtgaccg  1680
gctcctggag cagggctgcc tccctgcccc tgcccgcccc cgcccactg cactgcacca  1740
ccctgggcaa caccatttac tgcctcaacc ccaggtcac tgccaccttc acggtctctg  1800
gggggactgc ccagttccag gccaaggagc tgcagcccttt ccccttgggg agcaccgggg  1860
tcctcagtcc attcatcctg actctgcccc ctgaggaccg gctgcagacc tcactctgag  1920
tggcaggcag agaaccaaag ctgcttcgct gctctccagg gagaccctcc tgggatgggt  1980
ctgagaggcc ggggctcagg gaaggggctg ggatcggaac ttcctgctct tgtttctgga  2040
caactttccc cttctgcttt aaaggttgtc gattattttg aagcccagac tccctcagcc  2100
tctttctgcc cctcactcca cacccagact gtttcctgac tcaattccgt acctacttac  2160
agaccctctc agcttgctga cacccccctg tctgtgggga tccctattcc ctagagccag  2220
ggactgatgc gtctccacag acaaggactt ggctcgctgg agctctgctg agccgagaga  2280
ggagggggta gaaaacattc acacttccta tgctctgtca gcaggacagg gagcaaaaac  2340
gtccccaggc aacgccctcg cctctgggac tttctgcctg tcctaaggcc tcccaggta   2400
ccaaccccgt agctatctgg gtctgttttgg cactgtggat tctcaaggc ctagaaccct  2460
tgcctctgaa actggtccgc tggtgcagcc ctgctgtctg cagctcctgc ccataccccc  2520
agcccacacc aggccaggcc cactccgggg tcaccaccct ctgcagcctt gtggggctct  2580
cccagcccct ccagaaagccc accccacttc tcgccaaccc ccgatctcta aatgaggcct  2640
gagcgtcacc ctagttctgc ccctttttag ctgtgtagac ttggacgaga catttgactt  2700
cccttctctcc ttgtctataa aatgtggaca gtggacgtct gtcacccaag agagttgtgg  2760
gagacaagat cacagctatg agcacctcgc acggtgtcca ggatgcacag cacaatccat  2820
gatgcgtttt ctcccttac gcactttgaa acccatgcta gaaagtgaa tacatctgac   2880
tgtgctccac tccaacctcc agcctggatg tccctgtctg ggccttttt ctgttttta   2940
ttctatgttc agcaccactg gcaccaaata cattttaatt caccgaaagc            2990

SEQ ID NO: 17             moltype = DNA    length = 4837
FEATURE                   Location/Qualifiers
source                    1..4837
                          mol_type = other DNA
                          organism = Homo sapiens
SEQUENCE: 17
actgccagcc tgccatcagg cctctattgc agccctgaac catgatccag ggcaccttgg    60
agccagatgg tccctctgg ggctgggact gggacagtga caatgactgg gatagtgctg   120
tgctggccct cctggcgctg ctgtggtgg ctgccacagc gctggcctta cactggtttg   180
gctccgggca cgatcaagag gcggcagaac cggtgtccac agcccctcggg gctcaacctc   240
atcaggcagg aggagtcgag ctggccctgc aaccgaagtc taaggtcagt gatggcagcg   300
aggggcagag cccagggcag ggaaaccag agccccagg acgcggccag cagagccctg   360
tccctgctgc agcgccgggc gggggcctgg ccgccatggc ccggcttcca ctcaagacgg   420
ctgtcgagga ggcccgcaga gaggcattag acagcaacg gggcagtgcc accccgcgcg   480
cccccgagc ggaaggaaag gagcctccca ggccaggcac tgccttcctg ggcaggagcg   540
aagcagggag gatgtccgcc cccctcctga tccacttcaa tcctcggaag cctggcaggc   600
aagcaggagc ggagacaggt ggtgtcaggg cgtcctctcg ccaggccgca ggcccgcggg   660
ggcaacagga cactgacccc tggcaggcgg gcgcggggcc ctcgggctcg atgggggagg   720
gccggggccg gcggcggcgg atggacgctg gctcggagag cagagcccgc cgcccccgga   780
aactggaccc gctccgcctg ggcgccgcgg ggagcgtgtg gacgcggtg gacggggccg   840
cggccccgga cgccccacgcg cgcctcctcc cacaggacc cccactcgca caggagccgg   900
cactcccgga gctgcccgct ccccgcgccc tgcagcctgg gtctcagacg aaggctctg   960
gggcaaggg tggctggagc agggaggcct cggggtccc tgcccccgga ggaggctggc  1020
cctgggtcag cagggaggtc ccgggcaccc ggagctttgg cccagcccca gactccacgc  1080
gcccctggct agagagtccg cctcaaggtc gccactctca gtcccaaggg ccgggtgcca  1140
caggggccta cgatgccggc gaggccgggg ctgacagctc ccgagataac agtcctgccg  1200
```

```
ctgacctggg gcccacccgg ccccccggagc aagcaaagcc ggctgcagcc ggccacagcc    1260
gcgcgccctc ccggagccgt gagcctcgcc cgcgctccgc ctccccgccc gcagctcccg    1320
gcccggggtt cccacctgaa gccctgactc tcccctctcc ttcagacttt ttgcccctgg    1380
aggttaccca ggatccttcc gtgggcgaaa atctcagagc ggcgcagcc ccaagttcag    1440
cctcagccca agtcttaact tcagctccag cctcagtcct agcccagcc ctggcttcat    1500
cccccagctc agcaccaacc tcagccacca cctcaacctc atcccccacc tcagcccag    1560
ccccagctcc aacctcagct ccaacttcaa ccccagcccc agcccaagt ccagctgcag    1620
ccgcaactcc agcccagcc ccagtcccag tccaaccct cacaccccca tcccccagccc    1680
taacccagt cccaaccca gccctaagcc cagctccaa tccagcccta accccagccg    1740
catccccagc cctaacccca gtcccaaccc cagccctaag cccagctcca actccagcc    1800
caacccccagc cgcatccct gccccagccc ccacctcagc cccaacccca accccagccg    1860
catccctgc cccagctgac gggtcaaagc ctcaggagag tgtggctctc cccaggcgct    1920
accaggaggg gcaggtctca gccagctggg gaaaccttat tgccatggtt cttagaagcc    1980
accccttccc caggcaagac aggccccaag ggagtgtccc gagggcggtt cccggagcc    2040
ccgtgggtcc cagcacttcc acacactctg aggacagaca cggcccctct tcttcagtgg    2100
ggacagtcat agggacaggt acaggggggcc tggttgaggc tggaggtcag ccacagccaa    2160
gaagctccga gaccaacgga tcgcccagcc cagaccctcc cccaggccta agagggagag    2220
gaaccaggga gaaaagtcta gacccgctgc cccaagccgc gatgcccagg ggcccccgcac    2280
agcccccgc gcagaggccg cctgcccccg cggcctcctc ctctgcgagg cgctcacagc    2340
cggtaccccca gctacggaaa cgcagcaggt gcgaaatcgc cccgagctcg gagcaggagg    2400
tcaggccggc cgcctcgggg gaccctcaag gggaggcgcc gggggagggg ggcagccctg    2460
ccggccgcag cggggcgctc acggaaaagc aggaggagc atggtgtttc    2520
tgcagaggcc cggggggttgg ggggtggtg aggggccccg gaagcccagc tcccgggccc    2580
tggagcccgc cacgcggca gccctgcggg ggcggctgga cctgggcagt tgcctggacg    2640
tgctggcctt tgcccagcag cacgagagc ccggcctggc gcaggagacc tacgcgctga    2700
tgagcgacaa cctgctgcga gtgctgggaa acccgtgcct ctaccgccgg ctgagccgga    2760
ccgaccgcga gcgcatcctc agcctgcgga ccggccagga ccgggcggtg ctggcgtcc    2820
tcgtactgcc cagcctctac caggggggcc gctcagggct cccccaggggc cctcgtggcg    2880
aggagcctcc tgcggcggcc cctgtgtccc tgcctctacc tgcgcacctg catgtgttca    2940
accccccggga gaacacctgg cggccccctga cccaggtgcc cgaggaggcc ccgcttcgg    3000
gctgcggtct ctgcaccatg cacaactacc tgtttctggc gggggggcatc cgtggctccg    3060
gtgccaaggc cgtctgctcc aacgaggtct tctgctacaa ccctctgacc aacatctgga    3120
gccaggttcg gcccatgcag caggcccgag cccagctcaa gctggtggcc ctggacgggc    3180
tgctctatgc catcggtggc gaatgcctgt acagcatgga gtgctacgac ccgcgaacag    3240
acgcctggac cccacgacgcg ccactccccg caggcaccctt ccctgtggcc cacgaggctg    3300
tggcctgccg tgggggacatc tacgtcaccg ggggtcacctt cttctaccgc ctgctcaggt    3360
acagccccgt gaaggatgct tgggacgagt gcccatacag tgccagccac cggcgttcca    3420
gcgacatcgt ggcactgggg ggcttcctgt accgcttcga cctgctgcgg ggcatgggcg    3480
ccgccgtgat gcgctacaac acagtgaccg gctcctggag gctctgcccc tccctgcccc    3540
tgcccgcccc cgccccactg cactgcacca ccctgggcaa caccatttac tgcctcaacc    3600
cccaggtcac tgccaccttc acggtctctg gggggactgc ccagttccag gccaaggagc    3660
tgcagcccctt cccctttgggg agcaccgggg tcctcagtcc attcatcctg actctgcccc    3720
ctgaggaccg gctgcagacc tcactctgag tggcaggcag agaaccaaag ctgcttcgt    3780
gctctccagg gagaccctcc tgggatgggc ctgagaggcc ggggctcagg gaaggggctg    3840
ggatcggaac ttcctgctct tgtttctgga caacttccc cttctgcttt aaaggttgtc    3900
gattattttg aagcccagac tccctcagcc tctttctgcc cctcactcca cacccagact    3960
gtttcctgac tcaattccgt acctacttac agaccctcgc agcttgctga caccccccgg    4020
tctgtgggac tccctattcc ctagagccag ggactgatgc gtctccacag acaaggactt    4080
ggctcgctgg agctctgctg agccgagaga ggagggggta gaaaacattc acacttccta    4140
tgctctgtca gcaggacagg gagcaaaaac gtccccagge aacgcccttcg cctctgggac    4200
tttctgcctg tcctaaggcc tccccaggta ccaacccgcgt agctatctgg gtctgtttgg    4260
cactgtggat tctcaagggc ctagaaccct tgcctctgaa actggtccgc tggtgcagcc    4320
ctgctgtctg cagctcctgc ccatacccc agcccacacc aggccaggcc cactccgggc    4380
tcaccacct ctgcagcctt gtggggctct cccagcccct ccagaagccc accccacttc    4440
tcgccaaccc ccgatctcta aatgaggcct gagcgtcacc ctagttctgc ccctttttag    4500
ctgtgtagac ttggacgaga catttgactt cccttctcc ttgtctataa aatgtggaca    4560
gtggacgtct gtcacccaag agagtgttgg gagacaagat cacagctatg agcacctcgc    4620
acggtgtcca ggatgcacag cacaatccat gatgcgtttt ctccccttac gcactttgaa    4680
acccatgcta gaaaagtgaa tacatctgac tgtgctccac tccaacctcc agcctggatg    4740
tccctgtctg ggccctttt ctgttttta ttctatgttc agcaccactg gcaccaaata    4800
cattttaatt caccgaaagc aaaaaaaaaa aaaaaaa                              4837

SEQ ID NO: 18         moltype = DNA  length = 2099
FEATURE               Location/Qualifiers
source                1..2099
                      mol_type = other DNA
                      organism = Homo sapiens
SEQUENCE: 18
ccacctcagc cccaacccca acccagccg catccctgc cccagctgac gggtcaaagc      60
ctcaggagag tgtggctctc cccaggcgct accaggaggg gcaggtctca gccagctggg    120
gaaaccttat tgccatggtt cttagaagcc accccttccc caggcaagac aggccccaag    180
ggagtgtccc gagggcggtt cccggagcc ccgtgggtcc cagcacttcc acacactctg    240
aggacagaca cggcccctct tcttcagtgg ggacagtcat agggacaggt acaggggggcc    300
tggttgaggc tggaggtcag ccacagccaa gaagctccga gaccaacgga tcgcccagcc    360
cagaccctcc cccaggccta agagggagag gaaccaggga gaaaagtcta gacccgctgc    420
cccaagccgc gatgcccagg ggcccccgcac agcccccgc gcagaggccg cctgcccccg    480
cggcctcctc ctctgcgagg cgctcacagc cggtaccccca gctacggaaa cgcagcaggt    540
gcgaaatcgc cccgagctcg gagcaggagg tcaggccggc cgcctcgggg gaccctcaag    600
ggggaggcgcc gggggagggg ggcagccctg ccggccgcag cggggcgctc acggaaaagc    660
```

```
aggaggaggc ccggaagctc atggtgtttc tgcagaggcc cggggggttgg ggggtggtgg    720
aggggccccg gaagcccagc tcccgggccc tggagcccgc cacggcggca gccctgcggc    780
ggcggctgga cctgggcagt tgcctggacg tgctggcctt tgcccagcag cacggagagc    840
ccggcctggc caggagacc tacgcgctga tgagcgacaa cctgctgcga gtgctgggag    900
acccgtgcct ctaccgcgg ctgagcgcg ccgaccgcga tcctc agcctgcgga    960
ccggccgggg ccgggcggtg ctgggcgtcc tcgtactgcc cagcctctac caggggggcc    1020
gctcagggct ccccaggggc cctcgtggcg aggagcctcc tgcggcggcc cctgtgtccc    1080
tgcctctacc tgcgcacctg catgtgttca accccgggga gaacacctgg cggcccctga    1140
cccaggtgcc cgaggaggcc ccgcttcggg gctgcgcgtc t ctgcaccatg cacaactacc    1200
tgtttctggc ggggggcatc cgtggcctcc ggtgccaagc cgtctgctcc aacgaggtct    1260
tctgctacaa ccctctgacc aacatctgga gccaggttcg gcccatgcag caggccccgag    1320
cccagctcaa gctggtggcc ctggacgggc tgctctatgc catcggtggc gaatgcctgt    1380
acagcatgga gtgctacgac ccgcgaacag acgcctggac ccccacgcgcg ccactccccg    1440
caggcacctt ccctgtggcc cacgaggctg tggcctgccg tggggacatc tacgtcaccg    1500
ggggtcacct cttctaccgc ctgctcaggt acagccccgt gaaggatgct tgggacgagt    1560
gcccatacag tgccagccac cggcgttcca gcgacatcgt ggcactgggg ggcttcctgt    1620
accgcttcga cctgctgcgg ggcatgggcg ccgccgtgat gcgctacaac acagtgaccg    1680
gctcctggag cagggctgcc tccctgcccc tgccccgcgg cacctgcaca    1740
ccctgggcaa caccatttac tgcctcaacc cccaggtcac tgccaccttc acggtctctg    1800
ggggggactgc ccagttccag gccaaggagc tgcagccctt cccccttgggg agcaccgggg    1860
tcctcagtcc attcatcctg actctgcccc ctgaggaccg gctgcagacc tcactctgag    1920
tggcaggcag agaaccaaag tgcttcgct gtctccagga gacccctcc tgggatgggc    1980
ctgagaggcc ggggctcagg gaaggggctg ggatcgggaac ttcctgctct tgtttctgga    2040
caactttccc cttctgcttt aaaggttgtc gattattttg aaaaaaaaaa aaaaaaaaa    2099

SEQ ID NO: 19           moltype = AA   length = 1235
FEATURE                 Location/Qualifiers
source                  1..1235
                        mol_type = protein
                        organism = Homo sapiens
SEQUENCE: 19
MIQGTLEPDG PLWGWDWDSD NDWDSAVLAL LALAVVAATA LALHWFGSGH DQEAAEPVST    60
ALGAQPHQAG GAELALQPKS KVSDGSEGQS PGQGKPEPPG RGQQSPVPAA APGGGLAAMA   120
RLPLKTAVEE ARREALGQQR GSATPAAPRA EGKEPPRPGT ALLGRSEAGG MSAPLLIHFT   180
PRSPGSEAEA ETGGVRASSR QAAGPAGQQD TGPWQAGAGP SGSMGRGRGR RRRMDAGSGD   240
RARRPRKLDP LRLGAAGSVW DAVDGAAALD AHARGLPTGP PLAQEPALPA LPAPRALQPG   300
SQTEGSGAKG GWSREASGVP APGGGWPWVS REVPGTRSFG PAPDSTRPWL ESPPQGRPLS   360
SQGPGATGAY DAGEAGADSS RDNSPAADLG PTRPPEQAKP AAAGHSRAPS RSREPRPRSA   420
SPPAAPGPGF PPEALTLPSP SDFLPLEVTQ DPSVGENLRA APAPSSASAQ VLTSAPASVL   480
APALASSPSS APTSATTSTS SPTSAPAPAP TSAPTSTPAP APSPAAAATP APAPVPVPTL   540
TPPSPALTPV PTPALSPAPT PALTPAASPA LTPVPTPALS PAPTPAPTPA ASPAPAPTSA   600
PTPTPAASPA PADGSKPQES VALPRRYQEG QVSASWGNLI AMVLRSHPFP RQDRPQGSVP   660
RAVPGSPVGP STSTHSEDRH GPSSSVGTVI GTGTGGLVEA GGQPQPRSSE TNGSPSPDPP   720
PGLRGEGTRE KSLDPLPQAA MPRGPAQPPA QRPPGPAASS SARRSQPVPQ LRKRSRCEIA   780
PSSEQEVRPA ASGDPQGEAP GEGGSPAGRS GALTEKQEEA RKLMVFLQRP GGWGVVEGPR   840
KPSSRALEPA TAAALRRRLD LGSCLDVLAF AQQHGEPGLA QETYALMSDN LLRVLGDPCL   900
YRRLSAADRE RILSLRTGRG RAVLGVLVLP SLYQGGRSGL PRGPRGEEPP AAAPVSLPLP   960
AHLHVFNPRE NTWRPLTQVP EEAPLRGCGL CTMHNYLFLA GGIRGSGAKA VCSNEVFCYN  1020
PLTNIWSQVR PMQQARAQLK LVALDGLLYA IGGECLYSME CYDPRTDAWT PRAPLPAGTF  1080
PVAHEAVACR GDIYVTGGHL FYRLLRYSPV KDAWDECPYS ASHRRSSDIV ALGGFLYRFD  1140
LLRGVGAAVM RYNTVTGSWS RAASLPLPAP APLHCTTLGN TIYCLNPQVT ATFTVSGGTA  1200
QFQAKELQPF PLGSTGVLSP FILTLPPEDR LQTSL                            1235

SEQ ID NO: 20           moltype = AA   length = 594
FEATURE                 Location/Qualifiers
source                  1..594
                        mol_type = protein
                        organism = Homo sapiens
SEQUENCE: 20
MVLRSHPFPR QDRPQGSVPR AVPGSPVGPS TSTHSEDRHG PSSSVGTVIG TGTGGLVEAG    60
GQPQPRSSET NGSPSPDPPP GLRGEGTREK SLDPLPQAAM PRGPAQPPAQ RPPGPAASSS   120
ARRSQPVPQL RKRSRCEIAP SSEQEVRPAA SGDPQGEAPG EGGSPAGRSG ALTEKQEEAR   180
KLMVFLQRPG GWGVVEGPRK PSSRALEPAT AAALRRRLDL GSCLDVLAFA QQHGEPGLAQ   240
ETYALMSDNL LRVLGDPCLY RRLSAADRER ILSLRTGRGR AVLGVLVLPS LYQGGRSGLP   300
RGPRGEEPPA AAPVSLPLPA HLHVFNPREN TWRPLTQVPE EAPLRGCGLC TMHNYLFLAG   360
GIRGSGAKAV CSNEVFCYNP LTNIWSQVRP MQQARAQLKL VALDGLLYAI GGECLYSMEC   420
YDPRTDAWTP RAPLPAGTFP VAHEAVACRG DIYVTGGHLF YRLLRYSPVK DAWDECPYSA   480
SHRRSSDIVA LGGFLYRFDL LRGVGAAVMR YNTVTGSWSR AASLPLPAPA PLHCTTLGNT   540
IYCLNPQVTA TFTVSGGTAQ FQAKELQPFP LGSTGVLSPF ILTLPPEDRL QTSL         594

SEQ ID NO: 21           moltype = AA   length = 495
FEATURE                 Location/Qualifiers
source                  1..495
                        mol_type = protein
                        organism = Homo sapiens
SEQUENCE: 21
MPRGPAQPPA QRPPGPAASS SARRSQPVPQ LRKRSRCEIA PSSEQEVRPA ASGDPQGEAP    60
GEGGSPAGRS GALTEKQEEA RKLMVFLQRP GGWGVVEGPR KPSSRALEPA TAAALRRRLD   120
LGSCLDVLAF AQQHGEPGLA QETYALMSDN LLRVLGDPCL YRRLSAADRE RILSLRTGRG   180
```

```
RAVLGVLVLP SLYQGGRSGL PRGPRGEEPP AAAPVSLPLP AHLHVFNPRE NTWRPLTQVP      240
EEAPLRGCGL CTMHNYLFLA GGIRGSGAKA VCSNEVFCYN PLTNIWSQVR PMQQARAQLK      300
LVALDGLLYA IGGECLYSME CYDPRTDAWT PRAPLPAGTF PVAHEAVACR GDIYVTGGHL      360
FYRLLRYSPV KDAWDECPYS ASHRRSSDIV ALGGFLYRFD LLRGVGAAVM RYNTVTGSWS      420
RAASLPLPAP APLHCTTLGN TIYCLNPQVT ATFTVSGGTA QFQAKELQPF PLGSTGVLSP      480
FILTLPPEDR LQTSL                                                      495

SEQ ID NO: 22           moltype = AA  length = 1235
FEATURE                 Location/Qualifiers
source                  1..1235
                        mol_type = protein
                        organism = Homo sapiens
SEQUENCE: 22
MIQGTLEPDG PLWGWDWDSD NDWDSAVLAL LALAVVAATA LALHWFGSGH DQEAAEPVST      60
ALGAQPHQAG GAELALQPKS KVSDGSEGQS PGQQGKPEPPG RGQQSPVPAA APGGGLAAMA    120
RLPLKTAVEE ARREALGQQR GSATPAAPRA EGKEPPRPGT ALLGRSEAGG MSAPLLIHFT     180
PRSPGSEAEA ETGGVRASSR QAAGPAGQQD TGPWQAGAGP SGSMGRGRGR RRRMDAGSGD     240
RARRPRKLDP LRLGAAGSVW DAVDGAAALD AHARGLPTGP PLAQEPALPA LPAPRALQPG     300
SQTEGSGAKG GWSREASGVP APGGGWPWVS REVPGTRSFG PAPDSTRPWL ESPPQGRPLS     360
SQGPGATGAY DAGEAGADSS RDNSPAADLG PTRPPEQAKP AAAGHSRAPS RSREPRPRSA     420
SPPAAPGPGF PPEALTLPSP SDFLPLEVTQ DPSVGENLRA APAPSSASAQ VLTSAPASVL     480
APALASSPSS APTSATTSTS SPTSAPAPAP TSAPTSTPAP APSPAAAATP APAPVPVPTL     540
TPPSPALTPV PTPALSPAPT PALTPAASPA LTPVPTPALS PAPTPAPTPA ASPAPAPTSA     600
PTPTPAASPA PADGSKPQES VALPRRYQEG QVSASWGNLI AMVLRSHPFP RQDRPQGSVP     660
RAVPGSPVGP STSTHSEDRH GPSSSVGTVI GTGTGGLVEA GGQPQPRSSE TNGSPSPDPP     720
PGLRGEGTRE KSLDPLPQAA MPRGPAQPPA QRPPGPAASS SARRSQPVPQ LRKRSRCEIA     780
PSSEQEVRPA ASGDPQGEAP GEGGSPAGRS GALTEKQEEA RKLMVFLQRP GGWGVVEGPR     840
KPSSRALEPA TAAALRRRLD LGSCLDVLAF AQQHGEPGLA QETYALMSDN LLRVLGDPCL     900
YRRLSAADRE RILSLRTGRG RAVLGVLVLP SLYQGGRSGL PRGPRGEEPP AAAPVSLPLP     960
AHLHVFNPRE NTWRPLTQVP EEAPLRGCGL CTMHNYLFLA GGIRGSGAKA VCSNEVFCYN    1020
PLTNIWSQVR PMQQARAQLK LVALDGLLYA IGGECLYSME CYDPRTDAWT PRAPLPAGTF    1080
PVAHEAVACR GDIYVTGGHL FYRLLRYSPV KDAWDECPYS ASHRRSSDIV ALGGFLYRFD    1140
LLRGMGAAVM RYNTVTGSWS RAASLPLPAP APLHCTTLGN TIYCLNPQVT ATFTVSGGTA    1200
QFQAKELQPF PLGSTGVLSP FILTLPPEDR LQTSL                              1235

SEQ ID NO: 23           moltype = AA  length = 594
FEATURE                 Location/Qualifiers
source                  1..594
                        mol_type = protein
                        organism = Homo sapiens
SEQUENCE: 23
MVLRSHPFPR QDRPQGSVPR AVPGSPVGPS TSTHSEDRHG PSSSVGTVIG TGTGGLVEAG      60
GQPQPRSSET NGSPSPDPPP GLRGEGTREK SLDPLPQAAM PRGPAQPPAQ RPPGPAASSS    120
ARRSQPVPQL RKRSRCEIAP SSEQEVRPAA SGDPQGEAPG EGGSPAGRSG ALTEKQEEAR    180
KLMVFLQRPG GWGVVEGPRK PSSRALEPAT AAALRRRLDL GSCLDVLAFA QQHGEPGLAQ    240
ETYALMSDNL LRVLGDPCLY RRLSAADRER ILSLRTGRGR AVLGVLVLPS LYQGGRSGLP    300
RGPRGEEPPA AAPVSLPLPA HLHVFNPREN TWRPLTQVPE EAPLRGCGLC TMHNYLFLAG    360
GIRGSGAKAV CSNEVFCYNP LTNIWSQVRP MQQARAQLKL VALDGLLYAI GGECLYSMEC    420
YDPRTDAWTP RAPLPAGTFP VAHEAVACRG DIYVTGGHLF YRLLRYSPVK DAWDECPYSA    480
SHRRSSDIVA LGGFLYRFDL LRGMGAAVMR YNTVTGSWSR AASLPLPAPA PLHCTTLGNT    540
IYCLNPQVTA TFTVSGGTAQ FQAKELQPFP LGSTGVLSPF ILTLPPEDRL QTSL          594

SEQ ID NO: 24           moltype = AA  length = 495
FEATURE                 Location/Qualifiers
source                  1..495
                        mol_type = protein
                        organism = Homo sapiens
SEQUENCE: 24
MPRGPAQPPA QRPPGPAASS SARRSQPVPQ LRKRSRCEIA PSSEQEVRPA ASGDPQGEAP      60
GEGGSPAGRS GALTEKQEEA RKLMVFLQRP GGWGVVEGPR KPSSRALEPA TAAALRRRLD    120
LGSCLDVLAF AQQHGEPGLA QETYALMSDN LLRVLGDPCL YRRLSAADRE RILSLRTGRG    180
RAVLGVLVLP SLYQGGRSGL PRGPRGEEPP AAAPVSLPLP AHLHVFNPRE NTWRPLTQVP    240
EEAPLRGCGL CTMHNYLFLA GGIRGSGAKA VCSNEVFCYN PLTNIWSQVR PMQQARAQLK    300
LVALDGLLYA IGGECLYSME CYDPRTDAWT PRAPLPAGTF PVAHEAVACR GDIYVTGGHL    360
FYRLLRYSPV KDAWDECPYS ASHRRSSDIV ALGGFLYRFD LLRGMGAAVM RYNTVTGSWS    420
RAASLPLPAP APLHCTTLGN TIYCLNPQVT ATFTVSGGTA QFQAKELQPF PLGSTGVLSP    480
FILTLPPEDR LQTSL                                                    495

SEQ ID NO: 25           moltype = DNA  length = 5124
FEATURE                 Location/Qualifiers
source                  1..5124
                        mol_type = genomic DNA
                        organism = Homo sapiens
SEQUENCE: 25
agaagcaggt tggctgtgat gacagcacag agctcaggaa cgctgcctga ggaccctggg      60
gcctacgagg aggagaagag ggcaggagct ggtggggtgc ttgcagagac cctgggctcc     120
tatcctgcca taagcctcgc tgtctcctga tatctgcagc caggcccttac tgacaccccc     180
aggcctgagt gcaagcagag accccaccat tcccaggccc tggaggactg tccaccttta     240
actgggcagc ccttggggca ggcgctggcc ggtgcctcag cccaggcctc tgtgctctgc     300
```

-continued

```
atgcactgcc agcctgccat caggcctcta ttgcagccct gaaccatgat ccagggcacc    360
ttggagccag atggtcccct ctggggctgg gactgggaca gtgacaatga ctgggatagt    420
gctgtgctgg ccctcctggc gctggctgtg gtggctgcca cagcgctggc cttacactgg    480
tttggctccg ggcacgatca agaggcggca gaaccggtgt ccacagccct cggggctcaa    540
cctcatcagg caggaggagc tgagctggcc ctgcaaccga agtctaaggt cagtgatggc    600
agcgagggc agagcccagg gcaggggaaa ccagagcccc caggacgcgg ccagcagagc    660
cctgtccctg ctgcagcgcc gggcggggc ctggccgcca tggcccggct tccactcaag    720
acggctgtcg aggaggcccg cagagaggca ttaggacagc aacggggcag tgccacccc    780
gcggccccc gagcggaagg aaaggagcct cccaggccag gcactgccct cctgggcagg    840
agcgaagcag gggggatgtc cgcccccctc ctgatccact tcactcctcg gagccctggc    900
agcgaagcgg aggcggagac aggtggtgtc agggcgtcct ctcgccaggc cgcaggcccc    960
gcggggcaac aggacactgg ccctggcag gcgggcgcgg ggcctcggg ctcgatgggg   1020
agaggccggg gccggcggcg gcggatggac gctggctcgg gagacagagc ccgccgcccc   1080
cggaaactgg acccgctccg cctgggcgcc gcggggagcg tgtgggacgc ggtggacggg   1140
gccgccgccc tggacgccca cgcgcgcggc ctccccacag gacccccact cgcccaggag   1200
cccgcactcc cggcgctgcc cgctccccgc gccctgcagc ctgggtctca gacgaaggc   1260
tctgggggcca agggtggctg gagcaggag gcctcgggg tccctgcccc cggaggaggc   1320
tggccctggg tcagcaggga ggtcccgggc acccggagct ttggcccagc cccagactcc   1380
acgcgcccct ggctagagag tccgcctcaa ggtcgcccac tctcgtccca agggccgggt   1440
gccacagggg cctacgatgc cggcgaggcc gggctgaca gctcccgaga taacagtcct   1500
gccgctgacc tggggcccac ccggccccg gagcaagcaa agccggctgc agccggccac   1560
agccgcgccc cctcccggag ccgtgagcct cgcccgcgct cgcctcccc gcccgcagct   1620
cccggcccgg ggttcccacc tgaagccctg actctcccct ctccttcaga ctttttgccc   1680
ctggaggtta cccaggatcc ttccgtgggc gaaaatctca gagcggcgcc agccccaagt   1740
tcagcctcag cccaagtctt aacttcagct ccagcctcag tcctagcccc agccctggct   1800
tcatccccca gctcagcacc aacctcagcc accacctcaa cctcatcccc cacctcagcc   1860
ccagccccag ctccaacctc agctccaact tcaaccccaa cccagccccc aagtccagct   1920
gcagccgcaa ctccagcccc agcccagtc cagtcccaa ccctcacacc cccatccca   1980
gccctaaccc cagtcccaac cccagcccta agcccagctc caactccagc cctaacccca   2040
gccgcatccc cagcccctaac cccagtccca accccagccc taagcccagc tccaactcca   2100
gcccaaccc cagccgcatc ccctgcccca gcccccacct cagccccaac cccaacccca   2160
gccgcatccc ctgcccage tgacgggtca aagcctcagg agagtgtggc tctcccagg   2220
cgctaccagg aggggcaggt tcagccagc tgggaaaacc ttattgccat ggttcttaga   2280
agccaccct tccccaggca agacaggccc caagggagtg tcccgagggc ggttcccggg   2340
agccccgtgg gtccagcac ttccacacac tctgaggaca gacacggccc ctcttcttca   2400
gtggggacag tcatagggac aggtacaggg ggcctggttg aggctggagg tcagccacag   2460
ccaagaagct ccgagaccaa cggatcgccc agcccagacc ctcccccagg cctaagagga   2520
gagggaacca gggagaaaag tctagacccg ctgcccaag ccgcgatgcc caggggcccc   2580
gcacagcccc ccgcgcagag gccgcctggc ccgcggcct cctcctctgc gaggcgctca   2640
cagccggtac cccagctacg gaaacgcagc aggtgcgaaa tcgccccgag ctcggagcag   2700
gaggtcaggc cggccgcctc gggggaccct caagggggag cgccgggga gggggcagc   2760
cctgccggcc gcagcgggc gctcacgaaa aagcaggagg aggcccgaag ctcatggtgt   2820
ttctgcagag gcccgggggt tgggggtgg tggagggcc ccggaagccc agctcccggg   2880
ccctggagcc cgccacgcg gcagcctgc ggcggcggct ggacctgggc agttgcctgg   2940
acgtgctggc ctttgcccag cagcacggag agccggcct ggcgcaggag acctacgcgc   3000
tgatgagcga caacctgctg cgagtgctgg agacccgtg cctctaccgc cggctgagcg   3060
cggccgaccg cgagcgcatc ctcagcctgc ggaccggcg gggccgggag gtgctgggcg   3120
tcctcgtact gcccagcctc taccaggggg gccgctcagg gctccccagg ggccctcgtg   3180
gcgaggagcc tcctgcgggcg gcccctgtgt ccctgcctct acctgcgcac ctgcatgtgt   3240
tcaacccccg ggagaacacc tggcggcccc tgacccaggt gcccgaggag gccccgcttc   3300
gggctgcgg tctctgcacc atgcacaact acctgttttct ggcgggggc atccgtgctt   3360
ccggtgccaa ggccgtctgc tccaacgagg tcttctgcta caaccctctg accaacatct   3420
ggagccaggt tcgcccatg cagcaggccc gagccagct caagctggtg gccctggacg   3480
ggctgctcta tgccatcggt ggcgaatgcc tgtacagcat ggagtgctac gacccgcgaa   3540
cagacgccctg gaccccacgc gcgccactcc ccgcaggcac cttccctgtg gcccacgagg   3600
ctgtggcctg ccgtggggac atctacgtca ccgggggtca cctcttctac cgcctgctca   3660
ggtacagccc cgtgaaggat gcttgggacg agtgcccata cagtgccagc caccggcgtt   3720
ccagcgacat cgtggcactg ggggctcc tgtaccgctt cgacctgctg cggggcgtgg   3780
gcgccgccgt gatgcgctac aacacagtga ccggctcctg gagcagggct gcctccctgc   3840
ccctgcccgc ccccgcccca ctgcctgca ccaccctgca caacaccatt tactgcctca   3900
accccaggt cactgccacc ttcacggtct ctgggggac tgcccagttc caggccaagg   3960
agctgcagcc cttcccttg gggagcaccg gggtcctcag tccattcatc ctgactctgc   4020
cccctgagga ccggctgcag acctcactct gagtggcagg cagagaacca aagctgcttc   4080
gctgctctcc agggagaccc tcctgggatg ggcctgagag gccgggctc agggaagggg   4140
ctgggatcgg aacttcctgc tcttgtttct ggacaacttt ccccttctgc tttaaaggtt   4200
gtcgattatt ttgaagccca gactccctca gcctctttct gccctcact ccacacccag   4260
actgtttcct gactcaattc cgtacctact tacagaccct ctcagcttgc tgacaccccc   4320
ctgtctgtgg gactccctat tccctagagc cagggactga tgcgtctcca cagacaagga   4380
cttggctcgc tggagctctg ctgagccgag agaggagggg gtagaaaaca ttcacacttc   4440
ctatgctctg tcagcaggac agggagcaaa aacgtcccca ggcaacgccc tcgcctctgg   4500
gactttctgc ctgtcctaag gcctcccag gtaccaaccc cgtagctatc tgggtctgtt   4560
tggcactgtg gattctcaag ggcctagaac ccttgcctct gaaactggtc cgctggtgca   4620
gccctgctgt ctgcagctcc tgcccatacc cccagccac accaggccag cccactccg   4680
ggctcaccac cctctgcagc cttgtgggc tctcccagcc cctccagaag cccaccccaa   4740
ttctcgccaa cccccgatct ctaaatgagg cctgagcgtc accctagttc tgccccttt   4800
tagctgtgta gacttggacg agacatttga cttccctttc tccttgtcta taaaatgtgg   4860
acagtggacg tctgtcaccc aagagagttg tgggagacaa gatcacagct atgagccct   4920
cgcacggtgt ccaggatgca cagcacaatc catgatgcgt tttctccct tacgcacttt   4980
gaaacccatg ctagaaaagt gaatacatct gactgtgctc cactccaacc tccagcctgg   5040
```

```
atgtccctgt ctgggccctt tttctgtttt ttattctatg ttcagcacca ctggcaccaa    5100
atacatttta attcaccgaa agca                                           5124

SEQ ID NO: 26           moltype = DNA  length = 5124
FEATURE                 Location/Qualifiers
source                  1..5124
                        mol_type = genomic DNA
                        organism = Homo sapiens
SEQUENCE: 26
agaagcaggt tggctgtgat gacagcacag agctcaggaa cgctgcctga ggaccctggg     60
gcctacgagg aggagaagag ggcaggagct ggtggggtgc ttgcagagac cctgggctcc    120
tatcctgcca taagcctcgc tgtctcctga tatctgcagc caggccctac tgacacccca    180
aggcctgagt gcaagcagag accccaccat tcccaggccc tggaggactg gtccaccttg    240
actgggcagc ccttggggca ggcgctggcc ggtgcctcag cccaggcctc tgtgctctgc    300
atgcactgcc agcctgccat caggcctcta ttgcagccct gaaccatgat ccagggcacc    360
ttggagccag atggtcccct ctggggctgg gactgggaca gtgacaatga ctgggatagt    420
gctgtgctgc ccctcctggc gctggctgtg gtggctgcca cagcgctggc cttacactgg    480
tttggctccg ggcacgatca agaggcggca gaaccggtgt ccacagccct cggggctcaa    540
cctcatcagg caggaggagc tgagctggcc ctgcaaccga agtctaaggt cagtgatggc    600
agcgagggge agagcccagg gcaggggaaa ccagagcccc caggacgcgg ccagcagagc    660
cctgtccctg ctgcagcgcc gggcggggc ctggccgcca tgcccggct tccactcaag     720
acggctgtcg aggaggcccg cagagaggca ttaggacagc aactgccacc tgccaccccc    780
gcggcccccc gagcggaagg aaaggagcct cccaggccag gcactgccct cctgggcagg    840
agcgaagcag gggggatgtc cgcccccctc ctgatccact tcactcctcg gagccctggc    900
agcgaagcgg aggcggagac aggtggtgtc agggcgtcct ctcgccaggc cgcaggcccc    960
gcggggcaac aggacactgg cccctggcag gcgggggcgg ggccctcggg ctcgatgggg   1020
agaggccggg gccggcggcg gcggatggac gctggctcgg gagacagagc ccgccgcccc   1080
cggaaactgg acccgctccg cctgggcgcc cggggagcg tgtgggacgc ggtggacggg    1140
gccgccgccc tggacgccca cgcgcgcggc ctccccacag accccccact cgcccaggag   1200
cccgcactcc cggcgctgcc cgctccccgc gccctgcagc ctgggtctca gacggaaggc   1260
tctgggccca agggtggctg gagcaggag gcctcgggg tccctgcccc cggaggaggc    1320
tggccctggg tcagcaggga ggtcccgggc accggagct ttggcccagc ccagactcc     1380
acgcgccct ggctagagag tccgcctcaa ggtcgcccac tctcgtccca agggccgggt   1440
gccacagggg cctacgatgc cggcgaggcc ggggctgaca gctcccgaga taacagtcct   1500
gccgctgacc tggggcccac ccggccccg gagcaagcaa agccggctgc agccggccac    1560
agccgcgcgc cctccggag ccgtgagcct cgcccgcgct ccgcctcccc gcccgcagct    1620
cccgccccgg ggttcccacc tgaagccctg actctcccct ctccttcaga ctttttgccc   1680
ctggaggtta cccaggatcc ttccgtgggc gaaaatctca gagcggcgcc agcccaagt    1740
tcagcctcag cccaagtctt aacttcagct ccagcctcag tcctagccca agccctgct    1800
tcatccccca gctcagcacc aacctcagcc accacctcaa cctcatcccc cacctcagcc   1860
ccagcccag ctcaacctc agctccaact caaccccag cccagccc aagtccagct      1920
gcagccgcaa ctccagcccc agcccagtc ccagtcccaa ccctcacacc cccatccca     1980
gccctaaccc cagtcccaac cccagcccta agcccagcc cctaaccca                2040
gccgcatccc cagccctaac cccagtccca accccagccc taagcccagc tccaactcca   2100
gccccaaccc cagccgcatc ccctgcccca gcccccacct cagcccaac cccaacccca    2160
gccgcatccc ctgcccagc tgacgggtca agcctcagg agagtgtggc tctcccagg     2220
cgctaccagg aggggcaggt ctcagccagc tggggaaacc ttattgccat ggttcttaga   2280
agccaccct tccccaggca agacaggcc caagggagtg tcccgaggge ggttcccggg    2340
agccccgtgg gtcccagcac ttccacacac tctgaggaca gacacggccc ctcttcttca   2400
gtggggacag tcatagggac aggtacaggg ggcctggttg aggctggagg tcagccacag   2460
ccaagaagct ccgagaccaa cggatcgccc agcccagcc ctcccccagg cctaagagga    2520
gagggaacca gggagaaaag tctagacccg ctgcccaag ccgcgatgcc caggggcccc    2580
gcacagcccc ccgcgcagag gccgcctggc ccgcggcct cctcctgc gaggcgctca     2640
cagccggtac cccagctacg gaaacgcagc aggtgcgaaa tcgcccccgag ctcggagcag   2700
gaggtcaggc cggccgcctc gggggaccct caaggggagg cgccgggga ggggggcagc    2760
cctgccggcc gcagcggggc gctcacggaa aagcaggagg aggcccggaa gctcatggtg   2820
tttctgcaga ggcccggggg ttgggggggtg tgagggggc ccggaagcc cagctcccgg    2880
gccctggagc ccgccacggc ggcagccctg cggcggcggc tggacctggg cagttgcctg   2940
gacgtgctgg cctttgccca gcagcacgga gagcccggcc tggcgcagga gacctacgcg   3000
ctgatgagcg acaaacctgct gcgagtgctg ggagaccgt gcctctaccg ccggctgagc    3060
gcggccgacc gcgagcgcat cctcagcctg cggaccggcc ggggccgggc ggtgctgggc   3120
gtcctcgtac tgcccagcct ctaccagggg ggccgctcag ggctcccag ggccctcgtg    3180
gcgaggagcc tcctgcggcg gccctgtgt ccctgcctct acctgcgcac ctgcatgtgt    3240
tcaaccccg ggagaacacc tggcggcccc tgacccaggg agcccgcttc                3300
ggggctgcgg tctctgcacc atgcacaact acctgtttct ggcggggggc atccgtggct   3360
ccggtgccaa ggccgtctgc tccaacgagg tcttctgcta caaccctctg accaacatct   3420
ggagccaggt tcgcccatg cagcaggccc gagcccagct caagctggtg gccctggacg    3480
ggctgctcta tgccatcgtt ggcgaatgcc tgtacagcat ggagtgctac gaccgcgaa    3540
cagacgccgt gaccccacgc gcgccactcc cgcaggcc cttccctgtg gcccacgagg    3600
ctgtggcctg ccgtggggac atctacgtca ccggggtca cctcttctac cgcctgctca   3660
ggtacagccc cgtgaaggat gcttgggacg agtgccata cagtgccagc caccggcgtt    3720
ccagcgacat cgtggcactg gggggcttcc tgtaccgctt cgacctgctg cggggcgtgg   3780
gcgccgccgt gatgcgctac aacacagtga ccggctcctg gagcagggct gcctccctgc   3840
ccctgccccc cgcccccca ctgcactgca ccaaccatt tactgcctca                3900
accccaggt cactgccacc ttcacggtct ctgggggac tgcccagttc caggccaagg     3960
agctgcagcc cttcccctg gggagcaccg ggtcctcag tccattcatc ctgactctgc    4020
cccctgagga ccggctgcag acctcactct gagtggcagg cagagaacca aagctgcttc   4080
gctgctctcc agggagaccc tcctgggatg ggcctgagag gccggggctc agggaagggg   4140
ctgggatcgg aacttcctgc tcttgtttct ggacaacttg cccccttctgc tttaaaggtt   4200
```

```
gtcgattatt ttgaagccca gactccctca gcctctttct gccccctcact ccacacccag    4260
actgtttcct gactcaattc cgtacctact tacagaccct ctcagcttgc tgacaccccc    4320
ctgtctgtgg gactccctat tccctagagc cagggactga tgcgtctcca cagacaagga    4380
cttggctcgc tggagctctg ctgagccgag agaggagggg gtagaaaaca ttcacacttc    4440
ctatgctctg tcagcaggac agggagcaaa aacgtcccca ggcaacgcgt ctgcctctgg    4500
gactttctgc ctgtcctaag gcctcccag gtaccaaccc cgtagctatc tgggtctgtt    4560
tggcactgtg gattctcaag ggcctagaac ccttgcctct gaaactggtc cgctggtgca    4620
gccctgctgt ctgcagctcc tgcccatacc cccagcccac accaggccag cccactccg    4680
ggctcaccac cctctgcagc cttgtggggc tctcccagcc cctccagaag cccaccccac    4740
ttctcgccaa cccccgatct ctaaatgagg cctgagcgtc accctagttc tgcccctttt    4800
tagctgtgta gacttggacg agacatttga cttccctttc tccttgtcta taaaatgtgg    4860
acagtggacg tctgtcaccc aagagagttg tgggagacaa gatcacagct atgagcacct    4920
cgcacggtgt ccaggatgca cagcacaatc catgatgcgt tttctcccct tacgcacttt    4980
gaaacccatg ctagaaaagt gaatacatct gactgtgctc cactccaacc tccagcctgg    5040
atgtccctgt ctgggccctt tttctgtttt ttattctatg ttcagcacca ctggcaccaa    5100
atacattta attcaccgaa agca                                             5124

SEQ ID NO: 27        moltype = RNA   length = 5124
FEATURE              Location/Qualifiers
source               1..5124
                     mol_type = mRNA
                     organism = Homo sapiens
SEQUENCE: 27
agaagcaggt tggctgtgat gacagcacag agctcaggaa cgctgcctga ggaccctggg     60
gcctacgagg aggagaagag ggcaggagct ggtggggtgc ttgcagagac cctgggctcc    120
tatcctgcca taagcctcgc tgtctcctga tatctgcagg cagccctac tgacaccccc    180
aggcctgagt gcaagcagag accccaccat tccagggcc tggaggactg gtccacctta    240
actgggcagc ccttggggca ggcgctggcc ggtgcctcag cccaggcctc tgtgctctgc    300
atgcactgcc agcctgccat caggcctcta ttgcagccct gaaccatgat ccagggcacc    360
ttggagccag atggtcccct ctgggggctg gactgggaca gtgacaatga ctgggatagt    420
gctgtgctgg ccctcctggc gctggctgtg gtggctgcca cagcgctggc cttacactgg    480
tttggctccg ggcacgatca agaggcggca gaaccggtgt ccacagccct cggggctcaa    540
cctcatcagg caggaggagc tgagctgcc ctgcaaccga agtctaaggt cagtgatggc    600
agcgagggc agagcccagg gcaggggaaa ccagagcccc caggacgcgg cagcagagc    660
cctgtccctg ctgcagcgcc gggcggggc ctggccgcca tggcccggct tccactcaag    720
acggctgtcg aggaggcccg cagagaggca ttaggacagc aacggggcag tgccaccccc    780
gcggcccccc gagcggaagg aaaggagcct cccaggccag gcactgccct cctgggcagg    840
agcgaagcag ggggggatgtc cgccccctc ctgatccact tcactcctcg gagccctggc    900
agcgagggca aggcggagac aggtggtgtc agggcgtcct ctcgccaggc cgcaggcccc    960
gcggggcaac aggacactgg cccctggcag gcgggcgcgg ggcctcgggg ctcgatgggg    1020
agaggccggg gccggcggcg gcggatggac gctggctcgg gagacagagc ccgccgcccc    1080
cggaaactgg acccgctccg cctgggcgcc gcgggagcg tgtgggacgc ggtggacggg    1140
gccgcgcgcc tggacgccca cgcgcgcggc ctcccccagg gaccccccact cgcccaggag    1200
cccgcactcc cggcgctgcc cgctcccccgc gccctgcagc ctgggtctca gacggaaggc    1260
tctggggcca agggtggctg gagcagggag gcctcggggg tccctgcccc cggaggaggc    1320
tggccctggg tcagcaggga ggtcccgggc accggagct ttggcccagc ccagactcc    1380
acgcgccct ggctagagag tccgcctcaa ggtcgcccac tctcgtccca agggccgggt    1440
gccacagggg cctacgatgc cggcgaggcc ggggctgaca gctcccgaga taacagtcct    1500
gccgctgacc tggggcccac ccggcccccg gagcaagcaa agccggctgc agccggccac    1560
agccgcgcgc cctccggag ccgtgagcct cgcccgcgct ccgcctcccc gcccgcagct    1620
cccggcccgg ggttcccacc tgaagcctg actctccct ctccttcaga cttttttgccc    1680
ctggaggtta cccaggatcc ttccgtgggc gaaaatctca gagcggcgcc agccccaagt    1740
tcagcctcag cccaagtctt aacttcagct ccagctcag tcctagcccc agccctggct    1800
tcatccccca gctcagcacc aacctcagcc accacctcaa cctcatcccc cacctcagcc    1860
ccagcccag ctccaacctc agctccaact tcaaccccag ccccagcccc aagtccagct    1920
gcagccgcaa ctccagcccc agcccagtc ccagtcccaa ccctcacacc ccatccccca    1980
gccctaaccc cagtcccaac cccagcccta agccagctc caactccagc cctaaccca    2040
gccgcatccc cagccctaac cccagtccca accccagccc taagcccagc tccaactcca    2100
gcccccaacc cagcccatc ccctgcccca gccccaccct cagcccccaa accccaacccca    2160
gccgcatccc ctgcccagc tgacgggtca aagcctcagg agagtgtggc tctcccagg    2220
cgctaccagg aggggcaggt ctcagccagc tggggaaacc ttattgccat ggttcttaga    2280
agccaccct tccccaggca agacaggccc caagggagtg tcccgagggc ggttcccggg    2340
agcccccgtgg gtcccagcac ttccacacac tctgaggaca gacacggccc ctcttcttca    2400
gtggggacag tcatagggac aggtacaggg ggctggttg gcctggaggg tcagccacag    2460
ccaagaagct ccgagaccaa cggatcgccc agcccagacc ctcccccagg cctaagagga    2520
gagggaacca gggagaaag tctagacccg ctgcccaag ccgcgatgcc caggggcccc    2580
gcacagcccc ccgcgcagag gccgcctggc cccgcggcct cctcctctgc gaggcgctca    2640
cagccggtac cccagctacg gaaacgcagc aggtgcgaaa tcgcccgag ctcggagcag    2700
gaggtcaggc cggccgcctc gggggaccct caaggggagg cgccggggga ggggggcagc    2760
cctgccggcc gcagcggggc gctcacgaaa aagcaggagg aggccgaag ctcatggtgt    2820
ttctgcagag gccggggggt tgggggggtgg tgagggggcc ccgaagcccc agctcccggg    2880
ccctggagcc cgcacggcg gcagccctgc ggcggcggct ggacctgggc agttgcctgg    2940
acgtgctggc ctttgcccag cagcacgag agccccgcct ggcgcaggag acctacgcgc    3000
tgatgagcga caactgctg cgagtgctg gagaccgtg cctctaccgg cggctgagcg    3060
cggccgaccg cgagcgcatc ctcagcctgc ggacccgcc gggccgggcg gtgctgggcg    3120
tcctcgtact gcccagctc taccagggg gcgctcagg gctcccagg ggccctcgtg    3180
gcgaggagc tcctgcggcg gccctgtgt ccctgcctct acctgcgcac ctgcatgtgt    3240
tcaaccccg ggagaacac tggcggcccc tgacccaggt gcccgaggag gccccgcttc    3300
ggggctgcgg tctctgcacc atgcacaact acctgttctct ggcgggggc atccgtggct    3360
```

-continued

```
ccggtgccaa ggccgtctgc tccaacgagg tcttctgcta caaccctctg accaacatct   3420
ggagccaggt tcggcccatg cagcaggccc gagcccagct caagctggtg gccctggacg   3480
ggctgctcta tgccatcggt ggcgaatgcc tgtacagcat ggagtgctac gacccgcgaa   3540
cagacgcctg gaccccacgc gcgccactcc ccgcaggcac cttccctgtg gcccacgagg   3600
ctgtgccctg ccgtggggac atctacgtca ccggggggtca cctcttctac cgcctgctca   3660
ggtacagccc cgtgaaggat gcttgggacg agtgcccata cagtgccagc caccggcgtt   3720
ccagcgacat cgtggcactg gggggcttcc tgtaccgctt cgacctgctg cggggcgtgg   3780
gcgccgccgt gatgcgctac aacacagtga ccggctcctg gagcagggct gcctccctgc   3840
ccctgcccgc ccccgcccca ctgcactgca ccacccctggg caacaccatt tactgcctca   3900
accccaggt cactgccacc ttcacggtct ctgggggggac tgcccagttc caggccaagg   3960
agctgcagcc cttcccttg gggagcaccg gggtcctcag tccattcatc ctgactctgc   4020
cccctgagga ccggctgcag acctcactct gagtggcagg cagagaacca aagctgcttc   4080
gctgctctcc agggagaccc tcctgggatg ggcctgagag gccggggctc agggaagggg   4140
ctgggatcgg aacttcctgc tcttgttttct ggacaacttc ccccttctgc tttaaaggtt   4200
gtcgattatt ttgaagcccca gactccctca gcctcttttct gccctcact ccacacccag   4260
actgttttcct gactcaattc cgtacctact tacagaccct ctcagcttgc tgacaccccc   4320
ctgtctgtgg gactccctat tccctagagc cagggactga tgcgtctcca cagacaagga   4380
cttggctcgc tggagctctg ctgagccgag agaggagggg gtagaaaaca ttcacacttc   4440
ctatgctctg tcagcaggac agggagcaaa aacgtcccca ggcaacgccc tcgcctctgg   4500
gactttctgc ctgtcctaag gcctcccccag gtaccaaccc cgtagctatc tgggtctgtt   4560
tggcactgtg gattctcaag ggcctagaac ccttgcctct gaaactggtc cgctggtgca   4620
gccctgctgt ctgcagctcc tgcccatacc cccagccacc accaggccag cgcccactccg   4680
ggctcaccac cctctgcagc cttgtgggggc tctcccagcc cctccagaag cccaccccac   4740
ttctcgccaa ccccccgatct ctaaatgagg cctgagcgtc accctagttc tgccccttttt   4800
tagctgtgta gacttggacg agacatttga cttccctttc tccttgtcta taaatgtggg   4860
acagtggacg tctgtcaccc aagagagttg tgggagacaa gatcacagct atgagccacct   4920
cgcacggtgt ccaggatgca cagcacaatc catgatgcgt tttctcccct tacgcacttt   4980
gaaacccatg ctagaaaagt gaatacatct gactgtgctc cactccaacc tccagcctgg   5040
atgtccctgt ctgggccctt tttctgttttt ttattctatg ttcagcacca ctggcaccaa   5100
atacatttta attcaccgaa agca                                         5124
```

```
SEQ ID NO: 28           moltype = RNA  length = 2989
FEATURE                 Location/Qualifiers
source                  1..2989
                        mol_type = mRNA
                        organism = Homo sapiens
SEQUENCE: 28
ccacctcagc cccaacccca accccagccg catcccctgc cccagctgac gggtcaaagc     60
ctcaggagag tgtggctctc cccaggcgct accaggaggg gcaggtctca gccagctggg   120
gaaaccttat tgccatggtt cttagaagcc accccttccc caggcaagac aggccccaag   180
ggagtgtccc gagggcggtt ccccggagcc ccgtgggtcc cagcacttcc acacactctg   240
aggacagaca cggcccctct tcttcagtgg ggacagtcat agggacaggt acaggggcc   300
tggttgaggc tggaggtcag ccacagccaa gaagctccga gccaacggaa tcgcccagcc   360
cagaccctcc cccaggccta agaggagagg gaaccaggga gaaaagtcta gaccccgctgc   420
cccaagccgc gatgcccagg ggccccgcac agccccccgc gcagaggccg cctgcccccg   480
cggcctcctc ctctgcgagg cgctcacagc cggtacccca gctacggaaa cgcagcaggt   540
gcgaaatcgc cccgagctcg gagcaggagg tcaggccggg gcctcggggg gaccctcaag   600
gggaggcgcc ggggggagggg ggcagccctg ccggccgcag cggggcgctc acggaaaagc   660
aggaggaggc ccgaagctca tggtgttttct gcagaggccc gggggttggg gggtggtgga   720
ggggccccgg aagcccagct cccgggccct ggagcccgcc acggcggcag ccctgcggcg   780
gcggctggac ctgggcagtt gcctggacgt gctggccttt gccagcagc acggagagcc   840
cggcctggcg caggagacct acgcgctgat gagcgacaac ctgctgcgag tgctgggaga   900
cccgtgcctc taccgccggc tgagcgcggc cgaccgcgag cgcatcctca gcctgcggac   960
cggccggggc cgggcggtgc tgggcgtcct cgtactgccc agcctctacc aggggggccg  1020
ctcagggctc cccaggggcc ctcgtggcga ggagcctcgc gggcggccgc ctgtgtccct  1080
gcctctacct gcgcacctgc atgtgttcaa ccccccgggag aacacctggc ggcccctgac  1140
ccaggtgccc gaggaggccc cgcttcgggg ctgcggtctc tgcaccatgc acaactacct  1200
gtttctggcg gggggcatcc gtggctccgg tgccaaggcc gtctgctcca acgaggtctt  1260
ctgctacaac cctctgacca acatctggag ccaggttcgg ccatgcagc aggcccgagc  1320
ccagctcaag ctggtggccc tggacgggct ctatgccatc ggcggcg aatgcctgta  1380
cagcatggag tgctacgacc cgcgaacaga cgcctggacc ccacgcgcgc cactcccccgc  1440
aggcaccttc cctgtggccc acgaggctgt ggcctgccgt ggggacatct acgtcaccgg  1500
gggtcacctc ttctaccgcc tgctcaggta cagccccgtg aaggatgctt gggacgagtg  1560
cccatacagt gccagccacc ggcgttccag cgacatcgtg gcactgggggg gcttcctgta  1620
ccgcttcgac ctgctgcggg gcgtgggcgc cgcgtgatg cgctacaaca cagtgaccgg  1680
ctcctggagc agggctgcct ccctgccccct gcccgccccc gccccactgc actgcaccac  1740
cctgggcaac accatttact gcctcaaccc ccaggtcact gccaccttca cggtctctgg  1800
ggggactgcc cagttccagg ccaaggagct gcagcccttc ccctggggga gcaccgggt  1860
cctcagtcca ttcatctga ctctgccccc tgaggaccgg ctgcagacct cactctgagt  1920
ggcaggcaga gaaccaaagc tgcttcgctg ctctccaggg agaccctcct gggatgggcc  1980
tgagaggccg ggctcaggg aaggggctgg gatcggaact tcctgctctt gtttctggac  2040
aactttcccc ttctgcttta aaggttgtcg attattttga agcccagact ccctcagcct  2100
ctttctgccc ctcactccac acccagctg tttcctgact caattccgta cctacttaca  2160
gaccctctca gcttgctgac acccccctgt ctgtgggact ccctattccc tagagccaga  2220
gactgatgcg tctccacaga caaggacttg gctcgctgga gctctgctga gccgagagag  2280
gagggggtag aaaacattca cacttcctat gctctgtcag caggacaggg agcaaaaacg  2340
tccccaggca acgccctcgc ctctgggact ttctgcctgt cctaaggcct cccaggtac  2400
caaccccgta gctatctggg tctgtttggc actgtgatt ctcaagggcc tagaacccctt  2460
gcctctgaaa ctggtccgct ggtgcagccc tgctgtctgc agctcctgcc catacccca  2520
```

-continued

```
gcccacacca ggccaggccc actccgggct caccaccctc tgcagccttg tggggctctc    2580
ccagcccctc cagaagccca ccccacttct cgccaacccc cgatctctaa atgaggcctg    2640
agcgtcaccc tagttctgcc ccttttagc tgtgtagact tggacgagac atttgacttc     2700
cctttctcct tgtctataaa atgtggacag tggacgtctg tcacccaaga gagttgtggg    2760
agacaagatc acagctatga gcacctcgca cggtgtccac gatgcacagc acaatccatg    2820
atgcgttttc tccccttacg cactttgaaa cccatgctag aaaagtgaat acatctgact    2880
gtgctccact ccaacctcca gcctggatgt ccctgtctgg gcccttttc tgttttttat     2940
tctatgttca gcaccactgg caccaaatac attttaattc accgaaagc               2989
```

```
SEQ ID NO: 29           moltype = RNA   length = 4836
FEATURE                 Location/Qualifiers
source                  1..4836
                        mol_type = mRNA
                        organism = Homo sapiens
SEQUENCE: 29
actgccagcc tgccatcagg cctctattgc agccctgaac catgatccag ggcaccttgg    60
agccagatgg tccctctgg ggctgggact gggacagtga caatgactgg gatagtgctg     120
tgctggccct cctggcgctg gctgtggtgg ctgccacagc gctggcctta cactggtttg    180
gctccgggca cgatcaagag gcggcagaac cggtgtccac agccctcggg gctcaacctc    240
atcaggcagg aggagctgag ctggccctgc aaccgaagtc taaggtcagt gatggcagcg    300
aggggcagag cccagggcag gggaaaccag agccccagg acgcggccag cagagccctg     360
tccctgctgc agcgccgggc ggggggcctg ccgccatgcc ccggcttcca ctcaagacgg    420
ctgtcgagga ggcccgcaga gaggcattag gacagcaacg gggcagtgcc accccgcgg    480
ccccccgagc ggaaggaaag gagcctccca ggccaggcac tgccctcctg ggcaggagcg    540
aagcagggg gatgtccgcc cccctcctga tccacttcac tcctcggagc cctggcagcg    600
aagcggggca ggagacaggt ggtgtcaggg cgtcctctcg ccaggccgca ggcccgcggg    660
ggcaacagga cactgccccc tggcaggcgg gcgcggggcc ctcgggctcg atggggagag    720
gccggggccg gcggcggcgg atggacgctg gctcggagca cagagcccgc cgcccccgga    780
aactggaccc gctccgcctg ggcgccgcgg ggagcgtgtg ggacgcggtg gacggggccg    840
ccgccctgga cgcccacgcg cgcggcctcc ccacaggacc cccactcgcc caggagcccg    900
cactcccggc gctgcccgct cccgcgcgcc tgcagcctgg gtctcagacg gaaggctctg    960
gggcaaggtc tggctggagc agggaggcct cgggggtccc tgcccccgga ggaggctggc    1020
cctgggtcag cagggaggtc ccgggcaccc ggagctttgg cccagcccca gactccacgc    1080
gccccctggct agagagtccg cctcaaggtc gcccactcc gtcccaaggg ccgggtgcca    1140
caggggccta cgatgccggc gaggccgggg ctgacagctc ccgagataac agtcctgccg    1200
ctgacctggg gccaccccgg ccccggagc aagcaaagcc ggctgcagcc ggccacagcc     1260
gcgcgccctc ccggagccgt gagcctgccc cgcgctccgc ctcccgccc gcagctcccg     1320
gcccggggtt cccacctgaa gccctgactc tcccctctcc ttcagacttt ttgccctgg     1380
aggttaccca ggatccttcc gtgggcgaaa atctcagagc ggccgcagcc ccaagttcag    1440
cctcagccca agtcttaact tcagctccag cctcagtcct agcccagcc ctggcttcat     1500
ccccccagctc agcaccaacc tcagccacca cctcaacctc atccccacc tcagccccag    1560
ccccagctcc aacctcagct ccaacttcaa ccccagccc agcccaagt ccagctgcag      1620
ccgcaactcc agccccagcc ccagtcccag tcccaacct caacccccca tccccagccg    1680
taacccccagt cccaaccca gcctaagcc cagctccaac tccagcccta accccagccg    1740
catcccccagc cctaaccca gtccaaccc cagcctaag cccagctcca actccagccc     1800
caaccccagc cgcatcccct gccccagccc ccacctcagc cccaacccca accccagccg    1860
catcccctgc cccagctgac gggtcaaagc tcaggagag tgtggctctc ccaggcgct     1920
accaggaggg gcaggtctca gccagctggg gaaaccttat tgccatggtt cttagaagct    1980
accccttccc caggcaagac aggccccaag ggagtgtccc gagggcggtt cccgggagcc    2040
ccgtgggtcc cagcacttcc acacactctg aggacagaca cggcccctct tcttcagtgg    2100
ggacagtcat agggacaggt acagggggcc tggttgaggc tggaggtcag ccacagccaa    2160
gaagctccga gaccaacgga tcgcccagcc cagaccctcc cccaggccta agaggagagg    2220
gaaccaggga gaaagtcta gaccgctgc cccaagccgc gatgcccagg ggccccgcac      2280
agcccccgc gcagaggccg cctggccccg cggcctcctc ctctgcgagg cgctcacagc    2340
cggtacccca gctacggaaa cgcagcaggt gcgaaatcgc tgcgagctcg gagcaggagg   2400
tcaggccggc cgcctcgggg gaccctcaag gggaggcgcc gggggagggg ggcagccctg    2460
ccggccgcag cggggcgctc acggaaaagc aggaggaggc ccgaagctca tggtgtttct    2520
gcagaggccc gggggttggg gggtggtgga ggggcccggg aagcccagct cccgggccct    2580
ggagcccgcc acggcggcag ccctgcgcg gcggctggac ctggcagtt gcctggacgt     2640
gctgcctttt gcccagcagc acggagagcc cggcctgcag caggagacct acgcgctgat    2700
gagcgacaac ctgctgcgag tgctgggaga cccgtgcctc taccgccggc tgagcgcggc    2760
cgaccgcgag cgcatcctca gcctgcggac cggccgggc cgggcggtgc tgggcgtcct    2820
cgtactgccc agcctctacc aggggggccg ctcagggctc ccaggggcc ctcgtggcga    2880
ggagcctcct gcggcggccc ctgtgtccct gcctctacct gcgcacctgc atgtgttcaa    2940
ccccccggag aacacctggc ggccctgac ccaggtgccc gaggaggccc cgcttcgggg    3000
ctgcggtctc tgcaccatgc acaactacct gtttctggcg ggggcatcc gtggctccgg    3060
tgccaaggcc gtctgctcca acgaggtctt ctgctacaac cctctgacca acatctggag    3120
ccaggttcgg cccatgcagc aggcccgagc ccagctcaag ctggtggccc tggacgggct    3180
gctctatgcc atcggtggcg aatgcctgta cagcatggga tgctacgacc cgcgaacaga    3240
cgcctggacc ccacgcgcgc cactccccgc aggcaccttc cctgtggccc acgaggctgt    3300
ggcctgccgt ggggacatct acgtcaccgg ggtcacctc ttctaccgcc tgctcaggta    3360
cagccccgtg aaggatgctt gggacgagtg cccatacagt gccagccacc ggcgttccag    3420
cgacatcgtg gcactggggg gcttcctgta ccgcttcgac ctgctgcggg gcgtgggcgc    3480
cgctgatgat cgctacaaca cagtgaccgg cctcctggac agggctgcct ccctgcccct    3540
gccccgcccc gcccactgc actgcaccac cctgggcaac accatttact gcctcaaccc    3600
ccaggtcact gccaccttca cggtctctgg ggggactgcc cagttccagg ccaaggagct    3660
gcagcccttc cccttgggga gcaccggggt cctcagtcca ttcatcctga ctctgccccc    3720
tgaggaccgg ctgcagacct cactctgagt ggcaggcaga gaaccaaagc tgcttcgctg    3780
ctctccaggg agacccctcct gggatgggcc tgagaggccg gggctcaggg aaggggctgg    3840
```

```
gatcggaact tcctgctctt gtttctggac aactttcccc ttctgcttta aaggttgtcg   3900
attattttga agcccagact ccctcagcct ctttctgccc ctcactccac acccagactg   3960
tttcctgact caattccgta cctacttaca gaccctctca gcttgctgac accccctgt   4020
ctgtgggact ccctattccc tagagccagg gactgatgcg tctccacaga caaggacttg   4080
gctcgctgga gctctgctga gccgagagag gagggggtga aaaacattca cacttcctat   4140
gctctgtcag caggacaggg agcaaaaacg tccccaggca acgccctcgc ctctgggact   4200
ttctgcctgt cctaaggcct ccccaggtac caacccgta gctatctggg tctgtttggc   4260
actgtggatt ctcaagggcc tagaacctt gcctctgaaa ctggtccgct ggtgcagccc   4320
tgctgtctgc agctcctgcc catacccca gcccacacca ggccaggccc actccgggct   4380
caccaccctc tgcagccttg tgggctctc ccagccctc cagaagccca ccccacttct   4440
cgccaacccc cgatctctaa atgaggcctg agcgtcaccc tagttctgcc cctttttagc   4500
tgtgtagact tggacgagac atttgacttc cctttctcct tgtctataaa atgtggacag   4560
tggacgtctg tcacccaaga gagttgtggg agacaagatc acagctatga gcacctgca   4620
cggtgtccag gatgcacagc acaatccatg atgcgttttc tcccttacg cactttgaaa   4680
cccatgctag aaaagtgaat acatctgact gtgctccact ccaacctcca gcctggatgt   4740
ccctgtctgg gcccttttc tgttttttat tctatgttca gcaccactgg caccaaatac   4800
attttaattc accgaaagca aaaaaaaaaa aaaaaa                            4836

SEQ ID NO: 30           moltype = RNA   length = 2098
FEATURE                 Location/Qualifiers
source                  1..2098
                        mol_type = mRNA
                        organism = Homo sapiens
SEQUENCE: 30
ccacctcagc cccaacccca accccagccg catccctgc cccagctgac gggtcaaagc    60
ctcaggagag tgtggctctc cccaggcgct accaggaggg gcaggtctca gccagctggg   120
gaaaccttat tgccatggtt cttagaagcc accccttccc caggcaagac aggcccaag    180
ggagtgtccc gagggcggtt cccgggagcc ccgtgggtcc cagcacttcc acacactctg   240
aggacagaca cggcccctct tcttcagtgg ggacagtcat agggacaggt acaggggcc    300
tggttgaggc tggaggtcag ccacagccaa gaagctccga gaccaacgga tcgcccagcc   360
cagaccctcc cccaggccta agaggagagg gaaccaggga gaaaagtcta gacccgctgc   420
cccaagccgc gatgcccagg ggccccgcac agccccccgc gcagaggccg cctgcccccg   480
cggcctcctc ctctgcgagg cgctcacagc cggtacccca gctacggaaa cgcagcaggt   540
gcgaaatcgc cccgagctcg gagcaggagg tcaggccggc cgcctcgggg gaccctcaag   600
gggaggcgcc gggggagggg ggcagccctc ccggccgaca cgggcgctc acggaaaagc   660
aggaggaggc ccgaagctca tggtgtttct gcagaggccc gggggttggg gggtggtgga   720
ggggcccgg aagcccagct cccggggcct ggagcccgcc acggcggcag ccctgcggcg   780
gcggctggac ctgggcagtt gcctggacgt gctggccttt gccagcagc acggagagcc   840
cggcctggcg caggagacct acgcgctgat gagcgacaac ctgctgcgag tgctgggaga   900
cccgtgcctc taccgccggc tgagcgcggc cgaccgcgag cgcatcctca gcctgcggac   960
cggccgggc cgggcggtgc tgggcgtcct cgtactgccc agcctctacc aggggggccg  1020
ctcagggctc cccaggggcc ctcgtggcga ggagcctcct cgcggcggcc ctgtgtccct  1080
gcctctacct gcgcacctgc atgtgttcaa ccccgggag aacacctggc ggccctgca   1140
ccaggtgccc gaggaggccc cgcttcgggg ctgcggtctc tgcaccatgc acaactacct  1200
gtttctggcg gggggcatcc gtggctccgg tgccaaggcc gtctgctcca acgaggtctt  1260
ctgctacaac cctctgacca acatctggag ccaggttcgg cccatgcagc aggcccgagc  1320
ccagctcaag ctggtggccc tggacgggct gctctatgcc atcggtgcgg aatgcctgta  1380
cagcatggag tgctacgacc cgcgaacaga cgcctggacc ccacgcgcgc cactcccgc   1440
aggcaccttc cctgtggccc acgaggctgt ggcctgccgt ggggacatct acgtcaccgg  1500
gggtcacctc ttctaccgcc tgctcaggta cagccccgtg aaggatgctt gggacgagtg  1560
cccatacagt gccagccacc ggcgttccag cgacatcgtg gcactggggg gcttcctgga  1620
ccgcttcgac ctgctgcggg gcgtgggcgc cgccgtgatg cgctacaaca cagtgaccgg  1680
ctcctggagc agggctgcct ccctgccccc gccgccccc gcccactgc actgcaccac   1740
cctgggcaac accatttact gcctcaaccc ccaggtcact gccaccttca cggtctctgg  1800
ggggactgcc cagttccagg ccaaggagct gcagcccttc ccctttggga gcaccggggt  1860
cctcagtcca ttcatcctga ctctgccccc tgaggaccgg ctgcagacct cactctgagt  1920
ggcaggcaga gaaccaaagc tgcttcgctg ctctccaggg agaccctcct gggatgggcc  1980
tgagaggccg gggctcaggg aaggggctgg gatcggaact tcctgctctt gtttctggac  2040
aactttcccc ttctgcttta aaggttgtcg attattttga aaaaaaaaaa aaaaaaa    2098

SEQ ID NO: 31           moltype = RNA   length = 5124
FEATURE                 Location/Qualifiers
source                  1..5124
                        mol_type = mRNA
                        organism = Homo sapiens
SEQUENCE: 31
agaagcaggt tggctgtgat gacagcacag agctcaggaa cgctgcctga ggaccctggg    60
gcctacgagg aggagaagag ggcaggagct ggtggggtgc ttgcagagac cctgggctcc   120
tatcctgcca taagcctcgc tgtctcctga tatctgcagc caggccctac tgacacccc    180
aggcctgagt gcaagcagag accccaccat tccagggccc tggaggactg gtccaccta    240
actgggcagc ccttggggca ggcgctggcc ggtgcctcag cccaggcctc tgtgctctgc   300
atgcactgcc agcctgccat caggcctcta ttgcagccct gaaccatgat ccagggcacc   360
ttggagccag atggtcccct ctgggctgg gactgggaca gtgacaatga ctgggatagt   420
gctgtgctgg ccctcctggc gctggtgtg ttgcctgca cagcgctggc ttacactgg     480
tttggctccg ggcacgatca agaggcggca gaaccggtgt ccacagccct cgggggctcaa  540
cctcatcagg caggaggagc tgagctgcc ctgaaccga agtctaaggt cagtgatggc   600
agcgaggggg agagcccagg gcaggggaaa ccagagcccc caggacgcgg ccagcagagc   660
cctgtccctg ctgcagcgcc gggcgggc ctggccgcca tggcccggct tccactcaag   720
acggctgtcg aggaggcccg cagagaggca ttaggacagc aacggggcag tgccacccc   780
```

```
gcggccccc  gagcggaagg  aaaggagcct  cccaggccag  gcactgccct  cctgggcagg  840
agcgaagcag  gggggatgtc  cgccccctc   ctgatccact  tcactcctcg  gagccctggc  900
agcgaagcgg  aggcggagac  aggtggtgtc  agggcgtcct  ctcgccaggc  cgcaggcccc  960
gcggggcaac  aggacactgg  cccctggcag  gcgggcgcgg  ggccctcggg  ctcgatgggg  1020
agaggccggg  gccggcggcg  gcggatggac  gctggctcgg  gagacagagc  ccgccgcccc  1080
cggaaactgg  acccgctccg  cctgggcgcc  gcggggagcg  tgtgggacgc  ggtggacggg  1140
gccgccgccc  tggacgccca  cgcgcgcggc  ctccccacag  gaccccccact cgcccaggag  1200
cccgcactcc  cggcgctgcc  cgctcccgc   gccctgcagc  ctgggtctca  gacggaaggc  1260
tctggggcca  agggtggctg  gagcaggag   gcctcggggg  tccctgcccc  cggaggaggc  1320
tggccctggg  tcagcaggga  ggtcccgggc  acccgggct   ttggccagc   cccagactcc  1380
acgcgcccct  ggctagagag  tccgcctcaa  ggtcgcccac  tctcgtccca  agggccgggt  1440
gccacagggg  cctacgatgc  cggcgaggcc  gggctgaca   gctcccgaga  taacagtcct  1500
gccgctgacc  tggggcccac  ccggccccg   gagcaagcaa  agccggctgc  agccggccac  1560
agccgcgcgc  cctcccggag  ccgtgagcct  cgccgcgct   ccgcctccc   gcccgcagct  1620
cccggcccgg  ggttcccacc  tgaagccctg  actctcccct  ctccttcaga  cttttttgccc  1680
ctggaggtta  cccaggatcc  ttccgtgggc  gaaaatctca  gagcggcgcc  agccccaagt  1740
tcagcctcag  cccaagtctt  aacttcagct  ccagcctcag  tcctagcccc  agccctggct  1800
tcatccccca  gctcagcacc  aacctcagcc  accacctcaa  cctcatccct  cacctcagcc  1860
ccagccccag  ctccaacctc  agctccaact  tcaaccccca  ccccagcccc  aagtccagct  1920
gcagccgcaa  ctccagcccc  agcccagtc   ccagtcccaa  ccctcacacc  cccatcccca  1980
gccctaaccc  cagtcccaac  cccagcccta  agccagctc   caactccagc  cctaacccca  2040
gccgcatccc  cagccctaac  cccagtccca  accccagccc  taagcccagc  tccaactcca  2100
gccccaaccc  cagccgcatc  ccctgcccca  gcccccacct  cagccccaac  cccaacccca  2160
gccgcatccc  ctgcccagc   tgacgggtca  aagcctcagg  agagtgtggc  tctccccagg  2220
cgctaccagg  aggggcaggt  ctcagccagc  tgggaaacc   ttattgccat  ggttcttaga  2280
agccaccct   tccccaggca  agacaggcc   caagggagtg  tcccgaggg   ggttcccagg  2340
agccccgtgg  gtcccagcac  ttccacacac  tctgaggaca  gacacgggcc  ctcttcttca  2400
gtggggacag  tcatagggac  aggtacaggg  ggctggttg   aggctggagg  tcagccacag  2460
ccaagaagct  ccgagaccaa  cggatcgccc  agccagacc   ctcccccagg  cctaagagga  2520
gagggaacca  gggagaaaag  tctagacccg  ctgcccaag   ccgcgatgcc  cagggcccc   2580
gcacagcccc  ccgcgcagag  gccgcctggc  cccgcggcct  cctcctctgc  gaggcgctca  2640
cagccggtac  cccagctacg  gaaacgcagc  aggtgcgaaa  tcgccccgag  ctcggagcag  2700
gaggtcaggc  cggccgcctc  ggggaccct   caagggagg   cgccgggga   ggggggcagc  2760
cctgccggcc  gcagcgggc   gctcacggaa  aagcaggagg  aggcccggaa  gctcatggtg  2820
tttctgcaga  ggccgggggg  ttgggggtg   gtggaggggc  cccggaagcc  cagctcccgg  2880
gccctggagc  ccgccacggc  ggcagccctg  cggcggcgge  tggacctggg  cagttgcctg  2940
gacgtgctgg  cctttgccca  gcagcacgga  gagcccggcc  tggcgcagga  gacctacgcg  3000
ctgatgagcg  acaacctgct  gcgagtgctg  ggagaccgt   gcctctaccg  ccggctgagc  3060
gcggccgacc  gcgagcgcat  cctcagcctg  cggaccgagc  ggggccgggc  ggtgctgggc  3120
gtcctcgtac  tgcccagcct  ctaccagggg  ggccgctcag  ggctcccag   ggccctcgtg  3180
gcgaggagc   tcctgcggcg  gccctgtgt   ccctgcctct  acctgcgcac  ctgcatgtgt  3240
tcaacccccg  ggagaacacc  tggcggcccc  tgacccaggt  gcccgaggag  gccccgcttc  3300
ggggctgcgg  tctctgcacc  atgcacaact  acctgttttct ggcggggggc  atccgtggct  3360
ccggtgccaa  ggccgtctgc  tccaacgagg  tcttctgcta  caaccctctg  accaacatct  3420
ggagccaggt  tcgccccatg  cagcaggcc   gagcccagct  caagctgtgt  gccctggacg  3480
ggctgctcta  tgccatcggt  ggcgaatgcc  tgtacacagat ggagtgctac  gacccgcgaa  3540
cagacgccgg  gaccccacgc  gcgccactcc  ccgcaggcac  cttccctgtg  gccacagagg  3600
ctgtggcctg  ccgtggggac  atctacgtca  ccggggtca   cctcttctac  cgcctgctca  3660
ggtacagccc  cgtgaaggat  gcttgggacg  agtgccccata cagtgccagc  caccggcgtt  3720
ccagcgacat  cgtggcactg  ggggcttcc   tgtaccgctt  cgacctgctg  cggggcgtgg  3780
gcgccgccgt  gatgcgctac  aacacagtga  ccggctcctg  gagcagggct  ggctccctgg  3840
ccctgccccgc  cccgccccca  ctgcactgca  ccaccctggg  caacaccatt  tactgcctca  3900
accccaggt   cactgccacc  ttcacggtct  ctgggggac   tgcccagttc  caggccaagg  3960
agctgcagcc  cttccccttg  gggagcaccg  gggtcctcag  tccattcatc  ctgactctgc  4020
ccctgaggca  ccggctgcag  acctcactct  gagtggcagg  cagagaacca  aagctgcttc  4080
gctgctctcc  agggagaccc  tcctgggatg  ggcctgagag  gccggggctc  agggaagggg  4140
ctgggatcgg  aacttcctgc  tctttgtttct ggacaacttt  ccccttctgc  tttaaaggtt  4200
gtcgattatt  ttgaagccca  gactccctca  gcctcttttct gccccctcact  ccacacccag  4260
actgtttcct  gactcaattc  cgtacctact  tacagaccct  ctcagcttgc  tgacaccccc  4320
ctgtctgtgg  gactccctat  tcccctagagc caggggactga tgcgtctcca  cagacaagga  4380
cttggctcgc  tggagctctg  ctgagccgag  agaggagggg  gtagaaaaca  ttcacacttc  4440
ctatgctctg  tcagcaggac  agggagcaaa  aacgtcccca  ggcaacgccc  tcgcctctgg  4500
gactttctgc  ctgtcctaag  gcctcccag   gtaccaaccc  cgtagctatc  tgggtctgtt  4560
tggcactgtg  gattctcaag  ggcctagaac  ccttgcctct  gaaactggtc  cgctggtgca  4620
gccctgctgt  ctgcagctcc  tgccatacc   cccagcccac  accaggccag  gccactccg   4680
ggctcaccac  cctctgcagc  cttgtgggc   tctcccagcc  cctccagaag  cccaccccac  4740
ttctcgccaa  ccccgatct   ctaaatgagg  cctgagcgtc  accctagttc  tgccccttt   4800
tagctgtgta  gacttggacg  agacatttga  cttccctttc  tccttgtcta  taaaatgtgg  4860
acagtggacg  tctgtcaccc  aagagagttg  tgggagacaa  gatcacagct  atgagcacct  4920
cgcacggtgt  ccaggatgca  cagcacaatc  catgatgcgt  tttctcccct  tacgcacttt  4980
gaaacccatg  ctagaaaagt  gaatacatct  gactgtgctc  cactccaacc  tccagcctgg  5040
atgtccctgt  ctgggccctt  tttctgtttt  ttattctatg  ttcagcacca  ctggcaccaa  5100
atacatttta  attcaccgaa  agca                                           5124

SEQ ID NO: 32          moltype = RNA   length = 2989
FEATURE                Location/Qualifiers
source                 1..2989
                       mol_type = mRNA
                       organism = Homo sapiens
```

```
SEQUENCE: 32
ccacctcagc cccaacccca accccagccg catcccctgc cccagctgac gggtcaaagc    60
ctcaggagag tgtggctctc cccaggcgct accaggaggg gcaggtctca gccagctggg   120
gaaaccttat tgccatggtt cttagaagcc acccctcc   caggcaagac aggcccaag    180
ggagtgtccc gagggcggtt cccgggagcc ccgtgggcc cagcacttcc acacactctg   240
aggacagaca cggcccctct tcttcagtgg ggacagtcat agggacaggt acaggggggcc   300
tggttgaggc tggaggtcag ccacagccaa gaagctccga gaccaacgga tcgcccagcc   360
cagaccctcc cccaggccta agaggagagg gaaccaggga gaaaagtcta gacccgctgc   420
cccaagccgc gatgcccagg ggccccgcac agccccccgc gcagaggccg cctggcccg    480
cggcctcctc ctctgcgagg cgctcacagc cggtacccca gctacggaaa cgcagcaggt   540
gcgaaatcgc cccgagctcg gagcaggagg tcaggccggc cgcctcgggg gaccctcaag   600
gggaggcgcc gggggagggg ggcagccctg ccggccgcag cggggcgctc acggaaaagc   660
aggaggaggc ccggaagctc atggtgtttc tgcagaggcc cggggggttgg ggggtggtgg   720
aggggccccg gaagcccagc tcccgggccc tggagcccgc cacggccgca gccctgcggc   780
ggcggctgga cctgggcagt tgcctggacg tgctggcctt tgcccagcag cacggagagc   840
ccggcctggc gcaggagacc tacgcgctga tgagcgacaa cctgctgcga gtgctgggag   900
acccgtgcct ctaccgccgg ctgagcgcgg ccgaccgcga gcgcatcctc agcctgcgga   960
ccggccgggg ccgggccggtg ctgggcgtcc tcgtactgcc cagcctctac caggggggcc  1020
gctcagggct ccccagggcc ctcgtggcga ggagcctcct gcggcggccc ctgtgtccct  1080
gcctctacct gcgcacctgc atgtgttcaa ccccgggag aacacctggc ggcccctgac  1140
ccaggtgccc gaggaggccc cgcttcgggg ctgcggtctc tgcaccatgc acaactacct  1200
gtttctggcg ggggggcatcc gtggctccgg tgccaaggcc gtctgctcca acgaggtctt  1260
ctgctacaac cctctgacca acatctggag ccaggttcgg cccatgcagc aggcccgagc  1320
ccagctcaag ctggtggccc tggacgggct gctctatgcc atcggtggcg aatgcctgta  1380
cagcatggag tgctacgacc cgcgaacaga cgcctggacc ccacgcgcgc cactccccg  1440
aggcaccttc cctgtggccc acgaggctgt ggcctgccgt gggacatctg acgtcaccgg  1500
gggtcacctc ttctaccgcc tgctcaggta cagcccctgt aaggatgctt gggacgagtg  1560
cccatacagt gccagccacc ggcgttccag cgacatcgtg gcactggggg gcttcctgta  1620
ccgcttcgac ctgctgcggg gcgtgggcgc cgccgtgatg cgctacaaca cagtgaccgg  1680
ctcctggaac aggctgcct ccctgcccct gcccgcccgc gcccactgc actgcaccac  1740
cctgggcaac accatttact gcctcaaccc caggtcact gccaccttca cggtctctgg  1800
ggggactgcc cagttccagg ccaaggagct gcagcccttc cccttgggga gcaccggggt  1860
cctcagtcca ttcatcctga ctctgccccc tgaggaccgg ctgcagacct cactctgagt  1920
ggcaggcaga gaaccaaagc tgcttcgctg ctctccaggg agaccctcct gggatgggcc  1980
tgagaggccg gggctcaggg aaggggctgg gatcggaact tcctgctctt gtttctggac  2040
aactttcccc ttctgcttta aaggttgtcg attattttga agcccagact ccctcagcct  2100
ctttctgccc ctcactccac acccagactg tttcctgact caattccgta cctacttaca  2160
gaccctctca gcttgctgac accccctgt ctgtgggact cccctatccc tagagccagg  2220
gactgatgcg tctccacaga caaggacttg gctcgctgga gtctgctga gccgagagag  2280
gaggggggtag aaaacattca cacttcctat gctctgtcag caggacaggg agcaaaaacg  2340
tccccaggca acgccctcgc ctctgggact ttctgcctgt cctaaggcct ccccaggtac  2400
caacccgta gctatctggg tctgtttggc actgtggatt tcaagggcc tagaacccctt  2460
gcctctgaaa ctggtccgct ggtgcagccc tgctgtctgc agctcctgcc cataccccca  2520
gcccacacca ggccaggccc actccggct caccaccctc tgcagccttg tggggctctc  2580
ccagccctc cagaagccca cccccacttct cgccaacccc cgatctctaa atgaggcctg  2640
agcgtcaccc tagttctgcc ccttttttagc tgtgtagact tggacgagac atttgacttc  2700
cctttctcct tgtctataaa atgtggacag tggacgtctg tcacccaaga gagttgtggg  2760
agacaagatc acagctatga gcacctcgca cggtgtccag gatgcacagc acaatccatg  2820
atgcgttttc tcccccttacg cactttgaaa cccatgctag aaaagtgaat acatctgact  2880
gtgctccact ccaacctcca gcctggatgt ccctgtctgg gcccttttc tgttttttat  2940
tctatgttca gcaccactgg caccaaatac attttaattc accgaaagc               2989

SEQ ID NO: 33      moltype = RNA  length = 4836
FEATURE            Location/Qualifiers
source             1..4836
                   mol_type = mRNA
                   organism = Homo sapiens
SEQUENCE: 33
actgccagcc tgccatcagg cctctattgc agccctgaac catgatccag ggcaccttgg    60
agccagatgg tcccctctgg ggctgggact gggacagtga caatgactgg ggatagtgctg   120
tgctggccct cctggcgctg gctgtggtgg ctgccacagc gctggcctta cactggtttg   180
gctccgggca cgatcaagag gcggcagaac cggtgtccac agccctcggg gctcaacctc   240
atcaggcagg aggagctgag ctggccctgc aaccgaagtc taaggtcagt gatggcagcg   300
aggggcagag cccaggggcag gggaaaccag agcccccgag acgcggccga cagagccctg   360
tccctgctgc agcgccgggc gggggcctgg ccgccatggc ccggcttcca ctcaagacgg   420
ctgtcgagga ggcccgcaga gaggcattag acagcaacg gggcagtgcc acccccgcgg   480
cccccgagc ggaaggaaag gagcctccca ggccaggcac tgccctcctg gcaggagcg   540
aagcagggg gatgtccgcc cccctcctga tccacttcac tcctcggagc cctggcagcg   600
aagcggaggc ggagacaggt ggtgtcaggg cgtcctctcg ccaggccgga ggcccgcgg   660
ggcaacagga cactgccccc tgcaggcgcg gcgcggggcc ctcgggctcg atggggagag   720
gccggggccg gcggcggcgg atggacgctg gctcggggaga cagagcccgc cgccccggga   780
aactggaccc gctccgcctg ggcgccgcgg ggagcgtgtg ggacgcggtg acggggccg   840
ccgcctgga cgccacgcg cgcggcctcc ccacaggacc cccactcgcc caggagcccg   900
cactcccggc gctgcccgct ccccgcgccc tgcacctgg gtctcagacg gaaggctctg   960
gggccaaggg tggctggagc agggaggcct cggggtccc tgcccccgga ggaggctggc  1020
cctgggtcag cagggaggtc ccgggcaccc ggagctttgg cccagcccca gactccacgc  1080
gcccctggct agagagtccg cctcaaggtc gcccactctc gtcccaaggg ccgggtgcca  1140
caggggccta cgatgccggc gaggccgggg ctgcagactc ccgagataac agtcctgccg  1200
ctgacctggg gcccacccgg cccccggagc aagcaaagcc ggctgcagcc ggccacagcc  1260
```

-continued

```
gcgcgccctc ccggagccgt gagcctcgcc cgcgctccgc ctccccgccc gcagctcccg 1320
gcccggggtt cccacctgaa gccctgactc tccctctcc ttcagacttt ttgcccctgg 1380
aggttaccca ggatccttcc gtgggcgaaa atctcagagc ggcgccagcc ccaagttcag 1440
cctcagccca agtcttaact tcagctccag cctcagtcct agcccagcc ctggcttcat 1500
cccccagctc agcaccaacc tcagccacca cctcaaccctc atccccacc tcagccccag 1560
ccccagctcc aacctcagct ccaacttcaa ccccagcccc agcccaagt ccagctgcag 1620
ccgcaactcc agcccagcc ccagtcccag tcccaaccct cacacccca tccccagccc 1680
taaccccagt cccaacccca gccctaagcc cagctccaac tccagccta accccagccg 1740
catcccagc cctaacccca gtcccaaccc cagccctaag cccagctca actccagccg 1800
caaccccagc cgcatcccct gccccagccc ccacctcagc cccaacccca accccagccg 1860
catcccctgc cccagctgac gggtcaaagc ctcaggagag tgtggctctc cccaggcgct 1920
accaggaggg gcaggtctca gccagctggg gaaaccttat tgccatggtt cttagaagcc 1980
accccttccc caggcaagac aggccccaag ggagtgtccc gagggcggtt cccggagcc 2040
ccgtggtccc cagcacttcc acacactctg aggacagaca cggcccctct tcttcagtgg 2100
ggacagtcat agggacaggt acaggggcc tggttgagc tggaggtcag ccacagccaa 2160
gaagctccga gaccaacgga tcgcccagcc cagaccctcc cccaggccta agaggagagg 2220
gaaccaggga gaaaagtcta gacccgctgc ccaagccgc gatgcccagg ggcccgcac 2280
agccccccgc gcagaggccg cctggccccg cggcctcctc ctctgcgagg cgctcacagc 2340
cggtacccca gctacggaaa cgcagcaggt gcgaaatcgc cccgagctcg gagcaggagg 2400
tcaggccggc cgcctcgggg gaccctcaag gggaggcgcc gggggagggg ggcagccctg 2460
ccggccgcag cggggcgctc acggaaaagc aggaggaggc ccggaagctc atggtgtttc 2520
tgcagaggcc cggggggttgg gggtggtgg aggggccccg gaagcccagc tcccggaccg 2580
tggagcccgc cacgcggca gccctgcggc ggcggctgga cctgggcagt tgcctggacg 2640
tgctggcctt tgcccagcag cacggagagc ccggcctggc gcaggagacc tacgcgctga 2700
tgagcgacaa cctgctgcga gtgctggag accccgtgcct ctaccgccgg ctgagcgcgg 2760
ccgaccgcga gcgcatcctc agcctgcgga ccggccgcgt gcgggcggtc cggtcgtcc 2820
tcgtactgcc cagcctctac caggggggcc gctcaggggct cccagggcc ctcgtgcga 2880
ggagcctcct gcggcggccc ctgtgtccct gcctctacct gcgcacctgc atgtgttcaa 2940
cccccggag aacacctggc ggcccctgac ccaggtgccc gaggaggccc cgcttcgggg 3000
ctgcggtctc tgcaccatgc acaactacct gtttctggcg ggggcatcc gtggctccgg 3060
tgccaaggcc gtctgctcca acgaggtctt ctgctacaac cctctgacca acatctggag 3120
ccaggttcgg cccatgcagc aggcccgagc ccagctcaag ctggtggccc tggacgggct 3180
gctctatgcc atcggtggcg aatgcctgta cagcatggag tgctacgacc cgcgaacaga 3240
cgctggacc ccacgcgc cactccccgc aggcacctc cctgtggccc acgaggctgt 3300
ggcctgccgt ggggacatct acgtcaccgg gggtcacctc ttctggccgcc tgctcaggta 3360
cagccccgtg aaggatgctt gggacgagtg cccatacagt gccagccacc ggcgttccag 3420
cgacatcgtg gcactggggg gcttcctgta ccgcttcgac ctgctgcggg gcgtgggcgc 3480
cgccgtgatg cgctacaaca cagtgaccgg ctcctggagc agggctgcct ccctgccct 3540
gcccgcctcc gcccactgc actgcaccac cctgggcaac accattact gcctcaaccc 3600
ccaggtcact gccaccttca cggtctctgg ggggactgcc cagttccagg ccaaggagct 3660
gcagcccttc cccttgggga gcaccggggt cctcagtcca ttcatcctga ctctgccccc 3720
tgaggaccgg ctgcagacct cactctgagt ggcaggcaga gaaccaaagc tgcttcgctg 3780
ctctccaggg agaccctcct gggatggcc tgagaggccg gggctcaggg aaggggctgg 3840
gatcggaact tcctgctctt gtttctggac aactttcccc ttctgcttta aaggttgtcg 3900
attattttga agcccagact ccctcagcct ctttctgccc ctcactccac acccagactg 3960
tttcctgact caattccgta cctacttaca gaccctctca gcttgctgac accccctgt 4020
ctgtgggact ccctattccc tagagccagg gactgatgcg tctccacaga caaggactg 4080
gctcgctgga gctctgctga gccgagagag gaggggtag aaaacattca cacttccat 4140
gctctgtcag caggacaggg agcaaaaacg tccccaggca acgcccctcgc ctctgggact 4200
ttctgcctgt cctaaggcct ccccaggtac caaccccgta gctatctggg tctgtttggc 4260
actgtggatt ctcaagggcc tagaacccctt gcctctgaaa ctggtccgct ggtgcagccc 4320
tgctgtctgc agctcctgcc cataccccca gcccacacca ggccaggccc actccgggct 4380
caccaccctc tgcagccttg tggggctctc ccagcccctc cagaagccca ccccacttct 4440
cgccaaccccc cgatctctaa atgaggcctg agcgtcaccc tagttctgcc cctttttagc 4500
tgtgtagact tggacgagac attttgactc cctttctgtc tgtctataaa atgtggacag 4560
tggacgtctg tcacccaaga gagttgtggg agacaagatc acagctatga gcacctcgca 4620
cggtgtccag gatgcacagc acaatccatg atgcgttttc tccccttacg cacttttgaaa 4680
cccatgctag aaaagtgaat acatctgact gtgctccact ccaacctcca gcctggatgt 4740
ccctgtctgg gcccttttc tgttttttat tctatgttca gcaccactgg caccaaatac 4800
attttaattc accgaaagca aaaaaaaaa aaaaaa                            4836
```

```
SEQ ID NO: 34           moltype = RNA   length = 2098
FEATURE                 Location/Qualifiers
source                  1..2098
                        mol_type = mRNA
                        organism = Homo sapiens
SEQUENCE: 34
ccacctcagc cccaacccca accccagccg catcccctgc cccagctgac gggtcaaagc  60
ctcaggagag tgtggctctc cccaggcgct accaggaggg gcaggtctca gccagctggg 120
gaaaccttat tgccatggtt cttagaagcc accccttccc caggcaagac aggccccaag 180
ggagtgtccc gagggcggtt cccggagcc ccgtgggtcc cagcacttcc acacactctg 240
aggacagaca cggcccctct tcttcagtgg ggacagtcat agggacaggt acaggggcc  300
tggttgagc tggaggtcag ccacagccaa gaagctccga gaccaacgga tcgcccagcc 360
cagaccctcc cccaggccta agaggagagg gaaccaggga gaaaagtcta gacccgctgc 420
cccaagccgc gatgcccagg ggcccgcac agccccccgc gcagaggccg cctggccccg 480
cggcctcctc ctctgcgagg cgctcacagc cggtacccca gctacggaaa cgcagcaggt 540
gcgaaatcgc cccgagctcg gagcaggagg tcaggccggc cgcctcgggg gaccctcaag 600
ggaggcgcc gggggagggg ggcagccctg ccggccgcag cggggcgctc acggaaaagc 660
aggaggaggc ccggaagctc atggtgtttc tgcagaggcc cggggggttgg gggtggtgg 720
```

```
agggggccccg gaagcccagc tcccgggcc tggagcccgc cacgcgggca gccctgcggc    780
ggcggctgga cctgggcagt tgcctggacg tgctggcctt tgcccagcag cacggagagc    840
ccggcctggc gcaggagacc tacgcgctga tgagcgacaa cctgctgcga gtgctgggag    900
acccgtgcct ctaccgccgg ctgagcgcgg ccgaccgcga gcgcatcctc agcctgcgga    960
ccggccgggg ccgggcggtg ctgggcgtcc tcgtactgcc cagcctctac caggggggcc   1020
gctcagggct ccccagggcc ctcgtgcgca ggagcctcct gcggcggccc ctgtgtccct   1080
gcctctacct gcgcacctgc atgtgttcaa ccccgggag aacacctggc ggcccctgac    1140
ccaggtgccc gaggaggccc cgcttcgggg ctgcggtctc tgcaccatgc acaactacct   1200
gtttctggcg gggggcatcc gtggctccgg tgccaaggcc gtctgctcca acgaggtctt   1260
ctgctacaac cctctgacca acatctggag ccaggttcgg cccatgcagc aggcccgagc   1320
ccagctcaag ctggtggccc tggacgggct gctctatgcc atcggtgcg aatgcctgta    1380
cagcatggag tgctacgacc cgcgaacaga cgcctggacc ccacgcgcgc cactcccgc    1440
aggcaccttc cctgtggccc acgaggctgt ggcctgccgt ggggacatct acgtcaccgg   1500
gggtcacctc ttctaccgcc tgctcaggta cagccccgg aaggatgctt gggacgagtg    1560
cccatacagt gccagccacc ggcgttccag cgacatcgtg gcactggggg gcttcctgta   1620
ccgcttcgac ctgctgcggg gcgtgggcgc cgccgtgatg cgctacaaca cagtgaccgg   1680
ctcctggagc agggctgcct ccctgcccct gcccgcccc gccccactgc actgcaccac    1740
cctgggcaac accatttact gcctcaaccc ccaggtcact gccaccttca cggtctctgg   1800
ggggactgcc cagttccagg ccaaggagct gcagcccttc cccttgggga ggaccgggt    1860
cctcagtcca ttcatcctga ctctgcccc tgaggaccgg ctgcagacct cactctgagt   1920
ggcaggcaga gaaccaaagc tgcttcgctg ctctccaggg agaccctcct gggatgggcc   1980
tgagaggccg gggctcaggg aaggggctgg gatcggaact tcctgctctt gtttctggac   2040
aacttccccc ttctgctttta aaggttgtcg attattttga aaaaaaaaa aaaaaaaa     2098

SEQ ID NO: 35           moltype = DNA   length = 5124
FEATURE                 Location/Qualifiers
source                  1..5124
                        mol_type = other DNA
                        organism = Homo sapiens
SEQUENCE: 35
agaagcaggt tggctgtgat gacagcacag agctcaggaa cgctgcctga ggaccctggg     60
gcctacgagg aggagaagag ggcaggagct ggtggggtgc ttgcagagac cctgggctcc    120
tatcctgcca taagcctcgc tgtctcctga tatctgcagc caggcccac tgacacccca     180
aggcctgagt gcaagcagag accccaccat tcccaggcc tggaggactg gtccaccta     240
actggcagc ccttggggca ggcgctggcc ggtgcctcag cccaggcctc tgtgtctctg    300
atgcactgcc agcctgccat caggcctcta ttgcagccct gaaccatgat ccagggcacc    360
ttggagccaa atggtcccct ctggggctgg gactgggaca gtgacaatga ctgggatagt    420
gctgtgctgg ccctcctggc gctggctgtg gtggctgcca cagcgctggc cttacactgg    480
tttggctccg ggcacgatca agaggcggca gaacgggtgt ccacagccgc tggggctcaa    540
cctcatcagg caggaggagc tgagctggcc ctgcaaccga agtctaaggt cagtgatggc    600
agcgaggggc agagcccagg gcaggggaaa ccagagcccc caggacgcgg ccagcagagc    660
cctgtccctg ctgcagcgcc gggcggggc ctggccgcca tgcccggct tccactcaag     720
acggctgtcg aggagcccg cagagaggca ttaggacagc aaggggcag tgccacccc      780
gcggcccccc gagcggaagg aaaggagcct cccaggccag gcactgccct cctgggcagg    840
agcgaagcag gggggatgtc cgccccccctc ctgatccact tcactcctcg gagccctggc    900
agcgaagcgg aggcggagac aggtggtgtc agggcgtcct ctcgcaggc cgcaggcccc    960
gcggggcaac aggacactgg cccctggcag cgggcgggc ggtctcggg gagacagagc    1020
agaggccggg gccggcggcg gcggatggac gctggctcgg gagacagagc ccgccgcccc   1080
cggaaactgg acccgctccg cctgggcgcc gcggggagcg tgtgggacgc ggtggacggg   1140
gccgccgccc tggacgccca cgcgcgcggc ctccccacag accccccact cgcccaggag   1200
cccgcactcc cggcgctgcc cgctcccgc gcctgcagc ctgggtctca gacggaaggc    1260
tctgggccca aggtggctg gagcaggag gcctcggggg tccctgcccc cggaggaggc    1320
tggccctggg tcagcaggga ggtcccgggc accggagct ttggcccagc ccagactcc     1380
acgcgccct ggctagagag tccgcctcaa ggtcgcccac tctcgtccca agggccgggt    1440
gccacagggg cctacgatgc cggcagggcc ggggctgaca gctcccgaga taacagtcct   1500
gccgctgacc tggggcccac ccggcccccg gagcaagcaa agccggctgc agccggccac   1560
agccgcgcgc cctcccggag ccgtgagcct cgcccgcgct ccgcctcccc gcccgcagct   1620
cccggcccgg ggttcccacc tgaagccctg actctcccct ctccttcaga cttttttgccc   1680
ctggaggtta cccaggatcc ttccgtgggc gaaaatctca gagcggcgcc agcccaagt    1740
tcagcctcag cccaagtctt aacttcagct ccagcctcag tcctagcccc agccctgct    1800
tcatccccca gctcagcacc aacctcagcc accactcaa cctcatcccc cacctcagcc   1860
ccagcccag ctccaacctc agctccaact tcaaccccag cccagcccc aagtccagct    1920
gcagccgcaa ctccagcccc agcccagtc ccagtcccaa ccctcacacc cccatcccca    1980
gccctaaccc cagtcccaac cccagcccta agcccagct ccaactccag cctaacccca    2040
gccgcatccc cagccctaac cccagtccca accccagccc taagcccagc tccaactcca    2100
gcccaacccc cagccgcatc ccctgcccca gccccaccct cagccccaac ccaacccca    2160
gccgcatccc ctgcccagc tgacgggtca aagcctcagg agagtgtggc tctccccagg   2220
cgctaccagg aggggcaggt ctcagccagc tggggaaacc ttattgccat ggttcttaga    2280
agccacccct tcccaggca agacaggccc caagggagtg tcccgagggc ggttcccagg   2340
agccccgtgg gtcccagcac ttccacacac tctgaggaca gacacgggcc ctcttcttca    2400
gtggggacag tcatagggac aggtacaggg ggcctggttg aggctggagg tcagccacag    2460
ccaagaagct ccgagaccaa cggatcgccc agccagacc ctccccagg cctaagagga    2520
gagggaacca gggagaaaag tctagacccg ctgcccaag ccgcgatgcc caggggcccc    2580
gcacagcccg gcgcgcagag gccgcctggc ccgcgtgcct cctcctctgc gaggcgctca    2640
cagccggtac cccagctacg gaaacgcagc aggtgcgaaa tcgccccgag ctcggagcag    2700
gaggtcaggc cggccgcctc ggggggaccct caaggggagg cgccggggga gggggcagc    2760
cctgccggcc gcagcgggc gctcacggaa aagcaggagg aggcccgaag ctcatggtgt   2820
ttctgcagag gccggggtg tggggggtgg tgagggggcc ccggaagccc agctcccggg   2880
ccctggagcc cgccacggcg gcagcccctgc ggcggcggct ggacctgggc agttgcctgg   2940
```

```
acgtgctggc ctttgcccag cagcacggag agcccggcct ggcgcaggag acctacgcgc   3000
tgatgagcga caacctgctg cgagtgctgg gagaccgtg  cctctaccgc cggctgagcg   3060
cggccgaccg cgagcgcatc ctcagcctgc ggaccggccg gggccgggcg gtgctgggcg   3120
tcctcgtact gcccagcctc taccagggggg gccgctcagg gctccccagg ggccctcgtg  3180
gcgaggagcc tcctgcgcg  gcccctgtgt ccctgcctct acctgcgcac ctgcatgtgt   3240
tcaacccccg ggagaacacc tggcggcccc tgacccaggt gcccgaggag gccccgcttc   3300
ggggctgcgg tctctgcacc atgcacaact acctgtttct ggcggggggc atccgtggct   3360
ccggtgccaa ggccgtctgc tccaacgagg tcttctgcta caaccctctg accaacatct   3420
ggagccaggt tcggcccatg cagcaggccc gagcccagct caagctggtg gccctggacg   3480
ggctgctcta tgccatcggt ggcgaatgcc tgtacagcat ggagtgctac gaccccgcgaa  3540
cagacgcctg gacccacgc  gcgccactcc ccgcaggcac cttccctgtg cccacgaggg   3600
ctgtggcctg ccgtggggac atctacgtca ccggggggtca cctcttctac cgcctgctca  3660
ggtacagccc cgtgaaggat gcttgggacg agtgcccata cagtgccagc caccggcgtt  3720
ccagcgacat cgtggcactg gggggcttcc tgtaccgctt cgacctgctg cggggcgtgg  3780
gcgccgccgt gatgcgctac aacacagtga ccggctcctg gagcagggct gcctccctgc  3840
ccctgcccgc ccccgcccca ctgcactgca ccacccctggg caacaccatt tactgcctca  3900
acccccaggt cactgccacc ttcacggtct ctgggggggac tgcccagttc caggccaagg  3960
agctgagcc  cttcccccttg gggagcaccg gggtcctcag tccattcatc ctgactctgc   4020
cccctgaggg ccggctgcag acctcactct gagtggcagg cagagaacca aagctgcttc   4080
gctgctctcc agggagaccc tcctgggatg ggcctgagag gccggggctc agggaagggg   4140
ctgggatcgg aacttcctgc tcttgttcct ggacaacttt cccctttctgc ttttaaaggttt 4200
gtcgattatt ttgaagccca gactccctca gcctcttttct gccccctcct ccacacccag  4260
actgtttcct gactcaattc cgtacctact tacagaccct ctcagcttgc tgacaccccc   4320
ctgtctgtgg gactccctat tccctagagc cagggactga tgcgtctcca cagacaagga   4380
cttggctcgc tggagctctg ctgagccgag agaggagggg gtagaaaaca ttcacacttc   4440
ctatgctctg tcagcaggac agggagcaaa aacgtcccca ggcaacgccc tcgcctctgg   4500
gactttctgc ctgtcctaag gcctcccag  gtaccaaccc cgtagctatc tgggtctgtt   4560
tggcactgtg gattctcaag ggcctagaac ccttgcctct gaaactggtc cgctggtgca   4620
gccctgctgt ctgcagctcc tgcccatacc cccagcccac accaggccag cccactccg   4680
ggctcaccac cctctgcagc cttgtggggc tctcccagcc ctccagaag  cccacccac    4740
ttctcgccaa ccccgatct  ctaaatgagg cctgagcgtc accctagttc tgcccctttt   4800
tagctgtgta gacttggacg agacatttga cttccctttc tccttgtcta taaaatgtgg   4860
acagtggacg tctgtcaccc aagagagttg tgggagacaa gatcacagct atgagcacct   4920
cgcacggtgt ccaggatgca cagcacaatc catgatgcgt tttctcccct tacgcacttt   4980
gaaacccatg ctagaaaagt gaatacatct gactgtgctc cactccaacc tccagcctgg   5040
atgtcccctgt ctgggcccctt tttctgttttt ttattctatg ttcagcacca ctggcaccaa  5100
atacatttta attcaccgaa agca                                         5124

SEQ ID NO: 36      moltype = DNA  length = 2989
FEATURE            Location/Qualifiers
source             1..2989
                   mol_type = other DNA
                   organism = Homo sapiens
SEQUENCE: 36
ccacctcagc cccaaccccca accccagccg catcccctgc cccagctgac gggtcaaagc    60
ctcaggagag tgtggctctc cccaggcgct accaggaggg gcaggtctca gccagctggg   120
gaaaccttat tgccatggtt cttagaagcc accccttcca caggcaagac aggccccaag   180
ggagtgtccc gagggcggtt cccgggagcc ccgtgggtcc cagcacttcc acacactctg   240
aggacagaca cggcccctct tcttcagtgg ggacagtcat agggacaggt acaggggggcc  300
tggttgaggc tggaggtcag ccacagccaa gaagctccga gaccaacgga tcgcccagcc   360
cagaccctcc cccaggccta agaggagagg gaaccaggga gaaaagtcta gacccgctgc   420
cccaagccgc gatgcccagg ggccccgcac agccccccgc gcagaggccg cctggccccg   480
cggcctcctc ctctgcgagg cgctcacagc cggtacccca gctacggaaa cgcagcaggt   540
gcgaaatcgc cccgagctcg gagcaggagg tcaggccggc cgcctcgggg gaccctcaag   600
gggaggcgcc gggggagggg ggcagccctg ccggccgcag cgggcgcgctc acggaaaagc   660
aggaggaggc ccgaagctca tggtgttct  gcagaggccc ggggggttggg gggtggtgga   720
ggggccccgg aagcccagct cccgggcct  ggagcccgcc acggcggcag ccctgcggcg   780
gcggctggac ctgggcagtt gcctggacgt gctggccttt gccagcagc  acggagagcc   840
cggcctggcg caggacaacct acgcgctgat gagcgacaac ctgctgcgag tgctgggaga   900
cccgtgcctc taccgccggc tgagcgcggc cgaccgcgag cgcatcctca gcctgcgggc   960
cggccgggcg cggcgtgc  tgggcgtcct cgtactgccc agcctctacc agggggggccg  1020
ctcagggctc ccaggggcc  ctcgtggcga ggagcctcct gcggcggccc ctgtgtccct   1080
gcctctacct gcgcacctgc atgtgttcaa ccccggag  aacacctggc ggcccctgac   1140
ccaggtgccc gaggaggccc cgcttcgggg ctgcggtctg tgcaccatgc acaactacct   1200
gtttctggcg ggggggcatcc cgtggctccg tgccaaggcc gtctgctcca acgaggtctt   1260
ctgctacaac cctctgacca catctggag  ccaggttcgg cccatgcagc aggcccgagc   1320
ccagctcaag ctggtggccc tggacgggct gctctatgcc atcggtggcg aatgcctgta   1380
cagcatggag tgctacgacc cgcgaacaga cgcctggacc cacgcgcgc  cactcccgc    1440
aggcaccttc cctgtgccca cgaggctgt  ggcctgccgt ggggacatct acgtcaccgg   1500
gggtcacctc ttctaccgcc tgctcaggta cagccccgtg aaggatgctt gggacgagtg   1560
cccatacagt gccagccacc ggcgttccag cgacatcgtg gcactggggg gcttcctgta   1620
ccgcttcgac ctgctgcggg gcgtgggcgc cgccgtgatg cgctacaaca cagtgaccgg   1680
ctcctggagc agggctgcct ccctgcccct gcccgcccc  gccccactgc actgcaccac   1740
cctgggcaac accatttact gcctcaaccc ccaggtcact gccaccttca cggtctctgg   1800
ggggactgcc cagttccagg ccaaggagct gcagcccttc cccttgggga gcacggggt    1860
cctcagtcca ttcatcctga ctctgccccc tgaggaccgg ctgcagacct cactctgagt   1920
ggcaggcaga gaaccaaagc tgcttcgctg ctctccaggg agaccctcct gggatgggcc   1980
tgagaggccg gggctcaggg aaggggctgg gatcggaact tcctgctctt gtttctggac   2040
aactttcccc ttctgcttta aaggttgtcg attatttga  agcccagact ccctcagcct   2100
```

```
ctttctgccc ctcactccac acccagactg tttcctgact caattccgta cctacttaca   2160
gaccctctca gcttgctgac accccctgt ctgtgggact ccctattccc tagagccagg   2220
gactgatgcg tctccacaga caaggacttg gctcgctgga gctctgctga gccgagagag   2280
gaggggggtag aaaacattca cacttcctat gctctgtcag caggacaggg agcaaaaacg   2340
tcccaggca acgccctcgc ctctgggact ttctgcctgt cctaaggcct cccaggtac    2400
caacccgta gctatctggg tctgtttggc actgtggatt ctcaagggcc tagaaccctt   2460
gcctctgaaa ctggtccgct ggtgcagccc tgctgtctgc agctcctgcc catacccca   2520
gcccacacca ggccaggccc actccgggct caccaccctc tgcagccttg tggggctctc   2580
ccagcccctc cagaagccca ccccacttct cgccaacccc cgatctctaa atgaggccgg   2640
agcgtcaccc tagttctgcc ccttttagc tgtgtagact tggacgagac atttgacttc   2700
cctttctcct tgtctataaa atgtggacag tggacgtctg tcacccaaga gagttgtggg   2760
agacaagatc acagctatga gcacctcgca cggtgtccag gatgcacagc acaatccatg   2820
atgcgttttc tccccttacg cactttgaaa cccatgctaa aaaagtgaat acatctgact   2880
gtgctccact ccaacctcca gcctggatgt ccctgtctgg gccctttttc tgtttttttat   2940
tctatgttca gcaccactgg caccaaatac attttaattc accgaaagc              2989

SEQ ID NO: 37         moltype = DNA   length = 4836
FEATURE               Location/Qualifiers
source                1..4836
                      mol_type = other DNA
                      organism = Homo sapiens
SEQUENCE: 37
actgccagcc tgccatcagg cctctattgc agccctgaac catgatccag ggcaccttgg   60
agccagatgg tccctctgg ggctgggact gggacagtga caatgactgg gatagtgctg   120
tgctggccct cctggcgctg gctgtggtgg ctgccacagc gctggcctta cactggtttg   180
gctccgggca cgatcaagag gcggcagaac cggtgtccac agccctcggg gctcaacctc   240
atcaggcagg aggagctgag ctggccctgc aaccgaagtc taaggtcagt gatggcagcg   300
aggggcagag cccagggcag gggaaaccag agccccagg acgcggccag cagagccctg   360
tccctgctgc agccgcgggc gggggcctgg ccgccatggc ccggcttcca ctcaagacgg   420
ctgtcgagga ggccgcagaa gaggcattag gacagcaacg ggcagtgcc accccgcgg   480
ccccccgagc ggaaggaaag gagcctccca ggccaggcac tgccctcctg ggcaggagcg   540
aagcagggg gatgtccgcc cccctcctga tccacttcac tcctcggagc cctggcagcg   600
aagcggaggc ggagacaggt ggtgtcaggg cgtcctctcg ccaggccgca ggccccgcgg   660
ggcaacagga cactggcccc tggcaggcgg gcgcggggcc ctcgggctcg atggggagag   720
gccagggccg gcggcggcgg atggacgctg gctcggagca cagagcccgc cgcccccgga   780
aactggaccc gctccgcctg ggcgccgcgg ggagcgtgtg ggacgcggtg gacggggccg   840
ccgccctgga cgccacgcg cgcggcctcc ccacaggacc cccactcgcc caggagcccg   900
cactcccggc gctgccccgct ccccgcgccc tgcagcctgg gtctcagacg gaaggctctg   960
gggccagggg tggctggagc agggagggcct cggggtccc tgccccccga ggaggctgc   1020
cctgggtcag cagggaggtc ccgggcaccc ggagctttgg cccagcccca gactccacgc   1080
gcccctggct agagagtccg cctcaaggtc gcccactctc gtcccaaggg ccgggtgcca   1140
caggggccta cgatgccggc gaggccgggg ctgacagctc ccgagataac agtcctgccg   1200
ctgacctggg gcccaccgg cccccggagc aagcaaagcc ggctgcagcc agccacagcc   1260
gcgcgccctc ccggagccgt gagcctcgcc cgcgctccgc ctcccgccc gcagctcccg   1320
gcccggggtt cccacctgaa gccctgactc tcccctctcc ttcagacttt ttgccctggg   1380
aggttaccca ggatccttcc gtgggcgaaa atctcagagc ggcgccagcc caagttcag   1440
cctcagccca agtcttaact tcagctccag cctcagtcct agcccccagcc ctggcttcat   1500
ccccccagctc agcaccaacc tcagccacca cctcaacctc atcccccacc tcagcccag   1560
ccccagctcc aacctcagct ccaacttcaa ccccagcccc agcccaagt ccagctgcag   1620
ccgcaactcc agcccccagcc ccagtcccag tccaaccct cacacccca tcccccagcc   1680
taaccccagt cccaaccca gccctaagcc cagctccaac ccagcccta accccagccg   1740
catcccccage cctaacccca gtcccaaccc cagccctaag cccagctcca actccagccc   1800
caaccccagc cgcatcccct gcccccagccc ccacctcagc cccaaccca accccagccg   1860
catcccctgc cccagctgac gggtcaaagc ctcaggagag tgtggctctc cccaggcgct   1920
accaggaggg gcaggtctca gccagctggg gaaaccttat tgccatggtt cttagaagcc   1980
acccccttccc caggcaagac aggccccaag ggagtgtccc gagggcggtt cccgggagcc   2040
ccgtgggtcc cagcacttcc acacactctg aggacagaca cggcccctct tcttcagtgg   2100
ggacagtcat agggacaggt acaggggcc tggttgaggc tggaggtcag ccacagccaa   2160
gaagctccga gaccaacgga tcgcccagcc cagaccctcc cccagcctg agaggagagg   2220
gaaccaggga gaaagtctca gaccgctgc cccaagccgc gatgcccagg ggcccgcac   2280
agccccgc gcagaggccg cctggcccg cggcctcctc ctctgcgagg cgctcacagc   2340
cggtacccca gctacggaaa cgcagcaggt gcgaaatcgc cccgagctcg gagcaggagg   2400
tcaggccggc cgcctcgggg gaccctcaag gggaggcgcc ggggagggg ggcagccctg   2460
ccggccgcag cggggcgctc acggaaaagc aggaggagcc ccgagctca tggtgtttct   2520
gcagaggccc gggggttggg gggtggtgga ggggccccgg aagcccagct cccgggccct   2580
ggagcccgcc acgcgcggcag ccctgcgcg cgggctggac ctgggcagtt gcctggacgt   2640
gctggcctttt gcccagcagc acggagagcc cggcctggcg caggagacct acgcgctgat   2700
gagcgacaac ctgctgcgag tgctgggaga cccgtgcctc taccgccggc tgagcgcggc   2760
cgaccgcgag cgcatcctca gcctgcgcgac cggccgggtgc tggcgtcct              2820
cgtactgccc agcctctacc aggggggccg ctcaggcctc ccaggggcc ctcgtggcga   2880
ggagcctcct gcgcgcggccc ctgtgtccct gcctctacct gcgcacctgc atgtgttcaa   2940
ccccccggag aacacctggc ggccctgac ccaggtgccc gaggagccc cgcttcgggg   3000
ctgcggtctc tgcaccatgc acaactacct gtttctggcg ggggcatcc gtggctccgg   3060
tgccaaggcc gtctgctcca cgaggtctt ctgctacaac acatctggag            3120
ccaggttcgg cccatgcagc aggcccgagc ccagctcaag ctggtggccc tggacgggct   3180
gctctatgcc atcggtggcg aatgcctgta cagcatggag tgctacgacc gcgaacagga   3240
cgcctggacc ccacgcgcgc cactcccgc aggcaccttc cctgtggccc acgaggctgt   3300
ggcctgccgt ggggacatct acgtcaccgg gggtcacctc ttctaccgcc tgctcaggta   3360
cagccccgtg aaggatgctt gggacgagtg cccatacagt gccagccacc ggcgttccag   3420
```

```
cgacatcgtg gcactggggg gcttcctgta ccgcttcgac ctgctgcggg gcgtgggcgc   3480
cgccgtgatg cgctacaaca cagtgaccgg ctcctggagc agggctgcct ccctgcccct   3540
gcccgccccc gccccactgc actgcaccac cctgggcaac accatttact gcctcaaccc   3600
ccaggtcact gccaccttca cggtctctgg ggggactgcc cagttccagg ccaaggagct   3660
gcagcccttc cccttgggga gcaccggggt cctcagtcca ttcatcctga ctctgccccc   3720
tgaggaccgg ctgcagacct cactctgagt ggcaggcaga gaaccaaagc tgcttcgctg   3780
ctctccaggg agacctcct gggatgggcc tgagaggccg gggctcaggg aaggggctgg   3840
gatcggaact tcctgctctt gtttctggac aactttcccc ttctgcttta aggttgtcg   3900
attattttga agcccagact ccctcagcct ctttctgccc ctcactccac acccagactg   3960
tttcctgact caattccgta cctacttaca gaccctctca gcttgctgac acccccctgt   4020
ctgtgggact ccctattccc tagagccagg gactgatgcg tctccacaga caaggacttg   4080
gctcgctgga gctctgctga gccgagagag gaggggtag aaaacattca cacttcctat   4140
gctctgtcag caggacaggg agcaaaaacg tccccaggca acgcctcgc ctctgggact   4200
ttctgcctgt cctaaggcct ccccaggtac caaccccgta gctatctggg tctgtttggc   4260
actgtggatt ctcaagggcc tagaaccctt gcctctgaaa ctggtccgct ggtgcagccc   4320
tgctgtctgc agctcctgcc catccccca gcccacacca ggccaggccc actccgggct   4380
caccaccctc tgcagccttg tggggctctc ccagcccctc cagaagccca ccccacttct   4440
cgccaacccc cgatctctaa atgaggcctg agcgtcacc tagttctgcc cctttttagc   4500
tgtgtagact tggacgagac atttgacttc cctttctcct tgtctataaa atgtggacag   4560
tggacgtctg tcacccaaga gagttgtggg agacaagatc acagctatga gcacctcgca   4620
cggtgtccag gatgcacagc acaatccatg atgcgttttc tccccttacg cactttgaaa   4680
cccatgctag aaaagtgaat acatctgact gtgctccact ccaacctcca gcctggatgt   4740
ccctgtctgg gccctttttc tgttttttat tctatgttca gcaccactgg caccaaatac   4800
attttaattc accgaaagca aaaaaaaaaa aaaaaa                             4836

SEQ ID NO: 38          moltype = DNA    length = 2098
FEATURE                Location/Qualifiers
source                 1..2098
                       mol_type = other DNA
                       organism = Homo sapiens
SEQUENCE: 38
ccacctcagc cccaacccca accccagccg catcccctgc cccagctgac gggtcaaagc   60
ctcaggagag tgtggctctc cccaggcgct accaggaggg gcaggtctca gccagctggg   120
gaaaccttat tgccatggtt cttagaagcc accccttccc caggcaagac aggccccaag   180
ggagtgtccc gagggcggtt cccgggagcc ccgtgggtcc cagcacttcc acacactctg   240
aggacagaca cggcccctct tcttcagtgg ggacagtcat agggacaggt acaggggcc   300
tggttgaggc tggaggtcag ccacagccaa gaagctccga gaccaacgga tcgcccagcc   360
cagaccctcc ccaggccta agaggagagg gaaccaggga gaaaagtcta gacccgctgc   420
cccaagccgc gatgcccagg ggccccgcac agccccccgc gcagaggccg cctggcccgg   480
cggcctcctc ctctgcgagg cgctcacagc cggtacccca gctacggaaa cgcagcaggt   540
gcgaaatcgc cccgagctcg gagcaggagg tcaggccggc cgcctcgggg gaccсctcaag   600
gggaggcgcg gggggaggg gcagccctg ccggccgcag cggggcgctc acggaaaagc   660
aggaggaggc ccgaagctca tggтgттттct gcagaggccc gggggttggg gggtggtgga   720
ggggcccccgg aagcccagct cccgggcct ggagcccgcc acggcggcag ccctgcggct   780
gcggctggac ctgggcagtt gcctggacgt gctggccttt gcccagcagc acggagagcc   840
cggcctggcg caggagacct acgcgctgat gagcgacaac ctgctgcgag tgctgggaga   900
cccgtgcctc taccgccggc tgagccgggc cgaccgcgag cgcatcctca gcctgcggac   960
cggccggggc cggccggtgc tgggcgtcct cgtactgccc agcctctacc aggggggccg   1020
ctcagggctc cccaggggcc ctcgtggcga ggagcctcct gcggcggccc ctgtgtccct   1080
gcctctacct gcgcacctgc atgtgtt caa cccccgggag aacacctggc ggcccctgac   1140
ccaggtgccc gaggaggccc cgcttcgggg ctgcggtcct tgcaccatgc acaactacct   1200
gtttctggcg ggggcatcc gtggctccgg tgccaaggcc gtctgctcca acgaggtctt   1260
ctgctacaac cctctgacca acatctggag ccaggtccgg cccatgcagc aggcccgagc   1320
ccagctcaag ctggtggccc tggacgggct gtctatgcc atcggtggcg aatgcctgta   1380
cagcatggag tgctacgacc cgcgaacaga cgcctgacc ccacgcgcgc cactccccgc   1440
aggcaccttc cctgtggccc acgaggctgt ggcctgccgt ggggacatct acgtcaccgg   1500
gggtcacctc ttttaccgcc tgctcaggta cagccccgtg aaggatgctt gggacgagtg   1560
cccatacagt gccagccacc ggcgttccag cgacatcgtg gcactggggg gcttcctgta   1620
ccgcttcgac ctgctgcggg gcgtgggcgc cgccgtgatg cgctacaaca cagtgaccgg   1680
ctcctggagc agggctgcct ccctgcccct gcccgccccc gccccactgc actgcaccac   1740
cctgggcaac accatttact gcctcaaccc ccaggtcact gccaccttca cggtctctgg   1800
ggggactgcc cagttccagg ccaaggagct gcagcccttc cccttgggga gcaccggggt   1860
cctcagtcca ttcatcctga ctctgccccc tgaggaccgg ctgcagacct cactctgagt   1920
ggcaggcaga gaaccaaagc tgcttcgctg ctctccaggg agaccctcct gggatgggcc   1980
tgagaggccg gggctcaggg aaggggctgg gatcggaact tcctgctctt gtttctggac   2040
aactttcccc ttctgcttta aggttgtcg attatttga aaaaaaaaaa aaaaaaa       2098

SEQ ID NO: 39          moltype = DNA    length = 5124
FEATURE                Location/Qualifiers
source                 1..5124
                       mol_type = other DNA
                       organism = Homo sapiens
SEQUENCE: 39
agaagcaggt tggctgtgat gacagcacag agctcaggaa cgctgcctga ggaccctggg   60
gcctacgagg aggagaagag ggcaggagct ggtgggtgc ttgcagagac cctgggctcc   120
tatcctgcca taagcctcgc tgtctcctga tatctcagc caggccctac tgacaccccc   180
aggcctgagt gcaagcagag accccaccat tcccaggccc tggaggactg tccacctta   240
actgggcagc ccttggggca ggcgctggcc ggtgcctcag cccaggcctc tgtgctctgc   300
atgcactgcc agcctgccat caggcctcta ttgcagccct gaaccatgat ccagggcacc   360
```

```
ttggagccag atggtcccct ctggggctgg gactgggaca gtgacaatga ctgggatagt    420
gctgtgctgg ccctcctggc gctggctgtg gtggctgcca cagcgctggc cttacactgg    480
tttggctccg ggcacgatca agaggcggca gaaccggtgt ccacagccct cggggctcaa    540
cctcatcagg caggaggagc tgagctggcc ctgcaaccga agtctaaggt cagtgatggc    600
agcgagggc agagcccagg gcagggaaa ccagagcccc caggacgcgg ccagcagagc    660
cctgtccctg ctgcagcgcc gggcggggc ctggccgcca tggcccggct tccactcaag    720
acggctgtcg aggaggcccg cagagaggca ttaggacagc aacggggcag tgccacccc    780
gcggccccc gagcggaagg aaaggagcct cccaggccag gcactgccct cctgggcagg    840
agcgaagcag ggggatgtc cgccccctc ctgatccact tcactcctcg gagccctggc    900
agcgaagcgg aggcggagac aggtggtgtc agggcgtcct ctcgccaggc cgcaggcccc    960
gcggggcaac aggacactgg cccctggcag gcgggcgcgg ggcctcgggg ctcgatgggg   1020
agaggccggg gccggcggcg gcggatggac gctggctcgg gagacagagc ccgccgcccc   1080
cggaaactgg acccgctccg cctgggcgcc gcggggagc tgtgggacgc ggtggacggg   1140
gccgcgcccc tggacgcca cgcgcgcggc cctcccacag gaccccccact cgcccaggag   1200
cccgcactcc cggcgctgcc cgctccccgc gccctgcagc ctgggtctca gacggaaggc   1260
tctgggccca agggtggctg gagcaggag gcctcggggg tccctgcccc cggaggaggc   1320
tggccctggg tcagcaggga ggtcccggc acccggagct ttggcccagc ccagactcc    1380
acgcgccct ggctagagag tccgcctcaa ggtcgcccac tctcgtccca agggccgggt   1440
gccacagggg cctacgatgc cggcgaggcc ggggctgaca gctcccgaga taacagtcct   1500
gccgctgacc tggggcccac ccggccccg gagcaagcaa agccggctgc agccggccac   1560
agccgcgcgc cctccggag ccgtgagcct cgcccgcgct ccgcctcccc gcccgcagct   1620
cccgccgg ggttcccacc tgaagccctg actctccctc ctccttcaga cttttttgccc   1680
ctggaggtta cccaggatcc ttccgtgggc gaaaatctca gagcggcgcc agccccaagt   1740
tcagcctcag cccaagtctt aacttcagct ccagcctcag tcctagcccc agccctggct   1800
tcatccccca gctcagcacc aacctcagcc accacctcaa cctcatcccc cacctcagcc   1860
ccagcccag ctccaacctc agctccaact tcaaccccag ccccagcccc aagtccagct   1920
gcagccgcaa ctccagcccc agccccagtc ccagtcccaa ccctcacacc ccatcccca   1980
gccctaaccc cagtcccaac cccagcccta agcccagctc caactccagc cctaaccca   2040
gccgcatccc cagcctaac cccagtccca accccagccc taagcccagc tccaactcca   2100
gccccaaccc cagccgcatc ccctgcccca gcccccacct cagccccaac cccaaccca   2160
gccgcatccc ctgccccagc tgacgggtca aagcctcagg agagtgtggc tctcccagg   2220
cgctaccagg aggggcaggt ctcagccagc tggggaaacc ttattgccat ggttcttaga   2280
agccaccct tccccaggca agacaggccc caagggagtg tcccgagggc ggttcccggg   2340
agcccgtgg gtcccagcac ttccacacac tctgaggaca gacacggccc ctcttcttca   2400
gtggggacag tcatagggac aggtacaggg ggcctggttg aggctggagg tcagccacag   2460
ccaagaagct ccgagaccaa cggatcgccc agcccagacc ctcccccagg cctaagagga   2520
gagggaacca gggagaaaag tctagacccg ctgccccaag ccgcgatgcc caggggcccc   2580
gcacagcccc ccgcgcagag gccgcctggc cccgcggcct cctcctctgc gaggcgctca   2640
cagccggtac cccagctacg gaaacgcagc aggtgcgaaa tcgccccgag ctcggagcag   2700
gaggtcaggc cggccgcctc gggggaccct caagggggag cgccggggga gggggcagc   2760
cctgccggcc gcagcgggc gctcacgaaa aagcaggagg aggcccggaa gctcatggtg   2820
tttctgcaga ggcccggggg ttgggggtg gtggagggc cccggaagcc cagctcccgg   2880
gccctggagc ccgccacggc ggcagccctc cggcggccgg cagttgcctg                 2940
gacgtgctgg cctttgccca gcagcacgga gagcccggcc tggcgcagga gacctacgcg   3000
ctgatgagcg acaacctgct gcgagtgctg ggagacccgt gcctctaccg ccggctgagc   3060
gcggccgacc gcgagcgcat cctcagcctg cggaccggcc ggggccgggc ggtgctgggc   3120
gtcctcgtac tgcccagcct ctaccagggg ggcgctcag ggctccccag ggccctcgtg   3180
gcgaggagcc tcctgcggcg gcccctgtgt ccctgcctct acctgcgcac ctgcatgtgt   3240
tcaacccccg ggagaacacc tggcggcccc tgacccaggt gcccgaggag gccccgcttc   3300
ggggctgcgg tctctgcacc atgcacaact acctgtttct ggcgggggc atccgtggct   3360
ccggtgccaa ggccgtctgc tccaacgagg tcttctgcta caaccctctg accaacatct   3420
ggagccaggt tcggcccatg cagcaggccc gagcccagct caagctggtg gccctgacg    3480
ggctgctcta tgccatcggt ggcgaatgcc tgtacagcat ggagtgctac gacccgcgaa   3540
cagacgcctg gaccccacgc gcgccactcc ccgcaggcac cttccctgtg gcccacgagg   3600
ctgtgccctg ccgtggggac atctacgtca ccgggggtca cctcttctac cgcctgctca   3660
ggtacagccc cgtgaaggat gcttgggacg agtgcccata cagtgccagc caccggcgtt   3720
ccagcgacat cgtggcactg gggggcttcc tgtaccgctt cgacctgctg cggggcgtgg   3780
gcgccgccgt gatgcgctac aacacagtga ccggctcctg gagcagggct gcctccctgc   3840
ccctgccgc ccccgcccca ctgccacctca ccacctggg caacaccatt tactgcctca   3900
accccaggt cactgccacc ttcacggtct ctgggggac tgcccagttc caggccaagg   3960
agctgcagcc cttcccttg gggagcaccg ggtcctcag tccattcatc ctgactctgc   4020
ccctgagga ccggctgcag acctcactct gagtggcagg cagagaacca aagctgcttc   4080
gctgctctcc agggagaccc tcctgggatg ggcctgagag gccgggggctc agggaagggg   4140
ctgggatcgg aacttcctgc tctttgtttct ggacaacttt cccttctgc tttaaaggtt   4200
gtcgattatt ttgaagccca gactccctca gcctctttct gcccctcact ccacacccag   4260
actgttttcct gactcaattc cgtacctact tacagaccct ctcagcttgc tgacacccc    4320
ctgtctgtgg gactccctat tccctagagc cagggactga tgcgtctcca cagacaagga   4380
cttggctcgc tggagctctg ctgagccgag agaggagggg gtagaaaaca ttcacacttc   4440
ctatgctctg tcagcaggac agggagcaaa aacgtcccca ggcaacgccc tcgcctctgg   4500
gactttctgc ctgtcctaag gcctcccag gtaccaacc cgtagctatc tgggtctgtt    4560
tggcactgtg gattctcaag ggctagaac ccttgcctct gaaactggtc cgctggtgca   4620
gccctgctgt ctgcagctcc tgcccatacc cccagcccac accaggccag cccactccg    4680
ggctcaccac ccctctgcagc cttgtggggc tctcccagcc cctccagaag cccacccac   4740
ttctcgccaa cccccgatct ctaaatgagg cctgagcgtc accctagttc tgcccctttt   4800
tagctgtgta gacttggacg agacatttga cttcccttc tccttgtcta taaaatgtgg   4860
acagtggacg tctgtcaccc aagagagttg tgggagacaa gatcacagct atgagccct    4920
cgcacggtgt ccaggatgca cagcacaatc catgatgcgt tttctcccct tacgcacttt   4980
gaaacccatg ctagaaaagt gaatacatct gactgtgctc cactccaacc tccagcctgg   5040
atgtccctgt ctgggcccttt tttctgtttt ttattctatg ttcagcacca ctggcaccaa   5100
```

-continued

```
atacatttta attcaccgaa agca                                           5124

SEQ ID NO: 40           moltype = DNA  length = 2989
FEATURE                 Location/Qualifiers
source                  1..2989
                        mol_type = other DNA
                        organism = Homo sapiens
SEQUENCE: 40
ccacctcagc cccaacccca accccagccg catcccctgc cccagctgac gggtcaaagc     60
ctcaggagag tgtggctctc cccaggcgct accaggaggg gcaggtctca gccagctggg    120
gaaaccttat tgccatggtt cttagaagcc acccctttcc caggcaagac aggcccccaag   180
ggagtgtccc gagggcggtt cccgggagcc ccgtgggtcc cagcacttcc acacactctg    240
aggacagaca cggcccctct tcttcagtgg ggacagtcat agggacaggt acaggggggcc   300
tggttgaggc tggaggtcag ccacagccaa gaagctccga gacaacggga tcgcccagcc    360
cagaccctcc cccaggccta agaggagagg gaaccaggga gaaaagtcta gacccgctgc    420
cccaagccgc gatgcccagg ggccccgcac agccccccgc gcagaggccg cctggccccg    480
cggcctcctc ctctgcgagg cgctcacagc cggtaccccca gctacggaaa cgcagcaggt    540
gcgaaatcgc cccgagctcg gagcagggag tcaggccggc ccctcgggg gaccctcaag    600
gggaggcgcc gggggagggg ggcagccctg ccggccgcag cggggcgctc acggaaaagc    660
aggaggaggc ccggaagctc atggtgtttc tgcagaggcc cggggggttgg ggggtggtgg    720
aggggccccg gaagcccagc tcccgggccc tggagcccgc cacggcggca gccctgcggc    780
ggcggctgga cctgggcagt tgcctggacg tgctggcctt tgcccagcag cacggagagc    840
ccggcctggc gcaggagacc tacgcgctga tgagcgacaa cctgctgcga gtgctggag    900
acccgtgcct ctaccgccgg ctgagcgcgg ccgaccgcga gcgcatcctc agcctgcgga    960
ccggccgggg ccgggcggtg ctgggcgtcc tcgtactgcc cagcctctac caggggggcc    1020
gctcagggct cccccagggcc ctcgtcagcg ggagcctcct gggcgggcc ctgtgtccct    1080
gcctctacct gcgcacctgc atgtgttcaa cccccgggag aacacctggc ggcccctgac    1140
ccaggtgccc gaggaggccc cgcttcgggg ctgcggtctc tgcaccatgc acaactacct    1200
gtttctggcg ggggcatcc gtggctccgg tgccaaggcc gtctgctcca acgaggtctt    1260
ctgctacaac cctctgacca acatctggag ccaggttcgg ccatgcagc aggcccgagc    1320
ccagctcaag ctggtggccc tggacgggct gctctatgcc atcggtgccg aatgcctgta    1380
cagcatggag tgctacgacc cgcgaacaga cgcctggacc ccacgcgcgc cactccccgc    1440
aggcaccttc cctgtggccc acgaggctgt ggcctgccgt ggggacatct acgtcaccgg    1500
gggtcacctc ttctaccgcc tgctcaggta cagccccgtg aaggatgctt gggacgagtg    1560
cccatacagt gccagccacc ggcgttccag cgacatcggg gcatggggg gcttcctgta    1620
ccgcttcgac ctgctgcggg gcgtgggcgc cgccgtgatg cgctacaaca cagtgaccgg    1680
ctcctggagc agggctgcct ccctgcccct gccgcccccc gcccactgc actgcaccac    1740
cctgggcaac accatttact gcctcaaccc ccaggtcact gccaccttca cggtctctgg    1800
ggggactgcc cagttccagg ccaaggagct gcagcccttc cccttggga gcaccggggt    1860
cctcagtcca ttcatcctga ctctgcccccc tgaggaccgg ctgcagacct cactctgagt    1920
ggcaggcaga gaaccaaagc tgcttcgctg ctctccaggg agaccctcct gggatgggcc    1980
tgagaggccg gggctcaggg aaggggctgg gatcggaact tcctgctctt gtttctggac    2040
aactttcccc ttctgcttta aaggttgtcg attattttga agcccagact ccctcagcct    2100
ctttctgccc ctcactccac acccagactg tttcctgact caattccgta cctacttaca    2160
gaccctctca gcttgctgac accccccgt ctgtgggact cccctattccc tagagccagg    2220
gactgatgcg tctccacaga caaggacttg gctcgctgga gtctgctga gccgagagag    2280
gaggggtag aaaacattca cacttcctgt gctctgtcag caggacaggg agcaaaaacg    2340
tccccaggca acgccctcgc ctctgggact ttctgcctgt cctaaggcct ccccaggtac    2400
caaccccgta gctatctggg tctgtttggc actgtggatt tcaagggcc tagaaccctt    2460
gcctctgaaa ctggtccgct ggtgcagccc tgctgtctgc agctcctgcc cataccccca    2520
gcccacacca ggcaggccc actccgggct caccacccctc tgcaccttg tggggctctc    2580
ccagcccctc cagaagccca ccccacttct cgccaacccc cgatctctaa atgaggcctg    2640
agcgtcaccc tagttctgcc cctttttagc tgtgtagact tggacgagac atttgacttc    2700
cctttctcct tgtctataaa atgtggacag tggacgtctg tcacccaaga gagttgtggg    2760
agacaagatc acagctatga gcacctcgca cggtgtccag gatgcacagc acaatccatg    2820
atgcgttttc tcccccttacg cactttgaaa cccatgctag aaaagtgaat acatctgact   2880
gtgctccact ccaacctcca gcctggatgt ccctgtctgg gcccttttttc tgttttttat   2940
tctatgttca gcaccactgg caccaaatac attttaattc accgaaagc                2989

SEQ ID NO: 41           moltype = DNA  length = 4836
FEATURE                 Location/Qualifiers
source                  1..4836
                        mol_type = other DNA
                        organism = Homo sapiens
SEQUENCE: 41
actgccagcc tgccatcagg cctctattgc agccctgaac catgatccag ggcaccttgg     60
agccagatgg tcccctctgg ggctgggact ggacagtgat caatgactgg gatagtgctg    120
tgctggcccct cctggcgctg gctgtggtgg ctgccacagc gctggcctta cactggtttg    180
gctccgggca cgatcaagag gcggcagaac cggtgtccaa agccctcggg gctcaacctc    240
atcaggcagg aggagctgag ctggccctgc aaccgaagtc taaggtcagt gatgcagcag    300
aggggcagag cccagggcag gggaaaccag agccccagg acgcggccag cagagccctg    360
tccctgctgc agcgccgggc gggggcctgg ccgccatggg ccggcttcca ctcaagacgg    420
ctgtcgagga ggcccgcaga gaggcattag acagcaacg gggcagtgcc accccgcgcg    480
ccccccgagc ggaaggaaag gagcctccca ggccaggcac tgcctcctg gcaggaggg    540
aagcagggg gatgtccgcc ccctcctga tccacttcac tcctcggagc cctggcagcg    600
aagcggaggc ggagacaggt ggtgtcaggg cgtcctctcg ccaggccgca ggccccgcgg    660
ggcaacagga cactggcccc tgcaggcgg gcgcggggcc ctcgggctcg atggggagag    720
gccggggccg gcgcggcgg atgacgctg gctcgggaga cagagccgc cgcccccgga    780
aactggaccc gctccgcctg ggcgccgcgg ggagcgtgtg ggacgcggtg gacggggccg    840
```

-continued

```
ccgccctgga cgcccacgcg cgcggcctcc ccacaggacc cccactcgcc caggagcccg  900
cactccggc gctgcccgct ccccgcgccc tgcagcctgg gtctcagacg gaaggctctg   960
gggcaaggg tggctggagc agggaggcct cgggggtccc tgcccccgga ggaggctggc  1020
cctgggtcag cagggaggtc ccgggcaccc ggagctttgg cccagcccca gactccacgc  1080
gccctggct agagagtccg cctcaaggtc gcccactctc gtccaaggg gcgggtgcca    1140
caggggccta cgatgccggc gaggccgggg ctgacagctc ccgagataac agtcctgccg  1200
ctgacctggg gcccacccgg ccccggagc aagcaaagcc ggctgcagcc ggccacagcc   1260
gcgcgccctc ccggagccgt gagcctcgcc cgcgctccgc ctcccgccc gcagctcccg   1320
gcccggggtt cccacctgaa gccctgactc tcccctctcc ttcagacttt ttgccccctgg 1380
aggttaccca ggatccttcc gtgggcgaaa atctcagagc ggcgccagcc ccaagttcag   1440
cctcagccca agtcttaact tcagctccag cctcagtcct agcccagcc ctggcttcat    1500
cccccagctc agcaccaacc tcagccacca cctcaacctc atccccacc tcagcccag    1560
ccccagctcc aacctcagct ccaacttcaa ccccagcccc agcccaagt ccagctgcag    1620
ccgcaactcc agccccagcc ccagtcccag tcccaaccct cacaccccca tccccagccc   1680
taaccccagt cccaaccca gcctaagcc cagctccaac tccagcccta acccagccg    1740
catcccagc cctaacccca gtcccaaccc cagcctaag cccagctcca actccagccc    1800
caacccagc cgcatcccct gccccagccc ccacggcag cccaacccca acccagccg    1860
catcccctgc cccagctgac gggtcaaagc ctcaggagag tgtggctctc cccaggcgct    1920
accaggaggg gcaggtctca gccagctggg gaaaccttat tgccatggtt cttagaagcc   1980
accccttccc caggcaagac aggcccaag ggagtgtccc gagggcggtt cccgggagcc     2040
ccgtgggtcc cagcacttcc acacactctg aggacagaca cggcccctct tcttcagtgg    2100
ggacagtcat agggacaggt acaggggc tggttgaggc tggaggtcag cacagccaa     2160
gaagctccga gaccaacgga tcgcccagcc cagaccctcc cccaggccta agaggagagg    2220
gaaccaggga gaaagtctca gacccgctgc cccaagccgc gatgcccagg ggccccgcac    2280
agcccccgc gcagaggccg cctggccccg cggcctcctc ctctgcgagg cgctcacagc    2340
cggtaccca gctacggaaa cgcagcaggt gcgaaatcgc cccagctcg gagcaggagg    2400
tcaggccggc cgcctcgggg gaccctcaag gggaggcgcc ggggggaggg ggcagccctg    2460
ccggccgcag cggggcgctc acggaaaagc aggaggaggc ccggaagctc atggtgtttc    2520
tgcagaggcc cggggggttgg ggggtggtgg aggggccccg gaagcccagc tcccgggccc    2580
tggagccgc cacggcggca gccctgcggc ggcggctgga cctggcaggt tgcctggacg    2640
tgctggcctt tgcccagcag cacggagagc ccggcctggc gcaggagacc tacgcgctga    2700
tgagcgacaa cctgctgcga gtgctgggag accgtgcct ctaccgcgg ctgagcgcgg    2760
ccgaccgcga gcgcatcctc agcctgcgga ccggccgggg ccgggcggtg ctgggcgtcc    2820
tcgtactgcc cagcctctac caggggggcc gctcagggct cccgcagggcc ctcgtggcga    2880
ggagcctcct ccggcggccc ctgtgtccct gcctctacct gcgcaacctgc atgtgttcaa    2940
cccccgggag aacacctggc ggcccctgac ccaggtgccc gaggaggccc cgcttcgggg    3000
ctgcggtctc tgcaccatgc acaactacct gtttctggcg gggggcatcc gtggctccgg    3060
tgccaaggcc gtctgctcca acgaggtctt ctgctacaac cctctgacca acatctggag    3120
ccaggttcgg cccatgcagc aggcccgagc ccagctcacg ctggtggccc tggacggagg    3180
gctctatgcc atcggtggcg aatgcctgta cagcatggag tgctacgacc gcgaacaga    3240
cgcctggacc ccacgcgcgc cactcccgc aggcaccttc cctgtggccc acgaggctgt    3300
ggcctgccgt ggggacatct acgtcaccgg gggtcacctc ttctaccgcc tgctcaggta    3360
cagccccgtg aaggatgctt gggacgagtg ccatacagt gccagccacc ggcgttccag    3420
cgacatcgtg gcactggggg gcttcctgta ccgcttcgac ctgctgcggg gcgtgggcgc    3480
cgccgtgatg cgctacaaca cagtgaccgg ctcctggagc agggctgcct ccctgccct    3540
gcccgccccc gccccactgc actgcaccac cctgggcaac accatttact gcctcaaccc    3600
ccaggtcact gccaccttca cggtctctgg ggggactgcc cagttccagg ccaaggagct    3660
gcagcccttc cccttgggga gcaccggggt cctcagtcca ttcatcctga ctctgccccc    3720
tgaggaccgg ctgcagacct cactctgagt ggcaggcaga gaaccaaagc tgcttcgctg    3780
ctctccaggg agaccctcct gggatggcc tgagaggccg gggctcaggg aaggggctgg    3840
gatcggaact tcctgctctt gttctggac aactttccc ttctgcttta aaggttgtca    3900
attattttga agcccagact ccctcagcct ctttctgcc ctcactccac acccagactg    3960
tttcctgact caattccgta cctacttaca gaccctctca gcttgctgac accccctgt    4020
ctgtgggact cccatattccc tagagccagg gactgatgcg tctccacaga caaggacttg    4080
gctcgctgga gctctgctga gccgagagag gaggggtag aaaacattca cacttcctat    4140
gctctgtcag caggacaggg agcaaaaacg tccccaggca acgccctcgc ctctgggact    4200
ttctgcctgt cctaaggcct ccccaggtac caaccccgta gctatctggg tctgtttggc    4260
actgtggatt ctcaagggcc tagaacccctt gcctctgaaa ctggtccgct ggtgcagccc    4320
tgctgtctgc agctcctgcc catacccca gcccacacca ggcaggccc actccgggct    4380
caccaccctc tgcagccttg tgggctctc ccagcccctc cagaagccca cccactctt    4440
cgccaacccc cgatctctaa atgaggcctg agcgtcaccc tagttctgcc cctttttagc    4500
tgtgtagact tggacgagac atttgacttc cctttctcct tgtctataaa atgtggacag    4560
tggacgtctg tcacccaaga gagttgtggg agacaagatc acagctatga gcacctcgca    4620
cggtgtccag gatgcacagc acaatccatg atgcgttttc tcccttacg cactttgaaa    4680
cccatgctag aaaagtgaat acatctgact gtgctccact ccaacctcca gcctggatgt    4740
ccctgtctgg gccttttttc tgtttttttat tctatgttca gcaccactgg caccaaatac    4800
attttaattc accgaaagca aaaaaaaaaa aaaaaa                              4836

SEQ ID NO: 42        moltype = DNA   length = 2098
FEATURE              Location/Qualifiers
source               1..2098
                     mol_type = other DNA
                     organism = Homo sapiens
SEQUENCE: 42
ccacctcagc cccaaccca accccagccg catcccctgc cccagctgac gggtcaaagc    60
ctcaggagag tgtggctctc cccaggcgct accaggaggg gcaggtctca gccagctggg   120
gaaaccttat tgccatggtt cttagaagcc accccttccc caggcaagac aggcccaag    180
ggagtgtccc gagggcggtt cccggagcc ccgtgggtcc cagcacttcc acacactctg    240
aggacagaca cggcccctct tcttcagtgg ggacagtcat agggacaggt acaggggcc    300
```

-continued

```
tggttgaggc tggaggtcag ccacagccaa gaagctccga gaccaacgga tcgcccagcc    360
cagaccctcc cccaggccta agaggagagg gaaccaggga gaaaagtcta gaccgctgc    420
cccaagccgc gatgcccagg ggccccgcac agcccccgc gcagaggccg cctggccccg    480
cggcctcctc ctctgcgagg cgctcacagc cggtaccccca gctacggaaa cgcagcaggt    540
gcgaaatcgc cccgagctcg gagcagggca tcaggccggc cgcctcgggg gacccctcaag    600
gggaggcgcc gggggagggg ggcagccctg ccggccgcag cggggcgctc acggaaaagc    660
aggaggaggc ccggaagctc atggtgtttc tgcagaggcc cggggggttgg ggggtggtgg    720
aggggccccg gaagcccagc tcccgggccc tggagcccgc cacggcggca gccctgcggc    780
ggcggctgga cctgggcagt tgcctggacg tgctggcctt tgcccagcag cacggagagc    840
ccggctggc gcaggagacc tacgcgctga tgagcgacaa cctgctgcga gtgctgggag    900
acccgtgcct ctaccgccgg ctgagcgcgg ccgaccgcga gcgcatcctc agcctgcgga    960
ccggccgggg ccgggcggtg ctgggcgtcc tcgtactgcc cagcctctac caggggggcc   1020
gctcagggct ccccagggcc ctcgtggcga ggagcctcct gcggcggccc ctgtgtccct   1080
gcctctacct gcgcacctgc atgtgttcaa cccccgggca aacacctggc ggcccctgac   1140
ccaggtgccc gaggaggccc cgcttcgggg ctgcggtctc tgcaccatgc acaactacct   1200
gtttctggcg gggggcatcc gtggctccgg tgccaaggcc gtctgctcca acgaggtctt   1260
ctgctacaac cctctgacca catctggag ccaggttcgg cccatgcagc aggcccgagc   1320
ccagctcaag ctggtggccc tggacgggct gctctatgcc atcggtggcg aatgcctgta   1380
cagcatggag tgctacgacc cgcgaacaga cgcctggacc ccacgcgcgc cactccccgc   1440
aggcaccttc cctgtggccc acgaggctgt ggcctgccgt ggggacatct acgtcaccgg   1500
gggtcacctc ttctaccgcc tgctcaggta cagccccgtg aaggatgctt gggacgagtg   1560
cccatacagt gccagccacc ggcgttccag cgacatcggt ggactggggg gcttcctgta   1620
ccgcttcgac ctgctgcggg gcgtgggcgc cgccgtgatg cgctacaaca cagtgaccgg   1680
ctcctggagc agggctgcct ccctgccccct gcccgcccccc gcccactgc actgcaccac   1740
cctgggcaac accatttact gcctcaaccc caggtcact gccaccttca cggtctctgg   1800
ggggactgcc cagttccagg ccaaggagct gcagcccttc ccctggggga gcagcggggt   1860
cctcagtcca ttcatcctga ctctgccccc tgaggaccgg ctgcagacct cactctgagt   1920
ggcaggcaga gaaccaaagc tgcttcgctg ctctccaggg agaccctcct gggatgggcc   1980
tgagaggccg gggctcaggg aaggggctgg gatcggaact tcctgctctt gtttctggac   2040
aactttcccc ttctgcttta aaggttgtcg attattttga aaaaaaaaaa aaaaaaaa     2098
```

```
SEQ ID NO: 43         moltype = AA  length = 885
FEATURE               Location/Qualifiers
source                1..885
                      mol_type = protein
                      organism = Homo sapiens
SEQUENCE: 43
MIQGTLEPDG PLWGWDWDSD NDWDSAVLAL LALAVVAATA LALHWFGSGH DQEAAEPVST    60
ALGAQPHQAG GAELALQPKS KVSDGSEGQS PGQGKPEPPG RGQQSPVPAA APGGGLAAMA   120
RLPLKTAVEE ARREALGQQR GSATPAAPRA EGKEPPRPGT ALLGRSEAGG MSAPLLIHFT   180
PRSPGSEAEA ETGGVRASSR QAAGPAGQQD TGPWQAGAGP SGSMGRGRGR RRRMDAGSGD   240
RARRPRKLDP LRLGAAGSVW DAVDGAAALD AHARGLPTGP PLAQEPALPA LPAPRALQPG   300
SQTEGSGAKG GWSREASGVP APGGGWPWVS REVPGTRSFG PAPDSTRPWL ESPPQGRPLS   360
SQGPGATGAY DAGEAGADSS RDNSPAADLG PTRPPEQAKP AAAGHSRAPS RSREPRPRSA   420
SPPAAPGPGF PPEALTLPSP SDFLPLEVTQ DPSVGENLRA APAPSSASAQ VLTSAPASVL   480
APALASSPSS APTSATTSTS SPTSAPAPAP TSAPTSTPAP APSPAAAATP APAPVPVPTL   540
TPPSPALTPV PTPALSPAPT PALTPAASPA LTPVPTPALS LTPPAPTPA APAPAPTSA   600
PTPTPAASPA PADGSKPQES VALPRRYQEG QVSASWGNLI AMVLRSHPFP RQDRPQGSVP   660
RAVPGSPVGP STSTHSEDRH GPSSSVGTVI GTGTGGLVEA GGQPQPRSSE TNGSPSPDPP   720
PGLRGEGTRE KSLDPLPQAA MPRGPAQPPA QRPPGPAASS SARRSQPVPQ LRKRSRCEIA   780
PSSEQEVRPA ASGDPQGEAP GEGGSPAGRS GALTEKQEEA RSSWCFCRGP GVGGWWRGPG   840
SPAPGPWSPP RRQPCGGGWT WAVAWTCWPL PSSTESPAWR RRPTR                   885

SEQ ID NO: 44         moltype = AA  length = 244
FEATURE               Location/Qualifiers
source                1..244
                      mol_type = protein
                      organism = Homo sapiens
SEQUENCE: 44
MVLRSHPFPR QDRPQGSVPR AVPGSPVGPS TSTHSEDRHG PSSSVGTVIG TGTGGLVEAG    60
GQPQPRSSET NGSPSPDPPP GLRGEGTREK SLDPLPQAAM PRGPAQPPAQ RPPGPAASSS   120
ARRSQPVPQL RKRSRCEIAP SSEQEVRPAA SGDPQGEAPG EGGSPAGRSG ALTEKQEEAR   180
SSWCFCRGPG VGGWWRGPGS PAPGPWSPPR RQPCGGGWTW AVAWTCWPLP SSTESPAWRR   240
RPTR                                                                244

SEQ ID NO: 45         moltype = AA  length = 145
FEATURE               Location/Qualifiers
source                1..145
                      mol_type = protein
                      organism = Homo sapiens
SEQUENCE: 45
MPRGPAQPPA QRPPGPAASS SARRSQPVPQ LRKRSRCEIA PSSEQEVRPA ASGDPQGEAP    60
GEGGSPAGRS GALTEKQEEA RSSWCFCRGP GVGGWWRGPG SPAPGPWSPP RRQPCGGGWT   120
WAVAWTCWPL PSSTESPAWR RRPTR                                         145

SEQ ID NO: 46         moltype = AA  length = 975
FEATURE               Location/Qualifiers
source                1..975
                      mol_type = protein
```

```
                    organism = Homo sapiens
SEQUENCE: 46
MIQGTLEPDG PLWGWDWDSD NDWDSAVLAL LALAVVAATA LALHWFGSGH DQEAAEPVST    60
ALGAQPHQAG GAELALQPKS KVSDGSEGQS PGQGKPEPPG RGQQSPVPAA APGGGLAAMA   120
RLPLKTAVEE ARREALGQQR GSATPAAPRA EGKEPPRPGT ALLGRSEAGG MSAPLLIHFT   180
PRSPGSEAEA ETGGVRASSR QAAGPAGQQD TGPWQAGAGP SGSMGRGRGR RRRMDAGSGD   240
RARRPRKLDP LRLGAAGSVW DAVDGAAALD AHARGLPTGP PLAQEPALPA LPAPRALQPG   300
SQTEGSGAKG GWSREASGVP APGGGWPWVS REVPGTRSFG PAPDSTRPWL ESPPQGRPLS   360
SQGPGATGAY DAGEAGADSS RDNSPAADLG PTRPPEQAKP AAAGHSRAPS RSREPRPRSA   420
SPPAAPGPGF PPEALTLPSP SDFLPLEVTQ DPSVGENLRA APAPSSASAQ VLTSAPASVL   480
APALASSPSS APTSATTSTS SPTSAPAPAP TSAPTSTPAP APSPAAAATP APAPVPVPTL   540
TPPSPALTPV PTPALSPAPT PALTPAASPA LTPVPTPALS PAPTPAPTPA ASPAPAPTSA   600
PTPTPAASPA PADGSKPQES VALPRRYQEG QVSASWGNLI AMVLRSHPFP RQDRPQGSVP   660
RAVPGSPVGP STSTHSEDRH GPSSSVGTVI GTGTGGLVEA GGQPQPRSSE TNGSPSPDPP   720
PGLRGEGTRE KSLDPLPQAA MPRGPAQPPA QRPPGPAASS SARRSQPVPQ LRKRSRCEIA   780
PSSEQEVRPA ASGDPQGEAP GEGGSPAGRS GALTEKQEEA RKLMVFLQRP GGWGVVEGPR   840
KPSSRALEPA TAAALRRRLD LGSCLDVLAF AQQHGEPGLA QETYALMSDN LLRVLGDPCL   900
YRRLSAADRE RILSLRTGRG RAVLGVLVLP SLYQGGRSGL PRALVARSLL RRPLCPCLYL   960
RTCMCSTPGR TPGGP                                                   975

SEQ ID NO: 47          moltype = AA  length = 334
FEATURE                Location/Qualifiers
source                 1..334
                       mol_type = protein
                       organism = Homo sapiens
SEQUENCE: 47
MVLRSHPFPR QDRPQGSVPR AVPGSPVGPS TSTHSEDRHG PSSSVGTVIG TGTGGLVEAG    60
GQPQPRSSET NGSPSPDPPP GLRGEGTREK SLDPLPQAAM PRGPAQPPAQ RPPGPAASSS   120
ARRSQPVPQL RKRSRCEIAP SSEQEVRPAA SGDPQGEAPG EGGSPAGRSG ALTEKQEEAR   180
KLMVFLQRPG GWGVVEGPRK PSSRALEPAT AAALRRRLDL GSCLDVLAFA QQHGEPGLAQ   240
ETYALMSDNL LRVLGDPCLY RRLSAADRER ILSLRTGRGR AVLGVLVLPS LYQGGRSGLP   300
RALVARSLLR RPLCPCLYLR TCMCSTPGRT PGGP                              334

SEQ ID NO: 48          moltype = AA  length = 235
FEATURE                Location/Qualifiers
source                 1..235
                       mol_type = protein
                       organism = Homo sapiens
SEQUENCE: 48
MPRGPAQPPA QRPPGPAASS SARRSQPVPQ LRKRSRCEIA PSSEQEVRPA ASGDPQGEAP    60
GEGGSPAGRS GALTEKQEEA RKLMVFLQRP GGWGVVEGPR KPSSRALEPA TAAALRRRLD   120
LGSCLDVLAF AQQHGEPGLA QETYALMSDN LLRVLGDPCL YRRLSAADRE RILSLRTGRG   180
RAVLGVLVLP SLYQGGRSGL PRALVARSLL RRPLCPCLYL RTCMCSTPGR TPGGP        235
```

KELCH DOMAIN CONTAINING 7B (KLHDC7B) VARIANTS AND USES THEREOF

REFERENCE TO SEQUENCE LISTING

This application includes a Sequence Listing submitted electronically as a text file named 18923804001SEQ, created on May 1, 2021, with a size of 246 kilobytes. The Sequence Listing is incorporated herein by reference.

FIELD

The present disclosure relates generally to the treatment of subjects having hearing loss, methods of identifying subjects having an increased risk of developing hearing loss, and methods of detecting KLHDC7B variant nucleic acid molecules and variant polypeptides.

BACKGROUND

Auditory dysfunction in humans is an ongoing problem in the medical fields of otology and audiology. About 300 million people worldwide currently suffer from moderate to severe hearing loss, and this number is expected to increase to 700 million by the year 2015. Auditory dysfunction is a common consequence of aging in Western societies. Approximately 17 percent of Americans have hearing loss and half of that number are under the age of 65. It is predicted that the number of Americans with hearing loss will exceed 70 million by the year 2030.

Auditory dysfunctions typically arise from both acute and chronic exposures to loud sounds, ototoxic chemicals, and aging. Hearing impairments can be attributed to a wide variety of causes, including infections (e.g., otitis media), genetic predisposition, mechanical injury, tumors, loud sounds or prolonged exposure to noise, aging, and chemical-induced ototoxicity (e.g., antibiotics or platin drugs) that damages neurons and/or hair cells of the peripheral auditory system. This can be caused by acute noise or can be progressive over time. Sounds exceeding 85 decibels can cause hearing loss and is generated by sound sources such as, gun shots, exploding bombs, jet engines, power tools, and musical concerts. Other common everyday activities and products also give rise to high intensity noise such as use of hair dryers, MP3 players, lawn mowers, and blenders. Military personnel are particularly at risk for noise induced hearing loss due to typical military noise exposures. Side effects of noise-induced hearing loss include tinnitus (ringing in the ears), diminished speech understanding, hyperacusis, and various types of auditory processing impairments. Exposures to commonly used medications may also induce auditory dysfunctions. For instance, subjects treated with anticancer therapies, antibiotics, and other medications often develop hearing loss as a side effect. Furthermore, exposure to industrial chemicals and gasses may induce auditory impairments.

The prevalence of hearing loss after damage to the mammalian cochlea has been thought to be due to a lack of spontaneous regeneration of hair cells and/or neurons, the primary components to detect sound. Humans are born with about 15,000 inner ear hair cells and hair cells do not regenerate after birth. Supporting cells, which surround hair cells in the normal cochlear epithelium, have potential to differentiate into new hair cells in the neonatal mouse following ototoxic damage. Using lineage tracing, the new hair cells, predominantly outer hair cells, have been shown to arise from Lgr5-expressing inner pillar and third Deiters cells, and new hair cell generation has been shown to incrementally be increased by pharmacological inhibition of Notch.

Permanent damage to the hair cells of the inner ear results in sensorineural hearing loss, leading to communication difficulties in a large percentage of the population. Hair cells are the receptor cells that transduce the acoustic stimulus. Regeneration of damaged hair cells provide an avenue for the treatment of a condition that currently has no therapies other than prosthetic devices. Although hair cells do not regenerate in the mammalian cochlea, new hair cells in lower vertebrates are generated from epithelial cells, called supporting cells, that surround hair cells.

Currently, very few cases of hearing loss can actually be cured. Audiological devices such as hearing aids have limitations including the inability to improve speech intelligibility. Of those impacted by hearing impairments, less than 20 percent presently use hearing instruments. In cases of age-related, noise- or drug-induced auditory dysfunctions, often the only effective way to currently "treat" the disorder or reduce its severity is prevention, such as by avoiding excessive noise and using ear protectors, practicing a healthy lifestyle, and avoiding exposure to ototoxic drugs and substances if possible.

Thus, there remains a long felt need to protect auditory cells before injury and preserve/promote the function of existing cells after injury.

Kelch Domain Containing 7B (KLHDC7B) is a protein member of the Kelch superfamily, proteins involved in cellular processes such as cytoskeletal rearrangement and protein degradation, and also have roles in extracellular communication, cell morphology, gene expression and actin binding. In addition, members of this superfamily can be co-opted by a virus after an infection. Alterations in this protein superfamily have been associated with various types of cancer, including leukemia, lung, prostate, brain, and Hodgkin's disease. KLHDC7B was identified as being hypermethylated, yet upregulated, in breast cancer cells. Moderate levels of KLHDC7B expression were observed in hair cells of the ear, while outer hair cells seem to show slightly higher expression (gEAR portal).

SUMMARY

The present disclosure provides methods of identifying a subject having an increased risk for developing hearing loss, wherein the methods comprise: determining or having determined the presence or absence of a KLHDC7B missense variant nucleic acid molecule encoding a KLHDC7B predicted loss-of-function polypeptide in a biological sample obtained from the subject; wherein: i) when the subject is KLHDC7B reference, then the subject does not have an increased risk for developing hearing loss; and ii) when the subject is heterozygous or homozygous for a KLHDC7B missense variant nucleic acid molecule encoding a KLHDC7B predicted loss-of-function polypeptide, then the subject has an increased risk for developing hearing loss.

The present disclosure also provides methods of treating a subject with a therapeutic agent that treats or inhibits hearing loss, wherein the subject has hearing loss, the methods comprising the steps of: determining whether the subject has a KLHDC7B missense variant nucleic acid molecule encoding a KLHDC7B predicted loss-of-function polypeptide by: i) obtaining or having obtained a biological sample from the subject; and ii) performing or having performed a sequence analysis on the biological sample to determine if the subject has a genotype comprising the KLHDC7B missense variant nucleic acid molecule encoding a KLHDC7B predicted loss-of-function polypeptide; and administering or continuing to administer the therapeutic agent that treats or inhibits hearing loss in a standard dosage amount to a subject that is KLHDC7B reference; and administering or continuing to administer the therapeutic agent that treats or inhibits hearing loss in an amount that is the same as or greater than a standard dosage amount to a subject that is heterozygous or homozygous for the KLHDC7B missense variant nucleic acid molecule; wherein the presence of a genotype having the a KLHDC7B missense variant nucleic acid molecule encoding a KLHDC7B predicted loss-of-function polypeptide indicates the subject has an increased risk of developing hearing loss.

The present disclosure also provides methods of detecting a KLHDC7B missense variant nucleic acid molecule encoding a KLHDC7B predicted loss-of-function polypeptide in a subject comprising assaying a sample obtained from the subject to determine whether a nucleic acid molecule in the sample is: i) a genomic nucleic acid molecule comprising a nucleotide sequence: comprising an adenine at a position corresponding to position 3,778 according to SEQ ID NO:2, or the complement thereof; lacking a guanine at a position corresponding to position 2,807 according to SEQ ID NO:1, or the complement thereof; or lacking a guanine at a position corresponding to position 3,170 according to SEQ ID NO:1, or the complement thereof; ii) an mRNA molecule comprising a nucleotide sequence: comprising an adenine at a position corresponding to position 3,778 according to SEQ ID NO:7, or the complement thereof; comprising an adenine at a position corresponding to position 1,644 according to SEQ ID NO:8, or the complement thereof; comprising an adenine at a position corresponding to position 3,474 according to SEQ ID NO:9, or the complement thereof; comprising an adenine at a position corresponding to position 1,644 according to SEQ ID NO:10, or the complement thereof; lacking a guanine at a position corresponding to position 2,807 according to SEQ ID NO:3, or the complement thereof; lacking a guanine at a position corresponding to position 673 according to SEQ ID NO:4, or the complement thereof; lacking a guanine at a position corresponding to position 2,503 according to SEQ ID NO:5, or the complement thereof; lacking a guanine at a position corresponding to position 673 according to SEQ ID NO:6, or the complement thereof; lacking a guanine at a position corresponding to position 3,170 according to SEQ ID NO:3, or the complement thereof; lacking a guanine at a position corresponding to position 1,036 according to SEQ ID NO:4, or the complement thereof; lacking a guanine at a position corresponding to position 2,866 according to SEQ ID NO:5, or the complement thereof; or lacking a guanine at a position corresponding to position 1,036 according to SEQ ID NO:6, or the complement thereof; or iii) a cDNA molecule comprising a nucleotide sequence: comprising an adenine at a position corresponding to position 3,778 according to SEQ ID NO:15, or the complement thereof; comprising an adenine at a position corresponding to position 1,644 according to SEQ ID NO:16, or the complement thereof; comprising an adenine at a position corresponding to position 3,474 according to SEQ ID NO:17, or the complement thereof; comprising an adenine at a position corresponding to position 1,644 according to SEQ ID NO:18, or the complement thereof; lacking a guanine at a position corresponding to position 2,807 according to SEQ ID NO:11, or the complement thereof; lacking a guanine at a position corresponding to position 673 according to SEQ ID NO:12, or the complement thereof; lacking a guanine at a position corresponding to position 2,503 according to SEQ ID NO:13, or the complement thereof; lacking a guanine at a position corresponding to position 673 according to SEQ ID NO:14, or the complement thereof; lacking a guanine at a position corresponding to position 3,170 according to SEQ ID NO:11, or the complement thereof; lacking a guanine at a position corresponding to position 1,036 according to SEQ ID NO:12, or the complement thereof; lacking a guanine at a position corresponding to position 2,866 according to SEQ ID NO:13, or the complement thereof; or lacking a guanine at a position corresponding to position 1,036 according to SEQ ID NO:14, or the complement thereof.

The present disclosure also provides methods of detecting the presence of a KLHDC7B V1145M, V504M, V405M, K822fs, K181fs, K82fs, G943fs, G302fs, or G203fs variant polypeptide, comprising performing an assay on a sample obtained from a subject to determine whether a KLHDC7B protein in the sample: comprises a methionine at a position corresponding to position 1,145 according to SEQ ID NO:22, comprises a methionine at a position corresponding to position 504 according to SEQ ID NO:23, comprises a methionine at a position corresponding to position 405 according to SEQ ID NO:24, terminates at a position corresponding to position 885 according to SEQ ID NO:43 and lacks amino acids at positions corresponding to positions 886 to 1,235 of SEQ ID NO:19, terminates at a position corresponding to position 244 according to SEQ ID NO:44 and lacks amino acids at positions corresponding to positions 245 to 594 of SEQ ID NO:20, terminates at a position corresponding to position 145 according to SEQ ID NO:45 and lacks amino acids at positions corresponding to positions 146 to 495 of SEQ ID NO:21, terminates at a position corresponding to position 975 according to SEQ ID NO:46 and lacks amino acids at positions corresponding to positions 976 to 1,235 of SEQ ID NO:19, terminates at a position corresponding to position 334 according to SEQ ID NO:47 and lacks amino acids at positions corresponding to positions 335 to 594 of SEQ ID NO:20, and terminates at a position corresponding to position 235 according to SEQ ID NO:48 and lacks amino acids at positions corresponding to positions 236 to 495 of SEQ ID NO:21.

The present disclosure also provides therapeutic agents that treat or inhibit hearing loss for use in the treatment of hearing loss in a subject having: i) a genomic nucleic acid molecule having a nucleotide sequence encoding a KLHDC7B polypeptide, wherein the nucleotide sequence: comprises an adenine at a position corresponding to position 3,778 according to SEQ ID NO:2, or the complement thereof; lacks a guanine at a position corresponding to position 2,807 according to SEQ ID NO:1, or the complement thereof; or lacks a guanine at a position corresponding to position 3,170 according to SEQ ID NO:1, or the complement thereof; ii) an mRNA molecule having a nucleotide sequence encoding a KLHDC7B polypeptide, wherein the nucleotide sequence comprises: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof; or iii) a cDNA molecule having a nucleotide sequence encoding a KLHDC7B polypeptide, wherein the nucleotide sequence comprises: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof.

DESCRIPTION

Figure 1:
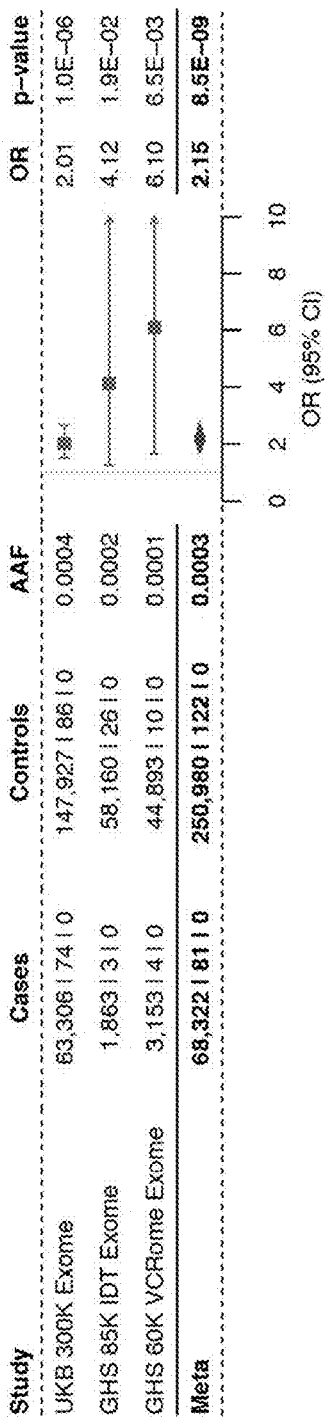
FIG. 1 (Panels A, B, and C) shows that a common missense variant, and rare, predicted loss-of-function (pLOF) variants in KLHDC7B are associated with increased risk for hearing loss. The association with the pLOF variants suggest that the missense is likely to be loss or of reduced function, and that reduction in KLHDC7B confers an increase in the risk for hearing loss.
Figure 1:
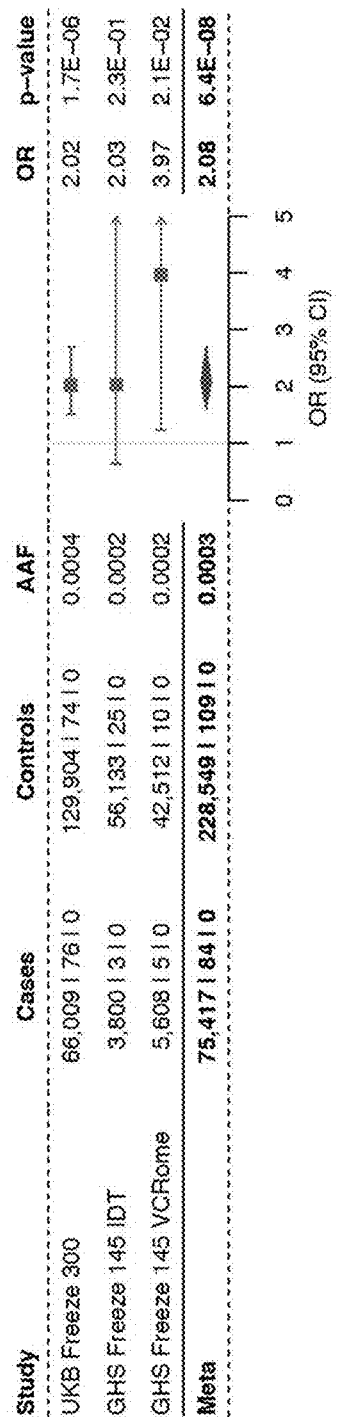
Figure 1:
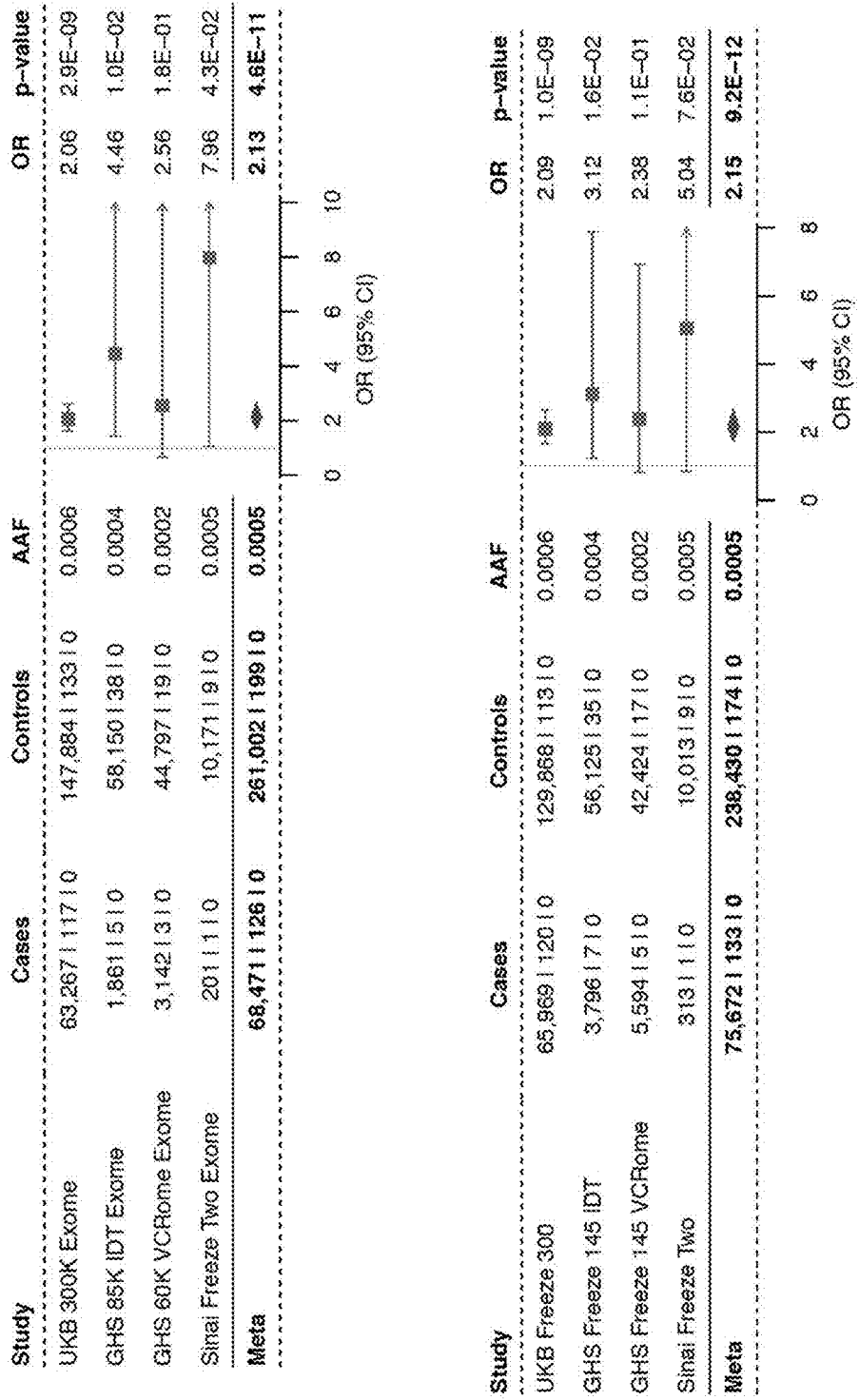

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

A rare variant in the KLHDC7B gene associated with an increased risk of developing hearing loss, such as conductive hearing loss, sensorineural hearing loss, or neural hearing loss, in humans has been identified in accordance with the present disclosure. For example, a genetic alteration that changes the guanine nucleotide of position 3,778 in the human KLHDC7B reference (see, SEQ ID NO:1) to adenine has been observed to indicate that the human having such an alteration may have an increased risk of developing hearing loss, such as conductive hearing loss, sensorineural hearing loss, or neural hearing loss. It is believed that no rare (minor allele frequency <1%) and predicted loss-of-function variants of the KLHDC7B gene or protein have any known association with hearing loss, such as conductive hearing loss, sensorineural hearing loss, or neural hearing loss. Altogether, the genetic analyses described herein surprisingly indicate that the KLHDC7B gene and, in particular, a variant in the KLHDC7B gene, associates with an increased risk of developing hearing loss, such as conductive hearing loss, sensorineural hearing loss, or neural hearing loss. Therefore, subjects that have a KLHDC7B variant nucleic acid molecule or polypeptide that associates with an increased risk of developing hearing loss, such as conductive hearing loss, sensorineural hearing loss, or neural hearing loss, may be treated such that hearing loss is prevented, the symptoms thereof are reduced, and/or development of symptoms is repressed. Accordingly, the present disclosure provides methods of leveraging the identification of such variants in subjects to identify or stratify risk in such subjects of developing hearing loss, such as conductive hearing loss, sensorineural hearing loss, or neural hearing loss, or to diagnose subjects as having an increased risk of developing hearing loss, such as conductive hearing loss, sensorineural hearing loss, or neural hearing loss, such that subjects at risk or subjects with active disease may be treated accordingly.

For purposes of the present disclosure, any particular subject can be categorized as having one of three KLHDC7B genotypes: i) KLHDC7B reference; ii) heterozygous for a KLHDC7B missense variant nucleic acid molecule encoding a KLHDC7B predicted loss-of-function polypeptide; or iii) homozygous for a KLHDC7B missense variant nucleic acid molecule encoding a KLHDC7B predicted loss-of-function polypeptide. A subject is KLHDC7B reference when the subject does not have a copy of a KLHDC7B missense variant nucleic acid molecule encoding a KLHDC7B predicted loss-of-function polypeptide. A subject is heterozygous for a KLHDC7B missense variant nucleic acid molecule encoding a KLHDC7B predicted loss-of-function polypeptide when the subject has a single copy of a KLHDC7B missense variant nucleic acid molecule encoding a KLHDC7B predicted loss-of-function polypeptide. A KLHDC7B missense variant nucleic acid molecule encoding a KLHDC7B predicted loss-of-function polypeptide is any KLHDC7B nucleic acid molecule (such as, a genomic nucleic acid molecule, an mRNA molecule, or a cDNA molecule) encoding a KLHDC7B polypeptide having a partial loss-of-function, a complete loss-of-function, a predicted partial loss-of-function, or a predicted complete loss-of-function. A subject who has a KLHDC7B polypeptide having a partial loss-of-function (or predicted partial loss-of-function) is hypomorphic for KLHDC7B. The KLHDC7B missense variant nucleic acid molecule encoding a KLHDC7B predicted loss-of-function polypeptide can be any nucleic acid molecule encoding KLHDC7B V1145M, V504M, V405M, K822fs, K181fs, K82fs, G943fs, G302fs, or G203fs. A subject is homozygous for a KLHDC7B missense variant nucleic acid molecule encoding a KLHDC7B predicted loss-of-function polypeptide when the subject has two copies of a KLHDC7B missense variant nucleic acid molecule encoding a KLHDC7B predicted loss-of-function polypeptide.

For subjects that are genotyped or determined to be heterozygous or homozygous for a KLHDC7B missense variant nucleic acid molecule encoding a KLHDC7B predicted loss-of-function polypeptide, such subjects have an increased risk of developing hearing loss, such as conductive hearing loss, sensorineural hearing loss, or neural hearing loss. For subjects that are genotyped or determined to be heterozygous or homozygous for a KLHDC7B missense variant nucleic acid molecule encoding a KLHDC7B predicted loss-of-function polypeptide, such subjects can be treated with an agent effective to treat hearing loss, such as conductive hearing loss, sensorineural hearing loss, or neural hearing loss.

In any of the embodiments described herein, the KLHDC7B missense variant nucleic acid molecule encoding a KLHDC7B predicted loss-of-function polypeptide can be any KLHDC7B nucleic acid molecule (such as, for example, genomic nucleic acid molecule, mRNA molecule, or cDNA molecule) encoding a KLHDC7B polypeptide having a partial loss-of-function, a complete loss-of-function, a predicted partial loss-of-function, or a predicted complete loss-of-function. For example, the KLHDC7B missense variant nucleic acid molecule encoding a KLHDC7B predicted loss-of-function polypeptide can be any nucleic acid molecule encoding KLHDC7B V1145M, V504M, V405M, K822fs, K181fs, K82fs, G943fs, G302fs, or G203fs. In some embodiments, the KLHDC7B missense variant nucleic acid molecule encodes KLHDC7B V1145M. In some embodiments, the KLHDC7B missense variant nucleic acid molecule encodes KLHDC7B V504M. In some embodiments, the KLHDC7B missense variant nucleic acid molecule encodes KLHDC7B V405M. In some embodiments, the KLHDC7B missense variant nucleic acid molecule encodes KLHDC7B K822fs. In some embodiments, the KLHDC7B missense variant nucleic acid molecule encodes KLHDC7B K181fs. In some embodiments, the KLHDC7B missense variant nucleic acid molecule encodes KLHDC7B K82fs. In some embodiments, the KLHDC7B missense variant nucleic acid molecule encodes KLHDC7B G943fs. In some embodiments, the KLHDC7B missense variant nucleic acid molecule encodes KLHDC7B G302fs. In some embodiments, the KLHDC7B missense variant nucleic acid molecule encodes KLHDC7B G203fs.

In any of the embodiments described herein, the KLHDC7B predicted loss-of-function polypeptide can be any KLHDC7B polypeptide having a partial loss-of-function, a complete loss-of-function, a predicted partial loss-of-function, or a predicted complete loss-of-function. In any of the embodiments described herein, the KLHDC7B predicted loss-of-function polypeptide can be any of the KLHDC7B polypeptides described herein including, for example, KLHDC7B V1145M, V504M, V405M, K822fs, K181fs, K82fs, G943fs, G302fs, or G203fs. In some embodiments, the KLHDC7B predicted loss-of-function polypeptide is KLHDC7B V1145M. In some embodiments, the KLHDC7B predicted loss-of-function polypeptide is KLHDC7B V504M. In some embodiments, the KLHDC7B predicted loss-of-function polypeptide is KLHDC7B V405M. In some embodiments, the KLHDC7B predicted loss-of-function polypeptide is KLHDC7B K822fs. In some embodiments, the KLHDC7B predicted loss-of-function polypeptide is KLHDC7B K181fs. In some embodiments, the KLHDC7B predicted loss-of-function polypeptide is KLHDC7B K82fs. In some embodiments, the KLHDC7B predicted loss-of-function polypeptide is KLHDC7B G943fs. In some embodiments, the KLHDC7B predicted loss-of-function polypeptide is KLHDC7B G302fs. In some embodiments, the KLHDC7B predicted loss-of-function polypeptide is KLHDC7B G203fs.

In any of the embodiments described herein, hearing loss is conductive hearing loss, sensorineural hearing loss, or neural hearing loss. In any of the embodiments described herein, hearing loss is conductive hearing loss. In any of the embodiments described herein, hearing loss is sensorineural hearing loss. In any of the embodiments described herein, hearing loss is neural hearing loss.

Symptoms of hearing loss include, but are not limited to, hearing problem (muffling of speech and other sounds, difficulty understanding words, especially against background noise or in a crowd, or trouble hearing consonants), ringing in the ears, sensitivity to sound, and speech delay in a child.

The present disclosure also provides methods of treating a subject with a therapeutic agent that treats or inhibits hearing loss, wherein the subject has hearing loss. In some embodiments, the methods comprise determining whether the subject has a KLHDC7B missense variant nucleic acid molecule encoding a KLHDC7B predicted loss-of-function polypeptide by obtaining or having obtained a biological sample from the subject, and performing or having performed a sequence analysis on the biological sample to determine if the subject has a genotype comprising the KLHDC7B missense variant nucleic acid molecule encoding a KLHDC7B predicted loss-of-function polypeptide. The methods comprise administering or continuing to administer the therapeutic agent that treats or inhibits hearing loss in a standard dosage amount to a subject that is KLHDC7B reference. The methods further comprise administering or continuing to administer the therapeutic agent that treats or inhibits hearing loss in an amount that is the same as or greater than a standard dosage amount to a subject that is heterozygous or homozygous for the KLHDC7B missense variant nucleic acid molecule. The presence of a genotype having the KLHDC7B missense variant nucleic acid molecule encoding a KLHDC7B predicted loss-of-function polypeptide indicates the subject has an increased risk of developing hearing loss. In some embodiments, the subject is KLHDC7B reference. In some embodiments, the subject is heterozygous for a KLHDC7B missense variant nucleic acid molecule encoding a KLHDC7B predicted loss-of-function polypeptide. In some embodiments, the subject is homozygous for a KLHDC7B missense variant nucleic acid molecule encoding a KLHDC7B predicted loss-of-function polypeptide.

In some embodiments, the methods of treatment further comprise detecting the presence or absence of a KLHDC7B missense variant nucleic acid molecule encoding a KLHDC7B predicted loss-of-function polypeptide in a biological sample from the subject. As used throughout the present disclosure, a "KLHDC7B missense variant nucleic acid molecule encoding a KLHDC7B predicted loss-of-function polypeptide" is any KLHDC7B nucleic acid molecule (such as, for example, genomic nucleic acid molecule, mRNA molecule, or cDNA molecule) encoding a KLHDC7B polypeptide having a partial loss-of-function, a complete loss-of-function, a predicted partial loss-of-function, or a predicted complete loss-of-function.

Detecting the presence or absence of a KLHDC7B missense variant nucleic acid molecule encoding a KLHDC7B predicted loss-of-function polypeptide in a biological sample from a subject and/or determining whether a subject has a KLHDC7B missense variant nucleic acid molecule encoding a KLHDC7B predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The present disclosure also provides methods of treating a subject with a therapeutic agent that treats or inhibits hearing loss, wherein the subject has hearing loss. In some embodiments, the method comprises determining whether the subject has a KLHDC7B predicted loss-of-function polypeptide by obtaining or having obtained a biological sample from the subject, and performing or having performed an assay on the biological sample to determine if the subject has a KLHDC7B predicted loss-of-function polypeptide. The methods comprise administering or continuing to administer the therapeutic agent that treats or inhibits hearing loss in a standard dosage amount to a subject that is KLHDC7B reference. The methods further comprise administering or continuing to administer the therapeutic agent that treats or inhibits hearing loss in an amount that is the same as or greater than a standard dosage amount to a subject that has a KLHDC7B predicted loss-of-function polypeptide. The presence of a KLHDC7B predicted loss-of-function polypeptide indicates the subject has an increased risk of developing hearing loss. In some embodiments, the subject has a KLHDC7B predicted loss-of-function polypeptide. In some embodiments, the subject does not have a KLHDC7B predicted loss-of-function polypeptide.

Detecting the presence or absence of a KLHDC7B predicted loss-of-function polypeptide in a biological sample from a subject and/or determining whether a subject has a KLHDC7B predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit hearing loss include, but are not limited to: antioxidants, calcium-channel blockers, anti-inflammatory drugs (such as steroids), apoptosis inhibitors, D-methionine, ebselen, N-acetylcysteine, lipoic acid, combination of ebselen and allopurinol, resveratrol, neurotrophic factors (such as T-817MA), caspase inhibitors (such as z-DEVD-fmk), copper transport inhibitors (such as cimetidine and copper sulphate), and micronutrients with antioxidant vitamins.

In some embodiments, the dose of the therapeutic agents that treat or inhibit hearing loss can be increased by about 10%, by about 20%, by about 30%, by about 40%, by about 50%, by about 60%, by about 70%, by about 80%, or by about 90% for subjects that are heterozygous or homozygous for a KLHDC7B predicted loss-of-function variant (i.e., a greater amount than the standard dosage amount) compared to subjects that are KLHDC7B reference (who may receive a standard dosage amount). In some embodiments, the dose of the therapeutic agents that treat or inhibit hearing loss can be increased by about 10%, by about 20%, by about 30%, by about 40%, or by about 50%. In addition, the dose of therapeutic agents that treat or inhibit hearing loss in subjects that are heterozygous or homozygous for a KLHDC7B predicted loss-of-function variant can be administered more frequently compared to subjects that are KLHDC7B reference.

In some embodiments, the dose of the therapeutic agents that treat or inhibit hearing loss can be increased by about 10%, by about 20%, by about 30%, by about 40%, by about 50%, by about 60%, by about 70%, by about 80%, or by about 90% for subjects that are homozygous for a KLHDC7B predicted loss-of-function variant compared to subjects that are heterozygous for a KLHDC7B predicted loss-of-function variant. In some embodiments, the dose of the therapeutic agents that treat or inhibit hearing loss can be increased by about 10%, by about 20%, by about 30%, by about 40%, or by about 50%. In addition, the dose of therapeutic agents that treat or inhibit hearing loss in subjects that are homozygous for a KLHDC7B predicted loss-of-function variant can be administered more frequently compared to subjects that are heterozygous for a KLHDC7B predicted loss-of-function variant.

Administration of the therapeutic agents that treat or inhibit hearing loss can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit hearing loss can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in hearing loss, a decrease/reduction in the severity of hearing loss (such as, for example, a reduction or inhibition of development or hearing loss), a decrease/reduction in symptoms and hearing loss-related effects, delaying the onset of symptoms and hearing loss-related effects, reducing the severity of symptoms of hearing loss-related effects, reducing the severity of an acute episode, reducing the number of symptoms and hearing loss-related effects, reducing the latency of symptoms and hearing loss-related effects, an amelioration of symptoms and hearing loss-related effects, reducing secondary symptoms, preventing relapse to hearing loss, decreasing the number or frequency of relapse episodes, increasing latency between symptomatic episodes, increasing time to sustained progression, speeding recovery, and/or increasing efficacy of or decreasing resistance to alternative therapeutics, following administration of the agent or composition comprising the agent. A prophylactic effect may comprise a complete or partial avoidance/inhibition or a delay of hearing loss development/progression (such as, for example, a complete or partial avoidance/inhibition or a delay) following administration of a therapeutic protocol. Treatment of hearing loss encompasses the treatment of subjects already diagnosed as having any form of hearing loss at any clinical stage or manifestation, the delay of the onset or evolution or aggravation or deterioration of the symptoms or signs of hearing loss, and/or preventing and/or reducing the severity of hearing loss.

The present disclosure also provides methods of identifying a subject having an increased risk for developing hearing loss. In some embodiments, the method comprises determining or having determined in a biological sample obtained from the subject the presence or absence of a KLHDC7B missense variant nucleic acid molecule (such as a genomic nucleic acid molecule, mRNA molecule, and/or cDNA molecule) encoding a KLHDC7B predicted loss-of-function polypeptide. When the subject lacks a KLHDC7B missense variant nucleic acid molecule encoding a KLHDC7B predicted loss-of-function polypeptide (i.e., the subject is genotypically categorized as a KLHDC7B reference), then the subject does not have an increased risk for developing hearing loss. When the subject has a KLHDC7B missense variant nucleic acid molecule encoding a KLHDC7B predicted loss-of-function polypeptide (i.e., the subject is heterozygous or homozygous for a KLHDC7B missense variant nucleic acid molecule encoding a KLHDC7B predicted loss-of-function polypeptide), then the subject has an increased risk for developing hearing loss.

Determining whether a subject has a KLHDC7B missense variant nucleic acid molecule encoding a KLHDC7B predicted loss-of-function polypeptide in a biological sample from a subject and/or determining whether a subject has a KLHDC7B missense variant nucleic acid molecule encoding a KLHDC7B predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing hearing loss, the subject is further treated with a therapeutic agent that treats or inhibits hearing loss, as described herein. In some embodiments, when the subject is heterozygous or homozygous for a KLHDC7B missense variant nucleic acid molecule encoding a KLHDC7B predicted loss-of-function polypeptide, the subject is administered the therapeutic agent that treats or inhibits hearing loss in a dosage amount that is the same as or greater than a standard dosage amount. In some embodiments, when the subject is homozygous for a KLHDC7B missense variant nucleic acid molecule encoding a KLHDC7B predicted loss-of-function polypeptide, the subject is administered the therapeutic agent that treats or inhibits hearing loss in a dosage amount that is the same as or greater than the dosage amount administered to a subject that is heterozygous for a KLHDC7B missense variant nucleic acid molecule encoding a KLHDC7B predicted loss-of-function polypeptide. In some embodiments, the subject is KLHDC7B reference. In some embodiments, the subject is heterozygous for a KLHDC7B missense variant nucleic acid molecule encoding a KLHDC7B predicted loss-of-function polypeptide. In some embodiments, the subject is homozygous for a KLHDC7B missense variant nucleic acid molecule encoding a KLHDC7B predicted loss-of-function polypeptide.

The present disclosure also provides methods of detecting the presence or absence of a KLHDC7B missense variant genomic nucleic acid molecule encoding a KLHDC7B predicted loss-of-function polypeptide in a biological sample from a subject, and/or a KLHDC7B missense variant mRNA molecule encoding a KLHDC7B predicted loss-of-function polypeptide in a biological sample from a subject, and/or a KLHDC7B missense variant cDNA molecule encoding a KLHDC7B predicted loss-of-function polypeptide produced from an mRNA molecule in a biological sample from a subject. It is understood that gene sequences within a population and mRNA molecules encoded by such genes can vary due to polymorphisms such as single-nucleotide polymorphisms. The sequences provided herein for the KLHDC7B variant genomic nucleic acid molecule, KLHDC7B variant mRNA molecule, and KLHDC7B variant cDNA molecule are only exemplary sequences. Other sequences for the KLHDC7B variant genomic nucleic acid molecule, variant mRNA molecule, and variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any KLHDC7B variant nucleic acid molecule, preliminary processing designed to isolate or enrich the sample for the genomic DNA can be employed. A variety of techniques may be used for this purpose. When detecting the level of any KLHDC7B variant mRNA, different techniques can be used enrich the biological sample with mRNA. Various methods to detect the presence or level of an mRNA or the presence of a particular variant genomic DNA locus can be used.

In some embodiments, detecting a KLHDC7B missense variant nucleic acid molecule encoding a KLHDC7B predicted loss-of-function polypeptide in a subject comprises assaying or genotyping a biological sample obtained from the subject to determine whether a KLHDC7B genomic nucleic acid molecule in the biological sample, and/or a KLHDC7B mRNA molecule in the biological sample, and/or a KLHDC7B cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a KLHDC7B missense variant nucleic acid molecule encoding a KLHDC7B predicted loss-of-function polypeptide (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the nucleotide sequence comprises: an adenine at a position corresponding to position 3,778 according to SEQ ID NO:2 (for genomic nucleic acid molecules), an adenine at a position corresponding to position 3,778 according to SEQ ID NO:7 (for mRNA molecules), or an adenine at a position corresponding to position 3,778 according to SEQ ID NO:15 (for cDNA molecules obtained from mRNA molecules).

In some embodiments, the nucleotide sequence comprises: an adenine at a position corresponding to position 1,644 according to SEQ ID NO:8 (for mRNA molecules), or an adenine at a position corresponding to position 1,644 according to SEQ ID NO:16 (for cDNA molecules obtained from mRNA molecules).

In some embodiments, the nucleotide sequence comprises: an adenine at a position corresponding to position 3,474 according to SEQ ID NO:9 (for mRNA molecules), or an adenine at a position corresponding to position 3,474 according to SEQ ID NO:17 (for cDNA molecules obtained from mRNA molecules).

In some embodiments, the nucleotide sequence comprises: an adenine at a position corresponding to position 1,644 according to SEQ ID NO:10 (for mRNA molecules), or an adenine at a position corresponding to position 1,644 according to SEQ ID NO:18 (for cDNA molecules obtained from mRNA molecules).

In some embodiments, the nucleotide sequence: lacks a guanine at a position corresponding to position 2,807 according to SEQ ID NO:1 (for genomic nucleic acid molecules), lacks a guanine at a position corresponding to position 2,807 according to SEQ ID NO:3 (for mRNA molecules), or lacks a guanine at a position corresponding to position 2,807 according to SEQ ID NO:11 (for cDNA molecules obtained from mRNA molecules).

In some embodiments, the nucleotide sequence: lacks a guanine at a position corresponding to position 673 according to SEQ ID NO:4 (for mRNA molecules), or lacks a guanine at a position corresponding to position 673 according to SEQ ID NO:12 (for cDNA molecules obtained from mRNA molecules).

In some embodiments, the nucleotide sequence: lacks a guanine at a position corresponding to position 2,503 according to SEQ ID NO:5 (for mRNA molecules), or lacks a guanine at a position corresponding to position 2,503 according to SEQ ID NO:13 (for cDNA molecules obtained from mRNA molecules).

In some embodiments, the nucleotide sequence: lacks a guanine at a position corresponding to position 673 according to SEQ ID NO:6 (for mRNA molecules), or lacks a guanine at a position corresponding to position 673 according to SEQ ID NO:14 (for cDNA molecules obtained from mRNA molecules).

In some embodiments, the nucleotide sequence: lacks a guanine at a position corresponding to position 3,170 according to SEQ ID NO:1 (for genomic nucleic acid molecules), lacks a guanine at a position corresponding to position 3,170 according to SEQ ID NO:3 (for mRNA molecules), or lacks a guanine at a position corresponding to position 3,170 according to SEQ ID NO:11 (for cDNA molecules obtained from mRNA molecules).

In some embodiments, the nucleotide sequence: lacks a guanine at a position corresponding to position 1,036 according to SEQ ID NO:4 (for mRNA molecules), or lacks a guanine at a position corresponding to position 1,036 according to SEQ ID NO:12 (for cDNA molecules obtained from mRNA molecules).

In some embodiments, the nucleotide sequence: lacks a guanine at a position corresponding to position 2,866 according to SEQ ID NO:5 (for mRNA molecules), or lacks a guanine at a position corresponding to position 2,866 according to SEQ ID NO:13 (for cDNA molecules obtained from mRNA molecules).

In some embodiments, the nucleotide sequence: lacks a guanine at a position corresponding to position 1,036 according to SEQ ID NO:6 (for mRNA molecules), or lacks a guanine at a position corresponding to position 1,036 according to SEQ ID NO:14 (for cDNA molecules obtained from mRNA molecules).

In some embodiments, the nucleotide sequence: comprises an adenine at a position corresponding to position 3,778 according to SEQ ID NO:2, or the complement thereof; lacks a guanine at a position corresponding to position 2,807 according to SEQ ID NO:1, or the complement thereof; or lacks a guanine at a position corresponding to position 3,170 according to SEQ ID NO:1, or the complement thereof.

In some embodiments, the nucleotide sequence: comprises an adenine at a position corresponding to position 3,778 according to SEQ ID NO:7, or the complement thereof; comprises an adenine at a position corresponding to position 1,644 according to SEQ ID NO:8, or the complement thereof; comprises an adenine at a position corresponding to position 3,474 according to SEQ ID NO:9, or the complement thereof; comprises an adenine at a position corresponding to position 1,644 according to SEQ ID NO:10, or the complement thereof; lacks a guanine at a position corresponding to position 2,807 according to SEQ ID NO:3, or the complement thereof; lacks a guanine at a position corresponding to position 673 according to SEQ ID NO:4, or the complement thereof; lacks a guanine at a position corresponding to position 2,503 according to SEQ ID NO:5, or the complement thereof; lacks a guanine at a position corresponding to position 673 according to SEQ ID NO:6, or the complement thereof; lacks a guanine at a position corresponding to position 3,170 according to SEQ ID NO:3, or the complement thereof; lacks a guanine at a position corresponding to position 1,036 according to SEQ ID NO:4, or the complement thereof; lacks a guanine at a position corresponding to position 2,866 according to SEQ ID NO:5, or the complement thereof; or lacks a guanine at a position corresponding to position 1,036 according to SEQ ID NO:6, or the complement thereof.

In some embodiments, the nucleotide sequence: comprises an adenine at a position corresponding to position 3,778 according to SEQ ID NO:15, or the complement thereof; comprises an adenine at a position corresponding to position 1,644 according to SEQ ID NO:16, or the complement thereof; comprises an adenine at a position corresponding to position 3,474 according to SEQ ID NO:17, or the complement thereof; comprises an adenine at a position corresponding to position 1,644 according to SEQ ID NO:18, or the complement thereof; lacks a guanine at a position corresponding to position 2,807 according to SEQ ID NO:11, or the complement thereof; lacks a guanine at a position corresponding to position 673 according to SEQ ID NO:12, or the complement thereof; lacks a guanine at a position corresponding to position 2,503 according to SEQ ID NO:13, or the complement thereof; lacks a guanine at a position corresponding to position 673 according to SEQ ID NO:14, or the complement thereof; lacks a guanine at a position corresponding to position 3,170 according to SEQ ID NO:11, or the complement thereof; lacks a guanine at a position corresponding to position 1,036 according to SEQ ID NO:12, or the complement thereof; lacks a guanine at a position corresponding to position 2,866 according to SEQ ID NO:13, or the complement thereof; or lacks a guanine at a position corresponding to position 1,036 according to SEQ ID NO:14, or the complement thereof.

In some embodiments, the biological sample comprises a cell or cell lysate. Such methods can further comprise, for example, obtaining a biological sample from the subject comprising a KLHDC7B genomic nucleic acid molecule or mRNA molecule, and if mRNA, optionally reverse transcribing the mRNA into cDNA. Such assays can comprise, for example determining the identity of these positions of the particular KLHDC7B nucleic acid molecule. In some embodiments, the method is an in vitro method.

In some embodiments, the determining step, detecting step, or sequence analysis comprises sequencing at least a portion of the nucleotide sequence of the KLHDC7B genomic nucleic acid molecule, the KLHDC7B mRNA molecule, or the KLHDC7B cDNA molecule in the biological sample, wherein the sequenced portion comprises one or more variations that cause a loss-of-function (partial or complete) or are predicted to cause a loss-of-function (partial or complete).

In some embodiments, the determining step, detecting step, or sequence analysis comprises sequencing at least a portion of: the nucleotide sequence of the KLHDC7B genomic nucleic acid molecule in the biological sample, wherein the sequenced portion comprises a position corresponding to position 3,778 according to SEQ ID NO:2, or the complement thereof; the nucleotide sequence of the KLHDC7B mRNA molecule in the biological sample, wherein the sequenced portion comprises a position corresponding to position 3,778 according to SEQ ID NO:7, or the complement thereof; and/or the nucleotide sequence of the KLHDC7B cDNA molecule produced from the mRNA in the biological sample, wherein the sequenced portion comprises a position corresponding to position 3,778 according to SEQ ID NO:15, or the complement thereof. When the sequenced portion of the KLHDC7B nucleic acid molecule in the biological sample comprises an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises a position corresponding to position 1,644 according to SEQ ID NO:8, or the complement thereof; and/or the nucleotide sequence of the KLHDC7B cDNA molecule produced from the mRNA in the biological sample, wherein the sequenced portion comprises a position corresponding to position 1,644 according to SEQ ID NO:16, or the complement thereof. When the sequenced portion of the KLHDC7B nucleic acid molecule in the biological sample comprises an adenine at a position corresponding to position 1,644 according to SEQ ID NO:8, or an adenine at a position corresponding to position 1,644 according to SEQ ID NO:16, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises a position corresponding to position 3,474 according to SEQ ID NO:9, or the complement thereof; and/or the nucleotide sequence of the KLHDC7B cDNA molecule produced from the mRNA in the biological sample, wherein the sequenced portion comprises a position corresponding to position 3,474 according to SEQ ID NO:17, or the complement thereof. When the sequenced portion of the KLHDC7B nucleic acid molecule in the biological sample comprises an adenine at a position corresponding to position 3,474 according to SEQ ID NO:9, or an adenine at a position corresponding to position 3,474 according to SEQ ID NO:17, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises a position corresponding to position 1,644 according to SEQ ID NO:10, or the complement thereof; and/or the nucleotide sequence of the KLHDC7B cDNA molecule produced from the mRNA in the biological sample, wherein the sequenced portion comprises a position corresponding to position 1,644 according to SEQ ID NO:18, or the complement thereof. When the sequenced portion of the KLHDC7B nucleic acid molecule in the biological sample comprises an adenine at a position corresponding to position 1,644 according to SEQ ID NO:10, or an adenine at a position corresponding to position 1,644 according to SEQ ID NO:18, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises positions corresponding to positions 2,806-2,807 according to SEQ ID NO:25, or the complement thereof; the nucleotide sequence of the KLHDC7B mRNA molecule in the biological sample, wherein the sequenced portion comprises positions corresponding to positions 2,806-2,807 according to SEQ ID NO:27, or the complement thereof; and/or the nucleotide sequence of the KLHDC7B cDNA molecule produced from the mRNA in the biological sample, wherein the sequenced portion comprises positions corresponding to positions 2,806-2,807 according to SEQ ID NO:35, or the complement thereof. When the sequenced portion of the KLHDC7B nucleic acid molecule in the biological sample comprises a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises positions corresponding to positions 672-673 according to SEQ ID NO:28, or the complement thereof; and/or the nucleotide sequence of the KLHDC7B cDNA molecule produced from the mRNA in the biological sample, wherein the sequenced portion comprises positions corresponding to positions 672-673 according to SEQ ID NO:36, or the complement thereof. When the sequenced portion of the KLHDC7B nucleic acid molecule in the biological sample comprises a CG dinucleotide at positions corresponding to positions 672-673 according to SEQ ID NO:28, or a CG dinucleotide at positions corresponding to positions 672-673 according to SEQ ID NO:36, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises positions corresponding to positions 2,502-2,503 according to SEQ ID NO:29, or the complement thereof; and/or the nucleotide sequence of the KLHDC7B cDNA molecule produced from the mRNA in the biological sample, wherein the sequenced portion comprises positions corresponding to positions 2,502-2,503 according to SEQ ID NO:37, or the complement thereof. When the sequenced portion of the KLHDC7B nucleic acid molecule in the biological sample comprises a CG dinucleotide at positions corresponding to positions 2,502-2,503 according to SEQ ID NO:29, or a CG dinucleotide at positions corresponding to positions 2,502-2,503 according to SEQ ID NO:37, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B mRNA molecule in the biological sample, wherein the sequenced portion comprises positions corresponding to positions 672-673 according to SEQ ID NO:30, or the complement thereof; and/or the nucleotide sequence of the KLHDC7B cDNA molecule produced from the mRNA in the biological sample, wherein the sequenced portion comprises positions corresponding to positions 672-673 according to SEQ ID NO:38, or the complement thereof. When the sequenced portion of the KLHDC7B nucleic acid molecule in the biological sample comprises a CG dinucleotide at positions corresponding to positions 672-673 according to SEQ ID NO:30, or a CG dinucleotide at positions corresponding to positions 672-673 according to SEQ ID NO:38, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises positions corresponding to positions 3,169-3,170 according to SEQ ID NO:26, or the complement thereof; the nucleotide sequence of the KLHDC7B mRNA molecule in the biological sample, wherein the sequenced portion comprises positions corresponding to positions 3,169-3,170 according to SEQ ID NO:31, or the complement thereof; and/or the nucleotide sequence of the KLHDC7B cDNA molecule produced from the mRNA in the biological sample, wherein the sequenced portion comprises positions corresponding to positions 3,169-3,170 according to SEQ ID NO:39, or the complement thereof. When the sequenced portion of the KLHDC7B nucleic acid molecule in the biological sample comprises an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises the nucleotide sequence of the KLHDC7B mRNA molecule in the biological sample, wherein the sequenced portion comprises positions corresponding to positions 1,035-1,036 according to SEQ ID NO:32, or the complement thereof; and/or the nucleotide sequence of the KLHDC7B cDNA molecule produced from the mRNA in the biological sample, wherein the sequenced portion comprises positions corresponding to positions 1,035-1,036 according to SEQ ID NO:40, or the complement thereof. When the sequenced portion of the KLHDC7B nucleic acid molecule in the biological sample comprises an AG dinucleotide at positions corresponding to positions 1,035-1,036 according to SEQ ID NO:32, or an AG dinucleotide at positions corresponding to positions 1,035-1,036 according to SEQ ID NO:40, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises the nucleotide sequence of the KLHDC7B mRNA molecule in the biological sample, wherein the sequenced portion comprises positions corresponding to positions 2,865-2,866 according to SEQ ID NO:33, or the complement thereof; and/or the nucleotide sequence of the KLHDC7B cDNA molecule produced from the mRNA in the biological sample, wherein the sequenced portion comprises positions corresponding to positions 2,865-2,866 according to SEQ ID NO:41, or the complement thereof. When the sequenced portion of the KLHDC7B nucleic acid molecule in the biological sample comprises an AG dinucleotide at positions corresponding to positions 2,865-2,866 according to SEQ ID NO:33, or an AG dinucleotide at positions corresponding to positions 2,865-2,866 according to SEQ ID NO:41, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of: the nucleotide sequence of the KLHDC7B genomic nucleic acid molecule in the biological sample, wherein the sequenced portion comprises the nucleotide sequence of the KLHDC7B mRNA molecule in the biological sample, wherein the sequenced portion comprises positions corresponding to positions 1,035-1,036 according to SEQ ID NO:34, or the complement thereof; and/or the nucleotide sequence of the KLHDC7B cDNA molecule produced from the mRNA in the biological sample, wherein the sequenced portion comprises positions corresponding to positions 1,035-1,036 according to SEQ ID NO:42, or the complement thereof. When the sequenced portion of the KLHDC7B nucleic acid molecule in the biological sample comprises an AG dinucleotide at positions corresponding to positions 1,035-1,036 according to SEQ ID NO:34, or an AG dinucleotide at positions corresponding to positions 1,035-1,036 according to SEQ ID NO:42, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of the nucleotide sequence of the KLHDC7B genomic nucleic acid molecule in the biological sample, wherein the sequenced portion comprises: a position corresponding to position 3,778 according to SEQ ID NO:2, or the complement thereof; positions corresponding to positions 2,806-2,807 according to SEQ ID NO:25, or the complement thereof; or positions corresponding to positions 3,169-3,170 according to SEQ ID NO:26, or the complement thereof. When the sequenced portion of the KLHDC7B nucleic acid molecule in the biological sample comprises: an adenine at a position corresponding to position 3,778 according to SEQ ID NO:2, a CG dinucleotide at positions corresponding to positions 2,806-2,807 according to SEQ ID NO:25, or an AG dinucleotide at positions corresponding to positions 3,169-3,170 according to SEQ ID NO:26, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of the nucleotide sequence of the KLHDC7B mRNA molecule in the biological sample, wherein the sequenced portion comprises: a position corresponding to position 3,778 according to SEQ ID NO:7, or the complement thereof; a position corresponding to position 1,644 according to SEQ ID NO:8, or the complement thereof; a position corresponding to position 3,474 according to SEQ ID NO:9, or the complement thereof; a position corresponding to position 1,644 according to SEQ ID NO:10, or the complement thereof; positions corresponding to positions 2,806-2,807 according to SEQ ID NO:27, or the complement thereof; positions corresponding to positions 672-673 according to SEQ ID NO:28, or the complement thereof; positions corresponding to positions 2,502-2,503 according to SEQ ID NO:29, or the complement thereof; positions corresponding to positions 672-673 according to SEQ ID NO:30, or the complement thereof; positions corresponding to positions 3,169-3,170 according to SEQ ID NO:31, or the complement thereof; positions corresponding to positions 1,035-1,036 according to SEQ ID NO:32, or the complement thereof; positions corresponding to positions 2,865-2,866 according to SEQ ID NO:33, or the complement thereof; or positions corresponding to positions 1,035-1,036 according to SEQ ID NO:34, or the complement thereof. When the sequenced portion of the KLHDC7B nucleic acid molecule in the biological sample comprises: an adenine at a position corresponding to position 3,778 according to SEQ ID NO:7, an adenine at a position corresponding to position 1,644 according to SEQ ID NO:8, an adenine at a position corresponding to position 3,474 according to SEQ ID NO:9, an adenine at a position corresponding to position 1,644 according to SEQ ID NO:10, a CG dinucleotide at positions corresponding to positions 2,806-2,807 to SEQ ID NO:27, a CG dinucleotide at positions corresponding to positions 672-673 according to SEQ ID NO:28, a CG dinucleotide at positions corresponding to positions 2,502-2,503 according to SEQ ID NO:29, a CG dinucleotide at positions corresponding to positions 672-673 according to SEQ ID NO:30, an AG dinucleotide at positions corresponding to positions 3,169-3,170 according to SEQ ID NO:31, an AG dinucleotide at positions corresponding to positions 1,035-1,036 according to SEQ ID NO:32, an AG dinucleotide at positions corresponding to positions 2,865-2,866 according to SEQ ID NO:33, or an AG dinucleotide at positions corresponding to positions 1,035-1,036 according to SEQ ID NO:34, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises sequencing at least a portion of the nucleotide sequence of the KLHDC7B cDNA molecule in the biological sample, wherein the sequenced portion comprises: a position corresponding to position 3,778 according to SEQ ID NO:15, or the complement thereof; a position corresponding to position 1,644 according to SEQ ID NO:16, or the complement thereof; a position corresponding to position 3,474 according to SEQ ID NO:17, or the complement thereof; a position corresponding to position 1,644 according to SEQ ID NO:18, or the complement thereof; positions corresponding to positions 2,806-2,807 according to SEQ ID NO:35, or the complement thereof; positions corresponding to positions 672-673 according to SEQ ID NO:36, or the complement thereof; positions corresponding to positions 2,502-2,503 according to SEQ ID NO:37, or the complement thereof; positions corresponding to positions 672-673 according to SEQ ID NO:38, or the complement thereof; positions corresponding to positions 3,169-3,170 according to SEQ ID NO:39, or the complement thereof; positions corresponding to positions 1,035-1,036 according to SEQ ID NO:40, or the complement thereof; positions corresponding to positions 2,865-2,866 according to SEQ ID NO:41, or the complement thereof; or positions corresponding to positions 1,035-1,036 according to SEQ ID NO:42, or the complement thereof. When the sequenced portion of the KLHDC7B nucleic acid molecule in the biological sample comprises: an adenine at a position corresponding to position 3,778 according to SEQ ID NO:15, an adenine at a position corresponding to position 1,644 according to SEQ ID NO:16, an adenine at a position corresponding to position 3,474 according to SEQ ID NO:17, an adenine at a position corresponding to position 1,644 according to SEQ ID NO:18, a CG dinucleotide at positions corresponding to positions 2,806-2,807 to SEQ ID NO:35, a CG dinucleotide at positions corresponding to positions 672-673 according to SEQ ID NO:36, a CG dinucleotide at positions corresponding to positions 2,502-2,503 according to SEQ ID NO:37, a CG dinucleotide at positions corresponding to positions 672-673 according to SEQ ID NO:38, an AG dinucleotide at positions corresponding to positions 3,169-3,170 according to SEQ ID NO:39, an AG dinucleotide at positions corresponding to positions 1,035-1,036 according to SEQ ID NO:40, an AG dinucleotide at positions corresponding to positions 2,865-2,866 according to SEQ ID NO:41, or an AG dinucleotide at positions corresponding to positions 1,035-1,036 according to SEQ ID NO:42, then the KLHDC7B nucleic acid molecule in the biological sample is a KLHDC7B missense variant nucleic acid molecule encoding a KLHDC7B predicted loss-of-function polypeptide.

In some embodiments, the determining step, detecting step, or sequence analysis comprises: a) contacting the biological sample with a primer hybridizing to a portion of the nucleotide sequence of the KLHDC7B: genomic nucleic acid molecule that is proximate to a position corresponding to position 3,778 according to SEQ ID NO:2; mRNA molecule that is proximate to a position corresponding to position 3,778 according to SEQ ID NO:7; and/or cDNA molecule that is proximate to a position corresponding to position 3,778 according to SEQ ID NO:15; b) extending the primer at least through the position of the nucleotide sequence of the KLHDC7B: genomic nucleic acid molecule corresponding to position 3,778 according to SEQ ID NO:2; mRNA molecule corresponding to position 3,778 according to SEQ ID NO:7; and/or cDNA molecule corresponding to position 3,778 according to SEQ ID NO:15; and c) determining whether the extension product of the primer comprises an adenine at a position corresponding to position 3,778 according to SEQ ID NO:2, an adenine at a position corresponding to position 3,778 according to SEQ ID NO:7, and/or an adenine at a position corresponding to position 3,778 according to SEQ ID NO:15.

In some embodiments, the determining step, detecting step, or sequence analysis comprises: a) contacting the biological sample with a primer hybridizing to a portion of the nucleotide sequence of the KLHDC7B mRNA molecule that is proximate to a position corresponding to position 1,644 according to SEQ ID NO:8, and/or cDNA molecule that is proximate to a position corresponding to position 1,644 according to SEQ ID NO:16; b) extending the primer at least through the position of the nucleotide sequence of the KLHDC7B mRNA molecule corresponding to position 1,644 according to SEQ ID NO:8, and/or cDNA molecule corresponding to position 1,644 according to SEQ ID NO:16; and c) determining whether the extension product of the primer comprises an adenine at a position corresponding to position 1,644 according to SEQ ID NO:8, and/or an adenine at a position corresponding to position 1,644 according to SEQ ID NO:16.

In some embodiments, the determining step, detecting step, or sequence analysis comprises: a) contacting the biological sample with a primer hybridizing to a portion of the nucleotide sequence of the KLHDC7B mRNA molecule that is proximate to a position corresponding to position 3,474 according to SEQ ID NO:9, and/or cDNA molecule that is proximate to a position corresponding to position 3,474 according to SEQ ID NO:17; b) extending the primer at least through the position of the nucleotide sequence of the KLHDC7B mRNA molecule corresponding to position 3,474 according to SEQ ID NO:9, and/or cDNA molecule corresponding to position 3,474 according to SEQ ID NO:17; and c) determining whether the extension product of the primer comprises an adenine at a position corresponding to position 3,474 according to SEQ ID NO:9, and/or an adenine at a position corresponding to position 3,474 according to SEQ ID NO:17.

In some embodiments, the determining step, detecting step, or sequence analysis comprises: a) contacting the biological sample with a primer hybridizing to a portion of the nucleotide sequence of the KLHDC7B mRNA molecule that is proximate to a position corresponding to position 1,644 according to SEQ ID NO:10, and/or cDNA molecule that is proximate to a position corresponding to position 1,644 according to SEQ ID NO:18; b) extending the primer at least through the position of the nucleotide sequence of the KLHDC7B mRNA molecule corresponding to position 1,644 according to SEQ ID NO:10, and/or cDNA molecule corresponding to position 1,644 according to SEQ ID NO:18; and c) determining whether the extension product of the primer comprises an adenine at a position corresponding to position 1,644 according to SEQ ID NO:10, and/or an adenine at a position corresponding to position 1,644 according to SEQ ID NO:18.

In some embodiments, the determining step, detecting step, or sequence analysis comprises: a) contacting the biological sample with a primer hybridizing to a portion of the nucleotide sequence of the KLHDC7B: genomic nucleic acid molecule that is proximate to positions corresponding to positions 2,806-2,807 according to SEQ ID NO:25; mRNA molecule that is proximate to positions corresponding to positions 2,806-2,807 according to SEQ ID NO:27; and/or cDNA molecule that is proximate to positions corresponding to positions 2,806-2,807 according to SEQ ID NO:35; b) extending the primer at least through the position of the nucleotide sequence of the KLHDC7B: genomic nucleic acid molecule that is proximate to positions corresponding to positions 2,806-2,807 according to SEQ ID NO:25; mRNA molecule that is proximate to positions corresponding to positions 2,806-2,807 according to SEQ ID NO:27; and/or cDNA molecule that is proximate to positions corresponding to positions 2,806-2,807 according to SEQ ID NO:35; and c) determining whether the extension product of the primer comprises a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 672-673 according to SEQ ID NO:28; and/or cDNA molecule that is proximate to positions corresponding to positions 672-673 according to SEQ ID NO:36; b) extending the primer at least through the position of the nucleotide sequence of the KLHDC7B: mRNA molecule that is proximate to positions corresponding to positions 672-673 according to SEQ ID NO:28; and/or cDNA molecule that is proximate to positions corresponding to positions 672-673 according to SEQ ID NO:36; and c) determining whether the extension product of the primer comprises a CG dinucleotide at positions corresponding to positions 672-673 according to SEQ ID NO:28, or a CG dinucleotide at positions corresponding to positions 672-673 according to SEQ ID NO:36.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 2,502-2,503 according to SEQ ID NO:29; and/or cDNA molecule that is proximate to positions corresponding to positions 2,502-2,503 according to SEQ ID NO:37; b) extending the primer at least through the position of the nucleotide sequence of the KLHDC7B: mRNA molecule that is proximate to positions corresponding to positions 2,502-2,503 according to SEQ ID NO:29; and/or cDNA molecule that is proximate to positions corresponding to positions 2,502-2,503 according to SEQ ID NO:37; and c) determining whether the extension product of the primer comprises a CG dinucleotide at positions corresponding to positions 2,502-2,503 according to SEQ ID NO:29, or a CG dinucleotide at positions corresponding to positions 2,502-2,503 according to SEQ ID NO:37.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 672-673 according to SEQ ID NO:30; and/or cDNA molecule that is proximate to positions corresponding to positions 672-673 according to SEQ ID NO:38; b) extending the primer at least through the position of the nucleotide sequence of the KLHDC7B: mRNA molecule that is proximate to positions corresponding to positions 672-673 according to SEQ ID NO:30; and/or cDNA molecule that is proximate to positions corresponding to positions 672-673 according to SEQ ID NO:38; and c) determining whether the extension product of the primer comprises a CG dinucleotide at positions corresponding to positions 672-673 according to SEQ ID NO:30, or a CG dinucleotide at positions corresponding to positions 672-673 according to SEQ ID NO:38.

In some embodiments, the determining step, detecting step, or sequence analysis comprises: a) contacting the biological sample with a primer hybridizing to a portion of the nucleotide sequence of the KLHDC7B: genomic nucleic acid molecule that is proximate to positions corresponding to positions 3,169-3,170 according to SEQ ID NO:26; mRNA molecule that is proximate to positions corresponding to positions 3,169-3,170 according to SEQ ID NO:31; and/or cDNA molecule that is proximate to positions corresponding to positions 3,169-3,170 according to SEQ ID NO:39; b) extending the primer at least through the position of the nucleotide sequence of the KLHDC7B: genomic nucleic acid molecule that is proximate to positions corresponding to positions 3,169-3,170 according to SEQ ID NO:26; mRNA molecule that is proximate to positions corresponding to positions 3,169-3,170 according to SEQ ID NO:31; and/or cDNA molecule that is proximate to positions corresponding to positions 3,169-3,170 according to SEQ ID NO:39; and c) determining whether the extension product of the primer comprises: an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 1,035-1,036 according to SEQ ID NO:32; and/or cDNA molecule that is proximate to positions corresponding to positions 1,035-1,036 according to SEQ ID NO:40; b) extending the primer at least through the position of the nucleotide sequence of the KLHDC7B: mRNA molecule that is proximate to positions corresponding to positions 1,035-1,036 according to SEQ ID NO:32; and/or cDNA molecule that is proximate to positions corresponding to positions 1,035-1,036 according to SEQ ID NO:40; and c) determining whether the extension product of the primer comprises an AG dinucleotide at positions corresponding to positions 1,035-1,036 according to SEQ ID NO:32, or an AG dinucleotide at positions corresponding to positions 1,035-1,036 according to SEQ ID NO:40.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 2,865-2,866 according to SEQ ID NO:33; and/or cDNA molecule that is proximate to positions corresponding to positions 2,865-2,866 according to SEQ ID NO:41; b)

extending the primer at least through the position of the nucleotide sequence of the KLHDC7B: mRNA molecule that is proximate to positions corresponding to positions 2,865-2,866 according to SEQ ID NO:33; and/or cDNA molecule that is proximate to positions corresponding to positions 2,865-2,866 according to SEQ ID NO:41; and c) determining whether the extension product of the primer comprises an AG dinucleotide at positions corresponding to positions 2,865-2,866 according to SEQ ID NO:33, or an AG dinucleotide at positions corresponding to positions 2,865-2,866 according to SEQ ID NO:41.

In some embodiments, the determining step, detecting step, or sequence analysis comprises: a) contacting the biological sample with a primer hybridizing to a portion of the nucleotide sequence of the KLHDC7B: mRNA molecule that is proximate to positions corresponding to positions 1,035-1,036 according to SEQ ID NO:34; and/or cDNA molecule that is proximate to positions corresponding to positions 1,035-1,036 according to SEQ ID NO:42; b) extending the primer at least through the position of the nucleotide sequence of the KLHDC7B: mRNA molecule that is proximate to positions corresponding to positions 1,035-1,036 according to SEQ ID NO:34; and/or cDNA molecule that is proximate to positions corresponding to positions 1,035-1,036 according to SEQ ID NO:42; and c) determining whether the extension product of the primer comprises an AG dinucleotide at positions corresponding to positions 1,035-1,036 according to SEQ ID NO:34, or an AG dinucleotide at positions corresponding to positions 1,035-1,036 according to SEQ ID NO:42.

In some embodiments, the determining step, detecting step, or sequence analysis comprises: a) contacting the biological sample with a primer hybridizing to a portion of the nucleotide sequence of the KLHDC7B genomic nucleic acid molecule that is proximate to a position corresponding to position 3,778 according to SEQ ID NO:2, positions corresponding to positions 2,806-2,807 according to SEQ ID NO:25, or positions corresponding to positions 3,169-3,170 according to SEQ ID NO:26; b) extending the primer at least through the position of the nucleotide sequence of the KLHDC7B genomic nucleic acid molecule corresponding to position 3,778 according to SEQ ID NO:2, positions corresponding to positions 2,806-2,807 according to SEQ ID NO:25, or positions corresponding to positions 3,169-3,170 according to SEQ ID NO:26; and c) determining whether the extension product of the primer comprises: an adenine at a position corresponding to position 3,778 according to SEQ ID NO:2, a CG dinucleotide at positions corresponding to positions 2,806-2,807 according to SEQ ID NO:25, or an AG dinucleotide at positions corresponding to positions 3,169-3,170 according to SEQ ID NO:26.

In some embodiments, the determining step, detecting step, or sequence analysis comprises: a) contacting the biological sample with a primer hybridizing to a portion of the nucleotide sequence of the KLHDC7B mRNA molecule that is proximate to: a position corresponding to position 3,778 according to SEQ ID NO:7, a position corresponding to position 1,644 according to SEQ ID NO:8, a position corresponding to position 3,474 according to SEQ ID NO:9, a position corresponding to position 1,644 according to SEQ ID NO:10, positions corresponding to positions 2,806-2,807 according to SEQ ID NO:27, positions corresponding to positions 672-673 according to SEQ ID NO:28, positions corresponding to positions 2,502-2,503 according to SEQ ID NO:29, positions corresponding to positions 672-673 according to SEQ ID NO:30, positions corresponding to positions 3,169-3,170 according to SEQ ID NO:31, positions corresponding to positions 1,035-1,036 according to SEQ ID NO:32, positions corresponding to positions 2,865-2,866 according to SEQ ID NO:33, or positions corresponding to positions 1,035-1,036 according to SEQ ID NO:34; b) extending the primer at least through the position of the nucleotide sequence of the KLHDC7B mRNA molecule corresponding to: position 3,778 according to SEQ ID NO:7, position 1,644 according to SEQ ID NO:8, position 3,474 according to SEQ ID NO:9, position 1,644 according to SEQ ID NO:10, positions 2,806-2,807 according to SEQ ID NO:27, positions 672-673 according to SEQ ID NO:28, positions 2,502-2,503 according to SEQ ID NO:29, positions 672-673 according to SEQ ID NO:30, positions 3,169-3,170 according to SEQ ID NO:31, positions 1,035-1,036 according to SEQ ID NO:32, positions 2,865-2,866 according to SEQ ID NO:33, or positions 1,035-1,036 according to SEQ ID NO:34; and c) determining whether the extension product of the primer comprises: an adenine at a position corresponding to position 3,778 according to SEQ ID NO:7, an adenine at a position corresponding to position 1,644 according to SEQ ID NO:8, an adenine at a position corresponding to position 3,474 according to SEQ ID NO:9, an adenine at a position corresponding to position 1,644 according to SEQ ID NO:10, a CG dinucleotide at positions corresponding to positions 2,806-2,807 to SEQ ID NO:27, a CG dinucleotide at positions corresponding to positions 672-673 according to SEQ ID NO:28, a CG dinucleotide at positions corresponding to positions 2,502-2,503 according to SEQ ID NO:29, a CG dinucleotide at positions corresponding to positions 672-673 according to SEQ ID NO:30, an AG dinucleotide at positions corresponding to positions 3,169-3,170 according to SEQ ID NO:31, an AG dinucleotide at positions corresponding to positions 1,035-1,036 according to SEQ ID NO:32, an AG dinucleotide at positions corresponding to positions 2,865-2,866 according to SEQ ID NO:33, or an AG dinucleotide at positions corresponding to positions 1,035-1,036 according to SEQ ID NO:34.

In some embodiments, the determining step, detecting step, or sequence analysis comprises: a) contacting the biological sample with a primer hybridizing to a portion of the nucleotide sequence of the KLHDC7B cDNA molecule that is proximate to: a position corresponding to position 3,778 according to SEQ ID NO:15, a position corresponding to position 1,644 according to SEQ ID NO:16, a position corresponding to position 3,474 according to SEQ ID NO:17, a position corresponding to position 1,644 according to SEQ ID NO:18, positions corresponding to positions 2,806-2,807 according to SEQ ID NO:35, positions corresponding to positions 672-673 according to SEQ ID NO:36, positions corresponding to positions 2,502-2,503 according to SEQ ID NO:37, positions corresponding to positions 672-673 according to SEQ ID NO:38, positions corresponding to positions 3,169-3,170 according to SEQ ID NO:39, positions corresponding to positions 1,035-1,036 according to SEQ ID NO:40, positions corresponding to positions 2,865-2,866 according to SEQ ID NO:41, or positions corresponding to positions 1,035-1,036 according to SEQ ID NO:42; b) extending the primer at least through the position of the nucleotide sequence of the KLHDC7B cDNA molecule corresponding to: position 3,778 according to SEQ ID NO:15, position 1,644 according to SEQ ID NO:16, position 3,474 according to SEQ ID NO:17, position 1,644 according to SEQ ID NO:18, positions 2,806-2,807 according to SEQ ID NO:35, positions 672-673 according to SEQ ID NO:36, positions 2,502-2,503 according to SEQ ID NO:37, positions 672-673 according to SEQ ID NO:38, positions 3,169-3,170 according to SEQ ID NO:39, positions 1,035-1,036 according to SEQ ID NO:40, positions 2,865-2,866 according to SEQ ID NO:41, or positions 1,035-1,036 according to SEQ ID NO:42; and c) determining whether the extension product of the primer comprises: an adenine at a position corresponding to position 3,778 according to SEQ ID NO:15, an adenine at a position corresponding to position 1,644 according to SEQ ID NO:16, an adenine at a position corresponding to position 3,474 according to SEQ ID NO:17, an adenine at a position corresponding to position 1,644 according to SEQ ID NO:18, a CG dinucleotide at positions corresponding to positions 2,806-2,807 to SEQ ID NO:35, a CG dinucleotide at positions corresponding to positions 672-673 according to SEQ ID NO:36, a CG dinucleotide at positions corresponding to positions 2,502-2,503 according to SEQ ID NO:37, a CG dinucleotide at positions corresponding to positions 672-673 according to SEQ ID NO:38, an AG dinucleotide at positions corresponding to positions 3,169-3,170 according to SEQ ID NO:39, an AG dinucleotide at positions corresponding to positions 1,035-1,036 according to SEQ ID NO:40, an AG dinucleotide at positions corresponding to positions 2,865-2,866 according to SEQ ID NO:41, or an AG dinucleotide at positions corresponding to positions 1,035-1,036 according to SEQ ID NO:42.

In some embodiments, the assay comprises sequencing the entire nucleic acid molecule. In some embodiments, only a KLHDC7B genomic nucleic acid molecule is analyzed. In some embodiments, only a KLHDC7B mRNA is analyzed. In some embodiments, only a KLHDC7B cDNA obtained from KLHDC7B mRNA is analyzed.

In some embodiments, the determining step, detecting step, or sequence analysis comprises: a) amplifying at least a portion of the nucleic acid molecule that encodes the KLHDC7B polypeptide, wherein the amplified portion comprises: i) an adenine at a position corresponding to position 3,778 according to SEQ ID NO:2, or the complement thereof; ii) an adenine at a position corresponding to position 3,778 according to SEQ ID NO:7, or the complement thereof; and/or iii) an adenine at a position corresponding to position 3,778 according to SEQ ID NO:15, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an adenine at a position corresponding to position 3,778 according to SEQ ID NO:2, or the complement thereof; ii) an adenine at a position corresponding to position 3,778 according to SEQ ID NO:7, or the complement thereof; and/or iii) an adenine at a position corresponding to position 3,778 according to SEQ ID NO:15, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 1,644 according to SEQ ID NO:8, or the complement thereof; and/or an adenine at a position corresponding to position 1,644 according to SEQ ID NO:16, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 1,644 according to SEQ ID NO:8, or the complement thereof; and/or an adenine at a position corresponding to position 1,644 according to SEQ ID NO:16, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 3,474 according to SEQ ID NO:9, or the complement thereof; and/or an adenine at a position corresponding to position 3,474 according to SEQ ID NO:17, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 3,474 according to SEQ ID NO:9, or the complement thereof; and/or an adenine at a position corresponding to position 3,474 according to SEQ ID NO:17, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 1,644 according to SEQ ID NO:10, or the complement thereof; and/an adenine at a position corresponding to position 1,644 according to SEQ ID NO:18, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 1,644 according to SEQ ID NO:10, or the complement thereof; and/an adenine at a position corresponding to position 1,644 according to SEQ ID NO:18, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) a CG dinucleotide at positions corresponding to positions 2,806-2,807 according to SEQ ID NO:25, or the complement thereof; ii) a CG dinucleotide at positions corresponding to positions 2,806-2,807 to SEQ ID NO:27, or the complement thereof; and/or iii) a CG dinucleotide at positions corresponding to positions 2,806-2,807 to SEQ ID NO:35, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a CG dinucleotide at positions corresponding to positions 2,806-2,807 according to SEQ ID NO:25, or the complement thereof; ii) a CG dinucleotide at positions corresponding to positions 2,806-2,807 to SEQ ID NO:27, or the complement thereof; and/or iii) a CG dinucleotide at positions corresponding to positions 2,806-2,807 to SEQ ID NO:35; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) a CG dinucleotide at positions corresponding to positions 672-673 according to SEQ ID NO:28, or the complement thereof; and/or ii) a CG dinucleotide at positions corresponding to positions 672-673 according to SEQ ID NO:36, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a CG dinucleotide at positions corresponding to positions 672-673 according to SEQ ID NO:28, or the complement thereof; and/or ii) a CG dinucleotide at positions corresponding to positions 672-673 according to SEQ ID NO:36; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) a CG dinucleotide at positions corresponding to positions 2,502-2,503 according to SEQ ID NO:29, or the complement thereof; and/or ii) a CG dinucleotide at positions corresponding to positions 2,502-2,503 according to SEQ ID NO:37, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a CG dinucleotide at positions corresponding to positions 2,502-2,503 according to SEQ ID NO:29, or the complement thereof; and/or ii) a CG dinucleotide at positions corresponding to positions 2,502-2,503 according to SEQ ID NO:37; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) a CG dinucleotide at positions corresponding to positions 672-673 according to SEQ ID NO:30, or the complement thereof; and/or ii) a CG dinucleotide at positions corresponding to positions 672-673 according to SEQ ID NO:38, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a CG dinucleotide at positions corresponding to positions 672-673 according to SEQ ID NO:30, or the complement thereof; and/or ii) a CG dinucleotide at positions corresponding to positions 672-673 according to SEQ ID NO:38; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) an AG dinucleotide at positions corresponding to positions 3,169-3,170 according to SEQ ID NO:26, or the complement thereof; ii) an AG dinucleotide at positions corresponding to positions 3,169-3,170 according to SEQ ID NO:31, or the complement thereof; and/or iii) an AG dinucleotide at positions corresponding to positions 3,169-3,170 according to SEQ ID NO:39, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an AG dinucleotide at positions corresponding to positions 3,169-3,170 according to SEQ ID NO:26, or the complement thereof; ii) an AG dinucleotide at positions corresponding to positions 3,169-3,170 according to SEQ ID NO:31, or the complement thereof; and/or iii) an AG dinucleotide at positions corresponding to positions 3,169-3,170 according to SEQ ID NO:39; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) an AG dinucleotide at positions corresponding to positions 1,035-1,036 according to SEQ ID NO:32, or the complement thereof; and/or ii) an AG dinucleotide at positions corresponding to positions 1,035-1,036 according to SEQ ID NO:40, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an AG dinucleotide at positions corresponding to positions 1,035-1,036 according to SEQ ID NO:32, or the complement thereof; and/or ii) an AG dinucleotide at positions corresponding to positions 1,035-1,036 according to SEQ ID NO:40; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) an AG dinucleotide at positions corresponding to positions 2,865-2,866 according to SEQ ID NO:33, or the complement thereof; and/or ii) an AG dinucleotide at positions corresponding to positions 2,865-2,866 according to SEQ ID NO:41, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an AG dinucleotide at positions corresponding to positions 2,865-2,866 according to SEQ ID NO:33, or the complement thereof; and/or ii) an AG dinucleotide at positions corresponding to positions 2,865-2,866 according to SEQ ID NO:41; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: i) an AG dinucleotide at positions corresponding to positions 1,035-1,036 according to SEQ ID NO:34, or the complement thereof; and/or ii) an AG dinucleotide at positions corresponding to positions 1,035-1,036 according to SEQ ID NO:42, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an AG dinucleotide at positions corresponding to positions 1,035-1,036 according to SEQ ID NO:34, or the complement thereof; and/or ii) an AG dinucleotide at positions corresponding to positions 1,035-1,036 according to SEQ ID NO:42; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 3,778 according to SEQ ID NO:2, or the complement thereof; a CG dinucleotide at positions corresponding to positions 2,806-2,807 according to SEQ ID NO:25, or the complement thereof; or an AG dinucleotide at positions corresponding to positions 3,169-3,170 according to SEQ ID NO:26, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 3,778 according to SEQ ID NO:2, or the complement thereof; a CG dinucleotide at positions corresponding to positions 2,806-2,807 according to SEQ ID NO:25, or the complement thereof; or an AG dinucleotide at positions corresponding to positions 3,169-3,170 according to SEQ ID NO:26, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 according to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof; and d) detecting the detectable label.

In some embodiments, the determining step, detecting step, or sequence analysis comprises: a) amplifying at least a portion of the nucleic acid molecule that encodes the KLHDC7B polypeptide, wherein the amplified portion comprises: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 according to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof; b) labeling the amplified nucleic acid molecule with a detectable label; c)

contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,778 according to SEQ ID NO:2, or the complement thereof; an adenine at a position corresponding to position 3,778 according to SEQ ID NO:7, or the complement thereof; and/or an adenine at a position corresponding to position 3,778 according to SEQ ID NO:15, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 1,644 according to SEQ ID NO:8, or the complement thereof, and/or an adenine at a position corresponding to position 1,644 according to SEQ ID NO:16, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,474 according to SEQ ID NO:9, or the complement thereof, and/or an adenine at a position corresponding to position 3,474 according to SEQ ID NO:17, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 1,644 according to SEQ ID NO:10, or the complement thereof, and/or an adenine at a position corresponding to position 1,644 according to SEQ ID NO:18, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a CG dinucleotide at positions corresponding to positions 2,806-2,807 according to SEQ ID NO:25, or the complement thereof; a CG dinucleotide at positions corresponding to positions 2,806-2,807 to SEQ ID NO:27, or the complement thereof; or a CG dinucleotide at positions corresponding to positions 2,806-2,807 to SEQ ID NO:35, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a CG dinucleotide at positions corresponding to positions 672-673 according to SEQ ID NO:28, or the complement thereof; or a CG dinucleotide at positions corresponding to positions 672-673 according to SEQ ID NO:36, or the complement thereof; and detecting the detectable label. In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a CG dinucleotide at positions corresponding to positions 2,502-2,503 according to SEQ ID NO:29, or the complement thereof; or a CG dinucleotide at positions corresponding to positions 2,502-2,503 according to SEQ ID NO:37, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a CG dinucleotide at positions corresponding to positions 672-673 according to SEQ ID NO:30, or the complement thereof; or a CG dinucleotide at positions corresponding to positions 672-673 according to SEQ ID NO:38, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an AG dinucleotide at positions corresponding to positions 3,169-3,170 according to SEQ ID NO:26, or the complement thereof; an AG dinucleotide at positions corresponding to positions 3,169-3,170 according to SEQ ID NO:31, or the complement thereof; or an AG dinucleotide at positions corresponding to positions 3,169-3,170 according to SEQ ID NO:39, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an AG dinucleotide at positions corresponding to positions 1,035-1,036 according to SEQ ID NO:32, or the complement thereof; or an AG dinucleotide at positions corresponding to positions 1,035-1,036 according to SEQ ID NO:40, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an AG dinucleotide at positions corresponding to positions 2,865-2,866 according to SEQ ID NO:33, or the complement thereof; or an AG dinucleotide at positions corresponding to positions 2,865-2,866 according to SEQ ID NO:41, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an AG dinucleotide at positions corresponding to positions 1,035-1,036 according to SEQ ID NO:34, or the complement thereof; or an AG dinucleotide at positions corresponding to positions 1,035-1,036 according to SEQ ID NO:42, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,778 according to SEQ ID NO:2, or the complement thereof; a CG dinucleotide at positions corresponding to positions 2,806-2,807 according to SEQ ID NO:25, or the complement thereof; or an AG dinucleotide at positions corresponding to positions 3,169-3,170 according to SEQ ID NO:26, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof; and detecting the detectable label.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a KLHDC7B variant genomic sequence, variant mRNA sequence, or variant cDNA sequence and not the corresponding KLHDC7B reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a KLHDC7B variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an adenine at a position corresponding to position 3,778 according to SEQ ID NO:2 (genomic nucleic acid molecule), an adenine at a position corresponding to position 3,778 according to SEQ ID NO:7 (mRNA molecule), or an adenine at a position corresponding to position 3,778 according to SEQ ID NO:15 (cDNA molecule), the biological sample can be subjected to an amplification method using a primer pair that includes a first primer derived from the 5' flanking sequence adjacent to an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15, and a second primer derived from the 3' flanking sequence adjacent to an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15 to produce an amplicon that is indicative of the presence of the SNP at positions encoding an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15, and at least 1, 2, 3, 4, 5, 6, 7, 8, 9, 10, or more nucleotides on each side of positions comprising an adenine at a position corresponding to position 3,778 according to SEQ ID NO:2, an adenine at a position corresponding to position 3,778 according to SEQ ID NO:7, or an adenine at a position corresponding to position 3,778 according to SEQ ID NO:15.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an adenine at a position corresponding to position 1,644 according to SEQ ID NO:8 (mRNA molecule), or an adenine at a position corresponding to position 1,644 according to SEQ ID NO:16 (cDNA molecule), the biological sample can be subjected to an amplification method using a primer pair that includes a first primer derived from the 5' flanking sequence adjacent to an adenine at a position corresponding to position 1,644 according to SEQ ID NO:8, or an adenine at a position corresponding to position 1,644 according to SEQ ID NO:16, and a second primer derived from the 3' flanking sequence adjacent to an adenine at a position corresponding to position 1,644 according to SEQ ID NO:8, or an adenine at a position corresponding to position 1,644 according to SEQ ID NO:16 to produce an amplicon that is indicative of the presence of the SNP at positions encoding an adenine at a position corresponding to position 1,644 according to SEQ ID NO:8, or an adenine at a position corresponding to position 1,644 according to SEQ ID NO:16. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 1,644 according to SEQ ID NO:8, or an adenine at a position corresponding to position 1,644 according to SEQ ID NO:16, and at least 1, 2, 3, 4, 5, 6, 7, 8, 9, 10, or more nucleotides on each side of positions comprising an adenine at a position corresponding to position 1,644 according to SEQ ID NO:8, or an adenine at a position corresponding to position 1,644 according to SEQ ID NO:16.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an adenine at a position corresponding to position 3,474 according to SEQ ID NO:9 (mRNA molecule), or an adenine at a position corresponding to position 3,474 according to SEQ ID NO:17 (cDNA molecule), the biological sample can be subjected to an amplification method using a primer pair that includes a first primer derived from the 5' flanking sequence adjacent to an adenine at a position corresponding to position 3,474 according to SEQ ID NO:9, or an adenine at a position corresponding to position 3,474 according to SEQ ID NO:17, and a second primer derived from the 3' flanking sequence adjacent to an adenine at a position corresponding to position 3,474 according to SEQ ID NO:9, or an adenine at a position corresponding to position 3,474 according to SEQ ID NO:17 to produce an amplicon that is indicative of the presence of the SNP at positions encoding an adenine at a position corresponding to position 3,474 according to SEQ ID NO:9, or an adenine at a position corresponding to position 3,474 according to SEQ ID NO:17. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 3,474 according to SEQ ID NO:9, or an adenine at a position corresponding to position 3,474 according to SEQ ID NO:17, and at least 1, 2, 3, 4, 5, 6, 7, 8, 9, 10, or more nucleotides on each side of positions comprising an adenine at a position corresponding to position 3,474 according to SEQ ID NO:9, or an adenine at a position corresponding to position 3,474 according to SEQ ID NO:17.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an adenine at a position corresponding to position 1,644 according to SEQ ID NO:10 (mRNA molecule), or an adenine at a position corresponding to position 1,644 according to SEQ ID NO:18 (cDNA molecule), the biological sample can be subjected to an amplification method using a primer pair that includes a first primer derived from the 5' flanking sequence adjacent to an adenine at a position corresponding to position 1,644 according to SEQ ID NO:10, or an adenine at a position corresponding to position 1,644 according to SEQ ID NO:18, and a second primer derived from the 3' flanking sequence adjacent to an adenine at a position corresponding to position 1,644 according to SEQ ID NO:10, or an adenine at a position corresponding to position 1,644 according to SEQ ID NO:18 to produce an amplicon that is indicative of the presence of the SNP at positions encoding an adenine at a position corresponding to position 1,644 according to SEQ ID NO:10, or an adenine at a position corresponding to position 1,644 according to SEQ ID NO:18. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 1,644 according to SEQ ID NO:10, or an adenine at a position corresponding to position 1,644 according to SEQ ID NO:18, and at least 1, 2, 3, 4, 5, 6, 7, 8, 9, 10, or more nucleotides on each side of positions comprising an adenine at a position corresponding to position 1,644 according to SEQ ID NO:10, or an adenine at a position corresponding to position 1,644 according to SEQ ID NO:18.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: a CG dinucleotide at positions corresponding to positions 2,806-2,807 according to SEQ ID NO:25 (genomic nucleic acid molecule), a CG dinucleotide at positions corresponding to positions 2,806-2,807 to SEQ ID NO:27 (mRNA molecule), or a CG dinucleotide at positions corresponding to positions 2,806-2,807 to SEQ ID NO:35 (cDNA molecule), the biological sample can be subjected to an amplification method using a primer pair that includes a first primer derived from the 5' flanking sequence adjacent to a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35, and a second primer derived from the 3' flanking sequence adjacent to a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35 to produce an amplicon that is indicative of the presence of the SNP at positions encoding a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35, and at least 1, 2, 3, 4, 5, 6, 7, 8, 9, 10, or more nucleotides on each side of positions comprising a CG dinucleotide at positions corresponding to positions 2,806-2,807 according to SEQ ID NO:25, a CG dinucleotide at positions corresponding to positions 2,806-2,807 to SEQ ID NO:27, or a CG dinucleotide at positions corresponding to positions 2,806-2,807 to SEQ ID NO:35.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: a CG dinucleotide at positions corresponding to positions 672-673 according to SEQ ID NO:28 (mRNA molecule), or a CG dinucleotide at positions corresponding to positions 672-673 according to SEQ ID NO:36 (cDNA molecule), the biological sample can be subjected to an amplification method using a primer pair that includes a first primer derived from the 5' flanking sequence adjacent to a CG dinucleotide at positions corresponding to positions 672-673 according to SEQ ID NO:28, or a CG dinucleotide at positions corresponding to positions 672-673 according to SEQ ID NO:36 and a second primer derived from the 3' flanking sequence adjacent to a CG dinucleotide at positions corresponding to positions 672-673 according to SEQ ID NO:28, or a CG dinucleotide at positions corresponding to positions 672-673 according to SEQ ID NO:36 to produce an amplicon that is indicative of the presence of the SNP at positions encoding a CG dinucleotide at positions corresponding to positions 672-673 according to SEQ ID NO:28, or a CG dinucleotide at positions corresponding to positions 672-673 according to SEQ ID NO:36. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a CG dinucleotide at positions corresponding to positions 672-673 according to SEQ ID NO:28, or a CG dinucleotide at positions corresponding to positions 672-673 according to SEQ ID NO:36, and at least 1, 2, 3, 4, 5, 6, 7, 8, 9, 10, or more nucleotides on each side of positions comprising a CG dinucleotide at positions corresponding to positions 672-673 according to SEQ ID NO:28, or a CG dinucleotide at positions corresponding to positions 672-673 according to SEQ ID NO:36. In some embodiments, to determine whether a KLHDC7B nucleic acid molecule (genomic nucleic acid molecule, mRNA molecule, or cDNA molecule), or complement thereof, within a biological sample comprises a nucleotide sequence comprising: a CG dinucleotide at positions corresponding to positions 2,502-2,503 according to SEQ ID NO:29 (mRNA molecule), or a CG dinucleotide at positions corresponding to positions 2,502-2,503 according to SEQ ID NO:37 (cDNA molecule), the biological sample can be subjected to an amplification method using a primer pair that includes a first primer derived from the 5' flanking sequence adjacent to a CG dinucleotide at positions corresponding to positions 2,502-2,503 according to SEQ ID NO:29, or a CG dinucleotide at positions corresponding to positions 2,502-2,503 according to SEQ ID NO:37 and a second primer derived from the 3' flanking sequence adjacent to a CG dinucleotide at positions corresponding to positions 2,502-2,503 according to SEQ ID NO:29, or a CG dinucleotide at positions corresponding to positions 2,502-2,503 according to SEQ ID NO:37 to produce an amplicon that is indicative of the presence of the SNP at positions encoding a CG dinucleotide at positions corresponding to positions 2,502-2,503 according to SEQ ID NO:29, or a CG dinucleotide at positions corresponding to positions 2,502-2,503 according to SEQ ID NO:37. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a CG dinucleotide at positions corresponding to positions 2,502-2,503 according to SEQ ID NO:29, or a CG dinucleotide at positions corresponding to positions 2,502-2,503 according to SEQ ID NO:37, and at least 1, 2, 3, 4, 5, 6, 7, 8, 9, 10, or more nucleotides on each side of positions comprising a CG dinucleotide at positions corresponding to positions 2,502-2,503 according to SEQ ID NO:29, or a CG dinucleotide at positions corresponding to positions 2,502-2,503 according to SEQ ID NO:37.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: a CG dinucleotide at positions corresponding to positions 672-673 according to SEQ ID NO:30 (mRNA molecule), or a CG dinucleotide at positions corresponding to positions 672-673 according to SEQ ID NO:38 (cDNA molecule), the biological sample can be subjected to an amplification method using a primer pair that includes a first primer derived from the 5' flanking sequence adjacent to a CG dinucleotide at positions corresponding to positions 672-673 according to SEQ ID NO:30, or a CG dinucleotide at positions corresponding to positions 672-673 according to SEQ ID NO:38 and a second primer derived from the 3' flanking sequence adjacent to a CG dinucleotide at positions corresponding to positions 672-673 according to SEQ ID NO:30, or a CG dinucleotide at positions corresponding to positions 672-673 according to SEQ ID NO:38 to produce an amplicon that is indicative of the presence of the SNP at positions encoding a CG dinucleotide at positions corresponding to positions 672-673 according to SEQ ID NO:30, or a CG dinucleotide at positions corresponding to positions 672-673 according to SEQ ID NO:38. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a CG dinucleotide at positions corresponding to positions 672-673 according to SEQ ID NO:30, or a CG dinucleotide at positions corresponding to positions 672-673 according to SEQ ID NO:38, and at least 1, 2, 3, 4, 5, 6, 7, 8, 9, 10, or more nucleotides on each side of positions comprising a CG dinucleotide at positions corresponding to positions 672-673 according to SEQ ID NO:30, or a CG dinucleotide at positions corresponding to positions 672-673 according to SEQ ID NO:38.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an AG dinucleotide at positions corresponding to positions 3,169-3,170 according to SEQ ID NO:26 (genomic nucleic acid molecule), an AG dinucleotide at positions corresponding to positions 3,169-3,170 according to SEQ ID NO:31 (mRNA molecule), or an AG dinucleotide at positions corresponding to positions 3,169-3,170 according to SEQ ID NO:39 (cDNA molecule), the biological sample can be subjected to an amplification method using a primer pair that includes a first primer derived from the 5' flanking sequence adjacent to an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39, and a second primer derived from the 3' flanking sequence adjacent to an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39 to produce an amplicon that is indicative of the presence of the SNP at positions encoding an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39, and at least 1, 2, 3, 4, 5, 6, 7, 8, 9, 10, or more nucleotides on each side of positions comprising an AG dinucleotide at positions corresponding to positions 3,169-3,170 according to SEQ ID NO:26, an AG dinucleotide at positions corresponding to positions 3,169-3,170 according to SEQ ID NO:31, or an AG dinucleotide at positions corresponding to positions 3,169-3,170 according to SEQ ID NO:39.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an AG dinucleotide at positions corresponding to positions 1,035-1,036 according to SEQ ID NO:32 (mRNA molecule), or an AG dinucleotide at positions corresponding to positions 1,035-1,036 according to SEQ ID NO:40 (cDNA molecule), the biological sample can be subjected to an amplification method using a primer pair that includes a first primer derived from the 5' flanking sequence adjacent to an AG dinucleotide at positions corresponding to positions 1,035-1,036 according to SEQ ID NO:32, or an AG dinucleotide at positions corresponding to positions 1,035-1,036 according to SEQ ID NO:40 and a second primer derived from the 3' flanking sequence adjacent to an AG dinucleotide at positions corresponding to positions 1,035-1,036 according to SEQ ID NO:32, or an AG dinucleotide at positions corresponding to positions 1,035-1,036 according to SEQ ID NO:40 to produce an amplicon that is indicative of the presence of the SNP at positions encoding an AG dinucleotide at positions corresponding to positions 1,035-1,036 according to SEQ ID NO:32, or an AG dinucleotide at positions corresponding to positions 1,035-1,036 according to SEQ ID NO:40. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an AG dinucleotide at positions corresponding to positions 1,035-1,036 according to SEQ ID NO:32, or an AG dinucleotide at positions corresponding to positions 1,035-1,036 according to SEQ ID NO:40, and at least 1, 2, 3, 4, 5, 6, 7, 8, 9, 10, or more nucleotides on each side of positions comprising an AG dinucleotide at positions corresponding to positions 1,035-1,036 according to SEQ ID NO:32, or an AG dinucleotide at positions corresponding to positions 1,035-1,036 according to SEQ ID NO:40.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an AG dinucleotide at positions corresponding to positions 2,865-2,866 according to SEQ ID NO:33 (mRNA molecule), or an AG dinucleotide at positions corresponding to positions 2,865-2,866 according to SEQ ID NO:41 (cDNA molecule), the biological sample can be subjected to an amplification method using a primer pair that includes a first primer derived from the 5' flanking sequence adjacent to an AG dinucleotide at positions corresponding to positions 2,865-2,866 according to SEQ ID NO:33, or an AG dinucleotide at positions corresponding to positions 2,865-2,866 according to SEQ ID NO:41 and a second primer derived from the 3' flanking sequence adjacent to an AG dinucleotide at positions corresponding to positions 2,865-2,866 according to SEQ ID NO:33, or an AG dinucleotide at positions corresponding to positions 2,865-2,866 according to SEQ ID NO:41 to produce an amplicon that is indicative of the presence of the SNP at positions encoding an AG dinucleotide at positions corresponding to positions 2,865-2,866 according to SEQ ID NO:33, or an AG dinucleotide at positions corresponding to positions 2,865-2,866 according to SEQ ID NO:41. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an AG dinucleotide at positions corresponding to positions 2,865-2,866 according to SEQ ID NO:33, or an AG dinucleotide at positions corresponding to positions 2,865-2,866 according to SEQ ID NO:41, and at least 1, 2, 3, 4, 5, 6, 7, 8, 9, 10, or more nucleotides on each side of positions comprising an AG dinucleotide at positions corresponding to positions 2,865-2,866 according to SEQ ID NO:33, or an AG dinucleotide at positions corresponding to positions 2,865-2,866 according to SEQ ID NO:41.

In some embodiments, to determine whether a KLHDC7B nucleic acid molecule (genomic nucleic acid molecule, mRNA molecule, or cDNA molecule), or complement thereof, within a biological sample comprises a nucleotide sequence comprising: an AG dinucleotide at positions corresponding to positions 1,035-1,036 according to SEQ ID NO:34 (mRNA molecule), or an AG dinucleotide at positions corresponding to positions 1,035-1,036 according to SEQ ID NO:42 (cDNA molecule), the biological sample can be subjected to an amplification method using a primer pair that includes a first primer derived from the 5' flanking sequence adjacent to an AG dinucleotide at positions corresponding to positions 1,035-1,036 according to SEQ ID NO:34, or an AG dinucleotide at positions corresponding to positions 1,035-1,036 according to SEQ ID NO:42 and a second primer derived from the 3' flanking sequence adjacent to an AG dinucleotide at positions corresponding to positions 1,035-1,036 according to SEQ ID NO:34, or an AG dinucleotide at positions corresponding to positions 1,035-1,036 according to SEQ ID NO:42 to produce an amplicon that is indicative of the presence of the SNP at positions encoding an AG dinucleotide at positions corresponding to positions 1,035-1,036 according to SEQ ID NO:34, or an AG dinucleotide at positions corresponding to positions 1,035-1,036 according to SEQ ID NO:42. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an AG dinucleotide at positions corresponding to positions 1,035-1,036 according to SEQ ID NO:34, or an AG dinucleotide at positions corresponding to positions 1,035-1,036 according to SEQ ID NO:42, and at least 1, 2, 3, 4, 5, 6, 7, 8, 9, 10, or more nucleotides on each side of positions comprising an AG dinucleotide at positions corresponding to positions 1,035-1,036 according to SEQ ID NO:34, or an AG dinucleotide at positions corresponding to positions 1,035-1,036 according to SEQ ID NO:42.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a KLHDC7B predicted loss-of-function polypeptide comprising performing an assay on a sample obtained from a subject to determine whether a KLHDC7B polypeptide in the subject contains one or more variations that causes the polypeptide to have a loss-of-function (partial or complete) or predicted loss-of-function (partial or complete). The KLHDC7B predicted loss-of-function polypeptide can be any of the KLHDC7B truncated variant polypeptides described herein. In some embodiments, the methods detect the presence of KLHDC7B V1145M, V504M, V405M, K822fs, K181fs, K82fs, G943fs, G302fs, or G203fs. In some embodiments, the methods detect the presence of KLHDC7B V1145M. In some embodiments, the methods detect the presence of KLHDC7B V504M. In some embodiments, the methods detect the presence of KLHDC7B V405M. In some embodiments, the methods detect the presence of KLHDC7B K822fs. In some embodiments, the methods detect the presence of KLHDC7B K181fs. In some embodiments, the methods detect the presence of KLHDC7B K82fs. In some embodiments, the methods detect the presence of KLHDC7B G943fs. In some embodiments, the methods detect the presence of KLHDC7B G302fs. In some embodiments, the methods detect the presence of KLHDC7B G203fs.

In some embodiments, the methods comprise performing an assay on a sample obtained from a subject to determine whether a KLHDC7B polypeptide in the sample comprises a methionine at a position corresponding to position 1,145 according to SEQ ID NO:22. In some embodiments, the methods comprise performing an assay on a sample obtained from a subject to determine whether a KLHDC7B polypeptide in the sample comprises a methionine at a position corresponding to position 504 according to SEQ ID NO:23. In some embodiments, the methods comprise performing an assay on a sample obtained from a subject to determine whether a KLHDC7B polypeptide in the sample comprises a methionine at a position corresponding to position 405 according to SEQ ID NO:24.

In some embodiments, the methods comprise performing an assay on a sample obtained from a subject to determine whether the sample contains a KLHDC7B truncated variant polypeptide terminating at a position corresponding to position 885 according to SEQ ID NO:43. In some embodiments, the KLHDC7B truncated variant polypeptide lacks amino acids at positions corresponding to positions 886 to 1,235 of SEQ ID NO:19. In some embodiments, the KLHDC7B truncated variant polypeptide comprises or consists of SEQ ID NO:43.

In some embodiments, the methods comprise performing an assay on a sample obtained from a subject to determine whether the sample contains a KLHDC7B truncated variant polypeptide terminating at a position corresponding to position 244 according to SEQ ID NO:44. In some embodiments, the KLHDC7B truncated variant polypeptide lacks amino acids at positions corresponding to positions 245 to 594 of SEQ ID NO:20. In some embodiments, the KLHDC7B truncated variant polypeptide comprises or consists of SEQ ID NO:44.

In some embodiments, the methods comprise performing an assay on a sample obtained from a subject to determine whether the sample contains a KLHDC7B truncated variant polypeptide terminating at a position corresponding to position 145 according to SEQ ID NO:45. In some embodiments, the KLHDC7B truncated variant polypeptide lacks amino acids at positions corresponding to positions 146 to 495 of SEQ ID NO:21. In some embodiments, the KLHDC7B truncated variant polypeptide comprises or consists of SEQ ID NO:45.

In some embodiments, the methods comprise performing an assay on a sample obtained from a subject to determine whether the sample contains a KLHDC7B truncated variant polypeptide terminating at a position corresponding to position 975 according to SEQ ID NO:46. In some embodiments, the KLHDC7B truncated variant polypeptide lacks amino acids at positions corresponding to positions 976 to 1,235 of SEQ ID NO:19. In some embodiments, the KLHDC7B truncated variant polypeptide comprises or consists of SEQ ID NO:46.

In some embodiments, the methods comprise performing an assay on a sample obtained from a subject to determine whether the sample contains a KLHDC7B truncated variant polypeptide terminating at a position corresponding to position 334 according to SEQ ID NO:47. In some embodiments, the KLHDC7B truncated variant polypeptide lacks amino acids at positions corresponding to positions 335 to 594 of SEQ ID NO:20. In some embodiments, the KLHDC7B truncated variant polypeptide comprises or consists of SEQ ID NO:47.

In some embodiments, the methods comprise performing an assay on a sample obtained from a subject to determine whether the sample contains a KLHDC7B truncated variant polypeptide terminating at a position corresponding to position 235 according to SEQ ID NO:48. In some embodiments, the KLHDC7B truncated variant polypeptide lacks amino acids at positions corresponding to positions 236 to 495 of SEQ ID NO:21. In some embodiments, the KLHDC7B truncated variant polypeptide comprises or consists of SEQ ID NO:48.

In some embodiments, the detecting step comprises sequencing at least a portion of the polypeptide that comprises a position corresponding to position 1,145 according to SEQ ID NO:22 or SEQ ID NO:19. In some embodiments, the detecting step comprises sequencing at least a portion of the polypeptide that comprises a position corresponding to position 504 according to SEQ ID NO:23 or SEQ ID NO:20.

In some embodiments, the detecting step comprises sequencing at least a portion of the polypeptide that comprises a position corresponding to position 405 according to SEQ ID NO:24 or SEQ ID NO:21.

In some embodiments, the detecting step comprises sequencing at least a portion of a KLHDC7B polypeptide that may comprise positions corresponding to any positions that are C-terminal to position 885 according to SEQ ID NO:43. If amino acids are detected in the KLHDC7B polypeptide at positions corresponding to positions 886 to 1,235 according to SEQ ID NO:19, then such KLHDC7B polypeptide is a KLHDC7B reference polypeptide. An absence of positions 886 to 1,235 according to SEQ ID NO:19 in the KLHDC7B polypeptide indicates that the KLHDC7B polypeptide terminates at position 885 according to SEQ ID NO:43 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 244 according to SEQ ID NO:44. If amino acids are detected in the KLHDC7B polypeptide at positions corresponding to positions 245 to 594 according to SEQ ID NO:20, then such KLHDC7B polypeptide is a KLHDC7B reference polypeptide. An absence of positions 245 to 594 according to SEQ ID NO:20 in the KLHDC7B polypeptide indicates that the KLHDC7B polypeptide terminates at position 244 according to SEQ ID NO:44 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 145 according to SEQ ID NO:45. If amino acids are detected in the KLHDC7B polypeptide at positions corresponding to positions 146 to 495 according to SEQ ID NO:21, then such KLHDC7B polypeptide is a KLHDC7B reference polypeptide. An absence of positions 146 to 495 according to SEQ ID NO:21 in the KLHDC7B polypeptide indicates that the KLHDC7B polypeptide terminates at position 145 according to SEQ ID NO:45 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 975 according to SEQ ID NO:46. If amino acids are detected in the KLHDC7B polypeptide at positions corresponding to positions 976 to 1,235 according to SEQ ID NO:19, then such KLHDC7B polypeptide is a KLHDC7B reference polypeptide. An absence of positions 976 to 1,235 according to SEQ ID NO:19 in the KLHDC7B polypeptide indicates that the KLHDC7B polypeptide terminates at position 975 according to SEQ ID NO:46 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 334 according to SEQ ID NO:47. If amino acids are detected in the KLHDC7B polypeptide at positions corresponding to positions 335 to 594 according to SEQ ID NO:20, then such KLHDC7B polypeptide is a KLHDC7B reference polypeptide. An absence of positions 335 to 594 according to SEQ ID NO:20 in the KLHDC7B polypeptide indicates that the KLHDC7B polypeptide terminates at position 334 according to SEQ ID NO:47 and is a KLHDC7B predicted loss-of-function polypeptide.

In some embodiments, the detecting step comprises sequencing at least a portion of a KLHDC7B polypeptide that may comprise positions corresponding to any positions that are C-terminal to position 235 according to SEQ ID NO:48. If amino acids are detected in the KLHDC7B polypeptide at positions corresponding to positions 236 to 495 according to SEQ ID NO:21, then such KLHDC7B polypeptide is a KLHDC7B reference polypeptide. An absence of positions 236 to 495 according to SEQ ID NO:21 in the KLHDC7B polypeptide indicates that the KLHDC7B polypeptide terminates at position 235 according to SEQ ID NO:48 and is a KLHDC7B predicted loss-of-function polypeptide.

In some embodiments, the detecting step comprises an immunoassay for detecting the presence of a polypeptide that comprises a position corresponding to position 1,145 according to SEQ ID NO:22 or SEQ ID NO:19. In some embodiments, the detecting step comprises an immunoassay for detecting the presence of a polypeptide that comprises a position corresponding to position 504 according to SEQ ID NO:23 or SEQ ID NO:20. In some embodiments, the detecting step comprises an immunoassay for detecting the presence of a polypeptide that comprises a position corresponding to position 405 according to SEQ ID NO:24 or SEQ ID NO:21.

In some embodiments, the detecting step comprises an immunoassay for detecting the presence of a KLHDC7B polypeptide that comprises or consists of SEQ ID NO:43. In some embodiments, the KLHDC7B polypeptide consists of SEQ ID NO:43. In some embodiments, the detecting step comprises detecting at least a portion of a KLHDC7B polypeptide that may comprise positions corresponding to any positions that are C-terminal to position 885 according to SEQ ID NO:43. If amino acids are detected in the KLHDC7B polypeptide at positions corresponding to positions 886 to 1,235 according to SEQ ID NO:19, then such KLHDC7B polypeptide is a KLHDC7B reference polypeptide. A lack of detection of positions 886 to 1,235 according to SEQ ID NO:19 in the KLHDC7B polypeptide indicates that the KLHDC7B polypeptide terminates at position 885 according to SEQ ID NO:43 and is a KLHDC7B predicted loss-of-function polypeptide.

In some embodiments, the detecting step comprises an immunoassay for detecting the presence of a KLHDC7B polypeptide that comprises or consists of SEQ ID NO:44. In some embodiments, the KLHDC7B polypeptide consists of SEQ ID NO:44. In some embodiments, the detecting step comprises detecting at least a portion of a KLHDC7B polypeptide that may comprise positions corresponding to any positions that are C-terminal to position 244 according to SEQ ID NO:44. If amino acids are detected in the KLHDC7B polypeptide at positions corresponding to positions 245 to 594 according to SEQ ID NO:20, then such KLHDC7B polypeptide is a KLHDC7B reference polypeptide. A lack of detection of positions 245 to 594 according to SEQ ID NO:20 in the KLHDC7B polypeptide indicates that the KLHDC7B polypeptide terminates at position 244 according to SEQ ID NO:44 and is a KLHDC7B predicted loss-of-function polypeptide.

In some embodiments, the detecting step comprises an immunoassay for detecting the presence of a KLHDC7B polypeptide that comprises or consists of SEQ ID NO:45. In some embodiments, the KLHDC7B polypeptide consists of SEQ ID NO:45. In some embodiments, the detecting step comprises detecting at least a portion of a KLHDC7B polypeptide that may comprise positions corresponding to any positions that are C-terminal to position 145 according to SEQ ID NO:45. If amino acids are detected in the KLHDC7B polypeptide at positions corresponding to positions 146 to 495 according to SEQ ID NO:21, then such KLHDC7B polypeptide is a KLHDC7B reference polypeptide. A lack of detection of positions 146 to 495 according to SEQ ID NO:21 in the KLHDC7B polypeptide indicates that the KLHDC7B polypeptide terminates at position 145 according to SEQ ID NO:45 and is a KLHDC7B predicted loss-of-function polypeptide.

In some embodiments, the detecting step comprises an immunoassay for detecting the presence of a KLHDC7B polypeptide that comprises or consists of SEQ ID NO:46. In some embodiments, the KLHDC7B polypeptide consists of SEQ ID NO:46. In some embodiments, the detecting step comprises detecting at least a portion of a KLHDC7B polypeptide that may comprise positions corresponding to any positions that are C-terminal to position 975 according to SEQ ID NO:46. If amino acids are detected in the KLHDC7B polypeptide at positions corresponding to positions 976 to 1,235 according to SEQ ID NO:19, then such KLHDC7B polypeptide is a KLHDC7B reference polypeptide. A lack of detection of positions 976 to 1,235 according to SEQ ID NO:19 in the KLHDC7B polypeptide indicates that the KLHDC7B polypeptide terminates at position 975 according to SEQ ID NO:46 and is a KLHDC7B predicted loss-of-function polypeptide.

In some embodiments, the detecting step comprises an immunoassay for detecting the presence of a KLHDC7B polypeptide that comprises or consists of SEQ ID NO:47. In some embodiments, the KLHDC7B polypeptide consists of SEQ ID NO:47. In some embodiments, the detecting step comprises detecting at least a portion of a KLHDC7B polypeptide that may comprise positions corresponding to any positions that are C-terminal to position 334 according to SEQ ID NO:47. If amino acids are detected in the KLHDC7B polypeptide at positions corresponding to positions 335 to 594 according to SEQ ID NO:20, then such KLHDC7B polypeptide is a KLHDC7B reference polypeptide. A lack of detection of positions 335 to 594 according to SEQ ID NO:20 in the KLHDC7B polypeptide indicates that the KLHDC7B polypeptide terminates at position 334 according to SEQ ID NO:47 and is a KLHDC7B predicted loss-of-function polypeptide.

In some embodiments, the detecting step comprises an immunoassay for detecting the presence of a KLHDC7B polypeptide that comprises or consists of SEQ ID NO:48. In some embodiments, the KLHDC7B polypeptide consists of SEQ ID NO:48. In some embodiments, the detecting step comprises detecting at least a portion of a KLHDC7B polypeptide that may comprise positions corresponding to any positions that are C-terminal to position 235 according to SEQ ID NO:48. If amino acids are detected in the KLHDC7B polypeptide at positions corresponding to positions 236 to 495 according to SEQ ID NO:21, then such KLHDC7B polypeptide is a KLHDC7B reference polypeptide. A lack of detection of positions 236 to 495 according to SEQ ID NO:21 in the KLHDC7B polypeptide indicates that the KLHDC7B polypeptide terminates at position 235 according to SEQ ID NO:48 and is a KLHDC7B predicted loss-of-function polypeptide.

In some embodiments, when the subject does not have a KLHDC7B predicted loss-of-function polypeptide, then the subject does not have an increased risk for developing hearing loss or any of conductive hearing loss, sensorineural hearing loss, or neural hearing loss. In some embodiments, when the subject has a KLHDC7B predicted loss-of-function polypeptide, then the subject has an increased risk for developing hearing loss or any of conductive hearing loss, sensorineural hearing loss, or neural hearing loss.

The present disclosure also provides isolated nucleic acid molecules that hybridize to KLHDC7B variant genomic nucleic acid molecules, KLHDC7B variant mRNA molecules, and/or KLHDC7B variant cDNA molecules (such as any of the genomic variant nucleic acid molecules, mRNA variant molecules, and cDNA variant molecules disclosed herein). In some embodiments, the isolated nucleic acid molecules hybridize to a portion of the KLHDC7B nucleic acid molecule that includes a position corresponding to position 3,778 according to SEQ ID NO:2, position 3,778 according to SEQ ID NO:7, or position 3,778 according to SEQ ID NO:15. In some embodiments, the isolated nucleic acid molecules hybridize to a portion of the KLHDC7B nucleic acid molecule that includes a position corresponding to position 1,644 according to SEQ ID NO:8, or position 1,644 according to SEQ ID NO:16. In some embodiments, the isolated nucleic acid molecules hybridize to a portion of the KLHDC7B nucleic acid molecule that includes a position corresponding to position 3,474 according to SEQ ID NO:9, or position 3,474 according to SEQ ID NO:17. In some embodiments, the isolated nucleic acid molecules hybridize to a portion of the KLHDC7B nucleic acid molecule that includes a position corresponding to position 1,644 according to SEQ ID NO:10, or position 1,644 according to SEQ ID NO:18. In some embodiments, the isolated nucleic acid molecules hybridize to a portion of the KLHDC7B nucleic acid molecule that includes positions corresponding to positions 2,806-2,807 according to SEQ ID NO:25, positions corresponding to positions 2,806-2,807 according to SEQ ID NO:27, or positions corresponding to positions 2,806-2,807 according to SEQ ID NO:35. In some embodiments, the isolated nucleic acid molecules hybridize to a portion of the KLHDC7B nucleic acid molecule that includes positions corresponding to positions 672-673 according to SEQ ID NO:28, or positions corresponding to positions 672-673 according to SEQ ID NO:36. In some embodiments, the isolated nucleic acid molecules hybridize to a portion of the KLHDC7B nucleic acid molecule that includes positions corresponding to positions 2,502-2,503 according to SEQ ID NO:29, or positions corresponding to positions 2,502-2,503 according to SEQ ID NO:37. In some embodiments, the isolated nucleic acid molecules hybridize to a portion of the KLHDC7B nucleic acid molecule that includes positions corresponding to positions 672-673 according to SEQ ID NO:30, or positions corresponding to positions 672-673 according to SEQ ID NO:38. In some embodiments, the isolated nucleic acid molecules hybridize to a portion of the KLHDC7B nucleic acid molecule that includes positions corresponding to positions 3,169-3,170 according to SEQ ID NO:26; positions corresponding to positions 3,169-3,170 according to SEQ ID NO:31, or positions corresponding to positions 3,169-3,170 according to SEQ ID NO:39. In some embodiments, the isolated nucleic acid molecules hybridize to a portion of the KLHDC7B nucleic acid molecule that includes positions corresponding to positions 1,035-1,036 according to SEQ ID NO:32, or positions corresponding to positions 1,035-1,036 according to SEQ ID NO:40. In some embodiments, the isolated nucleic acid molecules hybridize to a portion of the KLHDC7B nucleic acid molecule that includes positions corresponding to positions 2,865-2,866 according to SEQ ID NO:33, or positions corresponding to positions 2,865-2,866 according to SEQ ID NO:41. In some embodiments, the isolated nucleic acid molecules hybridize to a portion of the KLHDC7B nucleic acid molecule that includes positions corresponding to positions 1,035-1,036 according to SEQ ID NO:34, or positions corresponding to positions 1,035-1,036 according to SEQ ID NO:42.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to KLHDC7B variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to KLHDC7B variant genomic nucleic acid molecules, KLHDC7B variant mRNA molecules, and/or KLHDC7B variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: position 3,778 according to SEQ ID NO:2, or the complement thereof; position 3,778 according to SEQ ID NO:7, or the complement thereof; or position 3,778 according to SEQ ID NO:15, or the complement thereof. In some embodiments, the alteration-specific probe or alteration-specific primer comprises a nucleotide sequence which is complementary to a portion of a nucleotide sequence comprising positions corresponding to: positions 3,778-3,780 according to SEQ ID NO:2, or the complement thereof; positions 3,778-3,780 according to SEQ ID NO:7, or the complement thereof; and/or positions 3,778-3,780 according to SEQ ID NO:15, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: position 1,644 according to SEQ ID NO:8, or the complement thereof; or position 1,644 according to SEQ ID NO:16, or the complement thereof. In some embodiments, the alteration-specific probe or alteration-specific primer comprises a nucleotide sequence which is complementary to a portion of a nucleotide sequence comprising positions corresponding to: positions 1,644-1,646 according to SEQ ID NO:8, or the complement thereof and/or positions 1,644-1,646 according to SEQ ID NO:16, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: position 3,474 according to SEQ ID NO:9, or the complement thereof; or position 3,474 according to SEQ ID NO:17, or the complement thereof. In some embodiments, the alteration-specific probe or alteration-specific primer comprises a nucleotide sequence which is complementary to a portion of a nucleotide sequence comprising positions corresponding to: positions 3,474-3,476 according to SEQ ID NO:9, or the complement thereof; and/or positions 3,474-3,476 according to SEQ ID NO:17, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: position 1,644 according to SEQ ID NO:10, or the complement thereof; or position 1,644 according to SEQ ID NO:18, or the complement thereof. In some embodiments, the alteration-specific probe or alteration-specific primer comprises a nucleotide sequence which is complementary to a portion of a nucleotide sequence comprising positions corresponding to: positions 1,644-1,646 according to SEQ ID NO:10, or the complement thereof; and/or positions 1,644-1,646 according to SEQ ID NO:18, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: a CG dinucleotide at positions corresponding to positions 2,806-2,807 according to SEQ ID NO:25, or the complement thereof; a CG dinucleotide at positions corresponding to positions 2,806-2,807 to SEQ ID NO:27, or the complement thereof; or a CG dinucleotide at positions corresponding to positions 2,806-2,807 to SEQ ID NO:35, or the complement thereof. In some embodiments, the alteration-specific probe or alteration-specific primer comprises a nucleotide sequence which is complementary to a portion of a nucleotide sequence comprising positions corresponding to: a CG dinucleotide at positions corresponding to positions 2,806-2,807 according to SEQ ID NO:25, or the complement thereof; a CG dinucleotide at positions corresponding to positions 2,806-2,807 to SEQ ID NO:27, or the complement thereof; or a CG dinucleotide at positions corresponding to positions 2,806-2,807 to SEQ ID NO:35, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: a CG dinucleotide at positions corresponding to positions 672-673 according to SEQ ID NO:28, or the complement thereof, or a CG dinucleotide at positions corresponding to positions 672-673 according to SEQ ID NO:36, or the complement thereof. In some embodiments, the alteration-specific probe or alteration-specific primer comprises a nucleotide sequence which is complementary to a portion of a nucleotide sequence comprising positions corresponding to: a CG dinucleotide at positions corresponding to positions 672-673 according to SEQ ID NO:28, or the complement thereof, or a CG dinucleotide at positions corresponding to positions 672-673 according to SEQ ID NO:36, or the complement thereof In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: a CG dinucleotide at positions corresponding to positions 2,502-2,503 according to SEQ ID NO:29, or the complement thereof, or a CG dinucleotide at positions corresponding to positions 2,502-2,503 according to SEQ ID NO:37, or the complement thereof. In some embodiments, the alteration-specific probe or alteration-specific primer comprises a nucleotide sequence which is complementary to a portion of a nucleotide sequence comprising positions corresponding to: a CG dinucleotide at positions corresponding to positions 2,502-2,503 according to SEQ ID NO:29, or the complement thereof, or a CG dinucleotide at positions corresponding to positions 2,502-2,503 according to SEQ ID NO:37, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: a CG dinucleotide at positions corresponding to positions 672-673 according to SEQ ID NO:30, or the complement thereof, or a CG dinucleotide at positions corresponding to positions 672-673 according to SEQ ID NO:38, or the complement thereof. In some embodiments, the alteration-specific probe or alteration-specific primer comprises a nucleotide sequence which is complementary to a portion of a nucleotide sequence comprising positions corresponding to: a CG dinucleotide at positions corresponding to positions 672-673 according to SEQ ID NO:30, or the complement thereof, or a CG dinucleotide at positions corresponding to positions 672-673 according to SEQ ID NO:38, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: an AG dinucleotide at positions corresponding to positions 3,169-3,170 according to SEQ ID NO:26, or the complement thereof; an AG dinucleotide at positions corresponding to positions 3,169-3,170 according to SEQ ID NO:31, or the complement thereof; or an AG dinucleotide at positions corresponding to positions 3,169-3,170 according to SEQ ID NO:39, or the complement thereof. In some embodiments, the alteration-specific probe or alteration-specific primer comprises a nucleotide sequence which is complementary to a portion of a nucleotide sequence comprising positions corresponding to: an AG dinucleotide at positions corresponding to positions 3,169-3,170 according to SEQ ID NO:26, or the complement thereof; an AG dinucleotide at positions corresponding to positions 3,169-3,170 according to SEQ ID NO:31, or the complement thereof; or an AG dinucleotide at positions corresponding to positions 3,169-3,170 according to SEQ ID NO:39, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: an AG dinucleotide at positions corresponding to positions 1,035-1,036 according to SEQ ID NO:32, or the complement thereof, or an AG dinucleotide at positions corresponding to positions 1,035-1,036 according to SEQ ID NO:40, or the complement thereof. In some embodiments, the alteration-specific probe or alteration-specific primer comprises a nucleotide sequence which is complementary to a portion of a nucleotide sequence comprising positions corresponding to: an AG dinucleotide at positions corresponding to positions 1,035-1,036 according to SEQ ID NO:32, or the complement thereof, or an AG dinucleotide at positions corresponding to positions 1,035-1,036 according to SEQ ID NO:40, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: an AG dinucleotide at positions corresponding to positions 2,865-2,866 according to SEQ ID NO:33, or the complement thereof, or an AG dinucleotide at positions corresponding to positions 2,865-2,866 according to SEQ ID NO:41, or the complement thereof. In some embodiments, the alteration-specific probe or alteration-specific primer comprises a nucleotide sequence which is complementary to a portion of a nucleotide sequence comprising positions corresponding to: an AG dinucleotide at positions corresponding to positions 2,865-2,866 according to SEQ ID NO:33, or the complement thereof, or an AG dinucleotide at positions corresponding to positions 2,865-2,866 according to SEQ ID NO:41, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a KLHDC7B polypeptide, wherein the portion comprises a position corresponding to: an AG dinucleotide at positions corresponding to positions 1,035-1,036 according to SEQ ID NO:34, or the complement thereof, or an AG dinucleotide at positions corresponding to positions 1,035-1,036 according to SEQ ID NO:42, or the complement thereof. In some embodiments, the alteration-specific probe or alteration-specific primer comprises a nucleotide sequence which is complementary to a portion of a nucleotide sequence comprising positions corresponding to: an AG dinucleotide at positions corresponding to positions 1,035-1,036 according to SEQ ID NO:34, or the complement thereof, or an AG dinucleotide at positions corresponding to positions 1,035-1,036 according to SEQ ID NO:42, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the KLHDC7B variant genomic nucleic acid molecules, KLHDC7B variant mRNA molecules, and/or KLHDC7B variant cDNA molecules disclosed herein. The primers described herein can be used to amplify KLHDC7B variant genomic nucleic acid molecules, KLHDC7B variant mRNA molecules, or KLHDC7B variant cDNA molecules, or a fragment thereof.

The present disclosure also provides pairs of primers comprising any of the primers described above. For example, if one of the primers' 3'-ends hybridizes to a guanine at a position corresponding to position 3,778 according to SEQ ID NO:1 (rather than adenine) in a particular KLHDC7B nucleic acid molecule, then the presence of the amplified fragment would indicate the presence of a KLHDC7B reference genomic nucleic acid molecule. Conversely, if one of the primers' 3'-ends hybridizes to an adenine at a position corresponding to position 3,778 according to SEQ ID NO:2 (rather than guanine) in a particular KLHDC7B nucleic acid molecule, then the presence of the amplified fragment would indicate the presence of the KLHDC7B variant genomic nucleic acid molecule. In some embodiments, the nucleotide of the primer complementary to the adenine at a position corresponding to position 3,778 according to SEQ ID NO:2 can be at the 3' end of the primer. In addition, if one of the primers' 3'-ends hybridizes to a guanine at a position corresponding to position 3,778 according to SEQ ID NO:3 (rather than adenine) in a particular KLHDC7B nucleic acid molecule, then the presence of the amplified fragment would indicate the presence of a KLHDC7B reference mRNA molecule. Conversely, if one of the primers' 3'-ends hybridizes to an adenine at a position corresponding to position 3,778 according to SEQ ID NO:7 (rather than guanine) in a particular KLHDC7B mRNA molecule, then the presence of the amplified fragment would indicate the presence of the KLHDC7B variant mRNA molecule. In some embodiments, the nucleotide of the primer complementary to the adenine at a position corresponding to position 3,778 according to SEQ ID NO:7 can be at the 3' end of the primer. In addition, if one of the primers' 3'-ends hybridizes to a guanine at a position corresponding to position 3,778 according to SEQ ID NO:11 (rather than adenine) in a particular KLHDC7B nucleic acid molecule, then the presence of the amplified fragment would indicate the presence of a KLHDC7B reference cDNA molecule. Conversely, if one of the primers' 3'-ends hybridizes to an adenine at a position corresponding to position 3,778 according to SEQ ID NO:15 (rather than guanine) in a particular KLHDC7B cDNA molecule, then the presence of the amplified fragment would indicate the presence of the KLHDC7B variant cDNA molecule. In some embodiments, the nucleotide of the primer complementary to the adenine at a position corresponding to position 3,778 according to SEQ ID NO:15 can be at the 3' end of the primer.

If, for example, one of the primers' 3'-ends hybridizes to a guanine at a position corresponding to position 1,644 according to SEQ ID NO:4 (rather than adenine) in a particular KLHDC7B nucleic acid molecule, then the presence of the amplified fragment would indicate the presence of a KLHDC7B reference mRNA molecule. Conversely, if one of the primers' 3'-ends hybridizes to an adenine at a position corresponding to position 1,644 according to SEQ ID NO:8 (rather than guanine) in a particular KLHDC7B mRNA molecule, then the presence of the amplified fragment would indicate the presence of the KLHDC7B variant mRNA molecule. In some embodiments, the nucleotide of the primer complementary to the adenine at a position corresponding to position 1,644 according to SEQ ID NO:8 can be at the 3' end of the primer. In addition, if one of the primers' 3'-ends hybridizes to a guanine at a position corresponding to position 1,644 according to SEQ ID NO:12 (rather than adenine) in a particular KLHDC7B nucleic acid molecule, then the presence of the amplified fragment would indicate the presence of a KLHDC7B reference cDNA molecule. Conversely, if one of the primers' 3'-ends hybridizes to an adenine at a position corresponding to position 1,644 according to SEQ ID NO:16 (rather than guanine) in a particular KLHDC7B cDNA molecule, then the presence of the amplified fragment would indicate the presence of the KLHDC7B variant cDNA molecule. In some embodiments, the nucleotide of the primer complementary to the adenine at a position corresponding to position 1,644 according to SEQ ID NO:16 can be at the 3' end of the primer.

If, for example, one of the primers' 3'-ends hybridizes to a guanine at a position corresponding to position 3,474 according to SEQ ID NO:5 (rather than adenine) in a particular KLHDC7B nucleic acid molecule, then the presence of the amplified fragment would indicate the presence of a KLHDC7B reference mRNA molecule. Conversely, if one of the primers' 3'-ends hybridizes to an adenine at a position corresponding to position 3,474 according to SEQ ID NO:9 (rather than guanine) in a particular KLHDC7B mRNA molecule, then the presence of the amplified fragment would indicate the presence of the KLHDC7B variant mRNA molecule. In some embodiments, the nucleotide of the primer complementary to the adenine at a position corresponding to position 3,474 according to SEQ ID NO:9 can be at the 3' end of the primer. In addition, if one of the primers' 3'-ends hybridizes to a guanine at a position corresponding to position 3,474 according to SEQ ID NO:13 (rather than adenine) in a particular KLHDC7B nucleic acid molecule, then the presence of the amplified fragment would indicate the presence of a KLHDC7B reference cDNA molecule. Conversely, if one of the primers' 3'-ends hybridizes to an adenine at a position corresponding to position 3,474 according to SEQ ID NO:17 (rather than guanine) in a particular KLHDC7B cDNA molecule, then the presence of the amplified fragment would indicate the presence of the KLHDC7B variant cDNA molecule. In some embodiments, the nucleotide of the primer complementary to the adenine at a position corresponding to position 3,474 according to SEQ ID NO:17 can be at the 3' end of the primer.

If, for example, one of the primers' 3'-ends hybridizes to a guanine at a position corresponding to position 1,644 according to SEQ ID NO:6 (rather than adenine) in a particular KLHDC7B nucleic acid molecule, then the presence of the amplified fragment would indicate the presence of a KLHDC7B reference mRNA molecule. Conversely, if one of the primers' 3'-ends hybridizes to an adenine at a position corresponding to position 1,644 according to SEQ ID NO:10 (rather than guanine) in a particular KLHDC7B mRNA molecule, then the presence of the amplified fragment would indicate the presence of the KLHDC7B variant mRNA molecule. In some embodiments, the nucleotide of the primer complementary to the adenine at a position corresponding to position 1,644 according to SEQ ID NO:10 can be at the 3' end of the primer. In addition, if one of the primers' 3'-ends hybridizes to a guanine at a position corresponding to position 1,644 according to SEQ ID NO:14 (rather than adenine) in a particular KLHDC7B nucleic acid molecule, then the presence of the amplified fragment would indicate the presence of a KLHDC7B reference cDNA molecule. Conversely, if one of the primers' 3'-ends hybridizes to an adenine at a position corresponding to position 1,644 according to SEQ ID NO:18 (rather than guanine) in a particular KLHDC7B cDNA molecule, then the presence of the amplified fragment would indicate the presence of the KLHDC7B variant cDNA molecule. In some embodiments, the nucleotide of the primer complementary to the adenine at a position corresponding to position 1,644 according to SEQ ID NO:18 can be at the 3' end of the primer.

If, for example, one of the primers' 3'-ends hybridizes to a CGG trinucleotide at positions corresponding to positions 2,806-2,808 according to SEQ ID NO:1 (rather than a CG dinucleotide at positions corresponding to positions 2,806-2,807 according to SEQ ID NO:25) in a particular KLHDC7B nucleic acid molecule, then the presence of the amplified fragment would indicate the presence of a KLHDC7B reference genomic nucleic acid molecule. Conversely, if one of the primers' 3'-ends hybridizes to a CG dinucleotide at positions corresponding to positions 2,806-2,807 according to SEQ ID NO:25 (rather than a CGG trinucleotide at positions corresponding to positions 2,806-2,808 according to SEQ ID NO:1) in a particular KLHDC7B nucleic acid molecule, then the presence of the amplified fragment would indicate the presence of the KLHDC7B variant genomic nucleic acid molecule. In some embodiments, the nucleotide of the primer complementary to the CG dinucleotide at positions corresponding to positions 2,806-2,807 according to SEQ ID NO:25 can be at the 3' end of the primer. In addition, if one of the primers' 3'-ends hybridizes to a CGG trinucleotide at positions corresponding to positions 2,806-2,808 according to SEQ ID NO:3 (rather than a CG dinucleotide at positions corresponding to positions 2,806-2,807 to SEQ ID NO:27) in a particular KLHDC7B nucleic acid molecule, then the presence of the amplified fragment would indicate the presence of a KLHDC7B reference mRNA molecule. Conversely, if one of the primers' 3'-ends hybridizes to a CG dinucleotide at positions corresponding to positions 2,806-2,807 to SEQ ID NO:27 (rather than CGG trinucleotide at positions corresponding to positions 2,806-2,808 according to SEQ ID NO:3) in a particular KLHDC7B mRNA molecule, then the presence of the amplified fragment would indicate the presence of the KLHDC7B variant mRNA molecule. In some embodiments, the nucleotide of the primer complementary to the CG dinucleotide at positions corresponding to positions 2,806-2,807 to SEQ ID NO:27 can be at the 3' end of the primer. In addition, if one of the primers' 3'-ends hybridizes to a CGG trinucleotide at positions corresponding to positions 2,806-2,808 according to SEQ ID NO:11 (rather than a CG dinucleotide at positions corresponding to positions 2,806-2,807 to SEQ ID NO:35) in a particular KLHDC7B nucleic acid molecule, then the presence of the amplified fragment would indicate the presence of a KLHDC7B reference cDNA molecule. Conversely, if one of the primers' 3'-ends hybridizes to a CG dinucleotide at positions corresponding to positions 2,806-2,807 to SEQ ID NO:35 (rather than CGG trinucleotide at positions corresponding to positions 2,806-2,808 according to SEQ ID NO:11) in a particular KLHDC7B cDNA molecule, then the presence of the amplified fragment would indicate the presence of the KLHDC7B variant cDNA molecule. In some embodiments, the nucleotide of the primer complementary to the CG dinucleotide at positions corresponding to positions 2,806-2,807 to SEQ ID NO:35 can be at the 3' end of the primer.

If, for example, if one of the primers' 3'-ends hybridizes to a CGG trinucleotide at positions corresponding to positions 672-674 according to SEQ ID NO:4 (rather than a CG dinucleotide at positions corresponding to positions 672-673 according to SEQ ID NO:28) in a particular KLHDC7B nucleic acid molecule, then the presence of the amplified fragment would indicate the presence of a KLHDC7B reference mRNA molecule. Conversely, if one of the primers' 3'-ends hybridizes to a CG dinucleotide at positions corresponding to positions 672-673 according to SEQ ID NO:28 (rather than CGG trinucleotide at positions corresponding to positions 672-674 according to SEQ ID NO:4) in a particular KLHDC7B mRNA molecule, then the presence of the amplified fragment would indicate the presence of the KLHDC7B variant mRNA molecule. In some embodiments, the nucleotide of the primer complementary to the CG dinucleotide at positions corresponding to positions 672-673 according to SEQ ID NO:28 can be at the 3' end of the primer. In addition, if one of the primers' 3'-ends hybridizes to a CGG trinucleotide at positions corresponding to positions 672-674 according to SEQ ID NO:12 (rather than a CG dinucleotide at positions corresponding to positions 672-673 according to SEQ ID NO:36) in a particular KLHDC7B nucleic acid molecule, then the presence of the amplified fragment would indicate the presence of a KLHDC7B reference cDNA molecule. Conversely, if one of the primers' 3'-ends hybridizes to a CG dinucleotide at positions corresponding to positions 672-673 according to SEQ ID NO:36 (rather than CGG trinucleotide at positions corresponding to positions 672-674 according to SEQ ID NO:12) in a particular KLHDC7B cDNA molecule, then the presence of the amplified fragment would indicate the presence of the KLHDC7B variant cDNA molecule. In some embodiments, the nucleotide of the primer complementary to the CG dinucleotide at positions corresponding to positions 672-673 according to SEQ ID NO:36 can be at the 3' end of the primer.

If, for example, if one of the primers' 3'-ends hybridizes to a CGG trinucleotide at positions corresponding to positions 2,502-2,504 according to SEQ ID NO:5 (rather than a CG dinucleotide at positions corresponding to positions 2,502-2,503 according to SEQ ID NO:29) in a particular KLHDC7B nucleic acid molecule, then the presence of the amplified fragment would indicate the presence of a KLHDC7B reference mRNA molecule. Conversely, if one of the primers' 3'-ends hybridizes to a CG dinucleotide at positions corresponding to positions 2,502-2,503 according to SEQ ID NO:29 (rather than CGG trinucleotide at positions corresponding to positions 2,502-2,504 according to SEQ ID NO:5) in a particular KLHDC7B mRNA molecule, then the presence of the amplified fragment would indicate the presence of the KLHDC7B variant mRNA molecule. In some embodiments, the nucleotide of the primer complementary to the CG dinucleotide at positions corresponding to positions 2,502-2,503 according to SEQ ID NO:29 can be at the 3' end of the primer. In addition, if one of the primers' 3'-ends hybridizes to a CGG trinucleotide at positions corresponding to positions 2,502-2,504 according to SEQ ID NO:13 (rather than a CG dinucleotide at positions corresponding to positions 2,502-2,503 according to SEQ ID NO:37) in a particular KLHDC7B nucleic acid molecule, then the presence of the amplified fragment would indicate the presence of a KLHDC7B reference cDNA molecule. Conversely, if one of the primers' 3'-ends hybridizes to CG dinucleotide at positions corresponding to positions 2,502-2,503 according to SEQ ID NO:37 (rather than CGG trinucleotide at positions corresponding to positions 2,502-2,504 according to SEQ ID NO:13) in a particular KLHDC7B cDNA molecule, then the presence of the amplified fragment would indicate the presence of the KLHDC7B variant cDNA molecule. In some embodiments, the nucleotide of the primer complementary to the CG dinucleotide at positions corresponding to positions 2,502-2,503 according to SEQ ID NO:37 can be at the 3' end of the primer.

If, for example, if one of the primers' 3'-ends hybridizes to a CGG trinucleotide at positions corresponding to positions 672-674 according to SEQ ID NO:6 (rather than a CG dinucleotide at positions corresponding to positions 672-673 according to SEQ ID NO:30) in a particular KLHDC7B nucleic acid molecule, then the presence of the amplified fragment would indicate the presence of a KLHDC7B reference mRNA molecule. Conversely, if one of the primers' 3'-ends hybridizes to a CG dinucleotide at positions corresponding to positions 672-673 according to SEQ ID NO:30 (rather than CGG trinucleotide at positions corresponding to positions 672-674 according to SEQ ID NO:6) in a particular KLHDC7B mRNA molecule, then the presence of the amplified fragment would indicate the presence of the KLHDC7B variant mRNA molecule. In some embodiments, the nucleotide of the primer complementary to the CG dinucleotide at positions corresponding to positions 672-673 according to SEQ ID NO:30 can be at the 3' end of the primer. In addition, if one of the primers' 3'-ends hybridizes to a CGG trinucleotide at positions corresponding to positions 672-674 according to SEQ ID NO:14 (rather than a CG dinucleotide at positions corresponding to positions 672-673 according to SEQ ID NO:38) in a particular KLHDC7B nucleic acid molecule, then the presence of the amplified fragment would indicate the presence of a KLHDC7B reference cDNA molecule. Conversely, if one of the primers' 3'-ends hybridizes to a CG dinucleotide at positions corresponding to positions 672-673 according to SEQ ID NO:38 (rather than CGG trinucleotide at positions corresponding to positions 672-674 according to SEQ ID NO:14) in a particular KLHDC7B cDNA molecule, then the presence of the amplified fragment would indicate the presence of the KLHDC7B variant cDNA molecule. In some embodiments, the nucleotide of the primer complementary to the CG dinucleotide at positions corresponding to positions 672-673 according to SEQ ID NO:38 can be at the 3' end of the primer.

If, for example, one of the primers' 3'-ends hybridizes to an AGG trinucleotide at positions corresponding to positions 3,169-3,171 according to SEQ ID NO:1 (rather than an AG dinucleotide at positions corresponding to positions 3,169-3,170 according to SEQ ID NO:26) in a particular KLHDC7B nucleic acid molecule, then the presence of the amplified fragment would indicate the presence of a KLHDC7B reference genomic nucleic acid molecule. Conversely, if one of the primers' 3'-ends hybridizes to an AG dinucleotide at positions corresponding to positions 3,169-3,170 according to SEQ ID NO:26 (rather than an AGG trinucleotide at positions corresponding to positions 3,169-3,171 according to SEQ ID NO:1) in a particular KLHDC7B nucleic acid molecule, then the presence of the amplified fragment would indicate the presence of the KLHDC7B variant genomic nucleic acid molecule. In some embodiments, the nucleotide of the primer complementary to the AG dinucleotide at positions corresponding to positions 3,169-3,170 according to SEQ ID NO:26 can be at the 3' end of the primer. In addition, if one of the primers' 3'-ends hybridizes to an AGG trinucleotide at positions corresponding to positions 3,169-3,171 according to SEQ ID NO:3 (rather than an AG dinucleotide at positions corresponding to positions 3,169-3,170 according to SEQ ID NO:31) in a particular KLHDC7B nucleic acid molecule, then the presence of the amplified fragment would indicate the presence of a KLHDC7B reference mRNA molecule. Conversely, if one of the primers' 3'-ends hybridizes to an AG dinucleotide at positions corresponding to positions 3,169-3,170 according to SEQ ID NO:31 (rather than AGG trinucleotide at positions corresponding to positions 3,169-3,171 according to SEQ ID NO:3) in a particular KLHDC7B mRNA molecule, then the presence of the amplified fragment would indicate the presence of the KLHDC7B variant mRNA molecule. In some embodiments, the nucleotide of the primer complementary to the AG dinucleotide at positions corresponding to positions 3,169-3,170 according to SEQ ID NO:31 can be at the 3' end of the primer. In addition, if one of the primers' 3'-ends hybridizes to an AGG trinucleotide at positions corresponding to positions 3,169-3,171 according to SEQ ID NO:11 (rather than an AG dinucleotide at positions corresponding to positions 3,169-3,170 according to SEQ ID NO:39) in a particular KLHDC7B nucleic acid molecule, then the presence of the amplified fragment would indicate the presence of a KLHDC7B reference cDNA molecule. Conversely, if one of the primers' 3'-ends hybridizes to an AG dinucleotide at positions corresponding to positions 3,169-3,170 according to SEQ ID NO:39 (rather than AGG trinucleotide at positions corresponding to positions 3,169-3,171 according to SEQ ID NO:11) in a particular KLHDC7B cDNA molecule, then the presence of the amplified fragment would indicate the presence of the KLHDC7B variant cDNA molecule. In some embodiments, the nucleotide of the primer complementary to the AG dinucleotide at positions corresponding to positions 3,169-3,170 according to SEQ ID NO:39 can be at the 3' end of the primer.

If, for example, one of the primers' 3'-ends hybridizes to an AGG trinucleotide at positions corresponding to positions 1,035-1,037 according to SEQ ID NO:4 (rather than an AG dinucleotide at positions corresponding to positions 1,035-1,036 according to SEQ ID NO:32) in a particular KLHDC7B nucleic acid molecule, then the presence of the amplified fragment would indicate the presence of a KLHDC7B reference mRNA molecule. Conversely, if one of the primers' 3'-ends hybridizes to an AG dinucleotide at positions corresponding to positions 1,035-1,036 according to SEQ ID NO:32 (rather than AGG trinucleotide at positions corresponding to positions 1,035-1,037 according to SEQ ID NO:4) in a particular KLHDC7B mRNA molecule, then the presence of the amplified fragment would indicate the presence of the KLHDC7B variant mRNA molecule. In some embodiments, the nucleotide of the primer complementary to the AG dinucleotide at positions corresponding to positions 1,035-1,036 according to SEQ ID NO:32 can be at the 3' end of the primer. In addition, if one of the primers' 3'-ends hybridizes to an AGG trinucleotide at positions corresponding to positions 1,035-1,037 according to SEQ ID NO:12 (rather than an AG dinucleotide at positions corresponding to positions 1,035-1,036 according to SEQ ID NO:40) in a particular KLHDC7B nucleic acid molecule, then the presence of the amplified fragment would indicate the presence of a KLHDC7B reference cDNA molecule. Conversely, if one of the primers' 3'-ends hybridizes to an AG dinucleotide at positions corresponding to positions 1,035-1,036 according to SEQ ID NO:40 (rather than AGG trinucleotide at positions corresponding to positions 1,035-

1,037 according to SEQ ID NO:12) in a particular KLHDC7B cDNA molecule, then the presence of the amplified fragment would indicate the presence of the KLHDC7B variant cDNA molecule. In some embodiments, the nucleotide of the primer complementary to the AG dinucleotide at positions corresponding to positions 1,035-1,036 according to SEQ ID NO:40 can be at the 3' end of the primer.

If, for example, one of the primers' 3'-ends hybridizes to an AGG trinucleotide at positions corresponding to positions 2,865-2,867 according to SEQ ID NO:5 (rather than an AG dinucleotide at positions corresponding to positions 2,865-2,866 according to SEQ ID NO:33) in a particular KLHDC7B nucleic acid molecule, then the presence of the amplified fragment would indicate the presence of a KLHDC7B reference mRNA molecule. Conversely, if one of the primers' 3'-ends hybridizes to an AG dinucleotide at positions corresponding to positions 2,865-2,866 according to SEQ ID NO:33 (rather than AGG trinucleotide at positions corresponding to positions 2,865-2,867 according to SEQ ID NO:5) in a particular KLHDC7B mRNA molecule, then the presence of the amplified fragment would indicate the presence of the KLHDC7B variant mRNA molecule. In some embodiments, the nucleotide of the primer complementary to the AG dinucleotide at positions corresponding to positions 2,865-2,866 according to SEQ ID NO:33 can be at the 3' end of the primer. In addition, if one of the primers' 3'-ends hybridizes to an AGG trinucleotide at positions corresponding to positions 2,865-2,867 according to SEQ ID NO:13 (rather than an AG dinucleotide at positions corresponding to positions 2,865-2,866 according to SEQ ID NO:41) in a particular KLHDC7B nucleic acid molecule, then the presence of the amplified fragment would indicate the presence of a KLHDC7B reference cDNA molecule. Conversely, if one of the primers' 3'-ends hybridizes to an AG dinucleotide at positions corresponding to positions 2,865-2,866 according to SEQ ID NO:41 (rather than AGG trinucleotide at positions corresponding to positions 2,865-2,867 according to SEQ ID NO:13) in a particular KLHDC7B cDNA molecule, then the presence of the amplified fragment would indicate the presence of the KLHDC7B variant cDNA molecule. In some embodiments, the nucleotide of the primer complementary to the AG dinucleotide at positions corresponding to positions 2,865-2,866 according to SEQ ID NO:41 can be at the 3' end of the primer.

If, for example, one of the primers' 3'-ends hybridizes to an AGG trinucleotide at positions corresponding to positions 1,035-1,037 according to SEQ ID NO:6 (rather than an AG dinucleotide at positions corresponding to positions 1,035-1,036 according to SEQ ID NO:34) in a particular KLHDC7B nucleic acid molecule, then the presence of the amplified fragment would indicate the presence of a KLHDC7B reference mRNA molecule. Conversely, if one of the primers' 3'-ends hybridizes to an AG dinucleotide at positions corresponding to positions 1,035-1,036 according to SEQ ID NO:34 (rather than AGG trinucleotide at positions corresponding to positions 1,035-1,037 according to SEQ ID NO:6) in a particular KLHDC7B mRNA molecule, then the presence of the amplified fragment would indicate the presence of the KLHDC7B variant mRNA molecule. In some embodiments, the nucleotide of the primer complementary to the AG dinucleotide at positions corresponding to positions 1,035-1,036 according to SEQ ID NO:34 can be at the 3' end of the primer. In addition, if one of the primers' 3'-ends hybridizes to an AGG trinucleotide at positions corresponding to positions 1,035-1,037 according to SEQ ID NO:14 (rather than an AG dinucleotide at positions corresponding to positions 1,035-1,036 according to SEQ ID NO:42) in a particular KLHDC7B nucleic acid molecule, then the presence of the amplified fragment would indicate the presence of a KLHDC7B reference cDNA molecule. Conversely, if one of the primers' 3'-ends hybridizes to an AG dinucleotide at positions corresponding to positions 1,035-1,036 according to SEQ ID NO:42 (rather than AGG trinucleotide at positions corresponding to positions 1,035-1,037 according to SEQ ID NO:14) in a particular KLHDC7B cDNA molecule, then the presence of the amplified fragment would indicate the presence of the KLHDC7B variant cDNA molecule. In some embodiments, the nucleotide of the primer complementary to the AG dinucleotide at positions corresponding to positions 1,035-1,036 according to SEQ ID NO:42 can be at the 3' end of the primer.

In the context of the disclosure "specifically hybridizes" means that the probe or primer (such as, for example, the alteration-specific probe or alteration-specific primer) does not hybridize to a nucleic acid sequence encoding a KLHDC7B reference genomic nucleic acid molecule, a KLHDC7B reference mRNA molecule, and/or a KLHDC7B reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides molecular complexes comprising or consisting of any of the KLHDC7B nucleic acid molecules (genomic nucleic acid molecules, mRNA molecules, or cDNA molecules), or complement thereof, described herein and any of the alteration-specific primers or alteration-specific probes described herein. In some embodiments, the KLHDC7B nucleic acid molecules (genomic nucleic acid molecules, mRNA molecules, or cDNA molecules), or complement thereof, in the molecular complexes are single-stranded. In some embodiments, the KLHDC7B nucleic acid molecule is any of the genomic nucleic acid molecules described herein. In some embodiments, the KLHDC7B nucleic acid molecule is any of the mRNA molecules described herein. In some embodiments, the KLHDC7B nucleic acid molecule is any of the cDNA molecules described herein. In some embodiments, the molecular complex comprises or consists of any of the KLHDC7B nucleic acid molecules (genomic nucleic acid molecules, mRNA molecules, or cDNA molecules), or complement thereof, described herein and any of the alteration-specific primers described herein. In some embodiments, the molecular complex comprises or consists of any of the KLHDC7B nucleic acid molecules (genomic nucleic acid molecules, mRNA molecules, or cDNA molecules), or complement thereof, described herein and any of the alteration-specific probes described herein.

In some embodiments, the molecular complex comprises or consists of an alteration-specific primer or an alteration-specific probe hybridized to a genomic nucleic acid molecule comprising a nucleotide sequence encoding a KLHDC7B polypeptide, wherein the alteration-specific primer or the alteration-specific probe is hybridized to an adenine at a position corresponding to position 3,778 according to SEQ ID NO:2, or the complement thereof.

In some embodiments, the molecular complex comprises or consists of an alteration-specific primer or an alteration-specific probe that is hybridized to an ATG codon at positions corresponding to positions 3,778-3,780 according to SEQ ID NO:2.

In some embodiments, the molecular complex comprises or consists of a genomic nucleic acid molecule that comprises SEQ ID NO:2.

In some embodiments, the molecular complex comprises or consists of an alteration-specific primer or an alteration-specific probe hybridized to an mRNA molecule comprising a nucleotide sequence encoding a KLHDC7B polypeptide, wherein the alteration-specific primer or the alteration-specific probe is hybridized to: an adenine at a position corresponding to position 3,778 according to SEQ ID NO:7, or the complement thereof; an adenine at a position corresponding to position 1,644 according to SEQ ID NO:8, or the complement thereof; an adenine at a position corresponding to position 3,474 according to SEQ ID NO:9, or the complement thereof; an adenine at a position corresponding to position 1,644 according to SEQ ID NO:10, or the complement thereof; a CG dinucleotide at positions corresponding to positions 2,806-2,807 according to SEQ ID NO:27, or the complement thereof; a CG dinucleotide at positions corresponding to positions 672-673 according to SEQ ID NO:28, or the complement thereof; a CG dinucleotide at positions corresponding to positions 2,502-2,503 according to SEQ ID NO:29, or the complement thereof; a CG dinucleotide at positions corresponding to positions 672-673 according to SEQ ID NO:30, or the complement thereof; an AG dinucleotide at positions corresponding to positions 3,169-3,170 according to SEQ ID NO:31, or the complement thereof; an AG dinucleotide at positions corresponding to positions 1,035-1,036 according to SEQ ID NO:32, or the complement thereof; an AG dinucleotide at positions corresponding to positions 2,865-2,866 according to SEQ ID NO:33, or the complement thereof; or an AG dinucleotide at positions corresponding to positions 1,035-1,036 according to SEQ ID NO:34, or the complement thereof.

In some embodiments, the molecular complex comprises or consists of an alteration-specific primer or an alteration-specific probe that is hybridized to: an AUG codon at positions corresponding to positions 3,778-3,780 according to SEQ ID NO:7, an AUG codon at positions corresponding to positions 1,644-1,646 according to SEQ ID NO:8, an AUG codon at positions corresponding to positions 3,474-3,476 according to SEQ ID NO:9, or an AUG codon at positions corresponding to positions 1,644-1,646 according to SEQ ID NO:10.

In some embodiments, the molecular complex comprises or consists of an mRNA molecule that comprises SEQ ID NO:7, SEQ ID NO:8, SEQ ID NO:9, SEQ ID NO:10, SEQ ID NO:27, SEQ ID NO:28, SEQ ID NO:29, SEQ ID NO:30, SEQ ID NO:31, SEQ ID NO:32, SEQ ID NO:33, or SEQ ID NO:34.

In some embodiments, the molecular complex comprises or consists of an alteration-specific primer or an alteration-specific probe hybridized to a cDNA molecule comprising a nucleotide sequence encoding a KLHDC7B polypeptide, wherein the alteration-specific primer or the alteration-specific probe is hybridized to: an adenine at a position corresponding to position 3,778 according to SEQ ID NO:15, or the complement thereof; an adenine at a position corresponding to position 1,644 according to SEQ ID NO:16, or the complement thereof; an adenine at a position corresponding to position 3,474 according to SEQ ID NO:17, or the complement thereof; an adenine at a position corresponding to position 1,644 according to SEQ ID NO:18, or the complement thereof; a CG dinucleotide at positions corresponding to positions 2,806-2,807 to SEQ ID NO:35, or the complement thereof; a CG dinucleotide at positions corresponding to positions 672-673 according to SEQ ID NO:36, or the complement thereof; a CG dinucleotide at positions corresponding to positions 2,502-2,503 according to SEQ ID NO:37, or the complement thereof; a CG dinucleotide at positions corresponding to positions 672-673 according to SEQ ID NO:38, or the complement thereof; an AG dinucleotide at positions corresponding to positions 3,169-3,170 according to SEQ ID NO:39, or the complement thereof; an AG dinucleotide at positions corresponding to positions 1,035-1,036 according to SEQ ID NO:40, or the complement thereof; an AG dinucleotide at positions corresponding to positions 2,865-2,866 according to SEQ ID NO:41, or the complement thereof; or an AG dinucleotide at positions corresponding to positions 1,035-1,036 according to SEQ ID NO:42, or the complement thereof.

In some embodiments, the molecular complex comprises or consists of an alteration-specific primer or an alteration-specific probe that is hybridized to: an ATG codon at positions corresponding to positions 3,778-3,780 according to SEQ ID NO:15, an ATG codon at positions corresponding to positions 1,644-1,646 according to SEQ ID NO:16, an ATG codon at positions corresponding to positions 3,474-3,476 according to SEQ ID NO:17, or an ATG codon at positions corresponding to positions 1,644-1,646 according to SEQ ID NO:18.

In some embodiments, the molecular complex comprises or consists of a cDNA molecule that comprises SEQ ID NO:15, SEQ ID NO:16, SEQ ID NO:17, SEQ ID NO:18, SEQ ID NO:35, SEQ ID NO:36, SEQ ID NO:37, SEQ ID NO:38, SEQ ID NO:39, SEQ ID NO:40, SEQ ID NO:41, or SEQ ID NO:42.

In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The nucleotide sequence of a KLHDC7B reference genomic nucleic acid molecule (hg38 chr22:50,545,899-50,551,023; ENST00000648057.3) is set forth in SEQ ID NO:1. Referring to SEQ ID NO:1, position 3,778 is a guanine.

A variant genomic nucleic acid molecule of KLHDC7B exists, wherein the guanine at position 3,778 (referring to SEQ ID NO:1) is replaced with an adenine. The nucleotide sequence of this KLHDC7B variant genomic nucleic acid molecule is set forth in SEQ ID NO:2 (r536062310).

Another variant genomic nucleic acid molecule of KLHDC7B exists, wherein a guanine at position 2,807 (referring to SEQ ID NO:1) is deleted. The nucleotide sequence of this KLHDC7B variant genomic nucleic acid molecule is set forth in SEQ ID NO:25 (r5746113253).

Another variant genomic nucleic acid molecule of KLHDC7B exists, wherein a guanine at position 3,170 (referring to SEQ ID NO:1) is deleted. The nucleotide sequence of this KLHDC7B variant genomic nucleic acid molecule is set forth in SEQ ID NO:26 (r5749405486).

The nucleotide sequence of a KLHDC7B reference mRNA molecule is set forth in SEQ ID NO:3 (ENST00000648057.3). Referring to SEQ ID NO:3, position 3,778 is a guanine.

The nucleotide sequence of another KLHDC7B reference mRNA molecule is set forth in SEQ ID NO:4 (ENST00000395676.4). Referring to SEQ ID NO:4, position 1,644 is a guanine.

The nucleotide sequence of another KLHDC7B reference mRNA molecule is set forth in SEQ ID NO:5 (NM_138433.4). Referring to SEQ ID NO:5, position 3,474 is a guanine.

The nucleotide sequence of another KLHDC7B reference mRNA molecule is set forth in SEQ ID NO:6 (BC009980). Referring to SEQ ID NO:6, position 1,644 is a guanine.

A variant mRNA molecule of KLHDC7B exists, wherein the guanine at position 3,778 (referring to SEQ ID NO:3) is replaced with an adenine. The nucleotide sequence of this KLHDC7B variant mRNA molecule is set forth in SEQ ID NO:7 (ENST00000648057.3).

Another variant mRNA molecule of KLHDC7B exists, wherein the guanine at position 1,644 (referring to SEQ ID NO:4) is replaced with an adenine. The nucleotide sequence of this KLHDC7B variant mRNA molecule is set forth in SEQ ID NO:8 (ENST00000395676.4).

Another variant mRNA molecule of KLHDC7B exists, wherein the guanine at position 3,474 (referring to SEQ ID NO:5) is replaced with an adenine. The nucleotide sequence of this KLHDC7B variant mRNA molecule is set forth in SEQ ID NO:9 (NM_138433.4).

Another variant mRNA molecule of KLHDC7B exists, wherein the guanine at position 1,644 (referring to SEQ ID NO:6) is replaced with an adenine. The nucleotide sequence of this KLHDC7B variant mRNA molecule is set forth in SEQ ID NO:10 (BC009980).

Another variant mRNA molecule of KLHDC7B exists, wherein the guanine at position 2,807 (referring to SEQ ID NO:3) is deleted. The nucleotide sequence of this KLHDC7B variant mRNA molecule is set forth in SEQ ID NO:27 (ENST00000648057.3).

Another variant mRNA molecule of KLHDC7B exists, wherein the guanine at position 673 (referring to SEQ ID NO:4) is deleted. The nucleotide sequence of this KLHDC7B variant mRNA molecule is set forth in SEQ ID NO:28 (ENST00000395676.4).

Another variant mRNA molecule of KLHDC7B exists, wherein the guanine at position 2,503 (referring to SEQ ID NO:5) is deleted. The nucleotide sequence of this KLHDC7B variant mRNA molecule is set forth in SEQ ID NO:29 (NM_138433.4).

Another variant mRNA molecule of KLHDC7B exists, wherein the guanine at position 673 (referring to SEQ ID NO:6) is deleted. The nucleotide sequence of this KLHDC7B variant mRNA molecule is set forth in SEQ ID NO:30 (BC009980).

Another variant mRNA molecule of KLHDC7B exists, wherein the guanine at position 3,170 (referring to SEQ ID NO:3) is deleted. The nucleotide sequence of this KLHDC7B variant mRNA molecule is set forth in SEQ ID NO:31 (ENST00000648057.3).

Another variant mRNA molecule of KLHDC7B exists, wherein the guanine at position 1,036 (referring to SEQ ID NO:4) is deleted. The nucleotide sequence of this KLHDC7B variant mRNA molecule is set forth in SEQ ID NO:32 (ENST00000395676.4).

Another variant mRNA molecule of KLHDC7B exists, wherein the guanine at position 2,866 (referring to SEQ ID NO:5) is deleted. The nucleotide sequence of this KLHDC7B variant mRNA molecule is set forth in SEQ ID NO:33 (NM_138433.4).

Another variant mRNA molecule of KLHDC7B exists, wherein the guanine at position 1,036 (referring to SEQ ID NO:6) is deleted. The nucleotide sequence of this KLHDC7B variant mRNA molecule is set forth in SEQ ID NO:34 (BC009980).

The nucleotide sequence of a KLHDC7B reference cDNA molecule is set forth in SEQ ID NO:11 (ENST00000648057.3). Referring to SEQ ID NO:11, position 3,778 is a guanine.

The nucleotide sequence of another KLHDC7B reference cDNA molecule is set forth in SEQ ID NO:12 (ENST00000395676.4). Referring to SEQ ID NO:12, position 1,644 is a guanine.

The nucleotide sequence of another KLHDC7B reference cDNA molecule is set forth in SEQ ID NO:13 (NM_138433.4). Referring to SEQ ID NO:13, position 3,474 is a guanine.

The nucleotide sequence of another KLHDC7B reference cDNA molecule is set forth in SEQ ID NO:14 (BC009980). Referring to SEQ ID NO:14, position 1,644 is a guanine.

A variant cDNA molecule of KLHDC7B exists, wherein the guanine at position 3,778 (referring to SEQ ID NO:11) is replaced with an adenine. The nucleotide sequence of this KLHDC7B variant cDNA molecule is set forth in SEQ ID NO:15 (ENST00000648057.3).

Another variant cDNA molecule of KLHDC7B exists, wherein the guanine at position 1,644 (referring to SEQ ID NO:12) is replaced with an adenine. The nucleotide sequence of this KLHDC7B variant cDNA molecule is set forth in SEQ ID NO:16 (ENST00000395676.4).

Another variant cDNA molecule of KLHDC7B exists, wherein the guanine at position 3,474 (referring to SEQ ID NO:13) is replaced with an adenine. The nucleotide sequence of this KLHDC7B variant cDNA molecule is set forth in SEQ ID NO:17 (NM_138433.4). Another variant cDNA molecule of KLHDC7B exists, wherein the guanine at position 1,644 (referring to SEQ ID NO:14) is replaced with an adenine. The nucleotide sequence of this KLHDC7B variant cDNA molecule is set forth in SEQ ID NO:18 (BC009980).

Another variant cDNA molecule of KLHDC7B exists, wherein the guanine at position 2,807 (referring to SEQ ID NO:11) is deleted. The nucleotide sequence of this KLHDC7B variant cDNA molecule is set forth in SEQ ID NO:35 (ENST00000648057.3).

Another variant cDNA molecule of KLHDC7B exists, wherein the guanine at position 673 (referring to SEQ ID NO:12) is deleted. The nucleotide sequence of this KLHDC7B variant cDNA molecule is set forth in SEQ ID NO:36 (ENST00000395676.4).

Another variant cDNA molecule of KLHDC7B exists, wherein the guanine at position 2,503 (referring to SEQ ID NO:13) is deleted. The nucleotide sequence of this KLHDC7B variant cDNA molecule is set forth in SEQ ID NO:37 (NM_138433.4).

Another variant cDNA molecule of KLHDC7B exists, wherein the guanine at position 673 (referring to SEQ ID NO:14) is deleted. The nucleotide sequence of this KLHDC7B variant cDNA molecule is set forth in SEQ ID NO:38 (BC009980).

Another variant cDNA molecule of KLHDC7B exists, wherein the guanine at position 3,170 (referring to SEQ ID NO:11) is deleted. The nucleotide sequence of this KLHDC7B variant cDNA molecule is set forth in SEQ ID NO:39 (ENST00000648057.3).

Another variant cDNA molecule of KLHDC7B exists, wherein the guanine at position 1,036 (referring to SEQ ID NO:12) is deleted. The nucleotide sequence of this KLHDC7B variant cDNA molecule is set forth in SEQ ID NO:40 (ENST00000395676.4).

Another variant cDNA molecule of KLHDC7B exists, wherein the guanine at position 2,866 (referring to SEQ ID NO:13) is deleted. The nucleotide sequence of this KLHDC7B variant cDNA molecule is set forth in SEQ ID NO:41 (NM_138433.4).

Another variant cDNA molecule of KLHDC7B exists, wherein the guanine at position 1,036 (referring to SEQ ID NO:14) is deleted. The nucleotide sequence of this KLHDC7B variant cDNA molecule is set forth in SEQ ID NO:42 (BC009980).

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidase (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, gluta-thione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$ alkyl or $C_{2-10}$ alkenyl, and $C_{2-10}$ alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nC_{H3}]_2$, where n and m are from 1 to about 10. Other modifications at the 2' position include, but are not limited to, $C_{1-10}$ alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH2 and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:3, or SEQ ID NO:11). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a KLHDC7B polypeptide, wherein the nucleotide sequence comprises an adenine at a position corresponding to position 3,778 according to SEQ ID NO:2 means that if the nucleotide sequence of the KLHDC7B genomic nucleic acid molecule is aligned to the sequence of SEQ ID NO:2, the KLHDC7B sequence has an adenine residue at the position that corresponds to position 3,778 of SEQ ID NO:2. The same applies for mRNA molecules comprising a nucleotide sequence encoding a KLHDC7B polypeptide, wherein the nucleotide sequence comprises an adenine at a position corresponding to position 3,778 according to SEQ ID NO:7, and cDNA molecules comprising a nucleotide sequence encoding a KLHDC7B polypeptide, wherein the nucleotide sequence comprises an adenine at a position corresponding to position 3,778 according to SEQ ID NO:15. In other words, these phrases refer to a nucleic acid molecule encoding a KLHDC7B polypeptide, wherein the genomic nucleic acid molecule has a nucleotide sequence that comprises an adenine residue that is homologous to the adenine residue at position 3,778 of SEQ ID NO:2 (or wherein the mRNA molecule has a nucleotide sequence that comprises an adenine residue that is homologous to the adenine residue at position 3,778 of SEQ ID NO:7, or wherein the cDNA molecule has a nucleotide sequence that comprises an adenine residue that is homologous to the adenine residue at position 3,778 of SEQ ID NO:15).

As described herein, a position within a KLHDC7B genomic nucleic acid molecule that corresponds to position 3,778 according to SEQ ID NO:2, for example, can be identified by performing a sequence alignment between the nucleotide sequence of a particular KLHDC7B nucleic acid molecule and the nucleotide sequence of SEQ ID NO:2. A variety of computational algorithms exist that can be used for performing a sequence alignment to identify a nucleotide position that corresponds to, for example, position 3,778 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of a KLHDC7B reference polypeptide is set forth in SEQ ID NO:19. Referring to SEQ ID NO:19, the KLHDC7B reference polypeptide is 1,235 amino acids in length. Referring to SEQ ID NO:19, position 1,145 is valine, position 822 is lysine, and position 943 is glycine.

The amino acid sequence of another KLHDC7B reference polypeptide is set forth in SEQ ID NO:20. Referring to SEQ ID NO:20, the KLHDC7B reference polypeptide is 594 amino acids in length. Referring to SEQ ID NO:20, position 504 is valine, position 181 is lysine, and position 302 is glycine.

The amino acid sequence of another KLHDC7B reference polypeptide is set forth in SEQ ID NO:21. Referring to SEQ ID NO:21, the KLHDC7B reference polypeptide is 495 amino acids in length. Referring to SEQ ID NO:21, position 405 is valine, position 82 is lysine, and position 203 is glycine.

A KLHDC7B variant polypeptide exists (V1145M or Val1145Met), the amino acid sequence of which is set forth in SEQ ID NO:22. Referring to SEQ ID NO:22, the KLHDC7B variant polypeptide is 1,235 amino acids in length. Referring to SEQ ID NO:22, position 1,145 is methionine.

Another KLHDC7B variant polypeptide exists (V504M or Val504Met), the amino acid sequence of which is set forth in SEQ ID NO:23. Referring to SEQ ID NO:23, the KLHDC7B variant polypeptide is 594 amino acids in length. Referring to SEQ ID NO:23, position 504 is methionine.

Another KLHDC7B variant polypeptide exists (V405M or Val405Met), the amino acid sequence of which is set forth in SEQ ID NO:24. Referring to SEQ ID NO:24, the KLHDC7B variant polypeptide is 495 amino acids in length. Referring to SEQ ID NO:24, position 405 is methionine.

A KLHDC7B truncated variant polypeptide exists (K822fs or Lys822fs), the amino acid sequence of which is set forth in SEQ ID NO:43. Referring to SEQ ID NO:43, the KLHDC7B variant polypeptide is 885 amino acids in length. Referring to SEQ ID NO:43, the KLHDC7B variant polypeptide is truncated at position 885 and does not contain amino acids at positions corresponding to positions 886 to 1,235 of SEQ ID NO:19. Referring to SEQ ID NO:43, position 822 is serine.

Another KLHDC7B truncated variant polypeptide exists (K181fs or Lys181fs), the amino acid sequence of which is set forth in SEQ ID NO:44. Referring to SEQ ID NO:44, the KLHDC7B variant polypeptide is 244 amino acids in length. Referring to SEQ ID NO:44, the KLHDC7B variant polypeptide is truncated at position 244 and does not contain amino acids at positions corresponding to positions 245 to 594 of SEQ ID NO:20. Referring to SEQ ID NO:44, position 181 is serine.

Another KLHDC7B truncated variant polypeptide exists (K82fs or Lys82fs), the amino acid sequence of which is set forth in SEQ ID NO:45. Referring to SEQ ID NO:45, the KLHDC7B variant polypeptide is 145 amino acids in length. Referring to SEQ ID NO:45, the KLHDC7B variant polypeptide is truncated at position 145 and does not contain amino acids at positions corresponding to positions 146 to 495 of SEQ ID NO:21. Referring to SEQ ID NO:45, position 82 is serine.

Another KLHDC7B truncated variant polypeptide exists (G943fs or Gly943fs), the amino acid sequence of which is set forth in SEQ ID NO:46. Referring to SEQ ID NO:46, the KLHDC7B variant polypeptide is 975 amino acids in length. Referring to SEQ ID NO:46, the KLHDC7B variant polypeptide is truncated at position 975 and does not contain amino acids at positions corresponding to positions 976 to 1,235 of SEQ ID NO:19. Referring to SEQ ID NO:46, position 943 is arginine.

Another KLHDC7B truncated variant polypeptide exists (G302fs or Gly302fs), the amino acid sequence of which is set forth in SEQ ID NO:47. Referring to SEQ ID NO:47, the KLHDC7B variant polypeptide is 334 amino acids in length. Referring to SEQ ID NO:47, the KLHDC7B variant polypeptide is truncated at position 334 and does not contain amino acids at positions corresponding to positions 335 to 594 of SEQ ID NO:20. Referring to SEQ ID NO:47, position 302 is arginine.

Another KLHDC7B truncated variant polypeptide exists (G203fs or Gly203fs), the amino acid sequence of which is set forth in SEQ ID NO:48. Referring to SEQ ID NO:48, the KLHDC7B variant polypeptide is 235 amino acids in length. Referring to SEQ ID NO:48, the KLHDC7B variant polypeptide is truncated at position 235 and does not contain amino acids at positions corresponding to positions 236 to 495 of SEQ ID NO:21. Referring to SEQ ID NO:48, position 203 is arginine.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit hearing loss for use in the treatment of hearing loss (or for use in the preparation of a medicament for treating hearing loss) in a subject, wherein the subject has any of the genomic nucleic acid molecules, mRNA molecules, and/or cDNA molecules encoding a KLHDC7B polypeptide described herein. The therapeutic agents that treat or inhibit hearing loss can be any of the therapeutic agents that treat or inhibit hearing loss described herein.

In some embodiments, the subject comprises: a genomic nucleic acid molecule having a nucleotide sequence encoding a KLHDC7B polypeptide, wherein the nucleotide sequence comprises: an adenine at a position corresponding to position 3,778 according to SEQ ID NO:2, or the complement thereof; an mRNA molecule having a nucleotide sequence encoding a KLHDC7B polypeptide, wherein the nucleotide sequence comprises an adenine at a position corresponding to position 3,778 according to SEQ ID NO:7, or the complement thereof; a cDNA molecule having a nucleotide sequence encoding a KLHDC7B polypeptide, wherein the nucleotide sequence comprises an adenine at a position corresponding to position 3,778 according to SEQ ID NO:15, or the complement thereof; or a KLHDC7B polypeptide that comprises a methionine at a position corresponding to position 1,145 according to SEQ ID NO:22.

In some embodiments, the subject comprises: an mRNA molecule having a nucleotide sequence encoding a KLHDC7B polypeptide, wherein the nucleotide sequence comprises an adenine at a position corresponding to position 1,644 according to SEQ ID NO:8, or the complement thereof; a cDNA molecule having a nucleotide sequence encoding a KLHDC7B polypeptide, wherein the nucleotide sequence comprises an adenine at a position corresponding to position 1,644 according to SEQ ID NO:16, or the complement thereof; or a KLHDC7B polypeptide that comprises a methionine at a position corresponding to position 504 according to SEQ ID NO:23.

In some embodiments, the subject comprises: an mRNA molecule having a nucleotide sequence encoding a KLHDC7B polypeptide, wherein the nucleotide sequence comprises an adenine at a position corresponding to position 3,474 according to SEQ ID NO:9, or the complement thereof; a cDNA molecule having a nucleotide sequence encoding a KLHDC7B polypeptide, wherein the nucleotide sequence comprises an adenine at a position corresponding to position 3,474 according to SEQ ID NO:17, or the complement thereof; or a KLHDC7B polypeptide that comprises a methionine at a position corresponding to position 405 according to SEQ ID NO:24.

In some embodiments, the subject comprises: an mRNA molecule having a nucleotide sequence encoding a KLHDC7B polypeptide, wherein the nucleotide sequence comprises an adenine at a position corresponding to position 1,644 according to SEQ ID NO:10, or the complement thereof; a cDNA molecule having a nucleotide sequence encoding a KLHDC7B polypeptide, wherein the nucleotide sequence comprises an adenine at a position corresponding to position 1,644 according to SEQ ID NO:18, or the complement thereof.

In some embodiments, the subject comprises: a genomic nucleic acid molecule having a nucleotide sequence encoding a KLHDC7B polypeptide, wherein the nucleotide sequence comprises: a CG dinucleotide at positions corresponding to positions 2,806-2,807 according to SEQ ID NO:25, or the complement thereof; an mRNA molecule having a nucleotide sequence encoding a KLHDC7B polypeptide, wherein the nucleotide sequence comprises a CG dinucleotide at positions corresponding to positions 2,806-2,807 to SEQ ID NO:27, or the complement thereof; a cDNA molecule having a nucleotide sequence encoding a KLHDC7B polypeptide, wherein the nucleotide sequence comprises a CG dinucleotide at positions corresponding to positions 2,806-2,807 to SEQ ID NO:35, or the complement thereof; or a KLHDC7B polypeptide that comprises a serine at a position corresponding to position 822 according to SEQ ID NO:43.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises a CG dinucleotide at positions corresponding to positions 672-673 according to SEQ ID NO:28, or the complement thereof; a cDNA molecule having a nucleotide sequence encoding a KLHDC7B polypeptide, wherein the nucleotide sequence comprises a CG dinucleotide at positions corresponding to positions 672-673 according to SEQ ID NO:36, or the complement thereof; or a KLHDC7B polypeptide that comprises a serine at a position corresponding to position 181 according to SEQ ID NO:44.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises a CG dinucleotide at positions corresponding to positions 2,502-2,503 according to SEQ ID NO:29, or the complement thereof; a cDNA molecule having a nucleotide sequence encoding a KLHDC7B polypeptide, wherein the nucleotide sequence comprises a CG dinucleotide at positions corresponding to positions 2,502-2,503 according to SEQ ID NO:37, or the complement thereof; or a KLHDC7B polypeptide that comprises a serine at a position corresponding to position 82 according to SEQ ID NO:45.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises a CG dinucleotide at positions corresponding to positions 672-673 according to SEQ ID NO:30, or the complement thereof; or a cDNA molecule having a nucleotide sequence encoding a KLHDC7B polypeptide, wherein the nucleotide sequence comprises a CG dinucleotide at positions corresponding to positions 672-673 according to SEQ ID NO:38, or the complement thereof.

In some embodiments, the subject comprises: a genomic nucleic acid molecule having a nucleotide sequence encoding a KLHDC7B polypeptide, wherein the nucleotide sequence comprises: an AG dinucleotide at positions corresponding to positions 3,169-3,170 according to SEQ ID NO:26, or the complement thereof; an mRNA molecule having a nucleotide sequence encoding a KLHDC7B polypeptide, wherein the nucleotide sequence comprises an AG dinucleotide at positions corresponding to positions 3,169-3,170 according to SEQ ID NO:31, or the complement thereof; a cDNA molecule having a nucleotide sequence encoding a KLHDC7B polypeptide, wherein the nucleotide sequence comprises an AG dinucleotide at positions corresponding to positions 3,169-3,170 according to SEQ ID NO:39, or the complement thereof; or a KLHDC7B polypeptide that comprises an arginine at a position corresponding to position 943 according to SEQ ID NO:46.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises an AG dinucleotide at positions corresponding to positions 1,035-1,036 according to SEQ ID NO:32, or the complement thereof; a cDNA molecule having a nucleotide sequence encoding a KLHDC7B polypeptide, wherein the nucleotide sequence comprises an AG dinucleotide at positions corresponding to positions 1,035-1,036 according to SEQ ID NO:40, or the complement thereof; or a KLHDC7B polypeptide that comprises an arginine at a position corresponding to position 302 according to SEQ ID NO:47.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises an AG dinucleotide at positions corresponding to positions 2,865-2,866 according to SEQ ID NO:33, or the complement thereof; a cDNA molecule having a nucleotide sequence encoding a KLHDC7B polypeptide, wherein the nucleotide sequence comprises an AG dinucleotide at positions corresponding to positions 2,865-2,866 according to SEQ ID NO:41, or the complement thereof; or a KLHDC7B polypeptide that comprises an arginine at a position corresponding to position 203 according to SEQ ID NO:48.

In some embodiments, the subject comprises: a genomic nucleic acid molecule having a nucleotide sequence encoding a KLHDC7B polypeptide, wherein the nucleotide sequence comprises: an mRNA molecule having a nucleotide sequence encoding a KLHDC7B polypeptide, wherein the nucleotide sequence comprises an AG dinucleotide at positions corresponding to positions 1,035-1,036 according to SEQ ID NO:34, or the complement thereof; or a cDNA molecule having a nucleotide sequence encoding a KLHDC7B polypeptide, wherein the nucleotide sequence comprises an AG dinucleotide at positions corresponding to positions 1,035-1,036 according to SEQ ID NO:42, or the complement thereof.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Figure 2:
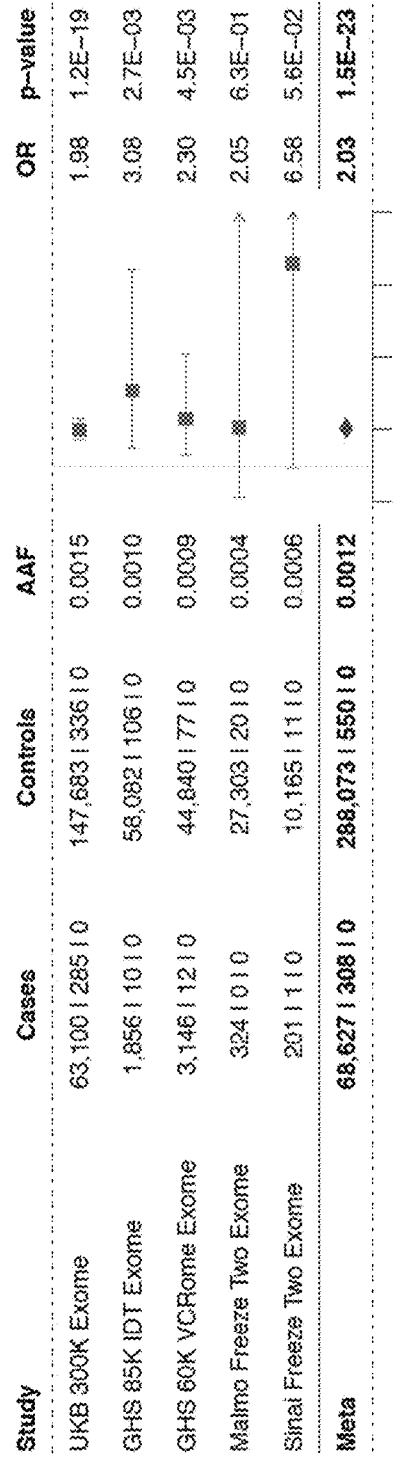
FIG. 2 shows an aggregate of rare (minor allele frequency <1%), pLOF variants in KLHDC7B is associated with hearing loss. This suggests that there are additional loss of function variants that increase the risk for hearing loss in carriers.
Figure 2:
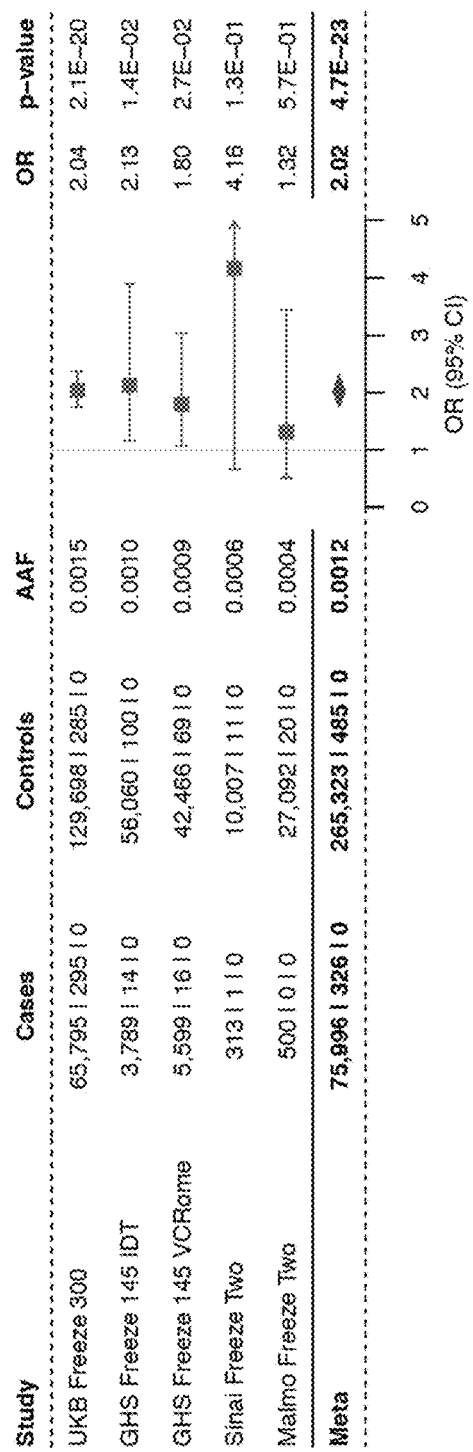

Example 1: A Missense Variant and Predicted Loss-of-Function Variants in KLHDC7B are Associated with Increased Risk for Hearing Loss A genome-wide and exome-wide analysis of self-reported and ICD code based hearing loss was carried out in UK Biobank, Geisinger (GHS) and other datasets. A common missense variant (FIG. 1, Panel C) and two rare, predicted loss-of-function (pLOF) variants (FIG. 1, Panels A and B) in KLHDC7B were associated with increased risk for hearing loss in meta-analysis of UK Biobank and 3 other cohorts. In addition, an aggregate of rare (minor allele frequency of less than 1%), pLOF variants in KLHDC7B also show an association with increased risk for hearing loss in the meta-analysis (FIG. 2) suggesting that KLHDC7B loss of function variants in addition to the two described in FIG. 1 confer an increased risk for hearing loss in carriers. The association with loss of function variants further suggests that reduced function of KLHDC7B is detrimental to hearing ability.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject having hearing loss with a therapeutic agent that treats or inhibits hearing loss, wherein the subject has been determined to have a Kelch Domain Containing 7B (KLHDC7B) missense variant nucleic acid molecule encoding KLHDC7B K181fs or KLHDC7B G302fs.

2. The method according to claim 1, wherein the KLHDC7B missense variant nucleic acid molecule is:
lacking a guanine at a position corresponding to position 2,807 according to SEQ ID NO:1; or lacking a guanine at a position corresponding to position 3,170 according to SEQ ID NO:1; or
an mRNA molecule having a nucleotide sequence: lacking a guanine at a position corresponding to position 673 according to SEQ ID NO:4, lacking a guanine at a position corresponding to position 673 according to SEQ ID NO:6, lacking a guanine at a position corresponding to position 1,036 according to SEQ ID NO:4, or lacking a guanine at a position corresponding to position 1,036 according to SEQ ID NO:6; or
a cDNA molecule produced from an mRNA molecule, wherein the cDNA molecule has a nucleotide sequence: lacking a guanine at a position corresponding to position 673 according to SEQ ID NO: 12, lacking a guanine at a position corresponding to position 673 according to SEQ ID NO: 14, lacking a guanine at a position corresponding to position 1,036 according to SEQ ID NO: 12, or lacking a guanine at a position corresponding to position 1,036 according to SEQ ID NO: 14.

3. The method of claim 1, wherein the subject has conductive hearing loss.

4. The method of claim 1, wherein the subject has sensorineural hearing loss.

5. The method of claim 1, wherein the subject has neural hearing loss.

6. The method of claim 1, wherein the subject has been determined to have a KLHDC7B missense variant nucleic acid molecule encoding KLHDC7B K181fs.

7. The method of claim 1, wherein the subject is heterozygous for the KLHDC7B missense variant nucleic acid molecule encoding KLHDC7B K181fs.

8. The method of claim 1, wherein the subject has been determined to have a KLHDC7B missense variant nucleic acid molecule encoding KLHDC7B G302fs.

9. The method of claim 1, wherein the subject is heterozygous for the KLHDC7B missense variant nucleic acid molecule encoding KLHDC7B G302fs.

10. The method of claim 1, wherein the KLHDC7B missense variant nucleic acid molecule is a genomic nucleic acid molecule having a nucleotide sequence lacking a guanine at a position corresponding to position 2,807 according to SEQ ID NO:1.

11. The method of claim 1, wherein the KLHDC7B missense variant nucleic acid molecule is a genomic nucleic acid molecule having a nucleotide sequence lacking a guanine at a position corresponding to position 3,170 according to SEQ ID NO:1.

12. The method of claim 1, wherein the KLHDC7B missense variant nucleic acid molecule is an mRNA molecule having a nucleotide sequence lacking a guanine at a position corresponding to position 673 according to SEQ ID NO:4.

13. The method of claim 1, wherein the KLHDC7B missense variant nucleic acid molecule is an mRNA molecule having a nucleotide sequence lacking a guanine at a position corresponding to position 673 according to SEQ ID NO:6.

14. The method of claim 1, wherein the KLHDC7B missense variant nucleic acid molecule is an mRNA molecule having a nucleotide sequence lacking a guanine at a position corresponding to position 1,036 according to SEQ ID NO:4.

15. The method of claim 1, wherein the KLHDC7B missense variant nucleic acid molecule is an mRNA molecule having a nucleotide sequence lacking a guanine at a position corresponding to position 1,036 according to SEQ ID NO:6.

16. The method of claim 1, wherein the KLHDC7B missense variant nucleic acid molecule is a cDNA molecule produced from an mRNA molecule, wherein the cDNA molecule has a nucleotide sequence lacking a guanine at a position corresponding to position 673 according to SEQ ID NO:12.

17. The method of claim 1, wherein the KLHDC7B missense variant nucleic acid molecule is a cDNA molecule produced from an mRNA molecule, wherein the cDNA molecule has a nucleotide sequence lacking a guanine at a position corresponding to position 673 according to SEQ ID NO: 14.

18. The method of claim 1, wherein the KLHDC7B missense variant nucleic acid molecule is a cDNA molecule produced from an mRNA molecule, wherein the cDNA molecule has a nucleotide sequence lacking a guanine at a position corresponding to position 1,036 according to SEQ ID NO:12.

19. The method of claim 1, wherein the KLHDC7B missense variant nucleic acid molecule is a cDNA molecule produced from an mRNA molecule, wherein the cDNA molecule has a nucleotide sequence lacking a guanine at a position corresponding to position 1,036 according to SEQ ID NO: 14.

* * * * *